(12) United States Patent
Cid-Nunez et al.

(10) Patent No.: US 8,946,205 B2
(45) Date of Patent: Feb. 3, 2015

(54) 1,2,4-TRIAZOLO[4,3-A]PYRIDINE DERIVATIVES AND THEIR USE AS POSITIVE ALLOSTERIC MODULATORS OF MGLUR2 RECEPTORS

(75) Inventors: Jose Maria Cid-Nunez, Toledo (ES); Ana Isabel De Lucas Olivares, Toledo (ES); Andres Avelino Trabanco-Suarez, Toledo (ES); Gregor James MacDonald, Beerse (BE)

(73) Assignees: Janssen Pharmaceuticals, Inc., Titusville, NJ (US); Addex Pharma, S.A., Geneva (CH)

( * ) Notice: Subject to any disclaimer, the term of this patent is extended or adjusted under 35 U.S.C. 154(b) by 344 days.

(21) Appl. No.: 13/319,558

(22) PCT Filed: May 11, 2010

(86) PCT No.: PCT/EP2010/002908
§ 371 (c)(1),
(2), (4) Date: Apr. 5, 2012

(87) PCT Pub. No.: WO2010/130422
PCT Pub. Date: Nov. 18, 2010

(65) Prior Publication Data
US 2012/0184527 A1 Jul. 19, 2012

(30) Foreign Application Priority Data
May 12, 2009 (EP) .................................... 09160067

(51) Int. Cl.
| | | |
|---|---|---|
| *A61K 31/553* | (2006.01) | |
| *A61K 31/437* | (2006.01) | |
| *A61K 31/538* | (2006.01) | |
| *A61K 31/506* | (2006.01) | |
| *C07D 471/04* | (2006.01) | |
| *C07D 519/00* | (2006.01) | |
| *A61K 45/06* | (2006.01) | |
| *A61K 31/444* | (2006.01) | |
| *A61K 9/00* | (2006.01) | |
| *A61K 9/06* | (2006.01) | |
| *A61K 9/08* | (2006.01) | |
| *A61K 9/10* | (2006.01) | |
| *A61K 9/20* | (2006.01) | |

(52) U.S. Cl.
CPC ............ *C07D 471/04* (2013.01); *C07D 519/00* (2013.01); *A61K 45/06* (2013.01); *A61K 31/437* (2013.01); *A61K 31/444* (2013.01); *A61K 31/553* (2013.01); *A61K 9/0014* (2013.01); *A61K 9/0095* (2013.01); *A61K 9/06* (2013.01); *A61K 9/08* (2013.01); *A61K 9/10* (2013.01); *A61K 9/2009* (2013.01); *A61K 9/2059* (2013.01)
USPC ... 514/211.09; 514/303; 514/275; 514/230.5; 546/119; 544/105; 544/331; 540/552

(58) Field of Classification Search
USPC .......... 514/211.09, 303, 230.5, 275; 546/119; 544/105, 331; 540/552
See application file for complete search history.

(56) References Cited

U.S. PATENT DOCUMENTS

| | | | |
|---|---|---|---|
| 2,976,146 A | * | 3/1961 | Salminen et al. .............. 430/385 |
| 4,051,244 A | | 9/1977 | Matiioda et al. |
| 4,066,651 A | | 1/1978 | Brittain et al. |
| 4,146,716 A | | 3/1979 | Cox et al. |
| 4,196,207 A | | 4/1980 | Webber et al. |
| 4,256,738 A | | 3/1981 | Woitun et al. |
| 4,358,453 A | | 11/1982 | Bristol et al. |

(Continued)

FOREIGN PATENT DOCUMENTS

| | | |
|---|---|---|
| BE | 841390 | 11/1976 |
| CA | 1019323 | 10/1977 |

(Continued)

OTHER PUBLICATIONS

Liu et al., The Journal of Neuroscience, (2006), 26(20):5309-5319.*

(Continued)

*Primary Examiner* — Niloofar Rahmani
(74) *Attorney, Agent, or Firm* — Baker & Hostetler LLP

(57) ABSTRACT

The present invention relates to novel triazolo[4,3-a]pyridine derivatives of Formula (I) wherein all radicals are as defined in the claims. The compounds according to the invention are positive allosteric modulators of the metabotropic glutamate receptor subtype 2 ("mGluR2"), which are useful for the treatment or prevention of neurological and psychiatric disorders associated with glutamate dysfunction and diseases in which the mGluR2 subtype of metabotropic receptors is involved. The invention is also directed to pharmaceutical compositions comprising such compounds, to processes to prepare such compounds and compositions, and to the use of such compounds for the prevention or treatment of neurological and psychiatric disorders and diseases in which mGluR2 is involved.

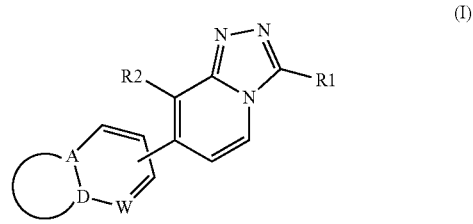

25 Claims, No Drawings

(56) References Cited

U.S. PATENT DOCUMENTS

| | | |
|---|---|---|
| 4,550,166 A | 10/1985 | Moran et al. |
| 4,866,074 A | 9/1989 | Spada et al. |
| 4,898,654 A | 2/1990 | Toda et al. |
| 4,978,663 A | 12/1990 | Effland et al. |
| 5,032,602 A | 7/1991 | Fey et al. |
| 5,130,442 A | 7/1992 | Meisel et al. |
| 5,175,157 A | 12/1992 | Psiorz et al. |
| 5,204,198 A | 4/1993 | Bugner et al. |
| 5,236,917 A | 8/1993 | Dunlap et al. |
| 5,254,543 A | 10/1993 | Hanko et al. |
| 5,260,293 A | 11/1993 | Baker et al. |
| 5,280,026 A | 1/1994 | Brown et al. |
| 5,332,750 A | 7/1994 | Mederski et al. |
| 5,356,911 A | 10/1994 | Muller-Gliemann et al. |
| 5,366,981 A | 11/1994 | Vecchietti et al. |
| 5,371,074 A | 12/1994 | Dunlap et al. |
| 5,374,513 A | 12/1994 | Ohzeki et al. |
| 5,378,720 A | 1/1995 | Hlasta et al. |
| 5,407,948 A | 4/1995 | Fey et al. |
| 5,418,243 A | 5/1995 | Angerbauer et al. |
| 5,424,435 A | 6/1995 | Hani et al. |
| 5,473,077 A | 12/1995 | Monn et al. |
| 5,498,774 A | 3/1996 | Mitsudera et al. |
| 5,500,420 A | 3/1996 | Maiese |
| 5,512,576 A | 4/1996 | Desai et al. |
| 5,532,242 A | 7/1996 | Cliffe |
| 5,596,012 A | 1/1997 | Dunlap et al. |
| 5,602,145 A | 2/1997 | Samanen |
| 5,650,422 A | 7/1997 | Dunlap et al. |
| 5,654,307 A | 8/1997 | Bridges et al. |
| 5,675,013 A | 10/1997 | Hani et al. |
| 5,710,274 A | 1/1998 | Yuan et al. |
| 5,723,463 A | 3/1998 | Hofgen et al. |
| 5,741,798 A | 4/1998 | Lazer et al. |
| 5,801,179 A | 9/1998 | Van Lommen et al. |
| 5,814,645 A | 9/1998 | Kanellakopulos et al. |
| 5,855,654 A | 1/1999 | Willingham et al. |
| 5,859,020 A | 1/1999 | Preuss et al. |
| 5,869,428 A | 2/1999 | Morishima et al. |
| 5,874,432 A | 2/1999 | Dunlap et al. |
| 5,922,773 A | 7/1999 | Lipton et al. |
| 5,948,911 A | 9/1999 | Pamukcu et al. |
| 5,958,931 A | 9/1999 | Adam et al. |
| 6,013,672 A | 1/2000 | Ye et al. |
| 6,022,869 A | 2/2000 | Faull |
| 6,054,588 A | 4/2000 | Adam et al. |
| 6,093,718 A | 7/2000 | Waterson et al. |
| 6,100,268 A | 8/2000 | Van Lommen et al. |
| 6,103,475 A | 8/2000 | Burnett, Jr. et al. |
| 6,107,342 A | 8/2000 | Adam et al. |
| 6,110,920 A | 8/2000 | Rochus et al. |
| 6,121,278 A | 9/2000 | Jackson et al. |
| 6,130,217 A | 10/2000 | Arnold et al. |
| 6,133,271 A | 10/2000 | Pamukcu et al. |
| 6,136,861 A | 10/2000 | Chenard |
| 6,143,783 A | 11/2000 | Monn et al. |
| 6,162,804 A | 12/2000 | Bilodeau et al. |
| 6,169,091 B1 | 1/2001 | Cockerill et al. |
| 6,172,058 B1 | 1/2001 | Tercero et al. |
| 6,204,292 B1 | 3/2001 | Kozikowski et al. |
| 6,262,068 B1 | 7/2001 | Atwal et al. |
| 6,262,074 B1 | 7/2001 | Otten et al. |
| 6,284,759 B1 | 9/2001 | He |
| 6,313,127 B1 | 11/2001 | Waterson et al. |
| 6,316,498 B1 | 11/2001 | Nakazato et al. |
| 6,333,428 B1 | 12/2001 | Nakazato et al. |
| 6,358,975 B1 | 3/2002 | Eliasson et al. |
| 6,361,571 B1 | 3/2002 | Goettel et al. |
| 6,403,588 B1 | 6/2002 | Hayakawa et al. |
| 6,407,094 B1 | 6/2002 | Adam et al. |
| 6,432,958 B1 | 8/2002 | He |
| 6,433,014 B1 | 8/2002 | Acher et al. |
| 6,455,528 B1 | 9/2002 | Adachi et al. |
| 6,465,484 B1 | 10/2002 | Bilodeau et al. |
| 6,472,392 B1 | 10/2002 | Starck et al. |
| 6,479,436 B1 | 11/2002 | Otten et al. |
| 6,498,180 B1 | 12/2002 | Collado Cano et al. |
| 6,509,328 B1 | 1/2003 | Adam et al. |
| 6,569,863 B1 | 5/2003 | Gerritsma et al. |
| 6,586,441 B2 | 7/2003 | Borroni et al. |
| 6,607,563 B2 | 8/2003 | Ohashi et al. |
| 6,664,250 B2 | 12/2003 | Atwal et al. |
| 6,670,307 B2 | 12/2003 | Schnatierer et al. |
| 6,835,726 B2 | 12/2004 | Cushing et al. |
| 7,393,549 B2 | 7/2008 | Ebinuma |
| 7,456,289 B2 | 11/2008 | Hsieh et al. |
| 7,572,807 B2 | 8/2009 | Li et al. |
| 7,579,360 B2 | 8/2009 | Li et al. |
| 7,700,593 B2 | 4/2010 | Chakrabarti et al. |
| 7,879,837 B2 | 2/2011 | Hayashi et al. |
| 7,960,563 B2 | 6/2011 | Johnson et al. |
| 7,977,325 B2 | 7/2011 | Schwede et al. |
| 8,252,937 B2 | 8/2012 | Cid-Nunez et al. |
| 8,299,101 B2 | 10/2012 | Cid-Nunez et al. |
| 8,399,493 B2 | 3/2013 | Bolea et al. |
| 2002/0009713 A1 | 1/2002 | Miller et al. |
| 2002/0022636 A1 | 2/2002 | Li et al. |
| 2002/0028813 A1 | 3/2002 | Jackson et al. |
| 2002/0041880 A1 | 4/2002 | Defeo-Jones et al. |
| 2002/0137770 A1 | 9/2002 | Nara et al. |
| 2002/0147362 A1 | 10/2002 | Kozikowski et al. |
| 2002/0193367 A1 | 12/2002 | Adam et al. |
| 2002/0198197 A1 | 12/2002 | Adam et al. |
| 2003/0055085 A1 | 3/2003 | Wagenen et al. |
| 2003/0109504 A1 | 6/2003 | Brotchie et al. |
| 2003/0130264 A1 | 7/2003 | Jaen |
| 2003/0134902 A1 | 7/2003 | Nakazoto et al. |
| 2003/0158155 A1 | 8/2003 | Hori et al. |
| 2003/0162802 A1 | 8/2003 | Guo et al. |
| 2003/0166639 A1 | 9/2003 | Adam et al. |
| 2003/0171380 A1 | 9/2003 | Arvanitis et al. |
| 2003/0199692 A1 | 10/2003 | Biediger et al. |
| 2003/0207882 A1 | 11/2003 | Stocker et al. |
| 2003/0207916 A1 | 11/2003 | Cheng et al. |
| 2004/0006114 A1 | 1/2004 | Coleman et al. |
| 2004/0034040 A1 | 2/2004 | Eggenweiler et al. |
| 2004/0043388 A1 | 3/2004 | Come et al. |
| 2004/0049032 A1 | 3/2004 | Charrier et al. |
| 2004/0053914 A1 | 3/2004 | Gharagozloo et al. |
| 2004/0063955 A1 | 4/2004 | Biediger et al. |
| 2004/0077599 A1 | 4/2004 | Curry |
| 2004/0097562 A1 | 5/2004 | Olesen et al. |
| 2004/0101833 A1 | 5/2004 | Lazdunski et al. |
| 2004/0102521 A1 | 5/2004 | Collado Cano et al. |
| 2004/0106791 A1 | 6/2004 | Yoakim et al. |
| 2004/0116489 A1 | 6/2004 | Massey et al. |
| 2004/0127936 A1 | 7/2004 | Salahieh et al. |
| 2004/0132723 A1 | 7/2004 | Yoakim et al. |
| 2004/0138204 A1 | 7/2004 | Harrington, Jr. |
| 2004/0138238 A1 | 7/2004 | Dhanoa et al. |
| 2004/0167123 A1 | 8/2004 | Prati et al. |
| 2004/0176385 A1 | 9/2004 | Nuss et al. |
| 2004/0204448 A1 | 10/2004 | Muller et al. |
| 2004/0220222 A1 | 11/2004 | Galley et al. |
| 2005/0004142 A1 | 1/2005 | Adams et al. |
| 2005/0026935 A1 | 2/2005 | Ford et al. |
| 2005/0054819 A1 | 3/2005 | Catalano et al. |
| 2005/0070538 A1 | 3/2005 | Cheng et al. |
| 2005/0113283 A1 | 5/2005 | Solow-cordero et al. |
| 2005/0187227 A1 | 8/2005 | Himmelsbach et al. |
| 2005/0245530 A1 | 11/2005 | Borzilleri et al. |
| 2006/0083676 A1 | 4/2006 | Lesage et al. |
| 2006/0240501 A1 | 10/2006 | Ebinuma |
| 2007/0032469 A1 | 2/2007 | Isaac et al. |
| 2007/0066582 A1 | 3/2007 | Herold et al. |
| 2007/0213323 A1 | 9/2007 | Imogai et al. |
| 2007/0275984 A1 | 11/2007 | Imogai et al. |
| 2008/0221179 A1 | 9/2008 | Gaul et al. |
| 2008/0286265 A1 | 11/2008 | Gaul et al. |
| 2008/0306077 A1 | 12/2008 | Clayton et al. |
| 2009/0031422 A1 | 1/2009 | Aaron et al. |
| 2009/0111855 A1 | 4/2009 | Gaul et al. |
| 2009/0124609 A1 | 5/2009 | Albrechet et al. |
| 2009/0124612 A1 | 5/2009 | Albrechet et al. |

(56) References Cited

U.S. PATENT DOCUMENTS

| | | |
|---|---|---|
| 2009/0203668 A1 | 8/2009 | Li et al. |
| 2009/0275751 A1 | 11/2009 | Nagato et al. |
| 2009/0318436 A1 | 12/2009 | Albrechet et al. |
| 2010/0063054 A1 | 3/2010 | Bressi et al. |
| 2010/0063092 A1 | 3/2010 | Cid-Nunez et al. |
| 2010/0087487 A1 | 4/2010 | Cid-Nunez et al. |
| 2010/0099715 A1 | 4/2010 | Cid-Nunez et al. |
| 2010/0166655 A1 | 7/2010 | Imogai et al. |
| 2010/0240688 A1 | 9/2010 | Cid-Nunez et al. |
| 2010/0240706 A1 | 9/2010 | Cid-Nunez et al. |
| 2010/0286206 A1 | 11/2010 | Cid-Nunez et al. |
| 2010/0292241 A1 | 11/2010 | Brnardic et al. |
| 2011/0009441 A1 | 1/2011 | Trabanco-Suarez et al. |
| 2011/0245232 A1 | 10/2011 | Braje et al. |
| 2011/0245247 A1 | 10/2011 | Braje et al. |
| 2011/0275624 A1 | 11/2011 | Cid-Nunez et al. |
| 2011/0306642 A1 | 12/2011 | Cid-Nunez et al. |
| 2012/0035167 A1 | 2/2012 | Cid-Nunez et al. |
| 2012/0135977 A1 | 5/2012 | Beshore et al. |
| 2012/0184525 A1 | 7/2012 | Cid-Nunez et al. |
| 2012/0184527 A1 | 7/2012 | Cic-Nunez et al. |
| 2012/0184528 A1 | 7/2012 | Cic-Nunez et al. |
| 2012/0309793 A1 | 12/2012 | Duvey et al. |
| 2013/0109052 A1 | 5/2013 | Yan et al. |
| 2013/0150412 A1 | 6/2013 | Cid-Nunez et al. |
| 2013/0196992 A1 | 8/2013 | Cid-Nunez et al. |
| 2013/0197019 A1 | 8/2013 | Cid-Nunez et al. |

FOREIGN PATENT DOCUMENTS

| | | |
|---|---|---|
| CA | 2035144 | 7/1991 |
| CN | 2390948 | 12/2000 |
| CN | 1842532 | 10/2006 |
| CN | 102002040 | 4/2011 |
| DE | 19507522 | 9/1996 |
| EP | 0082023 | 6/1983 |
| EP | 154190 | 9/1985 |
| EP | 0292840 | 11/1988 |
| EP | 0308020 | 3/1989 |
| EP | 0373423 | 6/1989 |
| EP | 0365486 | 4/1990 |
| EP | 0379806 | 8/1990 |
| EP | 0430385 | 6/1991 |
| EP | 0441718 | 8/1991 |
| EP | 447118 | 9/1991 |
| EP | 0447891 | 9/1991 |
| EP | 0478195 | 9/1991 |
| EP | 0452002 | 10/1991 |
| EP | 10482939 | 4/1992 |
| EP | 0530702 | 3/1993 |
| EP | 0542059 | 5/1993 |
| EP | 0547708 | 6/1993 |
| EP | 0548934 | 6/1993 |
| EP | 0557016 | 8/1993 |
| EP | 0612746 | 8/1994 |
| EP | 0626378 | 11/1994 |
| EP | 0728759 | 8/1996 |
| EP | 0799826 | 10/1997 |
| EP | 0838458 | 4/1998 |
| EP | 0856255 | 8/1998 |
| EP | 0903343 | 3/1999 |
| EP | 0955301 | 11/1999 |
| EP | 1006112 | 6/2000 |
| EP | 1203766 | 5/2002 |
| EP | 1277726 | 1/2003 |
| EP | 1459765 | 9/2004 |
| EP | 1764099 | 3/2007 |
| EP | 1764367 | 3/2007 |
| EP | 2039687 | 3/2009 |
| GB | 1392849 | 4/1975 |
| GB | 1502312 | 3/1978 |
| JP | 50106981 | 8/1975 |
| JP | 53082783 | 7/1978 |
| JP | 57052334 | 11/1982 |
| JP | 6110557 | 1/1986 |
| JP | 2277044 | 11/1990 |
| JP | H02503317 | 10/1991 |
| JP | 5204071 | 8/1993 |
| JP | 2124871 | 5/1994 |
| JP | 6211797 | 8/1994 |
| JP | 6211798 | 8/1994 |
| JP | 7070018 | 3/1995 |
| JP | 7101861 | 4/1995 |
| JP | 10029979 | 2/1998 |
| JP | 10045750 | 2/1998 |
| JP | 2000/072731 | 3/2000 |
| JP | 2000072751 | 3/2000 |
| JP | 2001/089367 | 4/2001 |
| JP | 2002/003401 | 1/2002 |
| JP | 2002/105085 | 4/2002 |
| JP | 2002308882 | 10/2002 |
| JP | 2003/012653 | 1/2003 |
| JP | 2004/525192 | 8/2004 |
| JP | 2004/339080 | 12/2004 |
| JP | 2005/531501 | 10/2005 |
| JP | 2008509714 | 4/2008 |
| JP | 2008/513414 | 5/2008 |
| RU | 1796625 | 2/1993 |
| RU | 12143433 | 12/1999 |
| SU | 509578 | 4/1976 |
| WO | WO 84/00544 | 2/1984 |
| WO | WO 84/00685 | 3/1984 |
| WO | WO 91/09848 | 7/1991 |
| WO | WO 92/18115 | 10/1992 |
| WO | WO 93/01195 | 1/1993 |
| WO | WO 93/15056 | 8/1993 |
| WO | WO 94/19315 | 9/1994 |
| WO | 9504733 | 2/1995 |
| WO | WO 95/04733 | 2/1995 |
| WO | WO 95/06032 | 3/1995 |
| WO | 9511233 | 4/1995 |
| WO | WO 95/17397 | 6/1995 |
| WO | WO 95/24393 | 9/1995 |
| WO | WO 95/35293 | 12/1995 |
| WO | WO 96/05828 | 2/1996 |
| WO | WO 96/06167 | 2/1996 |
| WO | WO 96/15108 | 5/1996 |
| WO | WO 96/22021 | 7/1996 |
| WO | WO 96/33974 | 10/1996 |
| WO | WO 96/37481 | 11/1996 |
| WO | WO 96/41639 | 12/1996 |
| WO | 9710238 | 3/1997 |
| WO | WO 97/10229 | 3/1997 |
| WO | 9721701 | 6/1997 |
| WO | WO 97/46532 | 12/1997 |
| WO | WO 97/48724 | 12/1997 |
| WO | WO 98/06724 | 2/1998 |
| WO | 9811075 | 3/1998 |
| WO | 9817668 | 4/1998 |
| WO | 9824780 | 6/1998 |
| WO | 9832762 | 7/1998 |
| WO | WO 98/38168 | 9/1998 |
| WO | WO 98/50384 | 11/1998 |
| WO | WO 99/06041 | 2/1999 |
| WO | WO 99/11622 | 3/1999 |
| WO | WO 99/11628 | 3/1999 |
| WO | WO 99/11649 | 3/1999 |
| WO | WO 99/12532 | 3/1999 |
| WO | WO 99/16755 | 4/1999 |
| WO | WO 99/18096 | 4/1999 |
| WO | WO 99/21992 | 5/1999 |
| WO | WO 99/31062 | 6/1999 |
| WO | WO 99/31066 | 6/1999 |
| WO | WO 99/32448 | 7/1999 |
| WO | WO 99/33829 | 7/1999 |
| WO | WO 99/36072 | 7/1999 |
| WO | WO 99/52893 | 10/1999 |
| WO | WO 99/53956 | 10/1999 |
| WO | 9962908 | 12/1999 |
| WO | 0003990 | 1/2000 |
| WO | WO 00/12089 | 3/2000 |
| WO | WO 00/21934 | 4/2000 |
| WO | 0034244 | 6/2000 |

(56) References Cited

FOREIGN PATENT DOCUMENTS

| | | |
|---|---|---|
| WO | WO 00/53605 | 9/2000 |
| WO | WO 00/61126 | 10/2000 |
| WO | WO 00/69816 | 11/2000 |
| WO | WO 00/73283 | 12/2000 |
| WO | WO 01/10846 | 2/2001 |
| WO | 0129025 | 4/2001 |
| WO | 0132632 | 5/2001 |
| WO | WO 01/32644 | 5/2001 |
| WO | WO 01/46190 | 6/2001 |
| WO | WO 01/53288 | 7/2001 |
| WO | 0156990 | 8/2001 |
| WO | WO 01/55132 | 8/2001 |
| WO | 0168097 | 9/2001 |
| WO | 0170731 | 9/2001 |
| WO | WO 01/72712 | 10/2001 |
| WO | 0183481 | 11/2001 |
| WO | WO 01/83421 | 11/2001 |
| WO | WO 01/83431 | 11/2001 |
| WO | WO 01/85716 | 11/2001 |
| WO | 0196308 | 12/2001 |
| WO | WO 02/02568 | 1/2002 |
| WO | 0210807 | 2/2002 |
| WO | 0212236 | 2/2002 |
| WO | WO 02/14282 | 2/2002 |
| WO | 0222598 | 3/2002 |
| WO | 0228837 | 4/2002 |
| WO | WO 02/051849 | 7/2002 |
| WO | 02074025 | 9/2002 |
| WO | WO 02/079498 | 10/2002 |
| WO | 02090333 | 11/2002 |
| WO | WO 02/094264 | 11/2002 |
| WO | 02096318 | 12/2002 |
| WO | 02096363 | 12/2002 |
| WO | WO 02/098869 | 12/2002 |
| WO | WO 02/102807 | 12/2002 |
| WO | WO 03/011293 | 2/2003 |
| WO | 03029209 | 4/2003 |
| WO | 03044021 | 5/2003 |
| WO | WO 03/035639 | 5/2003 |
| WO | WO 03/042989 | 5/2003 |
| WO | WO 03/047577 | 6/2003 |
| WO | WO 03/051481 | 6/2003 |
| WO | WO 03/051842 | 6/2003 |
| WO | 03059884 | 7/2003 |
| WO | 03062392 | 7/2003 |
| WO | WO 03/055878 | 7/2003 |
| WO | WO 03/059871 | 7/2003 |
| WO | 03065994 | 8/2003 |
| WO | 03068230 | 8/2003 |
| WO | 03068750 | 8/2003 |
| WO | WO 03/064428 | 8/2003 |
| WO | WO 03/070712 | 8/2003 |
| WO | WO 03/076405 | 9/2003 |
| WO | WO 03/082191 | 10/2003 |
| WO | WO 03/084610 | 10/2003 |
| WO | WO 03/092595 | 11/2003 |
| WO | WO 03/099808 | 12/2003 |
| WO | WO 03/104217 | 12/2003 |
| WO | WO 03/105846 | 12/2003 |
| WO | WO 04/000846 | 12/2003 |
| WO | WO 2004/004720 | 1/2004 |
| WO | WO 2004/011441 | 2/2004 |
| WO | WO 2004/014859 | 2/2004 |
| WO | WO 2004/014920 | 2/2004 |
| WO | 2004017950 | 3/2004 |
| WO | 2004018386 | 3/2004 |
| WO | 2004021984 | 3/2004 |
| WO | 2005021552 | 3/2004 |
| WO | WO 2004/019863 | 3/2004 |
| WO | WO 2004/024150 | 3/2004 |
| WO | 2004031189 | 4/2004 |
| WO | WO 2004/029060 | 4/2004 |
| WO | WO 2004/041818 | 5/2004 |
| WO | WO 2004/043927 | 5/2004 |
| WO | WO 2004/054979 | 7/2004 |
| WO | 2004072025 | 8/2004 |
| WO | WO 2004/065380 | 8/2004 |
| WO | WO 2004/067002 | 8/2004 |
| WO | 2004078175 | 9/2004 |
| WO | WO 2004/076413 | 9/2004 |
| WO | WO 2004/078176 | 9/2004 |
| WO | WO 2004/080981 | 9/2004 |
| WO | 2004092123 | 10/2004 |
| WO | 2004092135 | 10/2004 |
| WO | WO 2004/024936 | 10/2004 |
| WO | 2005002585 | 1/2005 |
| WO | WO 2005/007144 | 1/2005 |
| WO | 2005028445 | 3/2005 |
| WO | 2005040337 | 5/2005 |
| WO | 2005080356 | 9/2005 |
| WO | 2005097052 | 10/2005 |
| WO | WO 2005/100365 | 10/2005 |
| WO | WO 2005/123703 | 12/2005 |
| WO | 2006012622 | 2/2006 |
| WO | 2006014918 | 2/2006 |
| WO | 2006015158 | 2/2006 |
| WO | 2006015737 | 2/2006 |
| WO | 2006018727 | 2/2006 |
| WO | 2006020879 | 2/2006 |
| WO | 2006030031 | 3/2006 |
| WO | 2006030032 | 3/2006 |
| WO | WO 2006/029980 | 3/2006 |
| WO | WO 2006/047237 | 5/2006 |
| WO | WO 2006/057860 | 6/2006 |
| WO | WO 2006/057869 | 6/2006 |
| WO | 2006074041 | 7/2006 |
| WO | WO 2006/071730 | 7/2006 |
| WO | WO 2006/091496 | 8/2006 |
| WO | WO 2006/099972 | 9/2006 |
| WO | WO 2006/109876 | 10/2006 |
| WO | WO 2006/137350 | 12/2006 |
| WO | WO 2007/021308 | 2/2007 |
| WO | WO 2007/021309 | 2/2007 |
| WO | 2007027669 | 3/2007 |
| WO | 2007031558 | 3/2007 |
| WO | 2007039439 | 4/2007 |
| WO | 2007059257 | 5/2007 |
| WO | WO 2007/078523 | 7/2007 |
| WO | WO 2007/095024 | 8/2007 |
| WO | 2007103760 | 9/2007 |
| WO | WO 2007/104783 | 9/2007 |
| WO | 2007113276 | 10/2007 |
| WO | 2007122258 | 11/2007 |
| WO | 2007135527 | 11/2007 |
| WO | 2007135529 | 11/2007 |
| WO | 2008006540 | 1/2008 |
| WO | 2008008539 | 1/2008 |
| WO | 2008012622 | 1/2008 |
| WO | WO 2008/012623 | 1/2008 |
| WO | WO 2008/032191 | 3/2008 |
| WO | 2008045393 | 4/2008 |
| WO | 2008051197 | 5/2008 |
| WO | 2008057855 | 5/2008 |
| WO | 2008076225 | 6/2008 |
| WO | 2008078091 | 7/2008 |
| WO | 2008078100 | 7/2008 |
| WO | WO 2008/100715 | 8/2008 |
| WO | 2008107125 | 9/2008 |
| WO | 2008107479 | 9/2008 |
| WO | 2008107480 | 9/2008 |
| WO | 2008107481 | 9/2008 |
| WO | WO 2008/112483 | 9/2008 |
| WO | 2008124085 | 10/2008 |
| WO | WO 2008/130853 | 10/2008 |
| WO | WO 2008/145616 | 12/2008 |
| WO | WO 2008/150232 | 12/2008 |
| WO | WO 2008/150233 | 12/2008 |
| WO | WO 2009/004430 | 1/2009 |
| WO | 2009033702 | 3/2009 |
| WO | 2009033703 | 3/2009 |
| WO | 2009033704 | 3/2009 |
| WO | 2009045753 | 4/2009 |
| WO | 2009062676 | 5/2009 |
| WO | 2009091374 | 7/2009 |

(56) References Cited

FOREIGN PATENT DOCUMENTS

| WO | WO 2009/094265 | 7/2009 |
|---|---|---|
| WO | WO 2009/110901 | 9/2009 |
| WO | 2009124609 | 10/2009 |
| WO | WO 2009/140163 | 11/2009 |
| WO | WO 2009/140166 | 11/2009 |
| WO | WO 2009/148403 | 12/2009 |
| WO | WO 2010/009062 | 1/2010 |
| WO | 2010022076 | 2/2010 |
| WO | 2010022081 | 2/2010 |
| WO | 2010043396 | 4/2010 |
| WO | 2010063054 | 6/2010 |
| WO | 2010060589 | 7/2010 |
| WO | 2010089303 | 8/2010 |
| WO | 2010117926 | 10/2010 |
| WO | WO 2010/114726 | 10/2010 |
| WO | 2010025890 | 11/2010 |
| WO | 2010130422 | 11/2010 |
| WO | 2010130423 | 11/2010 |
| WO | 2010130424 | 11/2010 |
| WO | WO 2010/141360 | 12/2010 |
| WO | WO 2011/022312 | 2/2011 |
| WO | WO 2011/034741 | 3/2011 |
| WO | WO 2011/034828 | 3/2011 |
| WO | WO 2011/034830 | 3/2011 |
| WO | WO 2011/034832 | 3/2011 |
| WO | WO 2011/051490 | 5/2011 |
| WO | WO 2011/109277 | 9/2011 |
| WO | WO 2011/116356 | 9/2011 |
| WO | WO 2011/136723 | 11/2011 |
| WO | WO 2011/137046 | 11/2011 |
| WO | WO 2011/156245 | 12/2011 |
| WO | WO 2012/021382 | 2/2012 |
| WO | WO 2012/062750 | 5/2012 |
| WO | WO 2012/062751 | 5/2012 |
| WO | WO 2012/062752 | 5/2012 |
| WO | WO 2012/062759 | 5/2012 |
| WO | WO 2012/151136 | 11/2012 |
| WO | WO 2012/151139 | 11/2012 |
| WO | WO 2012/151140 | 11/2012 |

OTHER PUBLICATIONS

"Benneyworth et al.," "A Selective Positive Allosteric Modulator of Metabotropic Glutamate Receptor Subtype 2 Blocks a Hallucinogenic Drug Model of Psychosis," "Mol. Pharmacol., 2007, 72, 477-484."

Braga et al. "Making Crystals from Crystals: A Green Route to Crystal Engineering and Polymorphism" Chem. Commun. 2005, 3635-3645.

Chrostopoulos., "Allosteric Binding Sites on Cell-Sturcture Receptors: Novel Targets for Drug Discovery", Nature Rev., Mar. 2002, 1, 198-210.

"Eisa et al.," "Synthesis of some novel tetrazole derivatives as potential antimicrobial agents," "Pakistan J. of Scientific and Industrial Res, vol. 33, 1990, p. 417-420".

Galici et al. "Biphenyl-indanone A, a Positive Allosteric Modulator of the Metabotropic Glutamate Receptor Subtype 2, Has Antipsychotic- and Anxiolytic-Like Effects in Mice", Journal of Phamacology and Experimental Therapeutics, 2006, 318,1,173-185.

International Search Report dated Jul. 2, 2008 for application No. PCT/EP08/52767.

International Search Report dated Jun. 10, 2008 for application No. PCT/EP08/52766.

International Search Report dated Jun. 10, 2008 for application No. PCT/EP08/52768.

Johnson et al. Metabotropic glutamate 2 receptor potentiators: receptor modulation, frequency-dependent synaptic activity, and efficacy in preclinical anxiety and psychosis model(s), Psychopharmacology (2005) 179: 271-283.

Seddon "Pseudopolymorph: A Polemic" Crystal Growth & Design, 4(6), 1087, 2004.

Wikipedia, "Allosteric Regulation", 2010, 1-4.

Acta Chimica Slovencia, 2005, vol. 52, No. 4, pp. 391-397.

Al-Orman et al. "Studies with Polyfunctionally Substituted Heteroaromatics: New Routes for the Synthesis of Polyfunctionally Substituted Pyridines and 1,2,4-Triazolo[1,5-a]pyridines", Heteratom. Chemistry, vol. 6, No. 6, 1995, 545-551.

Azimov et al. Chemical Abstracts, 1986, abstract No. 78798, vol. 105 No. 10.

Azume et al., "Synthesis and reactions of 4-choloro-1, 2-dihydro-6-methyl-2-oxo-3-pyridinecarbonitrile", CA139:197340 (2003).

Boatman et al., "Alkylations at the Methyl or alpha-Methylene Group of 6- or 4-Alkyl-3-cyano-2(1)-pyridones through Dianions", Journal of Organic Chemistry, 1965, vol. 30 Pt 11, pp. 3593-3597.

Bohme et al., "Darstellng and Umsetzungen von 3-Arylamino-2-halogencrotononitilen", Chem. Ber., 1976, 109, 2908-2913.

Bradley et al. "Activation of Group II Metabotropic Glutamate Receptors Inhibits Synaptic Excitation of the Subsantia Nigra Pars Reticulata," J. of Neuroscience, May 1, 2000, 20(9):3085-3094.

Braish et al., "Construction of the (1x,5x,6x)-6-Amino-3-azabicyclo[3.1.0]hexane Ring System," Synlett, 1996, 1100-1102.

Brighty et al., "Synthesis of (1x,5x,6x)-6-Amino-3-azabicyclo[3.1.0]hexane, a Novel Achiral Diamine," Synlett, 1996, 1097-1099.

CA Office Action Apr. 23, 2010.

Cartmell et al. "Regulation of Neurotransmitter Release by Metabotropic Glutamate Receptors", J. Neurochem., p. 889-907, vol. 75, No. 3, 2000.

Clark et al., "Synthesis of Thieno[2,3-d]pyrimidines from 4,6-Dichloropyrimidine-5-carbaldehydes", Journal Heterocyclic Chem, 1993, vol. 30, 1065-1072.

Cook et al. "Diethylaminoalkyl Ester Hydrochlorides of N-Alkyl-4-carbostyrilcarboxylic Acids", J Am. Chem. Soc., 1952, 74, 543-554.

DiMichelle et al. "The Natural Course of Schizophrenia and Psychopathological Predictors of Outcome", (Mar.-Apr. 2004), 37(2), pp. 98-104 (abstract).

Duong et al. "A Biogenetic Like Synthesis of Perloline, 6-(3,4-Dimethoxyphenyl)-5-hydroxy-5,6-dihydrobenzo[c][2,7]naphthyridin-4(3H)-one", Aust. J. Chem., 1983, 36, 1431-1440.

Erlenmeyer et al., "Uber einige Derivate des 2-Aminothiazols", Helvetica Chim Acta, 1949, 35-38.

Ershov et al., Chemical Abstracts, 1985, vol. 103, Pt 21, pp. 678.

Euraisian Notification on the necessity to present additional matters from the Eurasian Patent Organization dated Dec. 17, 2008.

Feinberg et al, "The selective group mGlu2/3 receptor agonist LY379268 suppresses REM sleep and fast EEG in the rat," Pharmacology, Biochemistry and Behavior 73 (2002) 467-474.

Fuentes et al., "Synthesis of Heterocyclic Compounds; XL. Regioselective. synthesis of 4-subtituted 2-Amino-5-Cyano-6-methoxy-3-benzenesulfonylpyridines", Synthesis, 1984, pp. 768-770.

Galici et al., A Selective Allosteric Potentiator of Metabotropic Glutamate (mGlu) 2 Receptors Has Effects Similar to an Orthosteric mGlu2/3 Receptor Agonist in Mouse Models Predictive of Antipsychotic Activity, J of Pharmacology and Experimental Therapeutics, p. 1181-1187, vol. 315, No. 3.

Ghammamy et al., "Cetyltrimethylammonium Bromochromate: A New and Efficient Oxidant for Organic Substrates", Synthetic Communications, 2007, 37, 599-605.

Govek et al. Benzazoles as allosteric potentiators of metabotropic glutamate receptor 2 (mGluR2): Efficacy in an animal model for schizophrenia, Bioorg. Med. Chem Lett. 15 (2005) 4068-4072.

Grillon, et al., Anxiolytic effects of a novel group II metabotropic glutamate receptor agonist (LY354740) in the fear-potentiated startle paradigm in humans, Psychopharmacology (2003) 168:446-454.

Hamaguchi et al., "Effects of Hetero Atom Substituents in the decomposition of Pyrazolines: Abnormal Behavior of Methoxy Group Compared with Arylthio of Aryselenio Group.", Heterocycles, 1986, vol. 24, 2111-2115.

Hanfeld et al. "Synthese von 3-Cyan-6-methyl-4-pyridyl- und 3-cyan-4-methyl-6-pyridyl-pyrid-2(1H)-onen und -thionen", Pharmazie 43 (1988), H.11, 762-764.

Haper, "Agonist-Stimulated [35S]GTPyS Binding," Current Protocols in Pharmacology, 1998, Unit 2.6, 1-10.

(56) References Cited

OTHER PUBLICATIONS

Harriman et al. "Synthesis of 4-Substituted 4-Arylpiperidines", Tetrahedron Letters, 2000, 41, 8853-8856.
Helton et al. "Anxiolytic and Side-Effect Profile fo LY354740: A Potent, Highly Selective, Orally Active Agonist for Group II Metobotropic Glutamate Receptors", Journal of Phamacology and Experimental Therapeutics, 1998, 284, 2, 651-660.
Holden, "Excited by Glutamate", Science, p. 1866-1868, vol. 300, Jun. 20, 2003.
Hughes, "Progress in the Mitsunobu Reaction. A Review," Organic Preparations and Procedures International, 1996, 127-164.
Hughes, "The Mitsunobu Reaction", Organinc Reactions, 1992, vol. 42, 335-656.
International Search Report dated Oct. 26, 2009 for international application No. PCT/EP2009/006326.
International Search Report for International Application No. PCT/EP2007/052442 dated Sep. 7, 2007.
Jain et al. "A One-Step Preparation of Functionalized 3-Cyano-2-Pyridones", Tetrahedron Letters, 1995, 36, 19, 3307-3310.
Johnson et al. Discovery of Allosteric Potentiators for the Metabotropic Glutamate 2 Receptor: Synthesis and Subtype Selectivity of N-(4-(2-Methoxyphenoxy)phenyl)-N-(2,2,2-trifluorethylsulfonyl)pyrid-3-ylmethyl-amine, J. Med. Chem. 2003, 46, 3189-3192.
Johnson et al. Allosteric modulators of metabotropic glutamate receptors: lessons learnt from mGlu1, mGlu2 and mGlu5 potentiators and antagonists, Biochemical Society Transactions (2004) vol. 32, part 5, 881-887.
Johnson et al., Selective, Non-Amino Acid Allosteric mGlu2 Receptor Potentiators Inhibit Dural Plasma Protein Extravasation; A Potential Role in the Treatment of Migraine, Abstracts/Neuropharmacology 43 (2002) 291.
Kambe et al "A Convenient Method for the Preparation of 2-Pyridone Derivatives", 1977, vol. 12, pp. 841-842.
Kellner et al., Effects of metabotropic glutamate2/3 receptor agonist (LY544344/LY354740) on panic anxiety induced by cholecystokinin tetrapeptide in health humans: preliminary results, Psychopharmacology (2005) 179: 310-315.
Khimia Geterotsiklicheskikh Soedinenii, 1985, vol. 5, Pt 1985, 646-649.
Khimia Geterotsiklicheskikh Soedinenii, 1986, vol. 1986, Pt 8, 1118-1123.
Kilama et al. "A New Synthstic Approach to the C-D Ring Portion of Streptonigrin Analogues" Journal of Heterocyclic Chemistry, 1990, 27, 1437-1440.
Kiselyov et al., "A one pot synthesis of polysubstituted inidazo[1,2-a]pyridines", Tetrahedron Letters, 2006, 47, 2941-2944.
Kitano et al., "Synthesis and antifouling activity of 3-isocyanotheonellin and its analogues", Jour Chem Soc Perkin Trans, 2002, 2251-2255, The Royal Society of Chemistry.
Klemm et al. "Chemistry of Thienopyridines. VIII. Substitution Products Derived from Thieno[2,3-b] pyridine 7-Oxide(1)", Journal of Heterocyclic Chemistry, 1970, 7(1), 81-89.
Lan et al., Activation of Metabotropic Glutamate Receptor-1 Accelerates NMDA Receptor Trafficking, Abstracts/Neuropharmacology 43 (2002) 294.
Larock, "Comprehensive Organic Transformations", VCH Publishers, 1989, 595-596.
Lee et al., "Benzylic Bromination of Alkylbenzenes with Sodium Bromate-Bromotrimethylsilane", Bull. Korean Chem. Soc, 1995, vol. 16, pp. 371-374.
Malames et al. "N-Substituted Spirosuccinimide, Spiropyridazine, Spiroazetidine, and Acetic Acid Aidose Reductase Inhibitiors Derived From Isoquinoline-1,3-dinoes. 2", J Med Chem., 1994, 37(13), 2059-2070.
McElvain et al. "Piperidine Derivatives. XXX. 1,4-Dialkyl-4-arylpiperidines", J. Am. Chem. Soc, 1958, 80, 3915-3923.
Moldrich et al., Glutamate metabotropic receptors as targets for drug therapy in epilepsy, European Journal of Pharmacology 476 (2003) 3-16.
Mongin et al. "Advances in the directed metallation of azines and diazines (pyridines, pyrimidines, pyrazines, pyridazines, quinolines, benzodiazines and carbolines). Part 1: Metallation of Pyridines, quinolines and carbolines", Tetrahedron, 2001, 57(19), 4059-4090.
Moore et al. "Cycloadditions of Cyanoketenes to Cinnamylideneamines and Benzylideneamines. Synthetic Scope, Stereochemistry, and Mechanism", Journal Org. Chem. 1985, 50, 4231-4238.
Morrill et al., "Synthesis of 4-Arylpiperidines from 1-Benzyl-4piperidone: Application of the Sharpiro Reaction and Alkenylsilane Cross-coupling," Organic Letters, 2007, vol. 9, pp. 1505-1508.
Mutel et al., "Characterization of (2S,2'R,3'R)-2-(2',3'-[3H]-Dicarboxycyclopropyl)glycine Binding in Rat Brain," J Neurochemistry, 71(6), 1998, 2558-2564.
Mutel, "Therapeutic potential of non-competitive, subtype-selective metabotropic glutamate receptor ligands", Expert Opin. Ther. Patents (2002), 12 (12) p. 1845-1852.
Nakamura et al., "An Efficient Synthesis of Platelet-Activating Factor (PAF) J'IJ I-QAlkyl-2---(3-Isoxazolyl)-SN_Glycero-3-Phosphocholine, A New PAF Agonist. Utilization of the 3-Isoxazolyloxy Group as a Protected Hydroxyl." Tetrahedron Letters, 1990, vol. 31, 699-702.
Nakanishi, et al., Glutamate receptors: brain function and signal transduction, Brain Research Reviews 26 (1998) 230-235.
Nakano et al. "1-Alkyl-3-phenylpyridinium 1-Alkyl-2(1H)-pyridone 3-Phenyl 5-Phenyl", Annual Report of Tohoku College of Pharmacy, 1998, 45, 145-148.
Nell et al., "Preparation of 4-amino-3,5-dicyano-2-thiopyridines as cardiovascular agents", CA149:32326 (2008).
Ohishi et al., "Distribution of a metabotropic glutamate receptor, mGluR2, in the central nervous system of the rat and mouse: an immunohistochemical study with a monoclonal antibody," Neuroscience Research 30 (1998) 65-82.
Ojima et al., "Hydroformation of Fluoro Olefins, RfCH=CH2, Catalyzed by Group VIII Transition-Metal Catalysts. Crucial Factors for Extremly High Regioselectivity", Journal of American Chemical Society, 1987, 109, 7714-7720.
Pin et al., "New perspectives for the development of selective metabotropic glutamate receptor ligands," European J of Pharmacology, 1999, 375, 277-294.
Pinkerton, et al., Phenyl-tetrazolyl Acetophenones: Discovery of Positive Allosteric Potentiators for the Metabotropic Glutamate 2 Receptor, J. Med. Chem 2004, 47, 4595-4599.
Poisik, et al., Metabotropic glutamate receptor 2 modulates excitatory synaptic transmission in the rat globus pallidus, Neuropharmacology 49 (2005) 57-69.
Potts et al. "1,2,4-Triazoles. XII. Derivatives of the s-Triazolo[4,3-a]pyridine Ring System", Journal of Organic Chemistry, 1966, 251-260.
Potts et al. "1,2,4-Trizoles. XXV. The Effect of Pyridine Substitution on the Isomerization of s-Triazolo [4,3-a] pyridines into s-Triazolo [1,5-a] pyridines (1)", J. Heterocycl. Chem., 1970, 7, 1019-1027.
Prager et al. "The Synthesis of Peroline, 6-(3,4-Dimethoxyphenyl)-5-hydroxy-5,6-dihydrobenzo[c][2,7]naphthyridin-4(3H)-one", Aust. J. Chem., 1983, 36, 1441-1453.
Rani et al. "Thiazoline Analogues of Epiderstatin, New Inhibitors of Cell Cycle of TsFT-210 Cells", Journal of Antibiotics, 1995, 48(10), 1179-1181.
Renslo et al., "Synthesis of Aza-, Oxa-, and Thiabicyclo[3.1.0]hexane Heterocycles from a Common Synthetic Intermediate," Organic Letters, 2005, vol. 7, No. 13, 2627-2630, American Chemical Society, USA.
Roma et al., "1,8-Naphthyridines VII. New substituted 5-amino[1,2,4]triazolo[4,3-a] [1 ,8]naphthyridine-6-carboxamides and their isosteric analogues, exhibiting notable anti-inflammatory and/or analgesic activities, but no acute gastrolesivity", European Journal of Medical Chemistry. 2008, 43, 1665-1680.
Rosowsky et al. "2,4-Diaminothieno[2,3-d]pyrimidines as Antifolates and Antimalarials. 3. synthesis of 5,6-Disubstituted Derivatives and Related Tetracyclic Analogs", Journal of Medicinal Chemistry, 1973, 16,3,191-194.

(56) References Cited

OTHER PUBLICATIONS

Ryndina, et al., Torp-Ziegler Cyclization in the Synthesis of 3-Amino-4-Cyanopyrrole Derivatives, Chemistry of Heterocyclic Compounds, vol. 36, No. 12, 2000, pp. 1409-1420.
Schaffhauser et al., "In Vitro Binding Characteristics of a New Selective Group II Metabotropic Glutamate Receptor Radioligand, [3H]LY354740, in Rat Brain," Mol Pharmacology, 53, 228-233, 1998.
Schaffhauser et al., "Pharmacological Characterization and Identification of Amino Acids Involved in the Positive Modulation of Metabotropic Glutamate Receptor Subtype 2," Mol. Pharmacol 64:798-810, 2003, vol. 64, No. 4.
Schiefer et al. "The metabotropic glutamate receptor 5 antagonist MPEP and the mGluR2 agonist LY379268 modify disease progression in a transgenic mouse model of Huntington's disease," Brain Research 1019 (2004) 246-254.
Schoepp et al, "Pharmacological agents acting at subtypes of metabotropic glutamate receptors," Neuropharmacology 38 (1999) 1431-1476.
Schoepp et al., "Preclinical Pharmacology of mGlu2/3 Receptor Agonists: Novel Agents for Schizophrenia?", CNS & Neurological Disorders, 2002, 1, 215-225.
Senda et al. "Ring Transformation of Uracils to 2-Pyridones. Hydrolysis of 6-(Dimethylaminovinyl) Uracils" Heterocycles, 1978, 9, 6, 1-6.
Shiba et al. "Synthesis and binding affinities of methylvesamicol analogs for the acetylcholine transporter and sigma receptor", Bioorganic and Medicinal Chemistry, 2006, 14, 2620-2626.
Simmons et al., "Group II mGluR receptor agonists are effective in persistent and neuropathic pain models in rats," Pharmacology, Biochemistry and Behavior 73 (2002) 419-427.
SIPO Office Action Jun. 30, 2010.
Stewart et al. "Discovery of Inhibitors of Cell Adhesion Molecule Expression in Human Endothelial Cell. 1. Selective Inhibition of ICAM-1 and E-Selectin Expression", J Med Chem, 2001, 44, 998-1002.
Turck et al. "Advances in the directed metallation of azines and diazines (pyridines, pyrimidines, pyrazines, pyridazines, quinolines, benzodiazines and carbolines). Part 2: Metallation of pyrimidines, pyrazines, pyridazines and benzodiazines", Tetrahedron, 2001, 57(21), 4489-4505.
Tutonda et al. "Diels-Alder Reactions of the Heterodiene System in 2(1H)-Pyrazinones", Tetrahedron Letters, 1986, 27, 22, 2509-2512.
VanAllan et al. "Reactions of Some 4-Methylene-4H-pyran Derivatives with Primary and Secondary Amines", Journal of Heterocyclic Chemistry, 1970, 7, 495-507.
Vilsmaier et al., "Diastereoselective Syntheses of N-Protected Derivatives of Ia,5a,6fi-6-Amino-3-azabicyclo [3.101]hexane; A Route to Trovafloxacin 6fI-Diastereomer," Synthesis, 1998, 739-744.
Vippagunta et al., Crystalline Solids, Adv. Drug Deliv. Rev., 2001, 48, pp. 3-26.
Wang et al. "A simple and efficient automatable one step synthesis of triazolopyridines form carboxylic acids", Tetrahedron Letters, 2007, 48, 2237-2240.
Watanbe et al. "Pd/P(t-Bu)3-Catalyzed Synthesis of Aromatic Amines", Journal of TOSOH Research, 1999, vol. 43, 38-50.
Wenner et al, "Derivatives of 2-Pyridone", Journal of Organic Chemistry, 1946, vol. 11, pp. 751-759.
West Anthony R. Solid State Chemistry and Its Applications, Wiley, New York, 1988 pp. 358 & 365.
Yalyaheva et al.,Chemical Abstract, Heterocycles, p. 687, vol. 107, 1987.
Abi-Saab et al., "The NMDA Antagonist Model for Schizophrenia: Promise and Pitfalls", Pharmacopschiatry, 31, 1998, 104-109.
Abshire et al., "Injection of L-Allylglycine Into the Posterior Hypothalamus in Rats Causes Decreases in Local GABA Which Correlate with Increases in Heart Rate", Neuropharmacology, 1988, 27(11), 1171-1177.

Adam, "Symptomatic Treatment of Huntington Disease", Neurotherapeutics: the Journal of the American Society for Experimental Neurotherapeutics, Apr. 2008, 5, 181-197.
Adams et al., "Effect of Clozapine, Haloperidol, or M100907 on Phencyclidine-Activated Glutamate Efflux in the Prefrontal Cortex", Biol. Psychiatry 2001, 50(10), 750-757.
Adams, "A Long-Term, Phase 2, Multicenter, Randomized, Open-Label, Comparative Safety Study of Pomaglumetad Methionil (LY2140023 Monohydrate) Versus Atypical Antipsychotic Standard of Care in Patients with Schizophrenia", BMC Psychiatry 2013, 13(143), 1-9.
Addex Partner Completes ADX71149 Phase I Program, Press release Aug. 25, 2010, http://www.addextherapeutics.com/investors/press-releases/news-details/?tx_ttnews%5Btt_news%5D%20=103&cHash=91fade38b1d3dc85979989357b1a9281, retrieved on Aug. 22, 2013.
Addex Partner Doses First Patient in Phase 2 Clinical Study of ADX71149 for the Treatment of Major Depressive Disorder Patients with Anxiety Symptoms, Press Release Sep. 17, 2012, http://www.addextherapeutics.com/investors/press-releases/news-details/?tx_ttnews%5Btt_news%5D%20=214&cHash=12a9cc5ffefdb63c27d5b87a673f74eb, retrieved on Aug. 22, 2013.
Addex Partner to Initiate Phase 2 Clinical Trial of ADX71149 for the Treatment of Major Depressive Disorder with Anxiety Symptoms, Press Release Jun. 5, 2012 http://www.addextherapeutics.com/investors/press-releases/news-details/?tx_ttnews%5Btt_news%5D%20=204&cHash=1865c3b31d0b9042f84c017bb2b5f32c, retrieved on Aug. 22, 2013.
Addex Reports Top-line Data from a Successful Phase 2a Clinical Study with ADX71149 in Schizophrenia Patients, Press Release Nov. 5, 2012, http://www.addextherapeutics.com/investors/press-releases/news-details/?tx_ttnews%5Btt_news%5D%20=225&cHash=9e5e13cb042971e6135f8ac786ce7453 retrieved on Aug. 22, 2013.
Addington et al., "A depression rating scale for schizophrenics", Schizophr Res. 1990, 3(4), 247-251.
Ader et al., "Effects of Chlorpromazine on the Acquisition and Extinction of an Avoidance Response in the Rat", J. Pharmacol. Exp. Ther., 1957, 131, 144-148.
Agami et al., "An Efficient Synthesis of Polysubstituted 3-Halo-2(1H)-Pyridinones." Synthesis, 2002, 79-82.
Agari et al., "Intrapallidal Metabotropic Glutamate Receptor Activation in a Rat Model of Parkinson's Disease: Behavioral and Histological Analyses", Brain Res., 2008, 1203, 189-196.
Aghajanian et al., "Serotonin model of schizophrenia: Emerging role of glutamate Mechanisms", Brain Research Reviews, 2000, 31, 302-312.
Aghajanian, "Modeling 'Psychosis' in Vitro by Inducing Disordered Neuronal Network Activity in Cortical Brain Slices", Psychopharmacology 2009, 206(4), 575-585.
Agid et al., "How Can Drug Discovery for Psychiatric Disorders Be Improved?" Nature Reviews Drug Discovery, 2007, 6, 189-201.
Ago et al., "Activation of Metabotropic Glutamate 2/3 Receptors Attenuates Methamphetamine-Induced Hyperlocomotion and Increase in Prefrontal Serotonergic Neurotransmission", Psychopharmacology, 2011, 217, 443-452.
Ahnaou et al., "Modulation of Group II Metabotropic Glutamate Receptor (Mglu2) Elicits Common Changes in Rat and Mice Sleep-Wake Architecture", European Journal of Pharmacology, 2009, 603, 62-72.
Ainslie et al., "Practical Drug Evaluation Method", Arch Gen Psychiat, 1965, 12, 368-373.
Alagarsamy et al., "Coordinate Regulation of Metabotropic Glutamate Receptors", Current Opinion in Neurobiology, 2001, 11(3), 357-362.
Albasanz et al., "Internalization of Metabotropic Glutamate Receptor in C6 Cells Through Clathrin-Coated Vesicles", Molecular Brain Research, 2002, 99, 54-66.
Alderson et al., "Purification and Characterization of a Soluble Cyclic Nucleotide-Independent Ca2+-Calmodulin-Sensitive Protein Kinase from Rat Brain", J. Neurochem., 1986, 46, 594-603.

(56) References Cited

OTHER PUBLICATIONS

Aleppo et al., "Metabotropic Glutamate Receptors and Neuronal Toxicity", Advances in Experimental Medicine & Biology, 1992, 318, 137-145.
Alexander et al., "Metabotropic Glutamate Receptors as a Strategic Target for the Treatment of Epilepsy", Epilepsy Res., 2006, 71(1), 1-22.
Allen et al., "Group II Metabotropic Glutamate Receptor Activation Attenuates Traumatic Neuronal Injury and Improves Neurological Recovery After Traumatic Brain Injury", J Pharmacol. Exp. Ther., 1999, 290(1), 112-120.
Alley et al., "Memantine Lowers Amyloid-Beta Peptide Levels in Neuronal Cultures and in APP/PS1 Transgenic Mice", J Neurosci Res, 2010, 88, 143-154.
Al-Shamma et al., "Nelotanserin, a Novel Selective Human 5-Hydroxytryptamine2a Inverse Agonist for the Treatment of Insomnia", J Pharmacol Exp Ther, 2010, 332, 281-290.
Altamura et al., "Designing Outcome Studies to Determine Efficacy and Safety of Antipsychotics for 'Real World' Treatment of Schizophrenia", Int J Neuropsychopharmacol, 2010;13(7):971-973.
Altamura et al., "Plasma and Platelet Excitatory Amino Acids in Psychiatric Disorders", Am J Psychiatry, 1993, 150(11), 1731-1733.
Altamura et al., "Plasma Concentrations of Excitatory Amino Acids Serine, Glycine, Taurine and Histidine in Major Depression", Eur Neuropsychopharmacol, 1995; 5(Suppl), 71-75.
Amiri et al., "A Role for Leu118 of Loop E in Agonist Binding to the α7 Nicotinic Acetylcholine Receptor" Mol Pharmacol, 2008, 73, 1659-1667.
Amitai et al., "Effects of Metabotropic Glutamate Receptor 2/3 Agonism and Antagonism on Schizophrenia-Like Cognitive Deficits Induced by Phencyclidine in Rats", European Journal of Pharmacology, 2010, 639, 67-80.
Andreescu et al., "Comorbid Anxiety and Depression: Bête Noire or Quick Fix?", British Journal of Psychiatry 2012, 200:179-181.
Andreescu et al., "Effect of Comorbid Anxiety on Treatment Response and Relapse Risk in Late-Life Depression: Controlled Study", the British Journal of Psychiatry, 2007, 190, 344-349.
Andreescu et al., "The Default Mode Network in Late-Life Anxious Depression", Am J Geriatr Psychiatry, Nov. 2011, 19(11), 5 pages.
Andres et al., "2-(Dimethylaminomethyl)-Tetrahydroisoxazolopyridobenzazepine Derivatives. Synthesis of a New 5-HT2C Antagonist with Potential Anxiolytic Properties", Bioorganic & Medicinal Chemistry Letters, 2002, 12, 3573-3577.
Andres et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8699.
Angenstein et al., "Activation of Metabotropic Glutamate Receptors Increases Endogenous Protein Kinase C Substrate Phosphorylation in Adult Hippocampal Slices", Brain Research, 1997, 745(1-2), 46-54.
Angers et al., "Dimerization: An Emerging Concept for G Protein-Coupled Receptor Ontogeny and Function", Annu. Rev. Pharmacol. Toxicol., 2002, 42, 409-435.
Antuono, "Decreased Glutamate 1 Glutamine in Alzheimer's Disease Detected in Vivo with 1H-MRS at 0.5 T", Neurology, 2001, 56:737-742.
Anwyl "Metabotropic Glutamate Receptor-Dependent Long-Term Potentiation", Neuropharmacology, 2009, 56, 735-740.
Anwyl "Metabotropic Glutamate Receptors: Electrophysiological Properties and Role in Plasticity", Brain Res. Brain Res., 1999, 29, 83-120.
Aparicio-Legarza et al., "Deficits of [3h]D-Aspartate Binding to Glutamate Uptake Sites in Striatal and Accumbens Tissue in Patients with Schizophrenia", Neuroscience Letters, 1997, 232(1), 13-16.
Aparicio-Legarza et al., "Increased Density of Glutamate/N-Methyl-D-Aspartate Receptors in Putamen From Schizophrenic Patients", Neuroscience Letters,1998, 241(2-3), 143-146.

Armstrong et al., "Characterization of Competitive Inhibitors for the Transferase Activity of *Pseudomonas aeruginosa* Exotoxin A", Journal of Enzyme Inhibition and Medicinal Chemistry, 2002, 17(4), 235-246.
Arnt, "Differential Effects of Classical and Newer Antipsychotics on the Hypermotility Induced by Two Dose Levels of D-Amphetamine", European Journal of Pharmacology, 1995, 283, 55-62.
Arnt, "Pharmacological Specificity of Conditioned Avoidance Response Inhibition in Rats: Inhibition by Neuroleptics and Correlation to Dopamine Receptor Blockade", Acta Pharmacol. Toxicol., 1982, 51, 321-329.
Aronica et al., "Metabotropic Glutamate Receptors in Cultured Cerebellar Granule Cells: Developmental Profile", Journal of Neurochemistry, 1993, 60(2), 559-565.
Aronica et al., "Pharmacological Characterization of Metabotropic Glutamate Receptors in Cultured Cerebellar Granule Cells", Neurochemical Research, 1993, 18(5), 605-612.
Aronica et al., "Status Epilepticus-Induced Alterations in Metabotropic Glutamate Receptor Expression in Young and Adult Rats", J. Neurosci., 1997, 17(21), 8588-8595.
Aronson et al., "Triiodothyronine Augmentation in the Treatment of Refractory Depression. A Meta-Analysis", Arch Gen Psychiatry, 1996, 53, 842-848.
Arriza et al., "Functional Comparisons of Three Glutamate Transporter Subtypes Cloned From Human Motor Cortex", J. Neurosci., 1994, 14(9), 5559-5569.
Arundine, "Molecular Mechanisms of Glutamate-Dependent Neurodegeneration in Ischemia and Traumatic Brain Injury", Cellular and Molecular Life Sciences, 2004, 61, 657-668.
Atlante, "Glutamate Neurotoxicity, Oxidative Stress and Mitochondria", Febs Letters 497, 2001, 1-5.
Attwell et al., "Anticonvulsant and Glutamate Release-Inhibiting Properties of the Highly Potent Metabotropic Glutamate Receptor Agonist (2s,2'r, 3'r)-2-(2',3'-Dicarboxycyclopropyl)Glycine (Dcg-Iv)", Brain Res., 1998, 805(1-2), 138-143.
Auer et al., "Reduced Glutamate in the Anterior Cingulate Cortex in Depression: An in Vivo Proton Magnetic Resonance Spectroscopy Study", Biol Psychiatry, 2000, 47(4), 305-313.
Auerbach et al., "Mutations Causing Syndromic Autism Define an Axis of Synaptic Pathophysiology", Nature, 2011, 480, 63-68.
Aultman et al., "Distinct Contributions of Glutamate and Dopamine Receptors to Temporal Aspects of Rodent Working Memory Using a Clinically Relevant Task", Psychopharmacology (Berl), 2001, 153(3), 353-364.
Austin et al., "Symptomatic and Neuroprotective Effects Following Activation of Nigral Group III Metabotropic Glutamate Receptors in Rodent Models of Parkinson's Disease", British Journal of Pharmacology, 2010, 160, 1741-1753.
Australian Patent Application No. 2005/284098: Office Action dated Oct. 11, 2010, 2 pages.
Australian Patent Application No. 2007/224431: Office Action dated Mar. 19, 2010, 6 pages.
Australian Patent Application No. 2008/223795: Office Action dated May 29, 2012, 2 pages.
Australian Patent Application No. 2008/223796: Examiner's Report dated Nov. 3, 2010, 2 pages.
Australian Patent Application No. 2008/297877: Examiner's Report dated Oct. 31, 2012, 3 pages.
Awouters et al., "Astemizole: Effects on General Behavior and Interactions with the Central Nervous System", Jap. Pharmacol. & Therapeutics, 1991, 19, 73-89.
Ayalew et al., "Convergent Functional Genomics of Schizophrenia: From Comprehensive Understanding to Genetic Risk Prediction", Molecular Psychiatry 2012, 1-19.
Ayan-Oshodi et al., "Adverse Events in Healthy Subjects Exposed to Single and Multiple Doses of Ly2140023 Monohydrate", J Clin Psychopharmacol, 2012, 32, 408-411.
Backstrom, "Suppression of Alcohol Self-Administration and Cue-Induced Reinstatement of Alcohol Seeking by the Mglu2/3 Receptor Agonist Ly379268 and the Mglu8 Receptor Agonist (S)-3,4-Dcpg", Eur. J. Pharmacol., 2005, 528, 110-118.
Badawy et al., "Epilepsy: Ever-Changing States of Cortical Excitability" Neuroscience, 2012, 22, 89-99.

(56) References Cited

OTHER PUBLICATIONS

Baffa et al., "Norepinephrine and Serotonin Transporter Genes: Impact on Treatment Response in Depression", Neuropsychobiology, 2010, 62, 121-131.
Bagby et al., "Psychosocial and Clinical Predictors of Response to Pharmacotherapy for Depression" J Psychiatry Neurosci, 2002, 27(4), 250-7.
Bakker et al., "Activation of the Metabotropic Glutamate Receptor 2 (Mglu2) by Orthosteric and Allosteric Ligands", Poster 642.6/E30 Presented at the 40th Annual Meeting of Society for Neuroscience 2010, 1 page.
Bakker et al., "Reduction of Hippocampal Hyperactivity Improves Cognition in Amnestic Mild Cognitive Impairment", Neuron, 2012, 74(3), 467-474.
Balastrieri et al., "Assessing Mixed Anxiety-Depressive Disorder. A National Primary Care Survey", Psychiatry Research, 2010, 176, 197-201.
Balazs et al., "Metabotropic Glutamate Receptor Agonists Potentiate Cyclic Amp Formation Induced by Forskolin or Beta-Adrenergic Receptor Activation in Cerebral Cortical Astrocytes in Culture", Journal of Neurochemistry, 1998, 70(6), 2446-2458.
Bandelow et al., "Adjunct Quetiapine XR in Patients with Major Depressive Disorder: A Pooled Analysis of Data From Patients with Anxious Depression", Abstracts of the 19th European Congress of Psychiatry, Mar. 2011, 1 page.
Barda et al., "Sar Study of A Subtype Selective Allosteric Potentiator of Metabotropic Glutamate 2 Receptor, N-(4-Phenoxyphenyl)-N-(3-Pyridinylmethyl)Ethanesulfonamide", Bioorganic & Medicinal Chemistry Letters, 2004, 14, 3099-3102.
Barker et al., "A Temporally Distinct Role for Group I and Group II Metabotropic Glutamate Receptors in Object Recognition Memory", Learn. Mem., 2006, 13(2), 178-186.
Barnes et al., "A Review of Central 5-Ht Receptors and their Function", Neuropharmacology, 1999, 38, 1083-1152.
Bar-Peled et al., "Distribution of Glutamate Transporter Subtypes During Human Brain Development", J Neurochem., 1997, 69(6), 2571-2580.
Barrett, "Mglur2-Positive Allosteric Modulators: Therapeutic Potential for Treating Cocaine Abuse?", Neuropsychopharmacology, 2010, 35, 2007-2008.
Bartha et al., "Measurement of Glutamate and Glutamine in the Medial Prefrontal Cortex of Never-Treated Schizophrenic Patients and Healthy Controls by Proton Magnetic Resonance Spectroscopy", Archives of General Psychiatry, 1997, 54(10), 959-965.
Barton et al., "Comparison of the Effect of Glutamate Receptor Modulators in the 6 Hz and Maximal Electroshock Seizure Models", Epilepsy Research, 2003, 56, 17-26.
Basan et al., "Valproate for Schizophrenia", Cochrane Collaboration, Cochrane Database Syst Rev., 2008, 2, 38 pages.
Batchelor et al., "Novel Synaptic Potentials in Cerebellar Purkinje Cells: Probable Mediation by Metabotropic Glutamate Receptors", Neuropharmacology, 1993, 32(1), 11-20.
Battaglia et al., "Selective Activation of Group-II Metabotropic Glutamate Receptors Is Protective Against Excitotoxic Neuronal Death," European Journal of Pharmacology, 1998, 356(2-3), 271-274.
Bauer et al., "Extended Release Quetiapine as Adjunct to an Antidepressant in Patients with Major Depressive Disorder: Results of a Randomized, Placebo-Controlled, Double-Blind Study", J Clin Psychiatry 2009, 70(4), 540-549.
Bauzo et al., "Interactions Between the Mglur2/3 Agonist, Ly379268, and Cocaine on in Vivo Neurochemistry and Behavior in Squirrel Monkeys", Pharmacol. Biochem. Behav., 2009, 94(1), 204-210.
Bech et al., "Quantitative Rating of Depressive States", Acta Psychiatr Scand, 1975, 51(3), 161-170.
Bech, "Dose-Response Relationship of Pregabalin in Patients with Generalized Anxiety Disorder. A Pooled Analysis of Four Placebo-Controlled Trials", Pharmacopsychiatry, 2007, 40, 163-168.

Bech, "The Bech-Rafaelsen Melancholia Scale (Mes) in of Therapies in Depressive Disorders: A 20-Year Review of Its Use as Outcome Measure", Acta Psychiatr Scand, 2002, 106(4), 252-264.
Beesdo, "Incidence and Risk Patterns of Anxiety and Depressive Disorders and Categorization of Generalized Anxiety Disorder", Arch Gen Psychiatry, 2010, 67(1), 47-57.
Behrens et al., "Ketamine-Induced Loss of Phenotype of Fast-Spiking Interneurons is Mediated by Nadph-Oxidase", Science, 2007, 318, 1645-1647.
Belenikin et al., "Comparative Analysis of the Ligand-Binding Sites of the Metabotropic Glutamate Receptors Mglur1-Mglur8", Doklady Biochemistry & Biophysics., 2002, 386, 251-256.
Bell et al., "Altered Synaptic Function in Alzheimer's Disease", European Journal of Pharmacology, 2006, 545(1), 11-21.
Bellani et al., "Brain Anatomy of Major Depression II. Focus on Amygdala", Epidemiology and Psychiatric, Sciences, 2011, 20(1), 33-36.
Bellesi et al., "The Mglur2/3 Agonist Ly379268 Blocks the Effects of Glt-I Upregulation on Prepulse Inhibition of the Startle Reflex in Adult Rats", Neuropsychopharmacology, 2010, 1-8.
Bellesi et al., "The Mglur2/3 Agonist Ly379268 Blocks the Effects of Glt-1 Upregulation on Prepulse Inhibition of the Startle Reflex in Adult Rats", Neuropsychopharmacology, 2010, 35(6), 1253-1260.
Belousov et al., "Non-Cholinergic Excitation in Neurons After a Chronic Glutamate Receptor Blockade", Neuroreport, 2004, 15(1), 113-117.
Benarroch, "Metabotropic Glutamate Receptors: Synaptic Modulators and Therapeutic Targets for Neurologic Disease", Neurology, 2008, 70(12), 964-968.
Benca et al., "Sleep and Psychiatric Disorders. A Meta-Analysis", Arch Gen Psychiatry, 1992, 49, 651-670.
Beneyto et al., "Abnormal Glutamate Receptor Expression in the Medial Temporal Lobe in Schizophrenia and Mood Disorders", Neuropsychopharmacology, 2007, 32(9), 1888-1902.
Benilova et al., "The Toxic Aβ Oligomer and Alzheimer's Disease: An Emperor in Need of Clothes", Nature Neuroscience, 2012, 15(3), 349-357.
Benneyworth et al., "Chronic Phenethylamine Hallucinogen Treatment Alters Behavioral Sensitivity to a Metabotropic Glutamate 2/3 Receptor Agonist", Neuropsychopharmacology, 2008, 33(9), 2206-2216.
Benquet et al., "Two Distinct Signaling Pathways Upregulate Nmda Receptor Responses via Two Distinct Metabotropic Glutamate Receptor Subtypes", Journal of Neuroscience, 2002, 22(22), 9679-9686.
Benson et al., "A Comparison of Observational Studies and Randomized, Controlled Studies", N Engl J Med., 2000, 342(25), 1878-1886.
Bergink et al., "Metabotropic Glutamate II Receptor Agonists in Panic Disorder: A Double Blind Clinical Trial with Ly354740", International Clinical Psychopharmacology, 2005, 20, 291-293.
Berman et al., "The Efficacy and Safety of Aripiprazole as Adjunctive Therapy in Major Depressive Disorder: A Multicenter, Randomized, Double-Blind, Placebo-Controlled Study", J Clin Psychiatry, 2007, 68, 843-853.
Bermudo-Soriano, "New Perspectives in Glutamate and Anxiety", Pharmacol Biochem Behav, 2011, Epub, No Page Numbers, Doi:10.1016/J.Pbb.2011.04.010.
Berthele et al., "Distribution and Developmental Changes in Metabotropic Glutamate Receptor Messenger RNA Expression in the Rat Lumbar Spinal Cord", Developmental Brain Research, 1999, 112(1), 39-53.
Berthele et al., "Expression of Metabotropic Glutamate Receptor Subtype MRNA (Mglur1-8) in Human Cerebellum", Neuroreport, 1999, 10(18), 3861-3867.
Bertrand et al., "Common and Selective Molecular Determinants Involved in Metabotopic Glutamate Receptor Agonist Activity", J. Med. Chem., 2002, 45(15), 3171-3183.
Bespalov et al., "Behavioral Characterization of the Mglu Group II/III Receptor Antagonist, Ly-341495, in Animal Models of Anxiety and Depression", European Journal of Pharmacology 2008, 592, 96-102.
Bespalov et al., "Habituation Deficits Induced by Metabotropic Glutamate Receptors 2/3 Receptor Blockade in Mice: Reversal by

(56) References Cited

OTHER PUBLICATIONS

Antipsychotic Drugs", Journal of Pharmacology & Experimental Therapeutics, 2007, 320(2), 944-950.

Bessho et al., "Glutamate and Quisqualate Regulate Expression of Metabotropic Glutamate Receptor MRNA in Cultured Cerebellar Granule Cells", Journal of Neurochemistry, 1993, 60(1), 253-259.

Bessis et al., "Metabotropic Glutamate Receptors: Exciting Possibilities in Excitatory Transmission", Celltransmissions, 2000, 17, 3-10.

Bick et al., "Photo-Oxidative Cleavage: An Alternative Method for Degrading Bisbenzylisoquinoline Alkaloids", Journal of Natural Products, 1986, 49(3), 373-385.

Bijl et al., "Current and Residual Functional Disability Associated with Psychopathology: Findings from the Netherlands Mental Health Survey and Incidence Study (Nemesis)", Psychological Medicine, May 2000, 657-668.

Bilkei-Gorzo et al., "MCPP-Induced Anxiety in the Light-Dark Box in Rats—A New Method for Screening Anxiolytic Activity", Psychopharmacology (Berl), 1998, 136(3), 291-298.

Binder et al., "Association of Polymorphisms in Genes Regulating the Corticotropin-Releasing Factor System with Antidepressant Treatment Response", Arc Gen Psychiatry, 2010, 67(4), 369-370.

Black et al., "Compound A, A Novel, Potent and Selective Mglur2 Positive Allosteric Modulator: II. Effects in Models Predictive of Therapeutic Activity Against Cognitive Impairment Associated with Schizophrenia", Poster 767.7 Presented at the 40th Annual Meeting of Society for Neuroscience, Nov. 2010, 1 page.

Blaha et al., "Stimulation of the Ventral Subiculum of the Hippocampus Evokes Glutamate Receptor-Mediated Changes in Dopamine Efflux in the Rat Nucleus Accumbens", European Journal of Neuroscience, 1997, 9(5), 902-911.

Blanco et al., "Changes in the Prevalence of Non-Medical Prescription Drug Use and Drug Use Disorders in the United States: 1991-1992 and 2001-2002", Drug and Alcohol Dependence, 2007, 90, 252-260.

Bockaert et al., "Metabotropic Glutamate Receptors: An Original Family of G Protein-Coupled Coupled Receptors", Fundamental & Clinical Pharmacology, 1993, 7(9), 473-485.

Bockaert et al., "Molecular Tinkering of G Protein-Coupled Receptors: An Evolutionary Success", Embo Journal, 1999, 18(7), 1723-1729.

Bodick et al., "Protocols to Demonstrate Slowing of Alzheimer Disease Progression. Position Paper on the International Working Group on Harmonization of Dementia Drug Guidelines", Alzheimer Disease and Associated Disorders, 1997, 11(Suppl 3), 50-53.

Bohm et al., "Thieno Compounds Part 5: Basically Substituted Thieno[2,3-D]Pyrimidines", Pharmazie., 1986, 41, 23-25.

Boldyrev et al., "Homocysteine and its Derivatives as Possible Modulators of Neuronal and Non-Neuronal Cell Glutamate Receptors in Alzheimer's Disease", J Alzheimers. Dis, 2007, 11(2), 219-228.

Bolton et al., "Exploring the Correlates of Suicide Attempts Among Individuals with Major Depressive Disorder: Findings from the National Epidemiologic Survey on Alcohol and Related Conditions", J Clin Psychiatry, 2008, 69, 1139-1149.

Bonanno et al., "Chronic Antidepressants Reduce Depolarization-Evoked Glutamate Release and Protein Interactions Favoring Formation of Snare Complex in Hippocampus", J Neurosci 2005, 25, 3270-3279.

Bond et al., "Neuroprotective Effects of Ly379268, A Selective Mglu2/3 Receptor Agonist: Investigations Into Possible Mechanism of Action in Vivo", J Pharmacol. Exp. Ther., 2000, 294(3), 800-809.

Bond et al., "Pharmacology of Metabotropic Glutamate Receptor-Mediated Enhancement of Responses to Excitatory and Inhibitory Amino Acids on Rat Spinal Neurones in Vivo", Neuropharmacology, 1995, 34(8), 1015-1023.

Bonnefous et al., "Biphenyl-Indanones: Allosteric Potentiators of Metabotropic Glutamate Subtype 2 Receptor", Bioorg Med Chem Lett, 2005, 15, 4354-4358.

Boris-Moller et al., "Changes in the Extracellular Levels of Glutamate and Aspartate During Ischemia and Hypoglycemia. Effects of Hypothermia", Experimental Brain Research, 1998, 121(3), 277-284.

Borowitz et al., "Organophosphorus Chemistry. III. The Reactions of Triphenylphosphine with Secondary A-Bromo Ketones and with 2-Bromodimedone", Journal of Organic Chemistry, Dec. 1966, 4031-4037.

Bortolotto et al., "Roles of Metabotropic Glutamate Receptors in LTP and LTD in the Hippocampus", Current Opinion in Neurobiology, 1999, 9(3), 299-304.

Boules et al., "Neurotensin Agonists: Potential in the Treatment of Schizophrenia", CNS Drugs, 2007, 21(1), 13-23.

Bouvrais-Veret et al., "Microtubule-Associated Stop Protein Deletion Triggers Restricted Changes in Dopaminergic Neurotransmission", J. Neurochem., 2008, 104, 745-756.

Boyette et al., "Factor Structure of the Yale-Brown Obsessive-Compulsive Scale (Y-Bocs) in a Large Sample of Patients with Schizophrenia or Related Disorders and Comorbid Obsessive-Compulsive Symptoms", Psychiatry Res., 2011, 409-413.

Brabet et al., "Comparative Effect of L-CCG-I, DCG-IV and Gamma-Carboxy-L-Glutamate on all Cloned Metabotropic Glutamate Receptor Subtypes", Neuropharmacology, 1998, 37, 1043-1051.

Braff et al., "Human Studies of Prepulse Inhibition of Startle: Normal Subjects, Patient Groups, and Pharmacological Studies", Psychopharmacology, 2001, 156, 234-258.

Brauner-Osborne et al., "A New Highly Selective Metabotropic Excitatory Amino Acid Agonist: 2-Amino-4-(3-Hydroxy-5-Methylisoxazol-4-Yl)Butyric Acid", Journal of Medicinal Chemistry, 1996, 39(16), 3188-3194.

Brauner-Osborne et al., "Interaction of CPCCOET with a Chimeric Mglu1b and Calcium Sensing Receptor", Neuroreport, 1999, 10(18), 3923-3925.

Brauner-Osborne et al., "Molecular Pharmacology of 4-Substituted Glutamic Acid Analogues at Ionotropic and Metabotropic Excitatory Amino Acid Receptors", European Journal of Pharmacology, 1997, 335(2-3), R1-R3.

Brauner-Osborne et al., "Pharmacology of (S)-Homoquisqualic Acid and (S)-2-Amino-5-Phosphonopentanoic Acid [(S)-Ap5] at Cloned Metabotropic Glutamate Receptors", British Journal of Pharmacology, 1998, 123(2), 269-274.

Brauner-Osborne, "Structure, Pharmacology and Therapeutic Prospects of Family C G-Protein Coupled Receptors", Current Drug Targets, 2007, 8, 169-184.

Breier et al., "Association of Ketamine-Induced Psychosis with Focal Activation of the Prefrontal Cortex in Healthy Volunteers", Am J Psychiatry, 1997, 154, 805-811.

Bremner et al., "Development and Preliminary Psychometric Properties of an Instrument for the Measurement of Childhood Trauma: The Early Trauma Inventory", Depress Anxiety, 2000, 12(1), 1-12.

Bremner et al., "Psychometric Properties of the Early Trauma Inventory-Self Report", J Nerv Ment Dis, 2007, 195(3), 211-218.

Brnardic et al., "3-Aryl-5-Phenoxymethyl-1,3-Oxazolidin-2-Ones as Positive Allosteric Modulators of Mglur2 for the Treatment of Schizophrenia: Hit-To-Lead Efforts", Bioorg Med Chem Lett, 2010, 20, 3129-3133.

Broekkamp et al., "Major Tranquillizers can be Distinguished From Minor Tranquillizers on the Basis of Effects on Marble Burying and Swim-Induced Grooming in Mice", Eur. J. Pharmacol., 1986, 126, 223-229.

Bruno et al., "Activation of Class II or III Metabotropic Glutamate Receptors Protects Cultured Cortical Neurons Against Excitotoxic Degeneration", European Journal of Neuroscience, 1995, 7(9), 1906-1913.

Bruno et al., "Activation of Metabotropic Glutamate Receptors Coupled to Inositol Phospholipid Hydrolysis Amplifies NMDA-Induced Neuronal Degeneration in Cultured Cortical Cells", Neuropharmacology, 1995, 34(8), 1089-1098.

Bruno et al., "Excitatory Amino Acids and Neurotoxicity", Functional Neurology 1993, 8(4), 279-292.

(56) References Cited

OTHER PUBLICATIONS

Bruno et al., "Metabotropic Glutamate Receptors and Neurodegeneration", Progress in Brain Research, 1998, 116, 209-221.
Bruno et al., "Metabotropic Glutamate Receptors and Neuronal Degeneration in Culture", Advances in Neurology, 1996, 71, 47-52.
Bruno et al., "Molecular Dynamics Simulation of the Heterodimeric Mglur2/5ht(2a) Complex. An Atomistic Resolution Study of a Potential New Target in Psychiatric Conditions", J. Chem. Inf. Model., 2009, 49(6), 1602-1616.
Bruno et al., "Neuroprotection by Glial Metabotropic Glutamate Receptors is Mediated by Transforming Growth Factor-Beta", J. Neurosci., 1998, 18(23), 9594-9600.
Bruno et al., "The Neuroprotective Activity of Group-II Metabotropic Glutamate Receptors Requires New Protein Synthesis and Involves a Glial-Neuronal Signaling", J. Neurosci., 1997, 17(6), 1891-1897.
Bruno, "Metabotropic Glutamate Receptor Subtypes as Targets for Neuroprotective Drugs", Journal of Cerebral Blood Flow and Metabolism, 2001, 21,1013-1033.
Buisson et al., "The Inhibitory Mglur Agonist, S-4-Carboxy-3-Hydroxy-Phenylglycine Selectively Attenuates NMDA Neurotoxicity and Oxygen-Glucose Deprivation-Induced Neuronal Death", Neuropharmacology, 1995, 34(8), 1081-1087.
Bunch et al., "Excitatory Amino Acid Transporters as Potential Drug Targets", Expert Opin Ther Targets, 2009, 13(60), 719-731.
Bunney et al., "Norepinephrine in Depression Reactions. A Review", Arch Gen Psychiatry, 1965, 13(6), 483-494.
Burford et al., "Strategies for the Identification of Allosteric Modulators of G-Protein-Coupled Receptors", Biochem Pharmacol, 2011, 1-12.
Bushell et al., "Pharmacological Antagonism of the Actions of Group II and III Mglur Agonists in the Lateral Perforant Path of Rat Hippocampal Slices", Br. J Pharmacol., 1996, 117(7), 1457-1462.
Bustillo et al., "1H-MRS at 4 Tesla in Minimally Treated Early Schizophrenia", Mol Psychiatry, 2010, 15(6), 629-636.
Butterfield et al., "The Glutamatergic System and Alzheimer's Disease: Therapeutic Implications" CNS Drugs, 2003, 17(9), 641-652.
Byrnes et al., "Metabotropic Glutamate Receptors as Targets for Multipotential Treatment of Neurological Disorders", Neurotherapeutics, 2009, 6(1), 94-107.
Cacabelos et al., "The Glutamatergic System and Neurodegeneration in Dementia: Preventive Strategies in Alzheimer's Disease", International Journal of Geriatric Psychiatry, 1999, 14(1), 3-47.
Cai et al., "Local Potentiation of Excitatory Synapses by Serotonin and its Alteration in Rodent Models of Depression", Nature Neuroscience, 2013, 16(4), 464-472.
Calabresi, "Antiepileptic Drugs in Migraine: From Clinical Aspects to Cellular Mechanisms", Trends in Pharmacological Sci., 2007, 28(4), 188-195.
Campbell et al., "An Update on Regional Brain Volume Differences Associated with Mood Disorders", Curr Opin Psychiatry, 2006, 19(1), 25-33.
Canadian Patent Application No. 2,581,144: Office Action dated Dec. 4, 2012, 5 pages.
Canadian Patent Application No. 2,581,144: Office Action dated May 13, 2009, 5 pages.
Caraci et al., "Metabotropic Glutamate Receptors in Neurodegeneration/Neuroprotection: Still a Hot Topic?", Neurochemistry Intl, 2012, 61(4), 559-565.
Caraci et al., "Targeting Group II Metabotropic Glutamate (MGLU) Receptors for the Treatment of Psychosis Associated with Alzheimer's Disease: Selective Activation of Mglu2 Receptors Amplifies B-Amyloid Toxicity in Cultured Neurons, Whereas Dual Activation of Mglu2 and Mglu3 Receptors is Neuroprotective", Mol Pharmacol, 2011, 79, 618-626.
Carlsson et al., "Neurotransmitter Aberrations in Schizophrenia: New Perspectives and Therapeutic Implications", Life Sciences, 1997, 61(2), 75-94.
Carlsson, "The Neurochemical Circuitry of Schizophrenia", Pharmacopsychiatry, 2006, 39, S10-S14.
Carter, "Schizophrenia Susceptibility Genes Converge on Interlinked Pathways Related to Glutamatergic Transmission and Long-Term Potentiation, Oxidative Stress and Oligodendrocyte Viability", Schizophr. Res., 2006, 86(1-3), 1-14.
Cartmell et al., "Acute Increases in Monoamine Release in the Rat Prefrontal Cortex by the Mglu2/3 Agonist Ly379268 are Similar in Profile to Risperidone, Not Locally Mediated, and Can Be Elicited in the Presence of Uptake Blockade", Neuropharmacology, 2001, 40(7), 847-855.
Cartmell et al., "Attenuation of Specific Pcp-Evoked Behaviors by the Potent Mglu2/3 Receptor Agonist, Ly379268 and Comparison with the Atypical Antipsychotic, Clozapine", Psychopharmacology, 2000, 148, 423-429.
Cartmell et al., "Characterization of [3h]-(2s,2'r,3'r0-2-(2'3'-Dicarboxycyclopropyl)Glycine ([3h]-Dcg Iv) Binding to Metabotropic Mglu2 Receptor-Transfected Cell Membranes", British Journal of Pharmacology, 1998, 123, 497-504.
Cartmell et al., "Dopamine and 5-Ht Turnover are Increased by the Mglu2/3 Receptor Agonist Ly379268 in Rat Medial Prefrontal Cortex, Nucleus Accumbens and Striatum", Brain Res., 2000, 887(2), 378-384.
Cartmell et al., "Effect of Metabotropic Glutamate Receptor Activation on Receptor-Mediated Cyclic Amp Responses in Primary Cultures of Rat Striatal Neurones", Brain Res., 1998, 791(1-2), 191-199.
Cartmell et al., "The Metabotropic Glutamate 2/3 Receptor Agonists Ly354740 and Ly379268 Selectively Attenuate Phencyclidine Versus D-Amphetamine Motor Behavior in Rats", J Pharmacol Exp Ther, 1999, 291, 161-170.
Cartmell et al., "The Mglu(2/3) Receptor Agonist Ly379268 Selectively Blocks Amphetamine Ambulations and Rearing", Eur. J Pharmacol., 2000, 400(2-3), 221-224.
Cartmell et al., "The Potent, Selective Mglu2/3 Receptor Agonist Ly379268 Increases Extracellular Levels of Dopamine, 3,4-Dihydroxyphenylacetic Acid, Homovanillic Acid, and 5-Hydroxyindole-3-Acetic Acid in the Medial Prefrontal Cortex of the Freely Moving Rat", J Neurochem., 2000, 75(3), 1147-1154.
Cartmell et al., "Tolerance to the Motor Impairment, But Not the Reversal of PCP-Induced Motor Activities by Oral Administration of the Mglu2/3 Receptor Agonist, Ly379268", Naunyn Schmiedebergs Arch Pharmacol, 2000, 361, 39-46.
Casado et al., "GPCR Homomers and Heteromers: A Better Choice as Targets for Drug Development Than GPCR Monomers?", Pharmacology & Therapeutics, 2009, 124, 248-257.
Castagne et al., "Preclinical Behavioral Models for Predicting Antipsychotic Activity", Adv. Pharmacol., 2009, 57, 381-418.
Catania et al., "Desensitization of Metabotropic Glutamate Receptors in Neuronal Cultures", Journal of Neurochemistry, 1991, 56(4), 1329-1335.
Catania et al., "Group I Metabotropic Glutamate Receptors: A Role in Neurodevelopmental Disorders?", Mol Neurobiol, 2007, 35, 298-307.
Catania et al., "Homologous Desensitization of Metabolotropic Glutamate Receptors in Neuronal Cultures", Pharmacological Research, 1990, 22(Suppl 1), 79-80.
Catania et al., "Metabotropic Glutamate Receptor Heterogeneity in Rat Brain", Molecular Pharmacology, 1994, 45(4), 626-636.
Catania et al., "Metabotropic Glutamate Receptors are Differentially Regulated During Development", Neuroscience, 1994, 61(3), 481-495.
Catterall, "Structure and Function of Neuronal Ca2+ Channels and Their Role in Neurotransmitter Release", Cell Calcium, 1998, 24(5-6), 307-323.
Cavalli et al., "Multi-Target-Directed Ligands to Combat Neurodegenerative Diseases", J. Med. Chem., 2007-2008, 26 pages.
Cavanni et al., "Pharmacological Analysis of Carboxyphenylglycines at Metabotropic Glutamate Receptors", European Journal of Pharmacology, 1994, 269(1), 9-15.
Celanire et al., "Recent Advances in the Drug Discovery of Metabotropic Glutamate Receptor 4 (mGluR4) Activators for the Treatment of CNS and Non-CNS Disorders", Expert Opin. Drug Discovery, 2012, 7(3), 261-280.

(56) References Cited

OTHER PUBLICATIONS

Chaki "Group II Metabotropic Glutamate Receptor Agonists as a Potential Drug for Schizophrenia", European Journal of Pharmacology, 2010, 639, 59-66.
Chaki et al, "Anxiolytic- and Antidepressant-Like Profile of a New Crf1 Receptor Antagonist, R278995/Cra0450", Eur J Pharmacol, 2004, 485, 145-158.
Chaki et al., "Mglu2/3 and Mglu5 Receptors: Potential Targets for Novel Antidepressants", Neuropharmacology, 2013, 66, 40-52.
Chaki et al., "Targeting of Metabotropic Glutamate Receptors for the Treatment of Schizophrenia", Current Pharmaceutical Design, 2011, 17, 94-102.
Chakos et al., "Baseline Use of Concomitant Psychotropic Medications to Treat Schizophrenia in the Catie Trial", Psychiatr Serv., 2006, 57(8), 1094-1101.
Chakrabarty et al., "Glutamatergic Dysfunction in OCD", Neuropsychopharmacology, 2005, 30(9), 1735-1740.
Chakrasali et al., "Reaction of Acylketene S,N-Acetals with Malonyl Chloride: Synthesis of Novel 1,5-Substituted 4-Hydroxy-6-Methylthio-2 (1h)-Pyridones and 6,8-Substituted 4-Hydroxy-7-Methylthio-2,5-Dioxo-5,6-Dihydro-2h-Pyrano [3,2-C] Pyridines", Synthesis, Jan. 1988, 87-89.
Charney et al., "Increased Anxiogenic Effects of Caffeine in Panic Disorders", Arch Gen Psychiatry, 1985, 42, 233-243.
Charney et al., "Life Stress, Genes, and Depression: Multiple Pathways Lead to Increased Risk and New Opportunities for Intervention", Science's Stke, 2004, (225), Re5, 12 pages.
Charney et al., "Noradrenergic Function in Panic Anxiety. Effects of Yohimbine in Healthy Subjects and Patients with Agoraphobia and Panic Disorder", Arch. Gen. Psychiatry, 1984, 41, 751-763.
Chaudhari et al., "A Metabotropic Glutamate Receptor Variant Functions as a Taste Receptor", Nature Neuroscience, 2000, 3, 113-119.
Chavez-Noriega et al., "Metabotropic Glutamate Receptors: Potential Drug Targets for the Treatment of Schizophrenia", Current Drug Targets—CNS & Neurological Disorders, 2002, 1(3), 261-281.
Chavis et al., "Facilitatory Coupling Between a Glutamate Metabotropic Receptor and Dihydropyridine-Sensitive Calcium Channels in Cultured Cerebellar Granule Cells", J. Neurosci., 1995, 15(1), 135-143.
Chavis et al., "Modulation of Calcium Channels by Metabotropic Glutamate Receptors in Cerebellar Granule Cells", Neuropharmacology, 1995, 34(8), 929-937.
Chen et al., "Second-Generation Antipsychotics in Major Depressive Disorder: Update and Clinical Perspective", Curr Opin Psychiatry, 2011, 24, 19-17.
Chen, "The Chemical Biology of Clinically Tolerated NMDA Receptor Antagonists", Journal of Neurochemistry, 2006, 97, 1611-1626.
Chiarugi et al., "Novel Isoquinolinone-Derived Inhibitors of Poly(Adp-Ribose) Polymerase-1: Pharmacological Characterization and Neuroprotective Effects in an in Vitro Model of Cerebral Ischemia", Journal of Pharmacology and Experimental Therapeutics, 2003, 305(3), 943-949.
Chiechio et al., "Epigenetic Modulation of Mglu2 Receptors by Histone Deacetylase Inhibitors in the Treatment of Inflammatory Pain", Mol. Pharmacol., 2009, 75(5), 1014-1020.
Chiechio et al., "Metabotropic Glutamate Receptors and the Control of Chronic Pain", Curr Opin Pharmacol, 2012, 12, 28-34.
Chiechio et al., "Transcriptional Regulation of Type-2 Metabotropic Glutamate Receptors: An Epigenetic Path to Novel Treatments for Chronic Pain", Trends in Pharmacological Sciences, 2010, 31(4), 153-160.
Chilean Patent Application No. 2745-2008: Office Action dated Apr. 15, 2011, 2 pages.
Chilean Patent Application No. 671-2008: Office Action dated Oct. 29, 2010, 9 pages.
Chilean Patent Application No. 681-2007: Office Action dated Jan. 11, 2011, 6 pages.
Chin et al., "Amyloid Beta Protein Modulates Glutamate-Mediated Neurotransmission in the Rat Basal Forebrain: Involvement of Presynaptic Neuronal Nicotinic Acetylcholine and Metabotropic Glutamate Receptors", J. Neurosci., 2007, 27(35), 9262-9269.
Chin et al., "Awake Rat Pharmacological Magnetic Resonance Imaging as a Translational Pharmacodynamic Biomarker: Metabotropic Glutamate 2/3 Agonist Modulation of Ketamine-Induced Blood Oxygenation Level Dependence Signals", Jpet, 2011, 336, 709-715.
Chin et al., "Awake Rat Pharmacological MRI as a Translational Pharmacodynamic Biomarker: Mglur2/3 Agonist Modulation of Ketamine-Induced Bold Signals", Jpet, 2010, 22 pages.
Chinese Patent Application No. 200780009210.5: Office Action dated Jun. 19, 2012, 4 pages.
Chinese Patent Application No. 200880107135.0: Office Action dated Jul. 4, 2012, 4 pages.
Choi, "Methods for Antagonizing Glutamate Neurotoxicity", Cerebrovascular & Brain Metabolism Reviews, 1990, 2(2), 105-147.
Chojnacka-Wojcik et al., "Glutamate Receptor Ligands as Anxiolytics", Current Opinion in Investigational Drugs, 2001, 2(8), 1112-1119.
Christopolous et al., "G Protein-Coupled Receptor Allosterism and Complexing", Pharmacol Rev, 2002, 54, 323-374.
Cid et al., "Discovery of 1,4-Disubstituted 3-Cyano-2-Pyridones: A New Class of Positive Allosteric Modulators of the Metabotropic Glutamate 2 Receptor", J Med Chem, 2012, 55, 2388-2405.
Cid et al., "Discovery of 1,5-Disubstituted Pyridones: A New Class of Positive Allosteric Modulators of the Metabotropic Glutamate 2 Receptor", ACS Chem Neurosci, 2010, 1, 788-795.
Cid et al., "Discovery of 3-Cyclopropylmethyl-7-(4-Phenylpiperidin-1-Yl)-8-Trifluoromethyl[1,2,4]Triazolo[4,3-A]Pyridine (Jnj-42153605): A Positive Allosteric Modulator of the Metabotropic Glutamate 2 Receptor", J Med Chem, 2012, 55, 8770-8789.
Cid, "Discovery of a Potent and Orally Bioavailable Positive Allosteric Modulator of Mglur2 for the Treatment of CNS Disorders", Presentation Slides, 16th SCI/RSC Medicinal Chemistry Symposium, Cambridge, Sep. 2011, 26 pages.
Cid, "JNJ-42153605: A Novel Positive Allosteric Modulator of Mglur2 for the Treatment of CNS Disorders" Presentation Slides, RICT 2012—48th International Conference on Medicinal Chemistry, Poitiers 2012, 28 pages.
Citrome, "Adjunctive Aripiprazole, Olanzapine, or Quetiapine for Major Depressive Disorder: An Analysis of Number Needed to Treat, Number Needed to Harm, and Likelihood to Be Helped or Harmed", Postgraduate Medicine, 2010, 122(4), 39-48.
Clark et al., "Effects of the Mglu2/3 Receptor Agonist Ly379268 on Motor Activity in Phencyclidine-Sensitized Rats", Pharmacol. Biochem. Behav., 2002, 73(2), 339-346.
Clark, "Tripartite Model of Anxiety and Depression: Psychometric Evidence and Taxonomic Implications", J. Abnormal Psych., 1991, 100(3), 316-336.
Clayton et al., "Follow-Up and Family Study of Anxious Depression" Am J Psychiatry, 1991, 148, 1512-1517.
Cleary et al., "Factor Analysis of the Hamilton Depression Scale" Drugs Exptl Clin Res, 1977, 1(1-2), 115-120.
Clements et al., "The Time Course of Glutamate in the Synaptic Cleft", Science, 1992, 258(5087), 1498-1501.
Cleva et al., "Positive Allosteric Modulators of Type 5 Metabotropic Glutamate Receptors (mGluR5) and their Therapeutic Potential for the Treatment of CNS Disorders", Molecules, 2011, 16, 2097-2106.
Clinical Trials, "A Dose-Ranging Study of JNJ-40411813 in Healthy Male Volunteers", Available from http://clinicaltrials.gov/show/NCT01358006, retrieved on Aug. 1, 2013.
Clinical Trials, "A Study of [11C]JNJ-42491293, a Possible PET Ligand for the mGlu2 Receptor, in Healthy Adult Volunteers", Available from http://clinicaltrials.gov/show/NCT01359852, retrieved on Aug. 1, 2013.
Clinical Trials, "A Study of JNJ-40411813 as Supplementary Treatment to an Antidepressant in Adults with Depression and Anxiety Symptoms", Available from: http://clinicaltrials.gov/show/NCT01582815, retrieved on Aug. 1, 2013.
Clinical Trials, "AZD8529 Single Ascending Dose Study (Sad)", Clinicaltrials.Gov. No. NCT00755378, Available From: Http://Clinicaltrials.Gov/Show/Nct00755378, retrieved on Aug. 22, 2013.

(56) References Cited

OTHER PUBLICATIONS

Clinical Trials, "First-In-Patient Study to Assess the Safety and Tolerability and to Explore the Potential Therapeutic Efficacy of a Novel Glutamate Modulator as Monotherapy and as Add-On Therapy in Patients with Schizophrenia", Available From: Https://Www.Clinicaltrialsregister.Eu—Eudract No. 2010-023369-23, retrieved on Aug. 1, 2013.
Clinical Trials, "Investigation of the Safety, Tolerability and Potential Therapeutic Effects of JNJ-40411813 in Patients with Schizophrenia", Clinicaltrials Gov. No. NCT01323205, Available From: Http://Clinicaltrials.Gov/Show/NCT01323205, Retrieved Aug. 1, 2013.
Clinical Trials, "Ketamine Challenge Study with JNJ-40411813", Clinical Trials. Gov No. NCT01101659, Available From: Http://Clinicaltrials.Gov/Ct2/Show/Nct01101659, 2010, 3 pages.
Clinical Trials, "Study to Assess the Efficacy, Safety, and Tolerability of AZD8529 in Adult Schizophrenia Patients", Clinicaltrials.Gov. No. NCT00921804, Available From: Http://Clinicaltrials.Gov/Show/Nct00921804, retrieved on Aug. 23, 2013, 3 pages.
Clinical Trials, "The Effects Azd8529 on Cognition and Negative Symptoms in Schizophrenics", Clinicaltrials.Gov. No. NCT00986531, Available From: Http://Clinicaltrials.Gov/Show/Nct00986531, retrieved on Aug. 23, 2013, 2 pages.
Cloninger et al., "The Empirical Structure of Psychiatric Comorbidity and its Theoretical Significance", Comorbidity of Mood and Anxiety Disorders, 1990, 439-462.
Cohen et al., "A Global Measure of Perceived Stress", J Health Soc Behav, 1983 24(4), 385-396.
Colangelo et al., "Differential Effects of Acute Administration of Clozapine or Haloperidol on Local Cerebral Glucose Utilization in the Rat", Brain Research, 1997, 768, 273-278.
Collingridge et al., "Excitatory Amino Acid Receptors and Synaptic Plasticity", Trends in Pharmacological Sciences, 1990, 11(7), 290-296.
Collins et al., "Arachidonic Acid Metabolites and the Synaptic Potentiation Evoked by Activation of Metabotropic Glutamate Receptors", European Journal of Pharmacology, 1998, 342(2-3), 213-216.
Collins et al., "From Ligand Binding to Gene Expression: New Insights into the Regulation of G-Protein-Coupled Receptors", Trends in Biochemical Sciences, 1992, 17(1), 37-39.
Colpaert et al., "A Critical Study on Ro-4-1284 Antagonism in Mice", Arch. Int. Pharmacodyn., 1975, 215, 40-90.
Colzi et al., "Monoamine Oxidase-A Inhibitors and Dopamine Metabolism in Rat Caudatus: Evidence that an Increased Cytosolic Level of Dopamine Displaces Reversible Monoamine Oxidase-A Inhibitors in Vivo", J. Pharmacol. Exper. Therapeutics, 1993, 265, 103-111.
Comins et al., "N- Vs. O-Alkylation in the Mitsunobu Reaction of 2-Pyridone", Tetrahedron Letters, 1994, 35(18), 2819-2822.
Committee for Proprietary Medicinal Products (CPMP), European Agency for the Evaluation of Medicinal Products; Meeting Feb. 26, 1998, London (UK): Note for Guidance on the Clinical Investigation of Medicinal Products in the Treatment of Schizophrenia, 10.
Conigrave et al., "Allosteric Activation of Plasma Membrane Receptors—Physiological Implications and Structural Origins", Progress in Biophysics & Molecular Biology, 2003, 81(3), 219-40.
Conn et al., "Activation of Metabotropic Glutamate Receptors as a Novel Approach for the Treatment of Schizophrenia", Trends Pharmacol Sci, 2008, 30(1), 25-31.
Conn et al., "Allosteric Modulators of Gpers: A Novel Approach for the Treatment of CNS Disorders", Nature Reviews Drug Discovery, 2009, 8, 41-54.
Conn et al., "Metabotropic Glutamate Receptors in the Basal Ganglia Motor Circuit", Nature Reviews Neuroscience, 2005, 6, 787-798.
Conn et al., "Pharmacology and Functions of Metabotropic Glutamate Receptors", Annu Rev Pharmacol Toxicol, 1997, 37, 205-237.
Conn, "Physiological Roles and Therapeutic Potential of Metabotropic Glutamate Receptors", Annals of the New York Academy of Sciences, 2003, 1003, 12-21.
Connolly et al., "If at First You Don't Succeed: A Review of the Evidence for Antidepressant Augmentation, Combination and Switching Strategies", Drugs, 2011, 71(1), 43-64.
Cook et al., "Behavioral Effects of Some Psychopharmacological Agent", Ann. Ny Acad. Sci., 1957, 66, 740-752.
Cook et al., "Effects of Drugs on Avoidance and Escape Behavior", Fed. Proc. 23, 1964, 818-835.
Copani, "Activation of Metabotropic Glutamate Receptors Protects Cultured Neurons Against Apoptosis Induced By-Amyioid Peptide", Molecular Pharmacology, 1995, 47:890-897.
Copeland et al., "Positive Allosteric Modulation Reveals a Specific Role for Mglu2 Receptors in Sensory Processing in the Thalamus", J Physiol, 2012, 590.4, 937-951.
Corlett et al., "Glutamatergic Model Psychoses: Prediction Error, Learning, and Inference", Neuropsychopharmacology, 2011, 36(1), 294-315.
Corti, "The Use of Knock-Out Mice Unravels Distinct Roles for Mglu2 and Mglu3 Metabotropic Glutamate Receptors in Mechanisms of Neurodegeneration/Neuroprotection", J. Neurosci., 2007, 27(31), 8297-8308.
Coryell et al., "Effects of Anxiety on the Long-Term Course of Depressive Disorders", The British Journal of Psychiatry, 2012, 200, 210-215.
Costantino et al., "Modeling of Poly (Adp-Ribose) Polymerase (Parp) Inhibitors. Docking of Ligands and Quantitative Structure-Activity Relationship Analysis", Journal of Medicinal Chemistry, 2001, 440, 3786-3794.
Coyle, "The Gaba-Glutamate Connection in Schizophrenia: Which is the Proximate Cause?", Biochem. Pharmacol., 2004, 68(8), 1507-1514.
Cozzi et al., "Type 2 Metabotropic Glutamate (Mglu) Receptors Tonically Inhibit Transmitter Release in Rat Caudate Nucleus: in Vivo Studies with (2s,1's,2's,3'r)-2-(2'-Carboxy-3'-Phenylcyclopropyl)Glycine, A New Potent and Selective Antagonist", European Journal of Neuroscience, 1997, 9(7), 1350-1355.
Craddock et al., "The Genetics of Schizophrenia and Bipolar Disorder: Dissecting Psychosis", J Med Genet, 2005, 42, 193-204.
Cropley et al., "Molecular Imaging of the Dopaminergic System and its Association with Human Cognitive Function", Biol.Psychiatry, 2006, 59, 898-907.
Cube et al., "3-(2-Ethoxy-4-{4-[3-Hydroxy-2-Methyl-4-(3-Methylbutanoyl)-Phenoxy]Butoxy}Phenyl)Propanoic Acid: A Brain Penetrant Allosteric Potentiator at the Metabotropic Glutamate Receptor 2 (Mglur2)", Bioorganic & Medicinal Chemistry Letters, 2005, 15, 2389-2393.
Cummings, "Behavioral Effects of Memantine in Alzheimer Disease Patients Receiving Donepezil Treatment" Neurology 2006, 67, 57-63.
Cymbalta, "Highlights of Prescribing Information", 2004, 1 page.
Czapski et al., "Effect of Poly (Adp-Ribose) Polymerase Inhibitors on Oxidative Stress Evoked Hydroxyl Radical Level and Macromolecules Oxidation in Cell Free System of Rat Brain Cortex", Neuroscience Letters, 2004, 356, 45-48.
D'Alessandro et al., "The Identification of Structurally Novel, Selective, Orally Bioavailable Positive Allosteric Modulators of Mglur2", Bioorg Med Chem Lett, 2010, 20, 759-762.
D'Antoni et al., "Metabotropic Glutamate Receptors in Glial Cells", Neurochem. Res., 2008, 33(12), 2436-2443.
Dale et al., "Mechanisms of Metabotropic Glutamate Receptor Desensitization: Role in the Patterning of Effector Enzyme Activation", Neurochemistry Intl, 2002, 41, 319-326.
Dale et al., "Spatial-Temporal Patterning of Metabotropic Glutamate Receptor-Mediated Inositol 1,4,5-Triphosphate, Calcium, and Protein Kinase C Oscillations: Protein Kinase C-Dependent Receptor Phosphorylation Is Not Required", J. Biol. Chem., 2001, 276(38), 35900-35908.
Danner et al., "Integrating Patients' Views Into Health Technology Assessment: Analytic Hierarchy Process (Ahp) as a Method to Elicit Patient Preferences", Intl Journal of Technology Assessment in Health Care, 2011, 27(4), 369-375.
D'Ascenzo et al., "Mglur5 Stimulates Gliotransmission in the Nucleus Accumbens", Proc. Natl. Acad. Sci., 2007, 104(6), 1995-2000.

(56) References Cited

OTHER PUBLICATIONS

Dash et al., "Long-Term Homeostasis of Extracellular Glutamate in the Rat Cerebral Cortex Across Sleep and Waking States", J Neurosci, 2009, 29, 620-629.
Datta et al., "Microinjection of Glutamate into the Pedunculopontine Tegmentum Induces Rem Sleep and Wakefulness in the Rat", Am J Physiol., Regul Integr Comp Physiol, 2001, 280, R752-R759.
Davidson et al., "Achieving Remission with Venlafaxine and Fluoxetine in Major Depression: Its Relationship to Anxiety Symptoms", Depression and Anxiety, 2002, 16, 4-13.
Davidson et al., "Differential Effects of Neuroleptic and Other Psychotropic Agents on Acquisition of Avoidance in Rats", Life Sci., 1976, 18, 1279-1284.
Davis et al., "2,1-Benzisothiazoles. Xii. [1]. The Use of N-Substituted-2,1-Benzisothiazolium Salts as Synthetic Equivalents of O-Aminobenz-Aldehydes. A Simple Synthesis of Some 2-Quinolones", Journal of Heterocyclic Chemistry, 1983, 20, 1707-1708.
Davis, "Diazepam and Flurazepam: Effects on Conditioned Fear as Measured with the Potentiated Startle Paradigm", Psychopharmacology, 1979, 62, 1-7.
Davis, "Pharmacological and Anatomical Analysis of Fear Conditioning Using the Fear-Potentiated Startle Paradigm", Behavioral Neuroscience, 1986, 100, 814-824.
Dawson et al., "Novel Analysis for Improved Validity in Semi-Quantitative 2-Deoxyglucose Autoradiographic Imaging", Journal of Neuroscience Methods, 2008, 175, 25-35.
De Blasi et al., "Molecular Determinants of Metabotropic Glutamate Receptor Signaling", Trends in Pharmacological Sciences, 2001, 22 (3), 114-120.
De Boer et al., "Characterization of the Clinical Effect of a Positive Allosteric Modulator of the Metabotropic Glutamate Receptor-2", Society of Biological Psychiatry 67$^{th}$ Annual Scientific Convention, May 2012, 2 pages.
De Montis et al., "Selective Adenylate Cyclase Increase in the Limbic Area of Long-Term Imipramine-Treated Rats", European Journal of Pharmacology, 1990, 180(1), 169-174.
De Novellis et al., "Type I and II Metabotropic Glutamate Receptors Modulate Periaqueductal Grey Glycine Release: Interaction Between Mglu2/3 and A1 Adenosine Receptors", Neuropharmacology, 2002, 43(7), 1061-1069.
Dean, "The Cortical Serotonin2a Receptor and the Pathology of Schizophrenia: A Likely Accomplice", J. Neurochem., 2003, 85, 1-13.
Dedeurwaerdere et al., "Memantine-Induced Brain Activation as a Model for the Rapid Screening of Potential Novel Antipsychotic Compounds: Exemplified by Activity of an Mglu2/3 Receptor Agonist", Psychopharmacology, 2011, 214, 505-514.
Del Rio et al., "Differential Coupling of G-Protein-Linked Receptors to Ca2+ Mobilization Through Inositol(1,4,5)Trisphosphate or Ryanodine Receptors in Cerebellar Granule Cells in Primary Culture", European Journal of Neuroscience, 1999, 11(9), 3015-3022.
Del'guidice et al., "Messing Up with Traffic: Different Effects of Antipsychotic Agents on Glutamate Receptor Complexes in Vivo", Mol. Pharmacol., 2008, 73(5), 1339-1342.
Delille et al., "Heterocomplex Formation of 5-HT2A-Mglu2 and its Relevance for Cellular Signaling Cascades", Neuropharmacology, 2012, 1-8.
Delille et al., "The Two Faces of the Pharmacological Interaction of Mglu2 and 5-Ht2a—Relevance of Receptor Heterocomplexes and Interaction Through Functional Brain Pathways", Neuropharmacology, 2013, 70, 296-305.
Derks et al., "Kreapelin Was Right: A Latent Class Analysis of Symptom Dimensions in Patients and Controls", Schizophrenia Bull., 2012, 38(3), 495-505.
Desseilles et al., "Assessing the Adequacy of Past Antidepressant Trials: A Clinician's Guide to the Antidepressant Treatment Response Questionnaire", J Clin Psychiatry, 2011, 72(8), 1152-1154.
Dhami et al., "G Protein-Coupled Receptor Kinase 2 Regulator of G Protein Signaling Homology Domain Binds to Both Metabotropic Glutamate Receptor 1a and Galphaq to Attenuate Signaling", Journal of Biological Chemistry, 2004, 279(16), 16614-16620.
Dhami et al., "Regulation of Metabotropic Glutamate Receptor Signaling, Desensitization and Endocytosis", Pharmacol. Ther., 2006, 111(1), 260-271.
Dhanya et al., "Design and Synthesis of an Orally Active Metabotropic Glutamate Receptor Subtype-2 (Mglur2) Positive Allosteric Modulator (Pam) That Decreases Cocaine Self-Administration in Rats", J Med Chem, 2011, 54, 342-353.
Dhonnchadha et al., "Anxiolytic-Like Effects of 5-Ht2 Ligands on Three Mouse Models of Anxiety", Behavioural Brain Research, 2003, 140, 203-214.
Di Liberto et al., "Group II Metabotropic Glutamate Receptor Activation by Agonist Ly379268 Treatment Increases the Expression of Brain Derived Neurotrophic Factor in the Mouse Brain", Neuroscience, 2010, 165, 863-873.
Dingledine et al., "Excitatory Amino Acid Receptors in Epilepsy", Trends in Pharmacological Sciences, 1990, 11(8), 334-338.
Dingledine et al., "Peripheral Glutamate Receptors: Molecular Biology and Role in Taste Sensation", J Nutr, 2000, 130(4s Suppl):1039s-1042s.
Doherty et al., "Functional Interactions Between Cannabinoid and Metabotropic Glutamate Receptors in the Central Nervous System", Current Opinion in Pharmacology, 2003, 3(1), 46-53.
Doherty et al., "Rapid Internalization and Surface Expression of a Functional, Fluorescently Tagged G-Protein-Coupled Glutamate Receptor", Biochemical Journal, 1999, 341(Pt 2), 415-422.
Domschke et al., "Anxious Versus Non-Anxious Depression: Difference in Treatment Outcome", J Psychopharmacol, 2010, 24, 621-622.
D'onofrio et al., "Neuroprotection Mediated by Glial Group-II Metabotropic Glutamate Receptors Requires the Activation of the Map Kinase and the Phosphatidylinositol-3-Kinase Pathways", Journal of Neurochemistry, 2001, 78(3), 435-445.
Doreulee et al., "The Role of the Mglur Allosteric Modulation in the Nmda-Hypofunction Model of Schizophrenia", Georgian Medical News, 2009, 177, 59-65.
Doumazene et al., "A New Approach to Analyze Cell Surface Protein Complexes Reveals Specific Heterodimeric Metabotropic Glutamate Receptors", Faseb, 2011, 25, 66-77.
Doumazene, "Illuminating the Activation Mechanisms and Allosteric Properties of Metabotropic Glutamate Receptors", PNAS, 2013, 1-10.
Downey et al., "Ecdysone-Based System for Controlled Inducible Expression of Metabotropic Glutamate Receptor Subtypes 2,5, and 8", Journal of Biomolecular Screening, 2005, 10(8), 841-848.
Doyle et al., "Quantifying the Attenuation of the Ketamine Phmri Response in Humans: a Validation Using Antipsychotic and Glutamatergic Agents", Jpet Fast Forward, Jan. 31, 2013, 42 pages.
Drevets et al., "Functional Anatomical Correlates of Antidepressant Drug Treatment Assessed Using Pet Measures of Regional Glucose Metabolism", European Neuropsychopharmacology, 2002, 12, 527-544.
Drew et al., "Multiple Metabotropic Glutamate Receptor Subtypes Modulate Gabaergic Neurotransmission in Rat Periaqueductal Grey Neurons in Vitro", Neuropharmacology, 2004, 46(7), 927-934.
Dunayevich, "Efficacy and Tolerability of an Mglu2/3 Agonist in the Treatment of Generalized Anxiety Disorder", Neuropsychopharmacol., 2008, 33, 1603-1610.
Duncan et al., "Comparison of the Effects of Clozapine, Risperidone, and Olanzapine on Ketamine-Induced Alterations in Regional Brain Metabolism", Jpet, 2000, 293, 8-14.
Duncan et al., "Differential Effects of Clozapine and Haloperidol on Ketamine-Induced Brain Metabolic Activation", Brain Res, 1998, 812, 65-75.
Duncan et al., "Metabolic Mapping of the Rat Brain After Subanesthetic Doses of Ketamine: Potential Relevance to Schizophrenia", Brain Research, 1998, 787, 181-190.
Duncan et al., "Topographic Patterns of Brain Activity in Response to Swim Stress: Assessment by 2-Deoxyglucose Uptake and Expression of Fos-Like Immunoreactivity", J Neurosci, 1993, 13, 3932-3943.

(56) References Cited

OTHER PUBLICATIONS

Dunlop, "Glutamate-Based Therapeutic Approaches: Targeting the Glutamate Transport System", Current Opinion in Pharmacology, 2006, 6 (1), 103-107.

Duplantier et al., "3-Benzyl-1,3-Oxazolidin-2-Ones as Mglur2 Positive Allosteric Modulators: Hit to Lead and Lead Optimization", Bioorg Med Chem Lett, 2009, 19, 2524-2529.

Durand et al., "Role of Metabotropic Glutamate Receptors in the Control of Neuroendocrine Function", Neuropharmacology, 2008, 55(4), 577-583.

During, "Extracellular Hippocampal Glutamate and Spontaneous Seizure in the Conscious Human Brain", Lancet, 1993, 341, 1607-1610.

Dutar et al., "Pharmacological Characterization of an Unusual Mglur-Evoked Neuronal Hyperpolarization Mediated by Activation of Girk Channels", Neuropharmacology, 1999, 38(4), 467-475.

Egan et al., "Neurobiology of Schizophrenia", Current Opinion in Neurobiology, 1997, 7(5), 701-707.

Egashira et al., "Impaired Social Interaction and Reduced Anxiety-Related Behavior in Vasopressin V1a Receptor Knockout Mice", Behav Brain Res, 2007, 5 pages.

Ehlert, "Analysis of Allosterism in Functional Assays", J Pharmacol. Exp. Ther., 2005, 315(2), 740-754.

Eintrei et al., "Effects of Diazepam and Ketamine Administered Individually or in Combination on Regional Rates of Glucose Utilization in Rat Brain", Br J Anaesth, 1999, 82, 596-602.

Elia et al., "Genome-Wide Copy Number Variation Study Associates Metabotropic Glutamate Receptor Gene Networks with Attention Deficit Hyperactivity Disorder", Nature Genetics, 2011, 9 pages.

Ellenbroek et al., "Animal Models with Construct Validity for Schizophrenia", Behavioural Pharmacology, 1990, 1, 469-490.

Emmitte, "Recent Advances in the Design and Development of Novel Negative Allosteric Modulators of MgluS", Chem. Neurosci., 2011, 2, 411-432.

Engin et al., "The Effects of Intra-Cerebral Drug Infusions on Animals' Unconditioned Fear Reactions: A Systematic Review", Prog Neuropsychopharmacol Biol Psychiatry, 2008, 32, 1399-1419.

Enomoto et al., "Phencyclidine and Genetic Animal Models of Schizophrenia Developed in Relation to the Glutamate Hypothesis", Methods Find. Exp. Clin Pharmacol., 2007, 29(4), 291-301.

Ermolinsky et al., "Differential Changes in Mglu2 and Mglu3 Gene Expression Following Pilocarpine-Induced Status Epilepticus: A Comparative Real-Time Pcr Analysis", Brain Research, 2008, 1226, 173-180.

Esposito et al., "Patterns of Benzodiazepine Use in a Canadian Population Sample", Epidemiol Psichiatr Soc., 2009, 18(3), 248-254.

Etkin et al., "Common Abnormalities and Disorder-Specific Compensation During Implicit Regulation of Emotional Processing in Generalized Anxiety and Major Depressive Disorders", Am J Psychiatry, 2011, 168, 968-978.

Etkin, "Neurobiology of Anxiety: From Neural Circuits to Novel Solutions?", Depression and Anxiety, 2012, 29, 355-358.

Eurasian Patent Application No. 200801934/28: Office Action dated May 13, 2010, 4 pages.

Eurasian Patent Application No. 200901162/28: Office Action dated Apr. 18, 2011, 7 pages.

European Patent Application No. 05787278.0: Office Action dated May 11, 2012, 4 pages.

European Patent Application No. 07726932.2: Office Action dated Sep. 8, 2009, 10 pages.

European Patent Application No. 08717514.7: Office Action dated Jun. 28, 2010, 6 pages.

European Patent Application No. 08717515.4: Official Communication dated May 3, 2010, 5 pages.

European Patent Application No. 11181481.1: Office Action dated Dec. 6, 2012, 6 pages.

European Patent Application No. EP 08166832: Search Report dated May 8, 2009, 5 pages.

Ezquerra et al., "Efficient Reagents for the Synthesis of 5-, 7-, and 5,7-Substituted Indoles Starting from Aromatic Amines: Scopes and Limitations", J Org Chem, 1996, 61, 5804-5812.

Fagni et al., "Identification and Functional Roles of Metabotropic Glutamate Receptor-Interacting Proteins", Seminars in Cell & Developmental Biology, 2004, 15(3), 289-298.

Farabaugh et al., "Anxious Depression and Early Changes in the Hamd-17 Anxietysomatization Factor Items and Antidepressant Treatment Outcome", Int Clin Psychopharmacol., Jul. 2010, 25(4), 214-217.

Faries et al., "The Double-Blind Variable Placebo Lead-in Period: Results from Two Antidepressant Clinical Trials", Journal of Clinical Psychopharmacology, 2001, 21, 561-568.

Fava et al., "Anxiety Disorders in Major Depression" Comprehensive Psychiatry 2000, 41(2), 97-102.

Fava et al., "Clinical Correlates and Symptom Patterns of Anxious Depression Among Patients with Major Depressive Disorder in Star*D", Psychological Medicine, 2004, 34, 1299-1308.

Fava et al., "Difference in Treatment Outcome in Outpatients with Anxious Versus Nonanxious Depression: A Star*D Report", Am J Psychiatry, 2008, 165, 342-351.

Fava et al., "Major Depressive Subtypes and Treatment Response", Biol. Psychiatry, 1997, 42, 568-576.

Fava et al., "Reliability and Validity of the Massachusetts General Hospital Cognitive and Physical Functioning Questionnaire", Psychother Psychosom, 2009, 78(2), 91-97.

Fava et al., "The Efficacy and Tolerability of Duloxetine in the Treatment of Anxious Versus Non-Anxious Depression: A Post-Hoc Analysis of an Open-Label Outpatient Study", Annals of Clinical Psychiatry, 2007, 19(3), 187-195.

Fava et al., "The Problem of the Placebo Response in Clinical Trials for Psychiatric Disorders: Culprits, Possible Remedies, and a Novel Study Design Approach", Psychother Psychosom, 2003, 72, 115-127.

Fava et al., "What Clinical and Symptom Features and Comorbid Disorders Characterize Outpatients with Anxious Major Depressive Disorder: A Replication and Extension", Can J Psychiatry, Nov. 2006, 51(13), 823-835.

Fawcett et al., "Anxiety Syndromes and Their Relationship to Depressive Illness", J Clin Psychiatry, Aug. 1983, 44(8 Pt 2), 8-11.

Fawcett et al., "The Detection and Consequences of Anxiety in Clinical Depression", J Clin Psychiatry, 1997, 58(Suppl 8), 35-40.

Fawcett, "Treating Impulsivity and Anxiety in the Suicidal Patient", Ann NY Acad Sci., Apr. 2001, 932, 94-102.

FDA Center for Drug Evaluation and Research, "Introduction and Drug History", Pharmacology Reviews, 2003, NDA 21-487.

Feeley et al., "Mglurs: A Target for Pharmacotherapy in Parkinson Disease", Experimental Neurology, 2003, 184(Suppl-6), S30-S36.

Feenstra et al., "Local Activation of Metabotropic Glutamate Receptors Inhibits the Handling-Induced Increased Release of Dopamine in the Nucleus Accumbens But Not That of Dopamine or Noradrenaline in the Prefrontal Cortex: Comparison with Inhibition of Ionotropic Receptors", Journal of Neurochemistry, 1998, 70(3), 1104-1113.

Feinberg et al., "The Metabotropic Glutamate (Mglu)2/3 Receptor Antagonist Ly341495 [2s-2-Amino-2-(1s,2s-2-Carboxycyclopropyl-1-Yl)-3-(Xanth-9-Yl)Propanoic Acid] Stimulates Waking and Fast Electroencephalogram Power and Blocks the Effects of the Mglu2/3 Receptor Agonist Ly379268 [(−)-2-Oxa-4-Aminobicyclo[3.1.0]Hexane-4,6-Dicarboxylate] in Rats", Jpet, 2005, 312, 826-833.

Fell et al., "Activation of Metabotropic Glutamate (Mglu)2 Receptors Suppresses Histamine Release in Limbic Brain Regions Following Acute Ketamine Challenge", Neuropharmacology, 2010, 58, 632-639.

Fell et al., "Evidence for the Role of Mglu2 Not Mglu3 Receptors in the Preclinical Antipsychotic Pharmacology of the Mglu2/3 Receptor Agonist Ly404039", Journal of Pharmacology & Experimental Therapeutics, 2008, 326, 209-217.

Fell et al., "Group II Metabotropic Glutamate Receptor Agonists and Positive Allosteric Modulators as Novel Treatments for Schizophrenia", Neuropharmacology 2012, 62, 1473-1483.

Fell et al., "In Vitro and In Vivo Evidence for a Lack of Interaction with Dopamine D2 Receptors by the Metabotropic Glutamate 2/3

(56) References Cited

OTHER PUBLICATIONS

Receptor Agonists 1s,2s,5r,6s-2-Aminobicyclo[3.1.0]Hexane-2,6-Bicaroxylate Monohydrate (Ly354740) and (−)-2-Oxa-4-Aminobicyclo[3.1.0] Hexane-4,6-Dicarboxylic Acid (Ly379268)", Jpet, 2009, 331, 1126-1136.
Fell et al., "N-(4-((2-(Trifluoromethyl)-3-Hydroxy-4-(Isobutyryl)Phenoxy)Methyl)Benzyl)-1-Methyl-1h-Imidazole-4-Carboxamide (Thiic), A Novel Metabotropic Glutamate 2 Potentiator with Potential Anxiolytic/Antidepressant Properties: in Vivo Profiling Suggests a Link Between Behavioral and Central Nervous System Neurochemical Changes", Jpet, 2011, 336, 165-177.
Fendt et al., "Metabotropic Glutamate Receptors are Involved in Amygdaloid Plasticity", European Journal of Neuroscience, 2002, 15(9), 1535-1541.
Fenton et al., "The Role of a Prescription in Anxiety Medication Use, Abuse, and Dependence", Am J Psychiatry, 2010, 167, 1247-1253.
Ferraguti et al., "Activation of the Extracellular Signal-Regulated Kinase 2 by Metabotropic Glutamate Receptors", European Journal of Neuroscience, 1999, 11(6), 2073-2082.
Ferraguti et al., "Metabotropic Glutamate 1 Receptor: Current Concepts and Perspectives", Pharmacol Rev, 2008, 60, 536-581.
Ferraguti et al., "Metabotropic Glutamate Receptors", Cell Tissue Res, 2006, 326, 483-504.
Ferris et al., "Interactions Between Ly354740, a Group II Metabotropic Agonist and the Gabaa-Benzodiazepine Receptor Complex in the Rat Elevated Plus-Maze", J Psychopharmacol, 2001, 15, 76-82.
Feyissa et al., "Elevated Level of Metabotropic Glutamate Receptor 2/3 in the Prefrontal Cortex in Major Depression", Prog. Neuropsychopharmacol. Biol. Psychiatry, 2010, 34(2), 279-283.
File, "The Use of Social Interaction as a Method for Detecting Anxiolytic Activity of Chlordiazepoxide-Like Drugs", Journal of Neuroscience Methods, 1980, 2(3), 219-38.
Filinger, "Effect of a Reserpine-Like Agent on the Release and Metabolism of [3h]Na in Cell Bodies and Terminals", Gen. Pharmac., 1994, 25, 1039-1043.
Fiorella et al., "The Role of the 5-Ht2a and 5-Ht2c Receptors in the Stimulus Effects of Hallucinogenic Drugs I: Antagonist Correlation Analysis", Psychopharmacology, 1995, 121, 347-356.
Fisher et al., "Antinociceptive Effects Following Intrathecal Pretreatment with Selective Metabotropic Glutamate Receptor Compounds in a Rat Model of Neuropathic Pain", Pharmacology, Biochemistry and Behavior, 2002, 73, 411-418.
Fisher et al., "Intrathecal Administration of the Mglur Compound, (S)-4cpg, Attenuates Hyperalgesia and Allodynia Associated with Sciatic Nerve Constriction Injury in Rats", Pain, 1998, 77(1), 59-66.
Fisher et al., "Non-Peptide Rgd Surrogates Which Mimic a Gly-Asp B-Turn: Potent Antagonists of Platelet Glycoprotein IIb-IIIa", J. Med. Chem., 1997, 40, 2085-2101.
Fisher et al., "The Contribution of Metabotropic Glutamate Receptors (Mglurs) to Formalin-Induced Nociception", Pain, 1996, 68(2-3), 255-263.
Flint et al., "Anxious Depression in Elderly Patients: Response to Antidepressant Treatment", Am J Geriatr Psychiatry, 1997, 5(2), 107-115.
Flohr et al., "Poly(Adp-Ribosyl)Ation Accelerates DNA Repair in a Pathway Dependent on Cockayne Syndrome B Protein", Nucleic Acids Research, 2003, 31(18), 5332-5337.
Flor et al., "Molecular Cloning, Functional Expression and Pharmacological Characterization of the Human Metabotropic Glutamate Receptor Type 2", Eur J Neurosci, 1995, 7, 622-629.
Fonnum et al., "Role of Glutamate and Glutamate Receptors in Memory Function and Alzheimer's Disease", Annals of the New York Academy of Sciences, 1995, 757, 475-486.
Forstl, "Clinical Features of Alzheimer's Disease", Eur Arch Psychiatry Clin Neurosci, 1999, 249, 288-290.
Fraley, "Positive Allosteric Modulators of the Metabotropic Glutamate Receptor 2 for the Treatment of Schizophrenia", Expert Opin. Ther. Patents, 2009, 19(9), 1259-1275.
Franco et al., "Novel Pharmacological Targets Based on Receptor Heteromers", Brain Research Reviews, 2008, 58, 475-482.
Franco et al., "The Two-State Dimer Receptor Model: A General Model for Receptor Dimers", Molecular Pharmacology, 2006, 69, 1906-1912.
Frank et al., "Depression and Health-Related Quality of Life for Low-Income African-American Women in the U.S.", Quality of Life Research, 2005, 14, 2293-2301.
Frauli et al., "Among the Twenty Classical L-Amino Acids, Only Glutamate Directly Activates Metabotropic Glutamate Receptors", Neuropharmacology, 2006, 50(2), 245-253.
Freedman et al., "Desensitization of G Protein-Coupled Receptors", Recent Progress in Hormone Research, 1996, 51, 319-351.
Freedman, "Schizophrenia", N. Engl. J. Med., 2003, 349, 1738-1749.
French et al., Subfield-Specific Immediate Early Gene Expression Associated with Hippocampal Long-Term Potentiation in Vivo. European Journal of Neuroscience 2001, 13(5), 968-976.
Fribourg et al., "Decoding the Signaling of a Gper Heteromeric Complex Reveals a Unifying Mechanism of Action of Antipsychotic Drugs", Cell, 2011, 147, 1011-1023.
Fricker et al., "Effects of N-Acetylaspartylglutamate (Naag) at Group II Mglurs and Nmdar", Neuropharmacology, 2009, 56(6-7), 1060-1067.
Fujii et al., "A Chemical LTP Induced by Co-Activation of Metabotropic and N-Methyl-D-Aspartate Glutamate Receptors in Hippocampal Ca1 Neurons", Brain Research, 2004, 999(1), 20-28.
Fujii et al., "Lactams. IX. Generation of Latam Carbonyl Function in 1,3-Disubstituted Piperidines by Mercuric Acetate-Edta Oxidation: Effects of Hydrocarbon Substituents at the 3-Postion", Chem. Pharm. Bull., 1977, 25(9), 2336-2342.
Fujimoto et al., "Motor and Cognitive Function Evaluation Following Experimental Traumatic Brain Injury", Neurosci. and Biobehav. Rev., 2004, 28, 365-378.
Fujita et al., "Studies on 1-Alkyl-2(1h)-Pyridone Derivatives XXXII. The Friedel-Crafts Reaction of 1-Alkyl-2(1h)-Pyridone Derivatives with Acid Anhydride", Journal of the Pharmaceutical Society of Japan, 1990, 110, 449-452.
Furukawa et al., "Antidepressants Plus Benzodiazepines for Major Depression", The Cochrane Collaboration, 2009, 31 pages.
Fuxe et al., "Integrated Signaling in Heterodimers and Receptor Mosaics of Different Types of GPCRS of the Forebrain: Relevance for Schizophrenia", J Neural Transm, 2009, 116(8), 923-939.
Galimberti et al., "Long-Term Rearrangements of Hippocampal Mossy Fiber Terminal Connectivity in the Adult Regulated by Experience", Neuron 2006, 50, 749-763.
Gama et al., "Heterodimerization of Calcium Sensing Receptors with Metabotropic Glutamate Receptors in Neurons", J. Biol. Chem., 2001, 276(42), 39053-39059.
Garbaccio et al., "Discovery of Oxazolobenzimidazoles as Positive Allosteric Modulators for the Mglur2 Receptor", Acs Med Chem Lett, 2010, 1, 406-410.
Garrido-Sanabria et al., "Impaired Expression and Function of Group II Metabotropic Glutamate Receptors in Pilocarpine-Treated Chronically Epileptic Rats", Brain Res., 2008, 1240, 165-176.
Garriock et al., "Genetic Studies of Drug Response and Side Effects in the Star*D Study, Part 1", J Clin Psychiatry, 2009, 70(8), 1186-1187.
Gasparini et al., "Allosteric Modulators for Mglu Receptors", Curr Neuropharmacol, 2007, 5, 187-194.
Gavezzotti, "Are Crystal Structures Predictable?", Accounts of Chemical Research, 1994, 27, 309-314.
Gerber et al., "Metabotropic Glutamate Receptors: Intracellular Signaling Pathways", Current Opinion in Pharmacology, 2007, 7(1), 56-61.
Gerwitz et al., "Behavioral Evidence for Interactions Between a Hallucinogenic Drug and Group II Metabotropic Glutamate Receptors", Neuropsychopharmacology, 2000, 23, 569-576.
Gewald et al., "Heterocyclen Aus Ch-Aciden Nitrilen, VIII. 2-Amino-Thiophene Aus Methylenaktiven Nitrilen Carbonylverbindungen Und Schwefel", Chemische Berichte, 1966, 99, 94-100.

(56) References Cited

OTHER PUBLICATIONS

Gewald. "Heterocyclen Aus Ch-Aciden Nitrilen, VII. 2-Amino-Thiophene Aus A-Oxo-Mercaptanen Und Methylenaktiven Nitrilen", Chemische Berichte, 1965, 98, 3571-3577.
Geyer, "Are Cross-Species Measures of Sensorimotor Gating Useful for the Discovery of Procognitive Cotreatments for Schizophrenia?", Dialogues Clin Neurosci., 2006, 8(1), 9-16.
Ghose et al., "Differential Expression of Metabotropic Glutamate Receptors 2 and 3 in Schizophrenia: A Mechanism for Antipsychotic Drug Action?", Am J Psychiatry, 2009, 166, 812-820.
Gill et al., "Immunochemical Localization of the Metabotropic Glutamate Receptors in the Rat Heart", Brain Research Bulletin, 1999, 48(2), 143-146.
Gilling et al., "Potency, Voltage-Dependency, Agonist Concentration-Dependency, Blocking Kinetics and Partial Untrapping of the Uncompetitive N-Methyl-D-Aspartate (NMDA) Channel Blocker Memantine at Human Nmda (Glun1/Glun2a) Receptors", Neuropharmacology 2009, 56, 866-875.
Gilmour et al., "Diverse and Often Opposite Behavioural Effects of NMDA Receptor Antagonists in Rats: Implications for NMDA Antagonist Modelling of Schizophrenia", Psychopharmacology, 2009, 205, 203-216.
Giovannelli et al., "Comet Assay as a Novel Approach for Studying Dna Damage in Focal Cerebral Ischemia: Differential Effects of NMDA Receptor Antagonists and Poly(Adp-Ribose) Polymerase Inhibitors", Journal of Cerebral Blood Flow and Metabolism, 2002, 22, 697-704.
Girardi et al., "Differential Expression of Cerebellar Metabotropic Glutamate Receptors Mglur2/3 and Mglur4a After the Administration of a Convulsant Drug and the Adenosine Analogue Cyclopentyladenosine", Neurochem. Res., 2007, 32(7), 1120-1128.
Gjoni et al., "Receptor Activation Involving Positive Allosteric Modulation, Unlike Full Agonism, Does Not Result in Gabab Receptor Desensitization", Neuropharmacology, 2008, 55, 1293-1299.
Gleason et al., "Blockade of Phencyclidine-Induced Hyperlocomotion by Olanzapine, Clozapine, and Serotonin Receptor Subtype Selective Antagonists in Mice", Psychopharmacology, 1997, 129, 79-84.
Gleeson, "Generation of a Set of Simple, Interpretable Admet Rules of Thumb", J Med Chem, 2008, 51, 817-834.
Glick et al., "A Double-Blind Randomized Trial of Mood Stabilizer Augmentation Using Lamotrigine and Valproate for Patients with Schizophrenia Who Are Stabilized and Partially Responsive", J Clin Psychopharmacol, 2009, 29(3), 267-271.
Glick et al., "Concomitant Medications May Not Improve Outcome of Antipsychotic Monotherapy for Stabilized Patients with Non-Acute Schizophrenia", J Clin Psychiatry, 2006, 67(8), 1261-1265.
Glin et al., "The Intermediate Stage of Sleep in Mice", Physiology & Behavior, 1991, 50, 951-953.
Gnecco et al., "Oxidation of Chiral Non-Racemic Pyridinium Salts to Enantiopure 2-Pyridine and 3-Alkyl-2-Pyridones", Tetrahedron: Asymmetry, 1998, 9, 2027-2029.
Goff et al., "Lamotrigine as Add-On Therapy in Schizophrenia: Results of 2 Placebo-Controlled Trials", J Clin Psychopharmacol., 2007, 27(6), 582-589.
Goldberg et al., "Novel Non-Benzodiazepine Anxiolytics", Neuropharmacology, 1983, 22, 1499-1504.
Gonzalez-Maeso et al., "Identification of a Serotonin/Glutamate Receptor Complex Implicated in Psychosis", Nature, 2008, 452, 93-97.
Gonzalez-Maeso et al., "Psychedelics and Schizophrenia", Trends Neurosci., 2009, 32(4), 225-232.
Gonzalez-Maeso, "Hallucinogens Recruit Specific Cortical 5-Ht2a Receptor-Mediated Signaling Pathways to Affect Behavior", Neuron, 2007, 53, 439-452.
Gonzalez-Maeso, "Transcriptome Fingerprints Distinguish Hallucinogenic and Nonhallucinogenic 5-Hydroxytryptamine 2a Receptor Agonist Effects in Mouse Somatosensory Cortex", J. Neurosci., 2003, 23, 8836-8843.
Goodman et al., "The Yale-Brown Obsessive Compulsive Scale: I. Development, Use, and Reliability", Arch Gen Psychiatry, 1989, 46(11), 1006-1011.
Goodwin et al., "Advantages and Disadvantages of Combination Treatment with Antipsychotics", Nice. Eur Neuropsychoparmacol., 2009, 19(7), 520-532.
Gorcs et al., "Immunohistochemical Visualization of a Metabotropic Glutamate Receptor", Neuroreport, 1993, 4(3), 283-286.
Gorman et al., "A Hypothesized Role for Dendritic Remodeling in the Etiology of Mood and Anxiety Disorders", J Neuropsychiatry Clin Neurosci, 2010, 22(3), 256-264.
Gorman et al., "Anxiogenic Effects of Co2 and Hyperventilation in Patients with Panic Disorder", Am J Psychiatry, 1994, 151, 547-553.
Gorman, "Comorbid Depression and Anxiety Spectrum Disorders", Depression and Anxiety, 1996/1997, 4, 160-168.
Goudet et al., "Asymmetric Functioning of Dimeric Metabotropic Glutamate Receptors Disclosed by Positive Allosteric Modulators", J. Biol. Chem., 2005, 280(26), 24380-24385.
Goudet et al., "Metabotropic Receptors for Glutamate and Gaba in Pain", Brain Res. Rev., 2009, 60(1), 43-56.
Gouzoulis-Mayfrank, "Inhibition of Return in the Human 5ht2a Agonist and Nmda Antagonist Model of Psychosis", Neuropsychopharmacology, 2006, 31, 431-441.
Gouzoulis-Mayfrank, "Psychological Effects of (S)-Ketamine and N,N-Dimethyltryptamine (Dmt): A Double-Blind, Cross-Over Study in Healthy Volunteers", Pharmacopsychiatry, 2005, 38, 301-311.
Gozzi et al., "Differential Effects of Antipsychotic and Glutamatergic Agents on the Phmri Response to Phencyclidine", Neuropsychopharmacology, 2008, 33, 1690-1703.
Gray et al., "Functionalisation of 2-Methoxy-6-Methylpyridine", Synthetic Communications, 1994, 24(10), 1367-1379.
Gregory et al., "Allosteric Modulation of Metabotropic Glutamate Receptors: Structural Insights and Therapeutic Potential", Neuropharmacology, 2011, 60, 66-81.
Gregory et al., "Overview of Receptor Allosterism", Current Protocols in Pharmacology, 2010, 1.21.1-1.21.34.
Gregory et al., "Prefrontal Group II Metabotropic Glutamate Receptor Activation Decreases Performance on a Working Memory Task", Ann N Y. Acad. Sci., 2003, 1003, 405-409.
Groebe, "Screening for Positive Allosteric Modulators of Biological Targets", Drug Discov. Today, 2006, 11(13-14), 632-639.
Grueter et al., "Group II and III Metabotropic Glutamate Receptors Suppress Excitatory Synaptic Transmission in the Dorsolateral Bed Nucleus of the Stria Terminalis", Neuropsychopharmacology, 2005, 30(7), 1302-1311.
Gu et al., "Distribution of Metabotropic Glutamate 2 and 3 Receptors in the Rat Forebrain: Implications in Emotional Responses and Central Disinhibition", Brain Res, 2008, 1197, 47-62.
Gu et al., "Expression of Functional Metabotropic Glutamate Receptors in Primary Cultured Rat Osteoblasts. Cross-Talk with N-Methyl-D-Aspartate Receptors", J. Biol. Chem., 2000, 275(44), 34252-34259.
Gueremy et al. "2-Amino-6-Chloro-4-(N-Methyl-piperazino)Pyrimidines, Inhibitors of Spiropendol Binding", Journal of Medicinal Chemistry, 1982, 25, 1459-1465.
Guerineau et al., "G-Protein-Mediated Desensitization of Metabotropic Glutamatergic and Muscarinic Responses in Ca3 Cells in Rat Hippocampus", Journal of Physiology, 1997, 500(Pt 2), 487-496.
Guerineau et al., Activation of a Nonselective Cationic Conductance by Metabotropic Glutamatergic and Muscarinic Agonists in Ca3 Pyramidal Neurons of the Rat Hippocampus, J. Neurosci., 1995, 15(6), 4395-4407.
Guimaraes et al., "Ritanserin Facilitates Anxiety in a Simulated Public-Speaking Paradigm", Journal of Psychopharmacology, 1997, 11(3), 225-231.
Gunduz-Bruce, "The Acute Effects of Nmda Antagonism: from the Rodent to the Human Brain", Brain Res Rev, 2009, 60, 279-286.
Gupta et al., "Metabotropic Glutamate Receptor Protein Expression in the Prefrontal Cortex and Striatum in Schizophrenia", Synapse, 2005, 57(3), 123-131.

(56) References Cited

OTHER PUBLICATIONS

Gurevich et al., "Alterations in the Cortical Serotonergic System in Schizophrenia: A Postmortem Study", Biol. Psychiatry, 1997, 42, 529-545.
Haak et al., "Metabotropic Glutamate Receptor Activation Modulates Kainate and Serotonin Calcium Response in Astrocytes", J. Neurosci., 1997, 17(5), 1825-1837.
Heckler et al., "Selective Potentiation of the Metabotropic Glutamate Receptor Subtype 2 Blocks Phencyclidine-Induced Hyperlocomotion and Brain Activation", Neuroscience, 2010, 168(1), 209-218.
Hamilton, "A Rating Scale for Depression", J Neurol Neurosurg Psychiatry, 1960, 23, 56-62.
Hamilton, "Diagnosis and Rating of Anxiety, in Studies of Anxiety", MM Lader, Ed., Meedley Bros., Kent, 1969, 76-79.
Hamilton, "Standardised Assessment and Recording of Depressive Symptoms", Psychiatr Neurol Neurochir, 1969, 72(2), 201-205.
Hamilton, "The Assessment of Anxiety States by Rating", Br J Med Psychol, 1959, 32(1), 50-55.
Hampson et al., "Characterization of Two Alternatively Spliced Forms of a Metabotropic Glutamate Receptor in the Central Nervous System of the Rat", Neuroscience, 1994, 60(2), 325-336.
Handley et al., "Effects of Alpha-Adrenoceptor Agonists and Antagonists in a Maze-Exploration Model of Fear-Motivated Behavior", Naunyn-Schmied. Arch. Pharmacol., 327, 1-5, 1984.
Hanna et al., "Differentiating the Roles of Mglu2 and Mglu3 Receptors Using Ly541850, an Mglu2 Agonist/Mglu3 Antagonist", Neuropharmacology, 2012, 1-8.
Hannah et al., "Heterocomplex Formation of 5-Ht2a-Mglu2 and Its Relevance for Cellular Signaling Cascades", Neuropharmacology, 2012, 62, 2184-2191.
Hansen et al., "Glutamate Joins the Ranks of Immunomodulators", Nature Medicine, 2010, 16(8), 856-858.
Happe et al., "Agonist-Stimulated [35s]Gtpgammas Autoradiograph: Optimization for High Sensitivity", Eur J Pharmacol, 2001, 422, 1-13.
Harald et al., "Meta-Review of Depressive Subtyping Models", Journal of Affective Disorders, 2012, 139, 126-140.
Harich, "Stimulation of the Metabotropic Glutamate 2/3 Receptor Attenuates Social Novelty Discrimination Deficits Induced by Neonatal Phencyclidine Treatment", Psychopharmacology, 2007, 192, 511-519.
Haro et al., "The Clinical Global Impression-Schizophrenia Scale: A Simple Instrument to Measure the Diversity of Symptoms Present in Schizophrenia", Acta Psychiatr Scand Suppl., 2003, 416, 16-23.
Harrison et al., "The Group II Metabotropic Glutamate Receptor 3 (Mglur3, Mglu3, Grm3): Expression, Function and Involvement in Schizophrenia", J. Psychopharmacol., 2008, 22(3), 308-322.
Harrison, "Metabotropic Glutamate Receptor Agonists for Schizophrenia", The British Journal of Psychiatry, 2008, 192, 86-87.
Hartveit et al., "Expression of the Mrna of Seven Metabotropic Glutamate Receptors (Mglur1 to 7) in the Rat Retina. An in Situ Hybridization Study on Tissue Sections and Isolated Cells", Eur. J Neurosci., 1995, 7(7), 1472-1483.
Hascup et al., "An Allosteric Modulator of Metabotropic Glutamate Receptors (Mglur2), (+)-Tfmpip, Inhibits Retraint Stress-Induced Phasic Glutamate Release in Rat Prefrontal Cortex", Journal of Neurochemistry, 2012, 122, 619-627.
Hashimoto et al., "Increased Levels of Glutamate in Brains from Patients with Mood Disorders", Biol Psychiatry, 2007, 62(11), 1310-1316.
Hashimoto, "Emerging Role of Glutamate in the Pathophysiology of Major Depressive Disorder", Brain Research Reviews, 2009, 61, 105-123.
Hasin et al., "Epidemiology of Major Depressive Disorder. Results from the National Epidemiologic Survey on Alcoholism and Related Conditions", Arch Gen Psychiatry, 2005, 62, 1097-1106.
Hasler et al., "Reduced Prefrontal Glutamate/Glutamine and Gamma-Aminobutyric Acid Levels in Major Depression Determined Using Proton Magnetic Resonance Spectroscopy", Arch Gen Psychiatry, 2007, 64(2), 193-200.
Hawgood et al., "Anxiety Disorders and Suicidal Behavior: An Update", Current Opinion in Psychiatry, 2008, 21, 51-64.
He et al., "Conformational Color Polymorsphism and Control of Crystallization of 5-Methyl-2[(4-Methyl-2-Mitrophenyl0amino}-3-Thiophenecarbonitrile", Journal of Pharmaceutical Sciences, 2001, 90(3), 371-388.
Helton et al., "Ly354740: A Metabotropic Glutamate Receptor Agonist Which Ameliorates Symptoms of Nicotine Withdrawal in Rats", Neuropharmacology, 1997, 36(11/12), 1511-1516.
Hemstapat et al., "A Novel Family of Potent Negative Allosteric Modulators of Group II Metabotropic Glutamate Receptors", Jpet, 2007, 322, 254-264.
Henley et al., "Characterization of the Allosteric Modulatory Protein Associated with Non-Nmda Receptors", Biochemical Society Transactions, 1993, 21(1), 89-93.
Henry et al., "The MglurS Antagonist Mpep, But Not the Mglur2/3 Agonist Ly314582, Augments Pcp Effects on Prepulse Inhibition and Locomotor Activity", Neuropharmacology, 2002, 43(8), 1199-209.
Herdeis et al., "[4+2] Cycloadducts of 5-Benzyloxy-2-Pyrindone with Electron Deficient Dienophiles. Regio- and Stereochemistry", Heterocycles, 1989, 29(2), 287-296.
Herdeis et al., "A Facile Entry to the 2-Azabicyclo[2.2.2]Octane-6-One Skeleton Via [4+2]-Cycloaddition", Synthesis, Jan. 1988, 76-78.
Herdeis et al., "A Three-Step Synthesis of B-Aminolaevulinic Acid", Arch. Pharm., 1984, 317, 304-306.
Herdeis et al., "Stereochemistry and Reactivity of Phenylsulfonyl-Substituted 2-Azabicyclo[2.2.2]Octan-6-Ones", Arch. Pharm., 1990, 323, 937-942.
Heresco-Levy, "Glutamatergic Neurotransmission Modulators as Emerging New Drugs for Schizophrenia", Expert Opin Emerging Drugs, 2005, 10(4), 827-844.
Hermann et al., "Human Eeg Gamma Oscillations in Neuropsychiatric Disorders", Clinical Neurophysiology, 2005, 116, 2719-2733.
Hermans et al., "Structural, Signalling and Regulatory Properties of the Group I Metabotropic Glutamate Receptors: Prototypic Family C G-Protein-Coupled Receptors", Biochem. J., 2001, 359, 465-484.
Herminghaus, "Brain Metabolism in Alzheimer Disease and Vascular Dementia Assessed by In Vivo Proton Magnetic Resonance Spectroscopy", Psychiatry Research Neuroimaging, 2003, 123, 183-190.
Herrero et al., "Functional Switch from Facilitation to Inhibition in the Control of Glutamate Release by Metabotropic Glutamate Receptors", J. Biol. Chem., 1998 273(4), 1951-1958.
Herrero et al., "Positive Feedback of Glutamate Exocytosis by Metabotropic Presynaptic Receptor Stimulation", Nature, 1992, 360(6400), 163-166.
Herrero et al., "Rapid Desensitization of the Metabotropic Glutamate Receptor that Facilitates Glutamate Release in Rat Cerebrocortical Nerve Terminals", European Journal of Neuroscience, 1994, 6(1), 115-120.
Hettema "The Nosologic Relationship Between Generalized Anxiety Disorder and Major Depression", Depression and Anxiety, 2008, 25, 300-316.
Hetzenauer et al., "Individual Contribution of Metabotropic Glutamate Receptor (Mglu) 2 and 3 to C Expression Pattern Evoked by Mglu2/3 Antagonism", Psychopharmacology, 2008, 201, 1-13.
Hickinbottom, "Reactions of Organic Compounds", Gonti: Moscow, 1939, 360-2 (Russian with English Translation).
Higashida et al., "Subtype-Specific Coupling with Adp-Ribosyl Cyclase of Metabotropic Glutamate Receptors in Retina, Cervical Superior Ganglion and Ng108-15 Cells", Journal of Neurochemistry, 2003, 85, 1148-1158.
Higgins, "Pharmacological Manipulation of Mglu2 Receptors Influences Cognitive Performance in the Rodent", Neuropharmacology, 2004, 46, 907-917.
Hijzen et al., "Predictive Validity of the Potentiated Startle Response as a Behavioral Model for Anxiolytic Drugs", Psychopharmacology, 1995, 118, 150-154.
Hirao et al., "Preparation of Optically Active 8,8'-Disubstituted 1,1'-Biisoquinoline", Heterocycles, 1996, 42(1), 415-422.
Hlavackova et al., "Evidence for a Single Heptahelical Domain Being Turned on Upon Activation of a Dimeric GPCR", Embo, 2005, 24, 499-509.

(56) References Cited

OTHER PUBLICATIONS

Hoang et al., "Expression of Metabotropic Glutamate Receptors in Nodose Ganglia and the Nucleus of the Solitary Tract", Am J Physiol Heart Circ Physiol, 2001, 281, 457-462.
Hoeben et al., "Prediction of Serotonin 2a Receptor (5-Ht$_{2a}$r) Occupancy in Man From Nonclinical Pharmacology Data. Exposure Vs. 5-Ht$_{2a}$r Occupancy Modeling Used to Help Design a Positron Emission Tomography (Pet) Study in Healthy Male Subjects", Abstract, 2013 Annual Meeting of the Population Approach Group in Europe, 2 pages.
Hoffman et al., "Human and Economic Burden of Generalized Anxiety Disorder", Depression and Anxiety, 2008, 25, 72-90.
Hofmeijer-Sevink et al., "Clinical Relevance of Comorbidity in Anxiety Disorders: A Report From the Netherlands Study of Depression and Anxiety (NESDA)", Journal of Affective Disorders, 2012, 137, 106-112.
Hohnadel et al., "Effect of Repeated Nicotine Exposure on High-Affinity Nicotinic Acetylcholine Receptor Density in Spontaneously Hypertensive Rats", Neuroscience Letters, 2005, 382, 158-163.
Holcomb et al., "Effects of Noncompetitive Nmda Receptor Blockade on Anterior Cingulate Cerebral Blood Flow in Volunteers with Schizophrenia", Neuropsychopharmacology, 2005, 30, 2275-2282.
Holloway et al., "Prenatal Stress Induces Schizophrenia-Like Alterations of Serotonin 2a and Metabotropic Glutamate 2 Receptors in the Adult Offspring: Role of Maternal Immune System", J. Neurosci., 2013, 33(3), 1088-1098.
Holscher et al., "Metabotropic Glutamate Receptor Activation and Blockade: Their Role in Long-Term Potentiation, Learning and Neurotoxicity", Neuroscience & Biobehavioral Reviews, 1999, 23(3), 399-410.
Homayoun et al., "Activation of Metabotropic Glutamate 2/3 Receptors Reverses the Effects of Nmda Receptor Hypofunction on Prefrontal Cortex Unit Activity in Awake Rats", J. Neurophysiol., 2005, 93(4), 1989-2001.
Homayoun et al., "Group 5 Metabotropic Glutamate Receptors: Role in Modulating Cortical Activity and Relevance to Cognition", European Journal of Pharmacology, 2010, 639, 33-39.
Homayoun et al., "Orbitofrontal Cortex Neurons as a Common Target for Classic and Glutamatergic Antipsychotic Drugs", Proc. Natl. Acad. Sci. USA, 2008, 105(46), 18041-18046.
Honer et al., "Clozapine Alone Versus Clozapine and Risperidone with Refractory Schizophrenia", N Engl J Med., 2006, 354(5), 472-482.
Hook, "Neuroproteases in Peptide Neurotramission and Neurodegenerative Diseases Applications to Drug Discovery Research", Biodrugs, 2006, 20, 105-119.
Hopkins "Is There a Path Forward for Mglu2 Positive Allosteric Modulators for the Treatment of Schizophrenia?", ACS Chem. Neurosci., 2013, 4, 211-213.
Horiguchi et al., "Interaction of Mglu2/3 Agonism with Clozapine and Lurasidone to Restore Novel Object Recognition in Subchronic Phencyclidine-Treated Rats", Psychopharmacology, 2011, 217, 13-24.
Horiguchi et al., "Interactions Among the Atypical Antipsychotic Drug (APD), Lurasidone, 5-HT1A and Metabotropic Glutamate Receptor 2/3 (Mglur2/3) Agonism, and 5-HT2A Antagonism, to Attenuate Phencyclidine (PCP)-Induced Deficit in Rat Novel Object Recognition (NOR)" Poster 610.12 Presented at the 40$^{th}$ Annual Meeting of Society for Neuroscience, 2010, 1 page.
Hostetler, "PET Tracer Discovery for Subtype-Specific Mglur Allosteric Modulators: Challenges and Insights" Presentation Slides 7th International Meeting on Metabotropic Glutamate Receptors, Merck, Oct. 2011, 8 pages.
Houamed et al., "Cloning, Expression, and Gene Structure of a G Protein-Coupled Glutamate Receptor from Rat Brain", Science, 1991, 252(5010), 1318-1321.
Hovelso, "Therapeutic Potential of Metabotropic Glutamate Receptor Modulators", Current Neuropharmacology, 2012, 10, 12-48.
Hsia et al., "Evidence Against a Role for Metabotropic Glutamate Receptors in Mossy Fiber Ltp: the Use of Mutant Mice and Pharmacological Antagonists", Neuropharmacology, 1995, 34, 1567-1572.
Hu et al., "Altered Profile of Gene Expression in Rat Hearts Induced by Chronic Nicotine Consumption", Biochemical and Biophysical Research Communications, 2002, 297, 729-736.
Hu et al., "Emotion Enhances Learning Via Norepinephrine Regulation of Ampa-Receptor Trafficking", Cells, 2007, 131, 160-173.
Hu et al., "Glutamate Receptors in Preclinical Research on Alzheimer's Disease: Update on Recent Advances", Pharmacology, Biochemistry and Behavior, 2012, 100, 855-862.
Hu et al., "Identification of Glutamate Receptors and Transporters in Mouse and Human Sperm", Journal of Andrology, 2004, 25(1), 140-6.
Hu et al., "Pyrimidine Methyl Anilines: Selective Potentiators for the Metabotropic Glutamate 2 Receptor", Bioorganic & Medicinal Chemistry Letters, 2004, 14, 5071-5074.
Hu et al., "The Regulation of Dopamine Transmission by Metabotropic Glutamate Receptors", J. Pharmacol. Exp. Ther., 1999, 289(1), 412-416.
Huang et al., "Alzheimer Mechanisms and Therapeutic Strategies", Cell, 2012, 148, 1204-1222.
Huang et al., "Inhibition of Microtubule Formation by Metabotropic Glutamate Receptors", Journal of Neurochemistry, 2000, 74(1), 104-113.
Huang et al., "Interdomain Movements in Metabotropic Glutamate Receptor Activation", Proc Natl Acad Sci USA, 2011, 108, 15480-15485.
Huang et al., "Potentiation of the Novel Atypical Antipsychotic Drug Lurasidone-Induced Dopamine Efflux in Rat Medial Prefrontal Cortex and Hippocampus by DA D1 and Mglur2/3 Agonism but not D3 Receptor Antagonism" Poster 610.13 Presented at the 40$^{th}$ Annual Meeting of Society for Neuroscience, Nov. 2010, 1 page.
Huang et al., "Prevalence, Correlates, and Comorbidity of Nonmedical Prescription Drug Use and Drug Use Disorders in the United States: Results of the National Epidemiologic Survey on Alcohol and Related Conditions", J Clin Psychiatry, 2006, 67, 1062-1073.
Hucho et al., "Epac Mediates a Camp-To-Pkc Signaling in Inflammatory Pain: An Isolectin B4(+) Neuron-Specific Mechanism", Journal of Neuroscience, 2005, 25(26), 6119-6126.
Hucho et al., "Estrogen Controls Pkce-Dependent Mechanical Hyperalgesia Through Direct Action on Nociceptive Neurons", European Journal of Neuroscience, 2006, 24, 527-534.
Huey et al., "Development of Subtle Psychotic Symptoms with Memantine: A Case Report", J Clin Psychiatry, 2005, 66, 658-659.
Huntington Study Group, "Dosage Effects of Riluzole in Huntington's Disease: A Multicenter Placebo-Controlled Study", Neurology, 2003, 61, 1551-1556.
Iacovelli et al., "Regulation of Group II Metabotropic Glutamate Receptors by G Protein-Coupled Receptor Kinases: Mglu2 Receptors are Resistant to Homologous Desensitization", Mol Pharmacol., 2009, 75(4), 991-1003.
Iglesias et al., "Metabotropic Glutamate Receptor/Phospholipase C System in Female Rat Heart", Brain Res., 2007, 1153, 1-11.
Imogai et al., "Cis-Disubstituted Cyclopropanes via Asymmetric Catalytic Cyclopropenation: Synthesis of Cyclopropyl-Dehydroamino Acids and of Dictyopterene C.", Helvetica Chimica Acta, 1998, 81, 1754-1764.
Imre et al., "Dose-Response Characteristics of Ketamine Effect on Locomotion, Cognitive Function and Central Neuronal Activity", Brain Res. Bull, 2006, 69(3), 338-345.
Imre et al., "Effects of the Mglur2/3 Agonist Ly379268 on Ketamine-Evoked Behaviours and Neurochemical Changes in the Dentate Gyrus of the Rat", Pharmacology, Biochemistry and Behavior, 2006, 84, 392-399.
Imre et al., "Subchronic Administration of Ly354740 Does Not Modify Ketamine-Evoked Behavior and Neuronal Activity in Rats", Eur. J Pharmacol., 2006, 544(1-3), 77-81.
Imre, "The Preclinical Properties of a Novel Group II Metabotropic Glutamate Receptor Agonist Ly379268", CNS Drug Reviews, 2007, 13(4), 444-464.

(56) References Cited

OTHER PUBLICATIONS

Insel, et al., "Research Domain Criteria (Rdoc): Toward a New Classification Framework for Research on Mental Disorders", Am. J. Psychiatry, Jul. 2010, 167(7), 748-751.
Inta et al., "Mice with Genetically Altered Glutamate Receptors as Models of Schizophrenia: A Comprehensive Review", Neuroscience & Biobehavioral Reviews, 2010, 34(3), 285-94.
International Patent Application No. PCT/EP2011/69640: International Search Report dated Dec. 23, 2011, 3 pages.
International Patent Application No. PCT/EP2011/69641: International Search Report dated Dec. 23, 2011, 3 pages.
International Patent Application No. PCT/EP2011/69643: International Search Report dated Dec. 27, 2011, 4 pages.
International Patent Application No. PCT/EP2011/69654: International Search Report dated Dec. 23, 2011, 3 pages.
Ionescu et al., "Defining Anxious Depression: A Review of the Literature", CNS Spectrums, 2013, 1-9.
Iovieno et al., "Does the Presence of an Open-Label Antidepressant Treatment Period Influence Study Outcome in Clinical Trials Examining Augmentation/Combination Strategies in Treatment Partial Responders/Nonresponders with Major Depressive Disorder?", J Clin Psychiatry, 2012, 8 pages.
Irifune et al., "Riluzole, A Glutamate Release Inhibitor, Induces Loss of Righting Reflex, Antinociception, and Immobility in Response to Noxious Stimulation in Mice", Anesthesia & Analgesia, 2007, 104(6), 1415-1421.
Israeli Patent Application No. 192868: Office Action dated Dec. 21, 2011, 2 pages.
Itaya et al., "Purines. LXXV. Dimroth Rearrangement, Hydrolytic Deamination, and Pyrimidine-Ring Breakdown of 7-Alkylated 1-Alkoxyadenines: N(1)-C(2) Versus N(1)—C(6) Bond Fission", Chem. Pharm. Bull., 1997, 45 (5), 832-41.
Jablensky et al., "Polymorphisms Associated with Normal Memory Variation Also Affect Memory Impairment in Schizophrenia", Genes, Brain and Behavior, 2011, 10, 410-417.
Jane et al., "Potent Antagonists at the L-AP4- and (1s,3s)-ACPD-Sensitive Presynaptic Metabotropic Glutamate Receptors in the Neonatal Rat Spinal Cord", Neuropharmacology, 1996, 35(8), 1029-1035.
Janssens et al., "Glutamate Receptor Subunit Expression in Primary Neuronal and Secondary Glial Cultures", J Neurochem, 2001, 77, 1457-1474.
Japanese Patent Application No. 2007-531759: Office Action dated Jun. 27, 2011, 12 pages.
Japanese Patent Application No. 2008-558820: Office Action dated Aug. 28, 2012, 14 pages.
Japanese Patent Application No. 2009-552215: Office Action dated Dec. 18, 2012, 3 pages.
Japanese Patent Application No. 2010-524405: Office Action dated Jun. 5, 2012, 4 pages.
Japanese Patent Application No. 2010-553485: Office Action dated Jul. 11, 2013, 3 pages.
Javitt, "Glutamatergic Theories of Schizophrenia", ISR J Psychiatry Relat Sci, 2010, 47(1), 4-16.
Javitt et al., "Recent Advances in the Phenylcyclidine Model of Schizophrenia", Am J Psychiatry, 1991, 148, 1301-1308.
Jenkins et al., "Disturbances in Social Interaction Occur Along with Pathophysiological Deficits Following Sub-Chronic Phencyclidine Administration in the Rat", Behavioural Brain Research, 2008, 194, 230-235.
Jensen et al., "Allosteric Modulation of the Calcium-Sensing Receptor", Current Neuropharmacology, 2007, 5, 180-186.
Jin et al., "The Mglur2 Positive Allosteric Modulator Bina Decreases Cocaine Self-Administration and Cue-Induced Cocaine-Seeking and Counteracts Cocaine-Induced Enhancement of Brain Reward Function in Rats", Neuropsych., 2010, 35(10), 2021-2036.
Jingami et al., "Structure of the Metabotropic Glutamate Receptor", Current Opinion in Neurobiology, 2003, 13(3), 271-278.
Joffe et al., "Anxious and Nonanxious Depression", Am J Psychiatry, 1993, 150, 1257-1258.
Joffe et al., "Lifetime History of Depression and Anxiety Disorders as a Predictor of Quality of Life in Midlife Women in the Absence of Current Illness Episodes", Arch Gen Psychiatry, 2012, 69(5), 484-492.
Johansen et al., "Excitatory Amino Acid Receptor Ligands: Resolution, Absolute Stereochemistry, and Enantiopharmacology of 2-Amino-3-(4-Butyl-3-Hydroxyisoxazol-5-Yl)Propionic Acid", J of Medicinal Chem, 1998, 41(6), 930-939.
John et al., "Rapid Changes in Glutamate Levels in the Posterior Hypothalamus Across Sleep-Wake States in Freely Behaving Rats", American Journal of Physiology—Regulatory Integrative & Comparative Physiology, 2008, 295(6), R2041-2049.
Johnson et al., "Activation of Group II Metabotropic Glutamate Receptors Induces Long-Term Depression of Excitatory Synaptic Transmission in the Substantia Nigra Pars Reticulate", Neuroscience Letters, 2011, 504, 102-106.
Johnson et al., "Disruption of Gabaergic Tone in the Dorsomedial Hypothalamus Attenuates Responses in a Subset of Serotonergic Neurons in the Dorsal Raphe Nucleus Following Lactate-Induced Panic", J Psychopharmacol, 2008, 22, 642-652.
Johnson et al., "Glutamate Receptors as Therapeutic Targets for Parkinson's Disease", CNS Neurol Disord Drug Targets, 2009, 8, 475-491.
Johnson et al., "Group II Metabotropic Glutamate Receptor Type 2 Allosteric Potentiators Prevent Sodium Lactate-Induced Panic Like Response in Panic-Vulnerable Rats", J Psychopharmacol, 2013, 27, 152-161.
Johnson et al., "Species Variations in Transmembrane Region V of the 5-Hydroxytryptamine Type 2a Receptor Alter the Structure-Activity Relationship of Certain Ergolines and Tryptamines", Molecular Pharmacology, 1994, 45, 277-286.
Jones et al., "A Rotarod Suitable for Quantitative Measurements of Motor Incoordination in Naïve Mice", Naunyn Schmiedebergs Arch. Exper. Pathol. Pharmacol., 1968, 259, 211.
Jones et al., "Analgesic Effects of the Selective Group II (Mglu2/3) Metabotropic Glutamate Receptor Agonists Ly379268 and Ly389795 in Persistent and Inflammatory Pain Models After Acute and Repeated Dosing", Neuropharmacology, 2005, 49, 206-218.
Jones et al., "Discovery, Synthesis, and Structure-Activity Relationship Development of a Series of N-4-(2,5-Dioxopyrrolidin-1-Yl)Phenylpicolinamides (Vu0400195, MI182): Characterization of a Novel Positive Allosteric Modulator of the Metabotropic Glutamate Receptor 4 (Mglu4) with Oral Efficacy in an Antiparkinsonian Animal Model", J Med Chem, 2011, 54, 7639-7647.
Jones et al., "The Mglur2/3 Agonist Ly379268 Reverses Post-Weaning Social Isolation-Induced Recognition Memory Deficits in the Rat", Psychopharmacology, 2011, 214, 269-283.
Julio-Pieper et al., "Exciting Times Beyond the Brain: Metabotropic Glutamate Receptors in Peripheral and Non-Neural Tissues", Pharmacological Review, 2011, 63, 35-58.
Kagaya et al., "Heterologous Supersensitization Between Serotonin2 and Alpha 2-Adrenergic Receptor-Mediated Intracellular Calcium Mobilization in Human Platelets", Journal of Neural Transmission, 1992, 88(1), 25-36.
Kahn et al., "Group 2 Metabotropic Glutamate Receptors Induced Long Term Depression in Mouse Striatal Slices", Neurosci. Lett., 2001, 316(3), 178-182.
Kalivas et al., "Repeated Cocaine Administration Alters Extracellular Glutamate in the Ventral Tegmental Area", Journal of Neurochemistry, 1998, 70(4), 1497-1502.
Kappe et al., "Aktive Malonester Als Synthons Fur Heterocyclen: Eine Methode Zur Herstellung Von 4-Hydroxy-2(1h)-Pyridonen", Journal of Heterocyclic Chemistry, 1988, 463-468.
Kapur et al., "From Dopamine to Salience to Psychosis-Linking Biology, Pharmacology and Phenomenology of Psychosis", Schizophr.Res., 2005, 79, 59-68.
Karlsson et al., "Loss of Glial Glutamate and Aspartate Transporter (Excitatory Amino Acid Transporter 1) Causes Locomotor Hyperactivity and Exaggerated Responses to Psychotomimetics: Rescue by Haloperidol and Metabotropic Glutamate 2/3 Agonist", Biol. Psychiatry, 2008, 64(9), 810-814.
Kato "Molecular Genetics of Bipolar Disorder and Depression" Psychiatry and Clinical Neurosciences 2007, 61, 3-19.

(56) References Cited

OTHER PUBLICATIONS

Katon et al., "Major Depression: The Importance of Clinical Characteristics and Treatment Response to Prognosis", Depression and Anxiety, 2010, 27, 19-26.
Kaupmann et al., "Expression Cloning of Gaba(B) Receptors Uncovers Similarity to Metabotropic Glutamate Receptors", Nature, 1997, 386(6622), 239-246.
Kawabata et al., "Diversity of Calcium Signaling by Metabotropic Glutamate Receptors", J. Biol. Chem., 1998, 273(28), 17381-17385.
Kearney et al., "Intrasubthalamic Nucleus Metabotropic Glutamate Receptor Activation: A Behavioral, FOS Immunohistochemical and [14c]2-Deoxyglucose Autoradiographic Study", Neuroscience, 2000, 95(2), 409-416.
Kearney et al., "Metabotropic Glutamate Agonist-Induced Rotation: A Pharmacological, FOS Immunohistochemical, and [14c]-2-Deoxyglucose Autoradiographic Study", J Neurosci., 1997, 17(11), 4415-4425.
Kehne et al., "Anxiolytic Effects of Buspirone and Gepirone in the Fear-Potentiated Startle Paradigm", Psychopharmacology, 1988, 94, 8-13.
Keller et al., "Anxiety Symptom Relief in Depression Treatment Outcomes", J Clin Psychiatry, 1995, 56(Suppl 6), 22-29.
Kenakin et al., "Seven Transmembrane Receptors as Shapeshifting Proteins: The Impact of Allosteric Modulation and Functional Selectivity on New Drug Discovery", Pharmacological Reviews, 2010, 62(2), 265-304.
Kenakin et al., "Signalling Bias in New Drug Discovery: Detection, Quantification and Therapeutic Impact", Nature Reviews Drug Discovery, 2013, 12, 205-216.
Kenakin, "A Holistic View of GPCR Signaling", Nature Biotechnology, 2010, 28, 928-929.
Kenakin, "Allosteric Agonist Modulators", Journal of Receptors and Signal Transduction, 2007, 27(4), 247-259.
Kenakin, "Allosteric Modulators: The New Generation of Receptor Antagonist", Molecular Interventions, Aug. 2004, 4(4), 222-229.
Kenakin, "Collateral Efficacy in Drug Discovery: Taking Advantage of the Good (Allosteric) Nature of 7tm Receptors", Trends Pharmacol. Sci., 2007, 28(8), 407-415.
Kenakin, "Seven Transmembrane Receptors as Nature's Prototype Allosteric Protein: De-Emphasizing the Geography of Binding" Molecular Pharmacology 2008, 74, 541-543.
Kendler et al., "Major Depression and Generalized Anxiety Disorder: Same Genes, (Partly) Different Environments?", Arch Gen Psychiatry, 1992, 49, 716-722.
Kendler, "The Nosologic Validity of Paranoia (Simple Delusional Disorder)", Arch Gen Psychiatry, 1980, 37, 699-706.
Kennett et al., "Evidence That 5-Ht2c Receptor Antagonists are Anxiolytic in the Rat Geller-Seifter Model of Anxiety", Psychopharmacology, 1994, 114, 90-96.
Kenny et al., "Group II Metabotropic and Alpha-Amino-3-Hydroxy-5-Methyl-4-Isoxazole Propionate (Ampa)/Kainate Glutamate Receptors Regulate the Deficit in Brain Reward Function Associated with Nicotine Withdrawal in Rats", J Pharmacol. Exp. Ther., 2003, 306(3), 1068-1076.
Kenny et al., "The Ups and Downs of Addiction: Role of Metabotropic Glutamate Receptors", Trends in Pharmacological Sciences, 2004, 25(5), 265-272.
Kent, "Safety, Tolerability and Potential Therapeutic Efficacy of a Novel Glutamate Modulator as Adjunctive Treatment in Patients with Schizophrenia", Abstract No. 3160, American Psychiatric Association Annual Meeting, 2013, 1 page.
Kessler et al., "Comorbid Major Depression and Generalized Anxiety Disorders in the National Comorbidity Survey Follow-Up", Psychol Med., Mar. 2008, 38(3), 365-374.
Kessler et al., "Epidemiology of Anxiety Disorders", Current Topics in Behavioral Neurosciences, 2010, 2, 21-35.
Kessler et al., "Impairment in Pure and Comorbid Generalized Anxiety Disorder and Major Depression at 12 Months in Two National Surveys", American Journal of Psychiatry, 1999, 156(12), 1915-1923.
Kessler et al., "Lifetime and 12-Month Prevalence of DSM-III-R Psychiatric Disorders in the United States: Results From the National Comorbidity Survey", Arch Gen Psych, 1994, 51, 8-19.
Kessler et al., "Rethinking the Duration Requirement for Generalized Anxiety Disorder: Evidence from the National Comorbidity Survey Replication", Psychological Medicine, 2005, 7, 1073-1082.
Kessler et al., "The Epidemiology of Co-Ocurring Addictive and Mental Disorders: Implications for Prevention and Service Utilization", American Journal of Orthopsychiatry, 1996, 66(1), 17-31.
Kessler et al., "The Epidemiology of Major Depressive Disorder: Results from the National Comorbidity Survey Replication (NCS-R)", JAMA, 2003, 289(23), 3095-3105.
Kew et al., "Activity-Dependent Presynaptic Autoinhibition by Group II Metabotropic Glutamate Receptors at the Perforant Path Inputs to the Dentate Gyrus and Ca1", Neuropharmacology, 2001, 40, 20-27.
Kew et al., "Differential Regulation of Synaptic Transmission by Mglu2 and Mglu3 at the Perforant Path Inputs to the Dentate Gyrus and Ca1 Revealed in Mglu2 -/- Mice", Neuropharmacology, 2002, 43, 215-221.
Kew et al., "Ionotropic and Metabotropic Glutamate Receptor Structure and Pharmacology", Psychopharmacology, 2005, 179, 4-29.
Kew, "Positive and Negative Allosteric Modulation of Metabotropic Glutamate Receptors: Emerging Therapeutic Potential", Pharmacology & Therapeutics, 2004, 104, 233-244.
Kilbride et al., "Presynaptic Group II Mglur Inhibition of Short-Term Depression in the Medial Perforant Path of the Dentate Gyrus in Vitro", Neurophysiol, 2001, 85, 2509-2515.
Kilbride et al., "Presynaptic Inhibitory Action of the Group II Metabotropic Glutamate Receptor Agonists, Ly354740 and DCG-IV", European Journal of Pharmacology, 1998, 356, 149-157.
Kim et al., "Activation of Metabotropic Glutamate Receptors in the Rat Nucleus Accumbens Increases Locomotor Activity in a Dopamine-Dependent Manner", Journal of Pharmacology & Experimental Therapeutics, 1997, 283(2), 962-968.
Kim et al., "Group II Metabotropic Glutamate Receptor Stimulation Triggers Production and Release of Alzheimer's Amyloid B42 From Isolated Intact Nerve Terminals", Journal of Neuroscience, 2010, 30(11), 3870-3875.
Kim et al., "Metabotropic Glutamate Receptors in the Rat Nucleus Accumbens Contribute to Amphetamine-Induced Locomotion", Journal of Pharmacology & Experimental Therapeutics, 1998, 284(1), 317-322.
Kim et al., "Metabotropic Glutamate Receptors, Phosphorylation and Receptor Signaling", Journal of Neuroscience Research, 2008, 86, 1-10.
Kim et al., "Neurofilament-M Interacts with the D1 Dopamine Receptor to Regulate Cell Surface Expression and Desensitization", Journal of Neuroscience, 2002, 22(14), 5920-5930.
Kim et al., "Predictors of 12-Week Remission in a Nationwide Cohort of People with Depressive Disorders: The Crescend Study", Hum. Psychopharmacol Clin Exp, 2011, 26, 41-50.
Kingston et al., "Ly341495 is a Nanomolar Potent and Selective Antagonist of Group II Metabotropic Glutamate Receptors", Neuropharmacology, 1998, 37, 1-12.
Kingston et al., "Neuroprotection by Metabotropic Glutamate Receptor Agonists: Ly354740, Ly379268 and Ly389795", European Journal of Pharmacology, 1999, 377, 155-165.
Kingston et al., "Neuroprotective Actions of Novel and Potent Ligands of Group I and Group II Metabotropic Glutamate Receptors", Annals New York Academy of Sciences, 1999, 890, 438-449.
Kinon, "A Multicenter, Inpatient, Phase 2, Double-Blind, Placebo-Controlled Dose-Ranging Study of Ly2140023 Monohydrate in Patients with DSM-IV Schizophrenia", J. Clin. Psychopharmacology, 2011, 31(3), 349-355.
Kilts, "The Changing Roles and Targets for Animal Models of Schizophrenia", Biol. Psychiatr., 2001, 50, 845-855.
Klein "Mixed Anxiety Depression. For and Against", L'encéphale, 1993, 493-495.
Klein et al., "Glutamatergic Activation of Hippocampal Phospholipase D: Postnatal Fading and Receptor Desensitization", Journal of Neurochemistry, 1998, 70(4), 1679-1685.

(56) References Cited

OTHER PUBLICATIONS

Klodzinska et al., "Group II Mglu Receptor Agonists Inhibit Behavioural and Electrophysiological Effects of Doi in Mice", Pharmacology, Biochemistry and Behavior, 2002, 73(2), 327-332.
Klodzinska et al., "Roles of Group II Metabotropic Glutamate Receptors in Modulation of Seizure Activity", Naunyn Schmiedebergs Arch Pharmacol, 2000, 361, 283-288.
Klodzinska et al., "Selective Group II Glutamate Metabotropic Receptor Agonist Ly354740 Attenuates Pentetrazole- and Picrotoxin-Induced Seizures", Pol J Pharmacol, 1999, 51, 543-545.
Knesevich, "Validity of Hamilton Rating-Scale for Depression", Br J Psychiatry, 1977, 131, 49-52.
Kniazeff et al., "Closed State of Both Binding Domains of Homodimeric Mglu Receptors is Required for Full Activity", Nat Struct Mol Biol, 2004, 11, 706-713.
Knight et al., "Pharmacological Characterization of the Agonist Radioligand Binding Site of 5-Ht2a, 5-Ht2b and 5-Ht2c Receptors", Naunyn-Schmiedeberg's Arch Pharmacol, 2004, 370, 114-123.
Knoflach et al., "R1315, A Potent Orally Active Non-Competitive Group II Metabotropic Glutamate Receptor Antagonist with Cognitive Enhancing Properties", 5th International Meeting on Metabotropic Glutamate Receptors, Taormina Sicily—Italy, Sep. 2005, 1 page.
Kodama et al., "Enhanced Glutamate Release During Rem Sleep in the Rostromedial Medulla as Measured by in Vivo Microdialysis", Brain Res, 1998, 780, 178-181.
Koh et al., "Deficits in Social Behavior and Sensorimotor Gating in Mice Lacking Phospholipase Cb1", Genes, Brain and Behavior, 2008, 7, 120-128.
Koh et al., "Non-NMDA Receptor-Mediated Neurotoxicity in Cortical Culture", J. Neurosci., 1990, 10(2), 693-705.
Koh et al., "Treatment Strategies Targeting Excess Hippocampal Activity Benefit Aged Rats with Cognitive Impairment", Neuropsychopharmacology, 2010, 35, 1016-1025.
Komossa et al., "Second-Generation Antipsychotics for Major Depressive Disorder and Dysthymia (Review)", The Cochrane Collaboration, 2012, 222 pages.
Konarski et al., "Volumetric Neuroimaging Investigations in Mood Disorders: Bipolar Disorder Versus Major Depressive Disorder", Bipolar Disord, 2008, 10(1), 1-37.
Konieczny et al., "Ly354740, A Group II Metabotropic Glutamate Receptor Agonist with Potential Antiparkinsonian Properties in Rats", Naunyn Schmiedebergs Arch. Pharmacol., 1998, 358(4), 500-502.
Konstantakopoulos et al., "Lamotrigine Associated Exacerbation of Positive Symptoms in Paranoid Schizophrenia", Schizophr Res., 2008, 98(1-3), 325-326.
Koolschijn et al., "Brain Volume Abnormalities in Major Depressive Disorder: A Meta-Analysis of Magenetic Resonance Imaging Studies", Hum Brain Mapp, 2009, 30(11), 3719-3735.
Koroshetz et al., "Emerging Treatments for Stroke in Humans", Trends in Pharmacological Sciences, 1996, 17(6), 227-233.
Kostrzewa et al., "Supersensitized D1 Receptors Mediate Enhanced Oral Activity After Neonatal 6-Ohda. Pharmacology", Biochemistry & Behavior, 1991, 39(3), 677-682.
Kotlinska et al., "The Role of Group I Mglu Receptors in the Expression of Ethanol-Induced Conditioned Place Preference and Ethanol Withdrawal Seizures in Rats", European Journal of Pharmacology, 2011, 670, 154-161.
Koulen et al., "Group II and Group III Metabotropic Glutamate Receptors in the Rat Retina: Distributions and Developmental Expression Patterns", European Journal of Neuroscience, 1996, 8(10), 2177-2187.
Kowal et al., "A [35s]Gtpgammas Binding Assessment of Metabotropic Glutamate Receptor Standards in Chinese Hamster Ovary Cell Lines Expressing the Human Metabotropic Receptor Subtypes 2 and 4", Neuropharmacology, 1998, 37(2), 179-187.
Kowal et al., "Functional Calcium Coupling with the Human Metabotropic Glutamate Receptor Subtypes 2 and 4 by Stable Co-Expression with a Calcium Pathway Facilitating G-Protein Chimera in Chinese Hamster Ovary Cells", Biochemical Pharmacology, 2003, 66(5), 785-790.
Krieger, "The Plasma Level of Cortisol as a Predictor of Suicide", Diseases of the Nervous System, 1974, 35(5), 237-240.
Krishnan et al., "The Molecular Neurobiology of Depression", Nature, 2008, 455, 894-902.
Krivoy et al., "The Possible Involvement of Metabotropic Glutamate Receptors in Schizophrenia", European Neuropsychopharmacology, 2008, 18, 395-405.
Krohnke et al., "Methylketon-Addukte Der Chinolinium-Und Isochinolinium-Reihe", Justus Liebigs Annalen Der Chemie, 1956, 211-228.
Krystal et al., "Comparative and Interactive Human Psychopharmacologic Effects of Ketamine and Amphetamine: Implications for Glutamatergic and Dopaminergic Model Psychoses and Cognitive Function", Archives of General Psychiatry, 2005, 62(9), 985-994.
Krystal et al., "Neuroplasticity as a Target for the Pharmacotherapy of Anxiety Disorders, Mood Disorders, and Schizophrenia", Drug Discov. Today, 2009, 14(13-14), 690-697.
Krystal et al., "NMDA Receptor Antagonist Effects, Cortical Glutamatergic Function, and Schizophrenia: Toward a Paradigm Shift in Medication Development", Psychopharmacology, 2003, 169(3-4), 215-33.
Krystal et al., "Potential Psychiatric Applications of Metabotropic Glutamate Receptor Agonists and Antagonists", CNS Drugs, 2010, 24(8), 669-693.
Krystal et al., "Preliminary Evidence of Attenuation of the Disruptive Effects of the Nmda Glutamate Receptor Antagonist, Ketamine, on Working Memory by Pretreatment with the Group II Metabotropic Glutamate Receptor Agonist, Ly354740, in Healthy Human Subjects", Psychopharmacology (Berl)., 2005, 179(1), 303-309.
Krystal et al., "Subanesthetic Effects of the Noncompetitive NMDA Antagonist, Ketamine, in Humans. Psychotomimetic, Perceptual, Cognitive, and Neuroendocrine Responses", Arch Gen Psychiatry, 1994, 51(3), 199-214.
Krystal, "N-Methyl-D-Aspartate Glutamate Receptors and Alcoholism: Reward, Dependence, Treatment, and Vulnerability", Pharmacol. & Therapeutics, 2003, 99, 79-94.
Kubo et al., "Structural Basis for a Ca2+-Sensing Function of the Metabotropic Glutamate Receptors", Science, 1998, 279(5357), 1722-1725.
Kubokawa et al., "Cloning and Characterization of a Bifunctional Metabotropic Receptor Activated by Both Extracellular Calcium and Glutamate", Febs Letters, 1996, 392(1), 71-76.
Kucukibrahimoglu et al., "The Change in Plasma Gaba, Glutamine and Glutamate Levels in Fluoxetine- or S-Citalopram-Treated Female Patients with Major Depression", Eur J Clin Pharmacol, 2009, 65(6), 571-577.
Kufahl et al., "Enhanced Sensitivity to Attenuation of Conditioned Reinstatement by the Mglur2/3 Agonist Ly379268 and Increased Functional Activity of Mglur2/3 in Rats with a History of Ethanol Dependence", Neuropsychopharmacology, 2011, 1-12.
Kugaya et al., "Beyond Monoamines: Glutamatergic Function in Mood Disorders", CNS Spectr, 2005, 10, 808-819.
Kullmann et al., "Extrasynaptic Glutamate Spillover in the Hippocampus: Evidence and Implications", Trends Neurosci., 1998, 21(1), 8-14.
Kunishima et al., "Structural Basis of Glutamate Recognition by a Dimeric Metabotropic Glutamate Receptor", Nature, 2000, 407, 971-977.
Kuo, "Allosteric Cofactor-Mediated Enzyme Cooperativity: A Theoretical Treatment", Proc. Natl. Acad. Sci. USA, Sep. 1983, 80, 5243-5247.
Kurita et al., "Hdac2 Regulates Atypical Antipsychotic Responses through the Modulation of Mglu2 Promoter Activity", Nature Neuroscience, 2012, 15(9), 1245-1254.
Kurumaji et al., "Effects of Mk-801 Upon Local Cerebral Glucose Utilization in Conscious Rats and in Rats Anaesthetized with Halothane", J Cereb Blood Flow Metab, 1989, 9, 786-794.
Lahti et al., "Ketamine Activates Psychosis and Alters Limbic Blood Flow in Schizophrenia", Neuroreport, 1995, 6(6), 869-872.

(56) References Cited

OTHER PUBLICATIONS

Lam et al., "Effects of the Selective Metabotropic Glutamate Agonist Ly354740 in a Rat Model of Permanent Ischaemia", Neuroscience Letters, 1998, 254(2), 121-123.

Lambeng et al., "Selective Mglur2 Negative Allosteric Modulators Reverse the Scopolamine-Induced Memory Deficit in the Novel Object Recognition Test", Society for Neuroscience 40th Annual Meeting, Nov. 2010, 1 page.

Lambert et al., "Current Issues in Schizophrenia: Overview of Patient Acceptability, Functioning Capacity and Quality of Life", CNS Drugs, 2004,18(Suppl 2), 5-17.

Lamers et al., "Comorbidity Patterns of Anxiety and Depressive Disorders in a Large Cohort Study: the Netherlands Study of Depression and Anxiety (Nesda)", J Clin Psychiatry, 2011, 72(3), 341-348.

Lamotrigine, "Highlights of Prescribing Information", 2012, 1-64.

Landen et al., "A Randomized, Double-Blind, Placebo-Controlled Trial of Buspirone in Combination with an Ssri in Patients with Treatment-Refractory Depression", J Clin Psychiatry, 1998, 59, 664-668.

Landin et al., "The Impact of Restrictive Entry Criterion During the Placebo Lead-in Period", Biometrics, 2000, 56, 271-278.

Landmark, "Antiepileptic Drugs in Non-Epilepsy Disorders", CNS Drugs, 2008, 22(1), 27-47.

Landwehrmeyer, "Riluzole in Huntington's Disease: A 3-Year, Randomized Controlled Study", Ann Neurol, 2007, 62, 262-272.

Lane et al., "Bridging the Gap: Bitopic Ligands of G-Protein-Coupled Receptors", Trends in Pharmacological Sciences, Jan. 2013, 34(1), 59-66.

Lang et al., "Molecular Mechanisms of Depression Perspective on New Treatment Strategies", Cell Physiol Biochem, 2013, 31, 761-777.

Lang et al., "Molecular Mechanisms of Schizophrenia", Cell Physiol Biochem., 2007, 20(6), 687-702.

Langmead, "Ligand Properties and Behaviours in an Allosteric Age", Trends Pharmacol Sci, 2012, 33, 621-622.

Langmead, "Screening for Positive Allosteric Modulators: Assessment of Modulator Concentration-Response Curves as a Screening Paradigm", Journal of Biomolecular Screening, 2007, 668-676.

Large, "Do NMDA Receptor Antagonist Models of Schizophrenia Predict the Clinical Efficacy of Antipsychotic Drugs?", J Psychopharmacol, 2007, 21, 283-301.

Large, "The Potential Role of Lamotrigine in Schizophrenia", Psychopharmacol., 2005, 181, 415-436.

Larsson et al., "Neurochemical and Behavioral Studies on Ethanol and Nicotine Interactions", Neuroscience and Biobehavioral Reviews, 2004, 27, 713-720.

Laruelle et al., "Glutamate, Dopamine, and Schizophrenia: From Pathophysiology to Treatment", Ann Ny Acad Sci, 2003, 1003, 138-158.

Laruelle et al., "Relationships Between Radiotracer Properties and Image Quality in Molecular Imaging of the Brain with Positron Emission Tomography", Mol Imaging Biol, 2003, 5, 363-375.

Larzabal et al., "Distribution of the GrIup II Metabotropic Glutamate Receptors (Mglur2/3) in the Enteric Nervous System of the Rat", Neuroscience Letters, 1999, 276, 91-94.

Laughren et al., "Food and Drug Administration Perspective on Negative Symptoms in Schizophrenia as a Target for a Drug Treatment Claim", Schizophr Bull., 2006, 32(2), 220-222.

Laughren, "The Scientific and Ethical Basis for Placebo-Controlled Trials in Depression and Schizophrenia: An Fda Perspective", Eur Psychiatry, 2001, 16, 418-423.

Laurie et al., "Cloning, Distribution and Functional Expression of the Human Mglu6 Metabotropic Glutamate Receptor", Neuropharmacology, 1997, 36(2), 145-52.

Lavreysen et al., "[$^3$h]R214127: A Novel High-Affinity Radioligand for the Mglu1 Receptor Reveals a Common Binding Site Shared by Multiple Allosteric Antagonists", Mol Pharmacol, 2003, 63, 1082-1093.

Lavreysen et al., "A Study on the Molecular Interaction Between Mglu2 Receptor Agonists and Positive Allosteric Modulators", International Meeting on Metabotropic Glutamate Receptors, Poster, Sep. 2008, 1 page.

Lavreysen et al., "A Study on the Molecular Interaction Between Mglu2 Receptor Agonists and Positive Allosteric Modulators" Poster, Society for Neuroscience Annual Meeting, 2009, 1 page.

Lavreysen et al., "JNJ16259685, A Highly Potent, Selective and Systemically Active Mglu1 Receptor Antagonist" Neuropharmacology 2004, 47, 961-972.

Lavreysen et al., "JNJ-40068782: A Novel Potent, Selective and Systemically Active Positive Allosteric Modulator of the Mglu2 Receptor" Abstract, Society for Neuroscience Annual Meeting, 2010, 1 page.

Lavreysen et al., "Pharmacological Characterization of JNJ-40068782, A New Potent, Selective, and Systemically Active Positive Allosteric Modulator of the Mglu2 Receptor and Its Radioligand [3h]Jnj-40068782", J Pharmacol Exp Ther, Sep. 2013, 346, 514-527.

Lavreysen et al., "Therapeutic Potential of Group III Metabotropic Glutamate Receptors", Current Medicinal Chemistry, 2008, 15, 671-684.

Lavreysen, "The Development of Mglu2 Pams: Identification of JNJ-40068782 as a Novel Tool Compound", Allosteric Modulator Drug Discovery Congress, Nov. 2010, 34 pages.

Leach et al., "Allosteric Gper Modulators: Taking Advantage of Permissive Receptor Pharmacology", Trends in Pharmacological Sciences, 2007, 28(8), 382-389.

Leach et al., "Quantification of Allosteric Interactions Unit 1.22 at G Protein-Coupled Receptors Using Radioligand Binding Assays", Current Protocols in Pharmacology, Mar. 2011, 1.22.1-1.22.41.

Leber, "Observations and Suggestions on Antidementia Drug Development", Alzheimer Disease and Associated Disorders, 1996, 10 (Suppl 1), 31-35.

Lebois, "Neither Typical nor Atypical: Ly404039 Provides Proof of Concept That Selective Targeting of Mglur2/3 Receptors is a Valid Mechanism for Obtaining Antipsychotic Efficacy", Curr. Top. Med. Chem., 2008, 8(16), 1480-1481.

Lecci et al., "Pharmacological Validation of a Novel Animal Model of Anticipatory Anxiety in Mice", Psychopharmacology, 1990, 101, 255-261.

Lee et al., "Amyloid Precursor Protein Processing is Stimulated by Metabotropic Glutamate Receptors", National Academy of Sciences USA, 1995, 92(17), 8083-8087.

Lee et al., "Characterization of the Inward Current Induced by Metabotropic Glutamate Receptor Stimulation in Rat Ventromedial Hypothalamic Neurones", Journal of Physiology, 1997, 504(Pt 3), 649-663.

Lee et al., "Glutamategic Afferent Projections to the Dorsal Raphe Nucleus of the Rat", Brain Res, 2003, 963, 57-71.

Lee et al., "Low Doses of Cannabinoids Enhance the Antinociceptive Effects of Intracisternally Administered Mglurs Groups II and III Agonists in Formalin-Induced Tmj Nociception in Rats", Pain, 2008, 139(2), 367-375.

Lee et al., "The Effect of Mglur2 Activation on Signal Transduction Pathways and Neuronal Cell Survival", Brain Res., 2009, 1249, 244-250.

Lee et al., "The Mglu2/3 Receptor Agonist Ly354740 Suppresses Immobilization Stress-Induced Increase in Rat Prefrontal Cortical Bdnf Mrna Expression", Neuroscience Letters, 2006, 398, 328-332.

Lee, "The Role of Metabotropic Glutamate Receptors in Alzheimer's Disease", Acta Neurobiol Exp, 2004, 64, 89-98.

Leeson et al., "The Influence of Drug-Like Concepts on Decision-Making in Medicinal Chemistry", Nat Rev Drug Discovery, 2007, 6, 881-890.

Leever et al., "Identification of a Site in Glur1 and Glur2 That is Important for Modulation of Deactivation and Desensitization", Mol Pharmacol, 2003, 64(1), 5.

Lennon et al., "Metabotropic Glutamate Receptor Mglu2 is Resistant to Homologous Agonist-Induced Desensitilization But Undergoes Protein Kinase C-Mediated Heterologous Desensitization", Eur J Phamacol, 2010, 649, 29-37.

(56) References Cited

OTHER PUBLICATIONS

Lenox et al., "Mechanism of Action of Antidepressants and Mood Stabilizers" Neuropsychopharmacology: Tthe Fifth Generation of Progress, American College of Neuropsychopharmacology, 2002, 1139-1163.

Leo et al., "The Application of Nuclear Magnetic Resonance-Based Metabonomics to the Dominant-Submissive Rat Behavioral Model", Analytical Biochemistry, 2005, 339, 174-178.

Lerner et al., "The Work Limitations Questionnaire", Med Care, 2001, 39(1), 72-85.

Leucht et al., "Second-Generation Versus First-Generation Antipsychotic Drugs for Schizophrenia: A Meta-Analysis", Lancet, 2009, 373(9657), 31-41.

Levine et al., "Abstracts/Neuropharmacology", 2002, 43, 294-295.

Levitz et al., "Optical Control of Metabotropic Glutamate Receptors", Nature Neuroscience, 2013, 16(4), 507-516.

Lewis et al., "Cognitive Dysfunction in Schizophrenia: Convergence of Gamma-Aminobutyric Acid and Glutamate Alterations", Arch. Neurol., 2006, 63(10), 1372-1376.

Lewis, "The Molecular Choreography of a Store-Operated Calcium Channel", Nature, 2007, 446, 284-287.

Leysen et al., "[3h]Ketanserin (R 41 468), A Selective 3h-Ligand for Serotonin2 Receptor Binding Sites. Binding Properties, Brain Distribution, and Functional Role", Molecular Pharmacology, 1982, 21(2), 301-314.

Leysen et al., "Receptor Interactions of New Antipsychotics: Relation to Pharmacodynamics and Clinical Effects", Intl Journal of Psychiatry in Clinical Practice, 1998, 2, S3-S17.

Li et al., "Design and Synthesis of 4-Arylpiperidinyl Amide and N-Arylpiperdin-3-Yl-Cyclopropane Carboxamide Derivatives as Novel Melatonin Receptor Ligands", Bioorganic & Medicinal Chemistry Letters, 2011, 21, 1236-1242.

Li et al., "Evaluation of the Motor Initiation Hypothesis of Apd-Induced Conditioned Avoidance Decreases", Pharmacol. Biochem. Behav., 2004, 78, 811-819.

Lieberman et al., "A Randomized, Placebo-Controlled Study of Memantine as Adjunctive Treatment in Patients with Schizophrenia", Neuropsychopharmacology, 2009, 34, 1322-1329.

Lieberman et al., "Antipsychotic Drugs: Comparison in Animal Models of Efficacy, Neurotransmitter Regulation, and Neuroprotection", Pharmacol. Rev, 2008, 60(3), 358-403.

Lieberman et al., "Effectiveness of Antipsychotic Drugs in Patients with Chronic Schizophrenia", N Engl J Med., 2005, 353(12), 1209-1223.

Lieberman, "Serotonergic Basis of Antipsychotic Drug Effects in Schizophrenia", Biol. Psychiatry, 1998, 44, 1099-1117.

Liebowitz et al., "Biological Accompaniments of Lactate-Induced Panic", Psychopharmacology Bulletin, 1984, 20(1), 43-44.

Liebowitz et al., "Lactate Provocation of Panic Attacks. I. Clinical and Behavioral Findings", Archives of General Psychiatry, 1984, 41(8), 764-70.

Liechti et al., "Interactive Effects of the MgluS Receptor Angatonist Mpep and the Mglu2/3 Receptor Antagonist Ly341495 on Nicotine Self-Administration and Reward Deficits Associated with Nicotine Withdrawal in Rats", European Journal of Pharmacology, 2007, 554, 164-174.

Liechti et al., "Metabotropic Glutamate 2/3 Receptor Activation Induced Reward Deficits But Did Not Aggravate Brain Reward Deficits Associated with Spontaneous Nicotine Withdrawal in Rats", Biochemical Pharmacology, 2007, 74, 1299-1307.

Liechti et al., "Metabotropic Glutamate 2/3 Receptors in the Ventral Tegmental Area and the Nucleus Accumbens Shell are Involved in Behaviors Relating to Nicotine Dependence", Journal of Neuroscience, 2007, 27(34), 9077-9085.

Liechti et al., "Role of the Glutamatergic System in Nicotine Dependence Implications for the Discovery and Development of New Pharmacological Smoking Cessation Therapies", CNS Drugs, 2008, 22(9), 705-724.

Lilly, "Stops Phase III Development of Pomaglumetad Methionil for the Treatment of Schizophrenia Based on Efficacy Results", Press Release, Aug. 29, 2012, 1 page.

Lin et al., "A Meta-Analytic Review of Double-Blind, Placebo-Controlled Trials of Antidepressant Efficacy of Omega-3 Fatty Acids", J Clin Psychiatry, 2007, 68(7), 1056-1061.

Lindemann et al., "Ctep: A Novel, Potent, Long-Acting, and Orally Bioavailable Metabotropic Glutamate Receptor 5 Inhibitor", Jpet, 2011, 339, 474-486.

Linden et al., "Anxiolytic Activity of the Mglu2/3 Receptor Agonist Ly354740 on the Elevated Plus Maze is Associated with the Suppression of Stress-Induced C-Fos in the Hippocampus and Increases in C-Fos Induction in Several Other Stress-Sensitive Brain Regions", Neuropsychopharmacology, 2004, 29, 502-513.

Linden et al., "Comparison of C-Fos Induction in the Brain by the Mglu2/3 Receptor Antagonist Ly341495 and Agonist Ly354740: Evidence for Widespread Endogenous Tone at Brain Mglu2/3 Receptors In Vivo", Neuropharmacology, 2005, 49(Suppl 1), 120-134.

Linden et al., "Effects of Mglu2 or Mglu3 Receptor Deletions on Mglu2/3 Receptor Agonist (Ly354740)—Induced Brain C-Fos Expression: Specific Roles for Mglu2 in the Amygdala and Subcortical Nuclei, and Mglu3 in the Hippocampus", Neuropharmacology, 2006, 51, 213-228.

Linden et al., "Use of Mglur2 and Mglur3 Knockout Mice to Explore In Vivo Receptor Specificity of the Mglur2/3 Selective Agonist Ly341495", Neuropharmacology, 2009, 57, 172-182.

Linden, "Anxiolytic-Like Activity of the Mglu2/3 Receptor Agonist Ly354740 in the Elevated Plus Maze Test is Disrupted in Metabotropic Glutamate Receptor 2 and 3 Knock-Out Mice", Psychopharmacol., 2005, 179, 284-291.

Lindsley et al., "Progress Towards Validating the NMDA Receptor Hypofunction Hypothesis of Schizophrenia", Current Topics in Medicinal Chemistry, 2006, 6, 771-785.

Linn et al., "Activation of Metabotropic Glutamate Receptors Modulates the Voltage-Gated Sustained Calcium Current in a Teleost Horizontal Cell", Journal of Neurophysiology, 1999, 81(2), 425-434.

Lipton, "Excitatory Amino Acids as a Final Common Pathway for Neurologic Disorders", Mechanisms of Disease, New England Journal of Medicine, 1994, 330(9), 613-622.

Lissin et al., "An Immunocytochemical Assay for Activity-Dependent Redistribution of Glutamate Receptors from the Postsynaptic Plasma Membrane", Annals of the New York Academy of Sciences, 1999, 868, 550-553.

Litman, "AZD8529, A Positive Allosteric Modulator at the Mglur2 Receptor, Does Not Improve Symptoms in Schizophrenia: A Proof of Principle Study", NCDEU: An Annual Meeting Sponsored by Am Soc. of Clin. Psychopharmacology, Poster and Abstract, 2013, 3 pages.

Liu et al., "A Unified Theory of Two-Stage Adaptive Designs", Theory and Methods, 2002, 97, 1034-1041.

Liu et al., "Doubly Randomized Delayed-Start Design for Enrichment Studies with Responders or Nonresponders", Journal of Biopharmaceutical Statistics, 2012, 22(4), 737-757.

Liu et al., "Pharmacogenetic Analysis of the Mglu2/3 Agonist Ly2140023 Monohydrate in the Treatment of Schizophrenia", Pharmacogenomics Journal, 2010, 1-9.

Lopez-Rodriguez et al., "Changes in Extracellular Glutamate Levels in Rat Orbitofrontal Cortext During Sleep and Wakefulness", Arch Med Res, 2007, 38, 52-55.

Lorenzetti et al., "Structural Brain Abnormalities in Major Depressive Disorder: A Selective Review of Recent MRI Studies", J Affect Disord, 2009, 117(1-2), 1-17.

Lorrain et al., "Group II Mglu Receptor Activation Suppresses Norepinephrine Release in the Ventral Hippocampus and Locomotor Responses to Acute Ketamine Challenge", Neuropsychopharmacology, 2003, 28, 1622-1632.

Lou et al., "Allosteric Modulation of the Presynaptic Ca2+ Sensor for Vesicle Fusion", Nature, 2005, 435, 497-501.

Lourenco et al., "Differential Distribution of Metabotropic Glutamate Receptor Subtype MRNAS in the Thalamus of the Rat", Brain Research, 2000, 854(1-2), 93-105.

Lowe et al., "Effects of a Novel Mglu2/3 Receptor Agonist Prodrug, Ly2140023 Monohydrate, on Central Monoamine Turnover as

(56) References Cited

OTHER PUBLICATIONS

Determined in Human and Rat Cerebrospinal Fluid", Psychopharmacology, 2011, 1-12.
Lowry et al., "Serotonergic Systems, Anxiety, and Affective Disorder: Focus on the Dorsomedial Part of the Dorsal Raphe Nucleus", Annals of the New York Academy of Sciences, 2008, 1148, 86-94.
Lujan et al., "Glutamate and Gaba Receptor Signalling in the Developing Brain", Neuroscience, 2005, 130, 567-580.
Luscher et al., "Group I Mglur-Dependent Synaptic Long-Term Depression: Mechanisms and Implications for Circuitry and Disease", Neuron, 2010, 65, 445-459.
Lyon et al., "Altered Hippocampal Expression of Glutamate Receptors and Transporters in Grm2 and Grm3 Knockout Mice", Synapse, 2008, 62, 842-850.
Lyon et al., "Fractionation of Spatial Memory in Grm2/3 (Mglu2/Mglu3) Double Knockout Mice Reveals a Role for Group II Metabotropic Glutamate Receptors at the Interface Between Arousal and Cognition", Neuropsychopharmacology, 2011, 1-13.
Macchiarulo et al., "The Role of Electrostatic Interaction in the Molecular Recognition of Selective Agonists to Metabotropic Glutamate Receptors", Proteins, 2003, 50(4), 609-619.
Macdonald "The Design of Allosteric Modulators for the Treatment of CNS Disorders", $11^{th}$ Advances and Progress in Drug Design, Feb. 2012, 36 pages.
Macdonald, "The Design of Mglur Modulators for the Treatment of CNS Disorders" Presentation Slides, $6^{th}$ Anglo-Swedish Medicinal Chemistry Symposium, Stockholm, Jun. 19, 2013.
Macdonald, "Positive Allosteric Modulation of Mglur2 Receptors in the Treatment of CNS Disorders", $3^{rd}$ Symposium on GPCRS in Medicinal Chemistry, Oss, Sep. 2010, 29 pages.
Macek et al., "Differential Involvement of Group II and Group III Mglurs as Autoreceptors at Lateral and Medial Perforant Path Synapses", J Neurophysiol, 1996, 76(6), 3798-3806.
Macek et al., "Protein Kinase C and A3 Adenosine Receptor Activation Inhibit Presynaptic Metabotropic Glutamate Receptor (Mglur) Function and Uncouple Mglurs from Gtp-Binding Proteins", J. Neurosci., 1998, 18(16), 6138-6146.
Mackrill, "Protein-Protein Interactions in Intracellular Ca2+-Release Channel Function", Biochemical Journal, 1999, 337(Pt 3), 345-361.
Maeda et al., "Different Roles of Group I and Group II Metabotropic Glutamate Receptors on Phencyclidine-Induced Dopamine Release in the Rat Prefrontal Cortex", Neuroscience Letters, 2003, 336 (3), 171-174.
Maeng, "Cellular Mechanisms Underlying the Antidepressant Effects of Ketamine: Role of Alpha-Amino-3-Hydroxy-5-Methylisoxazole-4-Propionic Acid Receptors," Biol. Psychiatry, 2008, 63, 349-352.
Maione et al., "Characterisation of Mglurs Which Modulate Nociception in the Pag of the Mouse", Neuropharmacology,1998, 37(12), 1475-1483.
Makoff et al., "Molecular Characterization and Localization of Human Metabotropic Glutamate Receptor Type 3", Molecular Brain Research, 1996, 40(1), 55-63.
Malatynska et al., "Assessing Activity Onset Time and Efficacy for Clinically Effective Antidepressant and Antimanic Drugs in Animal Models Based on Dominant-Submissive Relationships", Neuroscience and Biobehavioral Reviews, 2007, 31, 904-919.
Malatynska et al., "Dominant-Submissive Behavior as Models of Mania and Depression", Neuroscience and Biobehavioral Reviews, 2005, 29(4-5), 715-37.
Malatynska et al., "Levels of Mrna for A-, B-, and Γ-Synuclein in the Brains of Newborn, Juvenile, and Adult Rats", J Mol Neurosci., 2006, 29(3), 269-77.
Malatynska et al., "Reduction of Dominant or Submissive Behaviors as Models for Antimanic or Antidepressant Drug Testing: Technical Considerations", J Neurosci Methods, 2007, 165(2), 175-182.
Malatynska et al., "Submissive Behavior in Mice as a Test for Antidepressant Drug Activity", Pharmacol Biochem Behavior, 2005, 82, 306-313.

Malenka et al., "Ltp and Ltd: An Embarrassment of Riches", Neuron, 2004, 44, 5-21.
Malherbe et al., "Identification of Essential Residues Involved in the Glutamate Binding Pocket of the Group II Metabotropic Glutamate Receptor", Molecular Pharmacology., 2001, 60 (5), 944-954.
Malherbe et al., "Opposite Effects of Zn on the in Vitro Binding of [3h]Ly354740 to Recombinant and Native Metabotropic Glutamate 2 and 3 Receptors", J Neurochem., 2005, 94(1), 150-160.
Malhi et al., "Recognizing the Anxious Face of Depression", Journal of Nervous and Mental Disease, 2002, 190(6), 366-73.
Malhotra et al., "NMDA Receptor Function and Human Cognition: The Effects of Ketamine in Healthy Volunteers", Neuropsychopharmacology, May 1996, 14(5), 301-307.
Mansbach et al., "Blockade of Potentiated Startle Responding in Rats by 5-Hydroxytryptamine1a Receptor Ligands", Eur. J. Pharmacology, 1988, 156, 375-383.
Marcotte, "Animal Models of Schizophrenia: A Critical Review", Psychiatry Neurosci., 2001, 26(5), 395-410.
Marcus et al., "The Efficacy and Safety of Aripiprazole as Adjunctive Therapy in Major Depressive Disorder: A Second Multicenter, Randomized, Double-Blind, Placebo-Controlled Study", Journal of Clinical Psychopharmacology, 2008, 28(2), 156-165.
Marek, "Metabotropic Glutamate2/3 (Mglu2/3) Receptors, Schizophrenia and Cognition", European Journal of Pharmacology, 2010, 639, 81-90.
Marek et al., "5-Hydroxytryptamine2a (5-Ht2a) Receptor Regulation in Rat Prefrontal Cortex: Interaction of a Phenethylamine Hallucinogen and the Metabotropic Glutamate2/3 Receptor Agonist Ly354740", Neuroscience Letters, 2006, 403(3), 256-260.
Marek et al., "Glutamatergic (N-Methyl-D-Aspartate Receptor) Hypofrontality in Schizophrenia: Too Little Juice or a Miswired Brain?", Molecular Pharmacology, 2010, 77(3), 317-326.
Marek et al., "Physiological Antagonism Between 5-Hydroxytryptamine2a and Group II Metabotropic Glutamate Receptors in Prefrontal Cortex", J. Pharm. Exper. Therapeut., 2000, 292, 76-87.
Marek et al., "The Electrophysiology of Prefrontal Serotonin Systems: Therapeutic Implications for Mood and Psychosis", Biol Psychiatry, 1998, 44, 1118-1127.
Marek, "Metabotropic Glutamate 2/3 Receptors as Drug Targets", Curr. Opin. Pharmacol., 2004, 4, 18-22.
Marino et al., "Glutamate-Based Therapeutic Approaches: Allosteric Modulators of Metabotropic Glutamate Receptors", Current Opinion in Pharmacology, 2006, 6, 98-102.
Markou, "The Role of Metabotropic Glutamate Receptors in Drug Reward, Motivation and Dependence", Drug News Perspect, 2007, 20(2), 103-108.
Marquet et al., "VIII. Nouvelle Methode De Synthese Des Furo[2,3-D]Pyrimidines Sustituees En Position 4 Et De Certains Thieno[2,3-D]Pyrimidines", Bulletin De La Societe Chimique De France, 1969, 12, 4344-4348.
Martella et al., "Enhanced Sensitivity to Group II Mglu Receptor Activation at Corticostriatal Synapses in Mice Lacking the Familial Parkinsonism-Linked Genes Pink1 or Parkin.", Exp. Neurol., 2009, 215(2), 388-396.
Martin et al., "Cellular Localization of a Metabotropic Glutamate Receptor in Rat Brain", Neuron, 1992, 9(2), 259-270.
Martin et al., "Cross-Talk Between Beta-Adrenergic and Metabotropic Glutamate Receptors in Rat C6 Glioma Cells", Biochimica Et Biophysica Acta, 1998, 1393(1), 186-192.
Mason, "Acamprosate in the Treatment of Alcohol Dependence", Expert Opin. Pharmacother., 2005, 6(12), 2103-2115.
Masu et al., "Sequence and Expression of a Metabotropic Glutamate Receptor", Nature, 1991, 349(6312), 760-765.
Matrisciano et al., "Activation of Group-II Metabotropic Glutamate Receptors Promotes DNA Demethylation in the Mouse Brain", Molecular Pharmacology, Apr. 2011, 52 pages.
Matrisciano et al., "Defective Group-II Metaboropic Glutamate Receptors in the Hippocampus of Spontaneously Depressed Rats", Neuropharmacology, 2008, 55(4), 525-531.
Matrisciano et al., "Group-II Metabotropic Glutamate Receptor Ligands as Adjunctive Drugs in the Treatment of Depression: A New

(56) References Cited

OTHER PUBLICATIONS

Strategy to Shorten the Latency of Antidepressant Medication?", Molecular Psychiatry, 2007, 12, 704-706.

Matrisciano et al., "Imipramine Treatment Up-Regulates the Expression and Function of Mglu2/3 Metabotropic Glutamate Receptors in the Rat Hippocampus", Neuropharmacology, 2002, 42(8), 1008-1015.

Matrisciano, "Metabotropic Glutamate Receptors and Neuroadaptation to Antidepressants: Imipramine-Induced Down-Regulation of B-Adrenergic Receptors in Mice Treated with Metabotropic Glutamate 2/3 Receptor Ligands", Journal of Neurochemistry, 2005, 93, 1345-1352.

Matrisciano, "Synergism Between Fluoxetine and the Mglu2/3 Receptor Agonist, Ly379268, in an In Vitro Model for Antidepressant Drug-Induced Neurogenesis", Neuropharmacology, 2008, 54, 428-437.

Maurel et al., "Cell-Surface Protein-Protein Interaction Analysis with Time-Resolved Fret and Snap-Tag Technologies: Application to Gper Oligomerization", Nat Methods, 2008, 5(6), 561-567.

Maxwell et al., "Ketamine Produces Lasting Disruptions in Encoding of Sensory Stimuli", J Pharmacol Exp Ther, 2006, 316, 315-324.

May et al., "Allosteric Modulation of G Protein-Coupled Receptors", Annu Rev Pharmacol Toxicol, 2007, 47, 14.1-14.51.

May et al., "Regional Serotonin Receptor Studies: Chronic Methysergide Treatment Induces a Selective and Dose-Dependent Decrease in Serotonin-2 Receptors in Mouse Cerebral Cortex", Life Sciences, 1986, 38(19), 1741-1747.

Mayers et al., "Antidepressants and Their Effect on Sleep", Hum Psychopharmacol., 2005, 20, 5333-559.

Mayo Clinic, "Mental Illness", 2012, 1-13.

McClintock et al., "Assessing Anxious Features in Depressed Outpatients" Int. J. Methods Psychiatr. Res. 20(4): E69-E82 (2011).

McDermott et al., "Design and Analysis of Two-Period Studies of Potentially Disease-Modifying Treatments", Controlled Clinical Trials, 2002, 23, 635-649.

McElroy, "A 52-Week, Open-Label Continuation Study of Lamotrigine in the Treatment of Bipolar Depression", J. Clin. Psychiatry, 2004, 204-210.

McEvoy et al., "Effectiveness of Clozapine Versus Olanzapine, Quetiapine, and Risperidone in Patients with Chronic Schizophrenia Who Did Not Respond to Prior Atypical Antipsychotic Treatment", Am J Psychiatry, 2006, 163(4), 600-610.

McIntyre et al., "Quetiapine Adjunct to Selective Serotonin Reuptake Inhibitors or Venlafaxine in Patients with Major Depression, Comorbid Anxiety, and Residual Depressive Symptoms: A Randomized, Placebo-Controlled Pilot Study", Depression and Anxiety, 2007, 24, 487-494.

Meador-Woodruff et al., "Glutamate Receptor Expression in Schizophrenic Brain", Brain Res., 2000, 31(2-3), 288-294.

Melancon et al., "Allosteric Modulation of 7 Transmembrane Spanning Receptors: Theory, Practice and Opportunities for CNS Drug Discovery", J Med Chem, 2012, 55(4), 1445-1464.

Melartin et al., "Current Comorbidity of Psychiatric Disorders Among DSM-IV Major Depressive Disorder Patients in Psychiatric Care in the Vantaa Depression Study", J Clin Psychiatry, 2002, 63, 126-134.

Meldrum et al., "Excitatory Amino Acid Neurotoxicity and Neurodegenerative Disease", Trends in Pharmacological Sciences, 1990, 11(9), 379-387.

Meldrum et al., "Glutamate Receptors and Trasnporters in Genetic and Acquired Models of Epilepsy", Epilepsy Res, 1999, 36, 189-204.

Meltzer et al., "Serotonin Receptors: Their Key Role in Drugs to Treat Schizophrenia", Prog. Neuropsychopharmacol. Biol. Psychiatry, 2003, 27(7), 1159-1172.

Meltzer, "Illuminating the Molecular Basis for Some Antipsychotic Drug-Induced Metabolic Burden", Proc. Natl. Acad. Sci. USA, 2007, 104(9), 3019-3020.

Merikangas et al., "Longitudinal Trajectories of Depression and Anxiety in a Prospective Community Study", Arch Gen Psychiatry, 2003, 60, 993-1000.

Metman, "Huntington's Disease A Randomized, Controlled Trial Using the NMDA-Antagonist Amantadine", Neurology, 2002, 59, 694-699.

Mexican Patent Application No. MX/a/2009/009422: Office Action dated Jun. 28, 2011, 5 pages.

Mezler et al., "Ly2140023, A Prodrug of the Group II Metabotropic Glutamate Receptor Agonist Ly-404039 for the Potential Treatment of Schizophrenia", Current Opinion in Investigational Drugs, 2010, 11(7), 833-845.

Michael et al., "Metabolic Changes Within the Left Dorsolateral Prefrontal Cortex Occurring with Electroconvulsive Therapy in Patients with Treatment Resistant Unipolar Depression", Psychol Med, 2003, 33(7), 1277-1284.

Michael et al., "Neurotrophic Effects of Eletroconvulsive Therapy: A Proton Magnetic Resonance Study of the Left Amygdalar Region in Patients with Treatment-Resistant Depression", Neuropsychopharmacology, 2003, 28(4), 720-725.

Michelson, "Clinical Studies with Mglur2/3 Agonists: Ly354740 Compared with Placebo in Patients with Generalized Anxiety Disorder", Neuropharmacol., 2005, 49, 257.

Miller, "Mechanisms of Action of Antipsychotic Drugs of Different Classes, Refractoriness to Therapeutic Effects of Classical Neuroleptics, and Individual Variation in Sensitivity to Their Actions: Part I", Current Neuropharmacology, 2009, 7, 302-314.

Miller et al., "Roles of Metabotropic Glutamate Receptors in Brain Plasticity and Pathology", Annals of the New York Academy of Sciences, 1995, 757, 460-474.

Mills et al., "Epidemiology and Reporting of Randomized Trials Employing Re-Randomization of Patient Groups: A Systematic Survey", Contemporary Clinical Trials, 2007, 28, 268-275.

Mitchell et al., "An Update on the Role of Glutamate in the Pathophysiology of Depression", Acta Psychiatrica Scandinavica, 2010, 122(3), 192-210.

Mitri et al., "Divergent Evolution in Metabotropic Glutamate Receptors. A New Receptor Activated by an Endogenous Ligand Different from Glutamate in Insects", Journal of Biological Chemistry, 2004, 279(10), 9313-9320.

Mittal et al., "Impact of Comorbid Anxiety Disorders on Health-Related Quality of Live Among Patients with Major Depressive Disorder", Psychiatric Services, 2006, 57(12), 1731-1737.

Miuller et al., "The Immunological Basis of Glutamatergic Disturbance in Schizophrenia: Towards an Integrated View", J Neural Transm, 2007, 72, 269-280.

Miyamoto et al., "Effects of Ketamine, Mk-801, and Amphetamine on Regional Brain 2-Deoxyglucose Uptake in Freely Moving Mice", Neuropsychopharmacology, 2000, 22, 400-412.

Miyamoto et al., "Treatments for Schizophrenia: A Critical Review of Pharmacology and Mechanisms of Action of Antipsychotic Drugs", Mol. Psychiatry, 2005, 10, 79-104.

Modafferi "Morphine Withdrawal Increases Metabotropic Glutamate 2/3 Receptors Expression in Nucleus Accumbens", Neurochemistry, 2008, 19(9), 911-914.

Moffitt et al., "Depression and Generalized Anxiety Disorder", Arch. Gen. Psychiatry, 2007, 64, 651-660.

Moghaddam et al., "Activation of Glutamatergic Neurotransmission by Ketamine: A Novel Step in the Pathway from NMDA Receptor Blockade to Dopaminergic and Cognitive Disruptions Associated with the Prefrontal Cortex", J Neurosci. 1997, 17(8), 2921-2927.

Moghaddam et al., "From Revolution to Evolution: the Glutamate Hypothesis of Schizophrenia and Its Implication for Treatment", Neuropsychopharmacology, 2012, 37, 4-15.

Moghaddam et al., "Reversal of Phencyclidine Effects by a Group II Metabotropic Glutamate Receptor Agonist in Rats", Science, 1998, 281, 1349-1352.

Moghaddam, "Targeting Metabotropic Glutamate Receptors for Treatment of the Cognitive Symptoms of Schizophrenia", Psychopharmacology, 2004, 174(1), 39-44.

Moldrich et al., "Anti-Epileptic Activity of Group II Metabotropic Glutamate Receptor Agonists (−)-2-Oxa-4-Aminobicyclo[3.1.0]Hexane-4,6-Dicarboxylate (Ly379268) and (−)-2-Thia-4-Aminobicyclo[3.1.0]Hexane-4,6-Dicarboxylate (Ly389795)", Neuropharmacology, 2001, 41, 8-18.

(56) References Cited

OTHER PUBLICATIONS

Moldrich et al., "Astrocyte Mglu(2/3)-Mediated Camp Potentiation is Calcium Sensitive: Studies in Murine Neuronal and Astrocyte Cultures", Neuropharmacology, 2002, 43(2), 189-203.

Moldrich et al., "Emerging Signalling and Protein Interactions Mediated via Metabotropic Glutamate Receptors", Curr. Drug Targets. CNS Neurol. Disord., 2003, 2(2), 109-122.

Molina et al., "Polymorphic Variation at the Serotonin 1-A Receptor Gene is Associated with Comorbid Depression and Generalized Anxiety", Psychiatry Genetics, 2011, 21, 195-201.

Molinaro et al., "Activation of Mglu2/3 Metabotropic Glutamate Receptors Negatively Regulates the Stimulation of Inositol Phospholipid Hydrolysis Mediated by 5-Hydroxytryptamine2a Serotonin Receptors in the Frontal Cortex of Living Mice", Mol. Pharmacol., 2009, 76(2), 379-387.

Mondon et al., "Synthesis of Narciprimine and Related Compounds", Chem. Ber., 1972, 105, 3726-3747.

Monn et al., "Design, Synthesis, and Pharmacological Characterization of (+)-2-Aminobicyclo[3.1.0]Hexane-2,6-Dicarboxylic Acid (Ly354740): A Potent, Selective, and Orally Active Group 2 Metabotropic Glutamate Receptor Agonist Possessing Anticonvulsant and Anxiolytic Properties", J Med Chem, 1997, 40, 528-537.

Monn et al., "Synthesis and Metabotropic Glutamate Receptor Activity of S-Oxidized Variants of (−)-4-Amino-2-Thiabicyclo-[3.1.0]Hexane-4,6-Dicarboxylate: Identification of Potent, Selective, and Orally Bioavailable Agonists for Mglu2/3 Receptors", J. Med. Chem., 2007, 50, 233-240.

Monn et al., "Synthesis, Pharmacological Characterization, and Molecular Modeling of Heterobicyclic Amino Acids Related to (+)-2-Aminobicyclo[3.1.0] Hexane-2,6-Dicarboxylic Acid (Ly354740): Identification of Two New Potent, Selective, and Systemically Active Agonists for Group II Metabotropic Glutamate Receptors", Journal of Medicinal Chemistry, 1999, 42(6), 1027-1040.

Monti et al., "Conventional and Power Spectrum Analysis of the Effects of Zolpidem on Sleep Eeg in Patients with Chronic Primary Insomnia", Sleep, 2000, 23, 1075-1084.

Mora et al., "Role of 5-Ht2a and 5-Ht2c Receptor Subtypes in the Two Types of Fear Generated by the Elevated T-Maze", Pharmacology Biochemistry and Behavior, 1997, 58, 1051-1057.

Moreno et al., "Group II Metabotropic Glutamate Receptors and Schizophrenia", Cell Mol. Life Sci., 2009, 66(23), 3777-3785.

Moreno et al., "Maternal Influenza Viral Infection Causes Schizophrenia-Like Alterations of 5-Ht2a and Mglu2 Receptors in the Adult Offspring", Journal of Neuroscience, 2011, 31(5), 1863-1872.

Moreno et al., "Metabotropic Glutamate Mglu2 Receptor is Necessary for the Pharmacological and Behavioral Effects Induced by Hallucinogenic 5-Ht2a Receptor Agonists", Neurosci. Lett., 2011, 493, 76-79.

Moreno et al., "Pindolol Augmentation of Treatment-Resistant Depressed Patients" J Clin Psychiatry 1997, 58, 437-439.

Morgan et al., "Is Persistent Ketamine Use a Valid Model of the Cognitive and Oculomotor Deficits in Schizophrenia?", Biol. Psychiatry, 2009, 65(12), 1099-1102.

Morikawa et al., "Two Intracellular Pathways Mediate Metabotropic Glutamate Receptor-Induced Ca2+ Mobilization in Dopamine Neurons", Journal of Neuroscience, 2003, 23(1), 149-157.

Morishima et al., "Enhanced Cocaine Responsiveness and Impaired Motor Coordination in Metabotropic Glutamate Receptor Subtype 2 Knockout Mice", Proc. Natl. Acad. Sci., 2005, 102(11), 4170-4175.

Morishita, "Clonazepam as a Therapeutic Adjunct to Improve the Management of Depression: A Brief Review", Hum Psychopharmacol Clin Exp, 2009, 24, 191-198.

Moroni et al., "Poly(Adp-Ribose) Polymerase Inhibitors Attenuate Necrotic But Not Apoptotic Neuronal Death in Experimental Models of Cerebral Ischemia", Cell Death and Differentiation, 2001, 8, 921-932.

Morpurgo et al., "Drug-Induced Modifications of Discriminated Avoidance Behavior in Rats", Psychopharmacol., 1965, 8, 91-99.

Morrison et al., "Schizophrenia: More Evidence for Less Glutamate", Expert Rev Neurother., 2007, 7 (1), 29-31.

Moussawi et al., "Group II Metabotropic Glutamate Receptors (Mglu2/3) in Drug Addiction", European Journal of Pharmacology, 2010, 639, 115-122.

Mudge et al., "Genomic Convergence Analysis of Schizophrenia: Mrna Sequencing Reveals Altered Synaptic Vesicular Transport in Post-Mortem Cerebellum", Plos One, 2008, 3(11) 1-24.

Mukhin et al., "Mglur Modulation of Post-Traumatic Neuronal Death: Role of NMDA Receptors", Neuroreport, 1997, 8(11), 2561-2566.

Muller, "Inflammation and the Glutamate System in Schizophrenia: Implications for Therapeutic Targets and Drug Development", Expert Opin. Ther. Targets, 2008, 12(12), 1497-1507.

Muly et al., "Group II Metabotropic Glutamate Receptors in Anxiety Circuitry: Correspondence of Physiological Response and Subcellular Distribution", J Comp Neurol., 2007, 505(6), 682-700.

Muntasir et al., "Inverse Agonist Activity of Sarpogrelate, a Selective 5-Ht2a-Receptor Antagonist, at the Constitutively Active Human 5-Ht2a Receptor", Journal of Pharmacological Sciences, 2006, 102(2), 189-195.

Murck et al., "State Markers of Depression in Sleep Eeg: Dependency on Drug and Gender in Patients Treated with Tianepine or Paroxetine", Neuropsychopharmacol. 2003, 28, 348-358.

Muto et al., "Structures of the Extracellular Regions of the Group II/III Metabotropic Glutamate Receptors", Proc. Natl. Acad. Sci. USA, 2007, 104(10), 3759-3764.

Nabeshima et al., "Animal Model of Schizophrenia. Dysfunction of Nmda Receptor-Signaling in Mice Following Withdrawal from Repeated Administration of Phencyclidine", Ann. N.Y. Acad. Sci., 2006, 1086, 160-168.

Nadin et al., "Synthesis of Tricyclic Pyridones by Radical Cyclization", Tetrahedron Letters, 1999, 40, 4073-4076.

Naimoli et al., "Compound A, A Novel Potent and Selective Mglur2 Positive Allosteric Modulator: III. Effects in Clinically Relevant Translational Cognition Models That Could be Used as Biomarkers" Poster 767.1 Presented at the 40th Annual Meeting of Society for Neuroscience, Nov. 2010, 1 page.

Nasca et al., "L-Acetylcarnitine Causes Rapid Antidepressant Effects Through the Epigenetic Induction of Mglu2 Receptors", Proceedings of the Nat. Acad. of Sci. of US, 2013, 110(12), 4804-4809.

Neale, "The Neurotransmitter N-Acetylaspartylglutamate in Models of Pain, Als, Diabetic Neuropathy CNS Injury and Schizophrenia", Trends in Pharmacological Sciences 2005, 26(9), 477-484.

Neki et al., "Metabotropic Glutamate Receptors Mglur2 and MglurS are Expressed in Two Non-Overlapping Populations of Golgi Cells in the Rat Cerebellum", Neuroscience, 1996, 75(3), 815-826.

Neki et al., "Pre- and Postsynaptic Localization of a Metabotropic Glutamate Receptor, Mglur2, in the Rat Brain: An Immunohistochemical Study with a Monoclonal Antibody", Neurosci. Lett., 1996, 202(3), 197-200.

Nelson, "Anxiety Does Not Predict Response to Duloxetine in Major Depression: Results of a Pooled Analysis of Individual Patient Data From 11 Placebo-Controlled Trials", Depression and Anxiety, 2010, 27, 12-18.

Nelson et al., "Anxiety Does Not Predict Response to Antidepressant Treatment in Late Life Depression: Results of a Meta-Analysis", Int J Geriatr Psychiatry, 2009, 24, 539-544.

Nelson et al., "Species Differences in the Pharmacology of the 5-Hydroxytrayptamine2 Receptor: Structurally Specific Differentiation by Ergolines and Tryptamines", Jpet, 1993, 265, 1272-1279.

Nelson, "Anxious Depression and Response to Treatment", Am J Psychiatry, 2008, 165(3), 297-299.

Nestler, "Common Molecular and Cellular Substrates of Addiction and Memory", Neurobiol. of Learning and Memory, 2002, 78, 637-647.

Neubig et al., "Specificity of Receptor-G Protein Coupling: Protein Structure and Cellular Determinants", Seminars in Neuroscience, 1998, 9, 189-197.

Neugebauer et al., "Groups II and III Metabotropic Glutamate Receptors Differentially Modulate Brief and Prolonged Nociception in Primate Stt Cells", J Neurophysiol, 2000, 84, 2998-3009.

(56) References Cited

OTHER PUBLICATIONS

Neugebauer et al., "Peripheral Metabotropic Glutamate Receptors as Drug Targets for Pain Relief", Expert Opinion on Therapeutic Targets, 2002, 6(3), 349-361.

Neugebauer et al., "Requirement of Metabotropic Glutamate Receptors for the Generation of Inflammation-Evoked Hyperexcitability in Rat Spinal Cord Neurons", European Journal of Neuroscience, 1994, 6(7), 1179-1186.

Neugebauer, "Metabotropic Glutamate Receptors—Important Modulators of Nociception and Pain Behavior", Pain, 2002, 98, 1-8.

"Neuroprotection as Initial Therapy in Acute Stroke, Third Report of an Ad Hoc Consensus Group Meeting", European Ad Hoc Consensus Group, Cerebrovascular Diseases 1998, 8(1), 59-72.

Ngomba et al., "Metabotropic Glutamate Receptors in the Thalamocortical Network: Strategic Targets for the Treatment of Absence Epilepsy", Epilepsia, 2011, 52(7), 1211-1222.

Ngomba et al., "The Preferential Mglu2/3 Receptor Antagonist, Ly341495, Reduces the Frequency of Spike-Wave Discharges in the Wag/Rij Rat Model of Absence Epilepsy", Neuropharmacology, 2005, 49, 89-103.

Nguyen et al., "An in Vivo Biosensor for Neurotransmitter Release and In Situ Receptor Activity", Nature Neuroscience, 2010, 13(1), 127-32.

Nicholls et al., "Mglur2 Acts Through Inhibitory G? Subunits to Regulate Transmission and Long-Term Plasticity at Hippocampal Mossy Fiber-Ca3 Synapses", Proc. Natl. Acad. Sci. USA, 2006, 103(16), 6380-6385.

Nicholls et al., "The Release and Uptake of Excitatory Amino Acids", Trends in Pharmacological Sciences, 1990, 11(11), 462-468.

Nicolas et al., "A Combined Marble Buyring-Locomotor Activity Test in Mice: A Practical Screening Test with Sensitivity to Different Classes of Anxiolytics and Antidepressants", Eur J Pharmacol., 2006, 547(1-3), 106-115.

Nicoletti et al., "Lesions of Putative Glutamatergic Pathways Potentiate the Increase of Inositol Phospholipid Hydrolysis Elicited by Excitatory Amino Acids", Brain Research, 1987, 436(1), 103-112.

Nicoletti et al., "Metabotropic Glutamate Receptors: Beyond the Regulation of Synaptic Transmission", Psychoneuroendocrinology, 2007, 32(Suppl 1), S40-S45.

Nicoletti et al., "Metabotropic Glutamate Receptors: from the Workbench to the Bedside", Neuropharmacology, 2011, 60, 1017-1041.

Nicoletti et al., "Metabotropic Glutamate Receptors: New Targets for the Control of Tumor Growth", Trends in Pharmacological Sciences, 2007, 206-213.

Nicoletti et al., "Pertussis Toxin Inhibits Signal Transduction at a Specific Metabolotropic Glutamate Receptor in Primary Cultures of Cerebellar Granule Cells", Neuropharmacology, 1988, 27(6), 551-556.

Nielson et al., "Phosphoramides XIV. Phosphorus Pentozide and Amine Hydrochlorides as Reagents in the Synthesis of Thieno{2,3-D]Pyrimidin-4(3h)-Ones", Chemica Scripta, 1981, 18, 135-138.

Niemegeers et al., "Direct Measurement of the Ph in the Stomach of the Conscious Rat, Using a Special Electrode", Experentia, 1979, 35, 1538-1539.

Niemegeers et al., "Interaction of Drugs with Apomorphine, Tryptamine, and Norepinephrine. A New 'In Vivo' Approach: the Atn-Test in Rats", Arch. Int. Pharmacodyn., 1977, 227, 238-253.

Niemegeers et al., "Protection of Rats from Compound 48/80-Induced Lethality. A Simple Test for Inhibitors of Mast Cell-Mediated Shock", Arch. Int. Pharmacodyn., 1978, 234, 164-176.

Nierenberg et al., "Lithium Augmentation of Nortriptyline for Subject Resistant to Multiple Antidepressants", J Clin Psychopharmacol, 2003, 23, 92-95.

Nijholt et al., "Neuronal Akap150 Coordinates Pka and Epac-Mediated Pkb/Akt Phosphorylation", Cellular Signaling, 2008, 20, 1715-1724.

Nikiforuk et al., "Effects of a Positive Allosteric Modulator of Group II Metabotropic Glutamate Receptors, Ly487379, on Cognitive Flexibility and Impulsive-Like Responding in Rats", Jpet, 2010, 335, 665-673.

Ninomiya et al., "Photocyclisation of Enamides. Part 14. Substituent Effects in the Photocyclisation of N-A,B-Unsaturated Acylanilides", J. Chem. Soc. Perkin Transactions, 1980, 1, 197-202.

Nishi et al., "Pharmacological Characterization of Metabotropic Glutamate Receptor-Mediated High-Affinity Gtpase Activity in Rat Cerebral Cortical Membranes", British Journal of Pharmacology, 2000, 130, 1664-1670.

Niswender et al., "Metabotropic Glutamate Receptors: Physiology, Pharmacology, and Disease", Annu Rev Pharmacol Toxicol, 2010, 50, 295-322.

Nofzinger et al., "Changes in Forebrain Function from Waking to Rem Sleep in Depression: Preliminary Analyses of [18f]Fdg Pet Studies", Psychiatry Res, 1999, 91, 59-78.

Noguchi et al., "Quantum Chemical Study on Conformational Properties of Bipyridine Cardiotonics", Chem. Pharm. Bull., 1993, 41(8), 1331-1336.

Nordquist, "Metabotropic Glutamate Receptor Modulation, Translational Methods, and Biomarkers: Relationships with Anxiety", Psychopharmacology, 2008, 199, 389-402.

Norman et al., "Structure-Activity Relationships of a Series of Pyrrolo[3,2-D]Pyrimidine Derivatives and Related Compounds as Neuropeptide Y5 Receptor Antagonists", J. Med. Chem., 2000, 43, 4288-4312.

O'Brien et al., "Molecular Mechanisms of Glutamate Receptor Clustering at Excitatory Synapses", Current Opinion in Neurobiology, 1998, 8(3), 364-369.

O'Connor et al., "Metabotropic Glutamate Receptor 7: At the Interface of Cognition and Emotion", European Journal of Pharmacology, 2010, 639, 123-131.

O'Neill et al., "Effects of Ischaemic Conditions on Uptake of Glutamate, Aspartate, and Noradrenaline by Cell Lines Derived from the Human Nervous System", Journal of Neurochemistry, 1994, 63(2), 603-611.

O'Neill et al., "Recent Developments in Metabotropic Glutamate Receptors as Novel Drug Targets", Drugs of the Future, 2010, 35, 307-324.

Odagaki et al., "Functional Coupling Between Metabotropic Glutamate Receptors and G-Proteins in Rat Cerebral Cortex Assessed by Guanosine-5'-O-(3-[35s]Thio)Triphosphate ([35s]Gtpys) Binding Assay", Basic & Clinical Pharmacology & Toxicology, 2011, 44 pages.

Odagaki et al., "Group II Metabotropic Glutamate Receptor-Mediated Activation of G-Proteins in Rat Hippocampal and Striatal Membranes", Neuroscience Letters, 2013, 24 pages.

Oehlrich, "Positive Allosteric Modulation of Mglur2 Receptors in the Treatment of CNS Disorders", Neuroscience Med Chem, 2012, 31 pages.

Ohishi et al., "Distribution of the Messenger Rna for Metabotropic Glutamate Receptor, Mglu2, in the Central Nervous System of the Rat", Neuroscience, 1993, 53, 1009-1018.

Olbrich et al., "Frontolimbic Glutamate Alterations in First Episode Schizophrenia: Evidence From a Magnetic Resonance Spectroscopy Study", World J Biol Psychiatry, 2008, 9(1), 59-63.

Oldenziel et al., "In Vivo Monitoring of Extracellular Glutamate in the Brain with a Microsensor", Brain Res., 2006, 1118(1), 34-42.

Olive, "Cognitive Effects of Group I Metabotropic Glutamate Receptor Ligands in the Context of Drug Addiction", European Journal of Pharmacology, 2010, 639, 47-58.

Olive, Metabotropic Glutamate Receptor Ligands as Potential Therapeutics for Addiction. Curr. Drug Abuse Rev 2009, 2 (1), 83-98.

Olivier et al., "Stress-Induced Hyperthermia and Anxiety: Pharmacological Validation", Eur J Pharmacol, 2003, 463, 117-132.

Olney et al., "NMDA Receptor Hypofunction Model of Schizophrenia", Journal of Psychiatric Research, 1999, 33, 523-533.

Olszewski et al., "Naag Peptidase Inhibition Reduces Locomotor Activity and Some Stereotypes in the Pcp Model of Schizophrenia Via Group II Mglur", J. Neurochem., 2004, 89(4), 876-885.

Olszewski et al., "Phencyclidine and Dizocilpine Induced Behaviors Reduced by N-Acetylaspartylglutamate Peptidase Inhibition Via Metabotropic Glutamate Receptors", Biol. Psychiatry, 2008, 63(1), 86-91.

(56) References Cited

OTHER PUBLICATIONS

Ong et al., "Localisation of Glutamate Receptors in the Substantia Nigra Pars Compacta of the Monkey", Journal Fur Hirnforschung, 1997, 38(3), 291-298.

Oquendo et al., "A Computer Algorithm for Calculating the Adequacy of Antidepressant Treatment in Unipolar and Bipolar Depression", J Clin Psychiatry, 2003, 64(7), 825-833.

Orlando, "The Role of Group I and Group II Metabotropic Glutamate Receptors in Modulation of Striatal Nmda and Quinolinic Acid Toxicity", Experimental Neurology, 2001, 167, 196-204.

Orlowski et al., "D- and L-Stereoisomers of Allylglycine: Convulsive Action and Inhibition of Brain L-Glutamate Decarboxylase", J Neurochem, 1977, 28, 349-353.

Orrenius et al., "Calcium Ions and Oxidative Cell Injury", Annals of Neurology, 1992, 32 (Suppl-42), S33-S42.

Osikowicz et al., "Glutamate Receptor Ligands Attenuate Allodynia and Hyperalgesia and Potentiate Morphine Effects in a Mouse Model of Neuropathic Pain", Pain, 2008, 139, 117-126.

Ossowska et al., "The Role of Glutamate Receptors in Antipsychotic Drug Action", Amino. Acids, 2000, 19(1), 87-94.

Ossowska et al., "The Striatum as a Target for Anti-Rigor Effects of an Antagonist of Mglur1, But Not an Agonist of Group II Metabotropic Glutamate Receptors", Brain Research, 2002, 950, 88-94.

O'suilleabhain, "A Randomized Trial of Amantadine in Huntington Disease", Arch Neurol, 2003, 60, 996-998.

Othmer et al., "Brain Functions and Psychiatric Disorders: A Clinical View", Diagnostic Dilemmas, Part I, The Psychiatryc Clinics of N.A., Sep. 1998, 21(3), 517-566.

Ottersen et al., "Organization of Glutamate Receptors at the Synapse", European Journal of Neuroscience, 1997, 9(11), 2219-2224.

Overstreet et al., "A 5-Ht1a Agonist and a 5-Ht2c Antagonist Reduce Social Interaction Deficit Induced by Multiple Ethanol Withdrawals in Rats", Psychopharmacology, 2003, 167, 344-352.

Ozawa et al., "Glutamate Receptors in the Mammalian Central Nervous System", Progress in Neurobiology, 1998, 54(5), 581-618.

Page et al., "Metabotropic Glutamate Receptors Inhibit Mechanosensitivity in Vagal Sensory Neurons", Gastroenterology, 2005, 128(2), 402-410.

Pajer et al., "Discovery of Blood Transcriptomic Markers for Depression in Animal Models and Pilot Validation in Subjects with Early-Onset Major Depression", Transl Psychiatry, 2012, 2(E101), 10 pages.

Pajonk et al., "Comparing the Efficacy of Atypical Antipsychotics in Open Uncontrolled Versus Double-Blind Controlled Trials in Schizophrenia", Psychopharmacology (Berl.), 2002, 162(1), 29-36.

Palazzo et al., "Metabotropic and Nmda Glutamate Receptors Participate in the Cannabinoid-Induced Antinociception", Neuropharmacology, 2001, 40(3), 319-326.

Palop et al., "Amyloid-B-Induced Neuronal Dysfunction in Alzheimer's Disease: From Synapses Toward Neural Networks", Nature Neuroscience, 2010, 13(7), 812-818.

Palucha et al., "Chronic Imipramine Treatment Reduces Inhibitory Properties of Group II Mglu Receptors Without Affecting Their Density or Affinity", Pharmacol. Rep., 2007, 59(5), 525-530.

Palucha et al., "Metabotropic Glutamate Receptor Ligands as Possible Anxiolytic and Antidepressant Drugs", Pharmacology & Therapeutics, 2007, 115, 116-147.

Palucha et al., "The Involvement of Glutamate in the Pathophysiology of Depression", Drug News Perspect, 2005, 18(4), 262-268.

Palucha, "Are Compounds Acting at Metabotropic Glutamate Receptors the Answer to Treating Depression?", Expert Opin. Investig. Drugs, 2006, 15(12), 1545-1553.

Palucha-Poniewiera et al., "On the Mechanism of the Antidepressant-Like Action of Group II Mglu Receptor Antagonist, Mgs0039", Psychopharmacology, 2010, 212, 523-535.

Panzer, "Are SSRIs Really More Effective for Anxious Depression?", Annals of Clinical Psychiatry, 2005, 17(1), 23-29.

Papakostas et al., "Augmentation of Antidepressants with Atypical Antipsychotic Medications for Treatment-Resistant Major Depressive Disorder: A Meta-Analysis", J Clin Psychiatry 2007, 68(6), 826-831.

Papakostas et al., "Efficacy of Bupropion and the Selective Serotonin Reuptake Inhibitors in the Treatment of Major Depressive Disorder with High Levels of Anxiety (Anxious Depression): A Pooled Analysis of 10 Studies", J Clin Psychiatry, 2008, 69(8), 1287-1292.

Papakostas et al., "Fluxetine-Clonazepam Cotherapy for Anxious Depression: An Exploratory, Post-Hoc Analysis of a Randomized, Double Blind Study", International Clinical Psychopharmacology, 2010, 25, 17-21.

Papakostas et al., "Predictors, Moderators, and Mediators (Correlates) of Treatment Outcome in Major Depressive Disorder", Dialogues Clin Neurosci., 2008, 10, 439-451.

Papakostas et al., "Severe and Anxious Depression: Combining Definitions of Clinical Sub-Types to Identify Patients Differentially Responsive to Selective Serotonin Reuptake Inhibitors", European Neuropsychopharmacology, 2012, 22, 347-355.

Papakostas et al., "Testing Anxious Depression as a Predictor and Moderator of Symptom Improvement in Major Depressive Disorder During Treatment with Escitalopram", Eur Arch Psychiatry Clin Neurosci, 2011, 261, 147-156.

Parmentier et al., "A Model for the Functioning of Family 3 Gpcrs", Trends in Pharmacological Sciences, 2002, 23(6), 268-274.

Parnot et al., "Toward Understanding Gpcr Dimers", Nature Structural & Molecular Biology, 2004, 11(8), 691-692.

Parry et al., "Functionalized Pyridylboronic Acids and Their Suzuki Cross-Coupling Reactions to Yield Novel Heteroarylpyridines", J. Org. Chem., 2002, 67, 7541-7543.

Parsons et al., "Memantine: A NMDA Receptor Antagonist That Improves Memory by Restoration of Homeostasis in the Glutamatergic System—Too Little Activation Is Bad, Too Much Is Even Worse", Neuropharmacology, 2007, 53, 699-723.

Passchier et al., "Measuring Drug-Related Receptor Occupancy with Positron Emission Tomography", Methods, 2002, 27, 278-286.

Pastorino et al., "Pin1 Protects Against Alzheimer's Disease: One Goal, Multiple Mechanisms", Intech, 2013, 36 pages.

Patil, "Activation of Mglu2/3 Receptors as a New Approach to Treat Schizophrenia: A Randomized Phase 2 Clinical Trial", Nature Medicine, 2007, 13(9), 1102-1107.

Patkar et al., "A Randomized, Double-Blind, Placebo-Controlled Trial of Augmentation with an Extended Release Formulation of Methylphenidate in Outpatients with Treatment-Resistant Depression", J Clin Psychopharmacol, 2006, 26, 653-656.

Paykel et al., "Response to Phenelzine and Amitriptyline in Subtypes of Outpatient Depression", Arch Gen Psychiatry, 1982, 39, 1041-1049.

Pehrson et al., "Impact of Metabotropic Glutamate 2/3 Receptor Stimulation on Activated Dopamine Release and Locomotion", Psychopharmacology, 2010, 211, 443-455.

Pellicciari et al., "Metabotropic Glutamate Receptors: Structure and New Subtype-Selective Ligands", Il Farmaco, 2001, 56(1-2), 91-94.

Pellicciari et al., "Metabotropic G-Protein-Coupled Glutamate Receptors as Therapeutic Targets", Current Opinion in Chemical Biology, 1999, 3(4), 433-440.

Pellicciari et al., "Modulation of Glutamate Receptor Pathways in the Search for New Neuroprotective Agents", Farmaco, 1998, 53(4), 255-261.

Penninx et al., "Two-Year Course of Depressive and Anxiety Disorders: Results from the Netherlands Study of Depression and Anxiety (Nesda)", Journal of Affective Disorders, 2011, 133, 76-85.

Pereira et al., "Study Pharmacologic of the Gabaergic and Glutamatergic Drugs on Seizures and Status Epilepticus Induced by Pilocarpine in Adult Wistar Rats", Neuroscience Letters, 2007, 419, 253-257.

Perkins et al., "Pharmacokinetics, Metabolism, and Excretion of the Intestinal Peptide Transporter 1 (Slc15a1)-Targeted Prodrug (1s,2s,5r,6s)-2-[(2's)-(2-Amino)Propionyl]Aminobicyclo[3.1.0. ]Hexen-2,6-Dicarboxylic Acid (Ly544344) in Rats and Dogs: Assessment of First-Pass Bioactivation and Dose Linearity", Drug Metabolism and Disposition, 2007, 35, 1903-1909.

(56) References Cited

OTHER PUBLICATIONS

Perroy et al., "The C Terminus of the Metabotropic Glutamate Receptor Subtypes 2 and 7 Specifies the Receptor Signaling Pathways", Journal of Biological Chemistry, 2001, 276(49), 45800-45805.
Petroff, "Glutamate-Glutamine Cycling in the Epileptic Human Hippocampus", Epilepsia, 2002, 43(7) 703-710.
Pettmann et al., "Neuronal Cell Death", Neuron, 1998, 20(4), 633-647.
Pfeiffer et al., "Benzodiazepines and Adequacy of Initial Antidepressant Treatment for Depression", J Clin Psychopharmacol, 2011, 31, 360-364.
Piccinin et al., "Interaction Between Ephrins and Mglu5 Metabotropic Glutamate Receptors in the Induction of Long-Term Synaptic Depression in the Hippocampus", Journal of Neuroscience, 2010, 30(8), 2835-2843.
Pietraszek et al., "The Role of Group I Metabotropic Glutamate Receptors in Schizophrenia", Amino Acids, 2006, 7 pages.
Pike, "Pet Radiotracers: Crossing the Blood-Brain Barrier and Surviving Metabolism", Trends Pharmacol Sci, 2009, 30, 431-440.
Pilc et al., "Mood Disorders: Regulation by Metabotropic Glutamate Receptors", Biochemical Pharmacology, 2008, 75, 997-1006.
Pin et al., "Evolution, Structure, and Activation Mechanism of Family 3/C G-Protein-Coupled Receptors", Pharmacology & Therapeutics, 2003, 98, 325-354.
Pin et al., "Get Receptive to Metabotropic Glutamate Receptors", Current Opinion in Neurobiology, 1995, 5(3), 342-349.
Pin et al., "Positive Allosteric Modulators for—Aminobutyric Acidb Receptors Open New Routes for the Development of Drugs Targeting Family 3 G-Protein-Coupled Receptors" Mol Pharmacol 2001, 60, 881-884.
Pin et al., "Release of Endogenous Amino Acids From Striatal Neurons in Primary Culture", Journal of Neurochemistry, 1986, 47(2), 594-603.
Pin et al., "The Metabotropic Glutamate Receptors: Structure and Functions", Neuropharmacology, 1995, 34(1), 1-26.
Pin et al., "Alternative Splicing Generates Metabotropic Glutamate Receptors Inducing Different Patterns of Calcium Release in *Xenopus* Oocytes", Proceedings of the National Academy of Sciences of the USA, 1992, 89(21), 10331-10335.
Pinhasov et al., "Reduction of Submissive Behavior Model for Antidepressant Drug Activity Testing: Study Using a Video-Tracking System", Behav Pharmacol, 2005, 16, 657-664.
Pinheiro et al., "Presynaptic Glutamate Receptors: Physiological Functions and Mechanisms of Action", Nat. Rev Neurosci., 2008, 9(6), 423-436.
Pinkerton et al., "Allosteric Potentiators of the Metabotropic Glutamate Receptor 2 (Mglu2). Part 1: Identification and Synthesis of Phenyl-Tetrazolyl Acetophenones", Bioorganic & Medicinal Chemistry Letters, 2004, 14, 5329-5332.
Pinkerton et al., "Allosteric Potentiators of the Metabotropic Glutamate Receptor 2 (Mglu2). Part 2: 4-Thiopyridyl Acetophenones as Non-Tetrazole Containing Mglu2 Receptor Potentiators", Bioorganic & Medicinal Chemistry Letters, 2004, 14, 5867-5872.
Pinkerton et al., "Substituted Acetophenones as Selective and Potent Allosteric Potentiators of the Metabotropic Glutamate Receptor 2 (Mglur2)", 229th ACS National Meeting, Mar. 2005, 1 page.
Pinkerton, "Allosteric Potentiators of the Metabotropic Glutamate Receptor 2 (Mglu2). Part 3: Identification and Biological Activity of Indanone Containing Mglu2 Receptor Potentiators", Bioorganic & Medicinal Chemistry Letters, 2005, 15, 1565-1571.
Pittenger et al., "Stress, Depression, and Neuroplasticity: A Convergence of Mechanisms", Neuropsychopharmacology, 2008, 33(1), 88-109.
Pitts et al., "Lactate Metabolism in Anxiety Neurosis",New England Journal of Medicine, 1967, 277, 1329-1336.
Pizzi et al., "Activation of Multiple Metabotropic Glutamate Receptor Subtypes Prevents NMDA-Induced Excitotoxicity in Rat Hippocampal Slices", European Journal of Neuroscience, 1996, 8(7), 1516-1521.
Popik et al., "Selective Agonist of Group II Glutamate Metabotropic Receptors, Ly354740, Inhibits Tolerance to Analgesic Effects of Morphine in Mice", British Journal of Pharmacology, 2000, 130, 1425-1431.
Porsolt et al., "Behavioural Despair in Mice: A Primary Screening Test for Antidepressants", Arch. Int. Pharmacodyn., 1977, 229, 327-336.
Porsolt et al., "Behavioural Despair in Rats: A New Model Sensitive to Antidepressant Treatments", Eur. J. Pharmacol., 1978, 47(4), 379-391.
Porter et al., "(S)-Homoquisqualate: A Potent Agonist at the Glutamate Metabotropic Receptor", British Journal of Pharmacology, 1992, 106(3), 509-510.
Posluns, "An Analysis of Chlorpromazine-Induced Suppression of the Avoidance Response.", Psychopharmacol. 3: 361-373 (1962).
Posner et al., "Columbia Classification Algorithm of Suicide Assessment (C-Casa): Classification of Suicidal Events in the FDA's Pediatric Suicidal Risk Analysis of Antidepressants", American Journal of Psychiatry, 2007, 164, 1035-1043.
Poyurovsky et al., "Lamotrigine Augmentation in Schizophrenia and Schizoaffective Patients with Obsessive-Compulsive Symptoms", J Psychopharmacol., 2010, 24(6), 861-866.
Prabakaran et al., "2-D Dige Analysis of Liver and Red Blood Cells Provides Further Evidence for Oxidative Stress in Schizophrenia", Journal of Proteome Research, 2007, 6, 141-149.
Pralong et al., "Cellular Perspectives on the Glutamate-Monoamine Interactions in Limbic Lobe Structures and Their Relevance for Some Psychiatric Disorders", Progress in Neurobiology, 2002, 67, 173-202.
Prezeau et al., "Functional Crosstalk Between Gpcrs: With or Without Oligomerization", Current Opinion in Pharmacology, 2010, 10, 6-13.
Prezeau et al., "Pharmacological Characterization of Metabotropic Glutamate Receptors in Several Types of Brain Cells in Primary Cultures", Mol Pharmacol, 1993, 45(4), 570-577.
Prina et al., "Co-occurrence of Anxiety and Depression Amongst Older Adults in Low and Middle Income Countries: Findings From the 10/66 Study", Psychological Medicine, Oct. 2011, 41(10), 2047-2056.
Priolo et al., "Panic-Like Attack Induced by Microinfusion Into the Locus Coeruleus of Antagonists and Inverse Agonists at Gabaa-Receptors in Rodents", Funct Neurol, 1991, 6, 393-403.
Profaci et al., "Group II Mglur Agonist Ly354740 and Naag Peptidase Inhibitor Effects on Prepulse Inhibition in Pcp and D-Amphetamine Models of Schizophrenia", Psychopharmacology, 2011, 216, 235-243.
Prous Science Integrity 2007—Chemical Structure Ly-404039.
Prous Science Integrity 2007—Chemical Synthesis Ly-2140023.
Pszczolkowski et al., "Effect of Metabotropic Glutamate Receptor Agonists and Signal Transduction Modulators on Feeding by a Caterpillar", Pharmacology, Biochemistry and Behavior, 2005, 82, 678-685.
Putt et al., "An Enzymatic Assay for Poly(Adp-Ribose) Polymerase-1 (Parp-1) via the Chemical Quantitation of Nad+: Application to the High-Throughput Screening of Small Molecules as Potential Inhibitors", Analytical Biochemistry, 2004, 326, 78-86.
Quitkin et al., "Placebo Run-in Period in Studies of Depressive Disorders: Clinical, Heuristic and Research Implications", British Journal of Psychiatry, 1998, 173, 242-248.
Raffray et al., "Apoptosis and Necrosis in Toxicology: A Continuum or Distinct Modes of Cell Death?", Pharmacology & Therapeutics, 1997, 75(3), 153-177.
Rao et al., "Anxious Depression: Clinical Features and Treatment", Current Psychiatry Reports, 2009, 11, 429-436.
Raskin et al., "Differential Response to Chlorpromazine, Imipramine, and Placebo. A Study of Subgroups of Hospitalized Depressed Patients", Arch Gen Psychiat, 1970, 23, 164-173.
Ravaris et al., "Phenelzine and Amitriptyline in the Treatment of Depression: A Comparison of Present and Past Studies", Arch Gen Psychiatry, 1980, 37, 1075-1080.
Recasens et al., "Metabotropic Glutamate Receptors as Drug Targets", Current Drug Targets, 2007, 8(5), 651-681.

(56) References Cited

OTHER PUBLICATIONS

Redondo et al., "Selective Heteronuclear Noe Enhancements in Benzoheterocycles. Effect of Ring Size on Indirect Three-Spin Effects", Magnetic Resonance in Chemistry, 1988, 26, 511-517.
Regier et al., "Comorbidity of Mental Disorders with Alcohol and Other Drug Abuse. Results From the Epidemiologic Catchment Area (Eca) Study", Jama, 1990, 264, 2511-2518.
Rehwald et al., "3-Amino-2(1h)-Quinolones by Cyclization of N-Acylated Anthranilic Acid Derivatives", Heterocycles, 1997, 45(3), 483-492.
Reiner et al., "Bdnf May Play a Differential Role in the Protective Effect of the Mglur2/3 Agonist Ly379258 on Striatal Projection Neurons in R6/2 Huntington's Disease Mice", Brain Research, 2012, 1473, 161-172.
Reis et al., "Reactions of Tricarbonyl(Vinylketene)Iron(0) Complexes with Imines", Organometallics, 1995, 14, 1586-1591.
Reynolds et al., "New Approaches to the Drug Treatment of Schizophrenia", Adv. Pharmacol., 1995, 32, 461-503.
Reynolds et al., "Sleep Research in Affective Illness: State of the Art Circa", Sleep, 1987, 10, 199-215.
Rhebergen et al., "The 7-Year Course of Depression and Anxiety in the General Population", Acta Psychiatr Scand, 2011, 123, 297-306.
Ribeiro et al., "Group I Metabotropic Glutamate Receptor Signaling and Its Implication in Neurological Disease", CNS & Neurological Disorders—Drug Targets, 2010, 9, 574-595.
Ribeiro et al., "Metabotropic Glutamate Receptor-Mediated Cell Signaling Pathways are Altered in a Mouse Model of Huntington's Disease", Journal of Neuroscience, 2010, 30(1), 316-324.
Richards et al., "Distribution and Abundance of Metabotropic Glutamate Receptor Subtype 2 in Rat Brain Revealed by [3h]Ly354740 Binding in Vitro and Quantitative Radioautography: Correlation with the Sites of Synthesis, Expression, and Agonist Stimulation of [35s]Gtps Binding", J Comp Neurology, 2005, 487, 15-27.
Richardson-Burns et al., Metabotropic Glutamate Receptor Mrna Expression in the Schizophrenic Thalamus, Biol. Psychiatry, 2000, 47(1), 22-28.
Rickels et al., "Efficacy of Extended-Release Venlafaxine in Nondepressed Outpatients with Generalized Anxiety Disorder", Am J Psychiatry, 2000, 157, 968-974.
Rickels et al., "Long-Term Diazepam Therapy and Clinical Outcome", Jama, 1983, 250, 767-771.
Ried et al., "Reactions with Cyclobutenediones, Ix. 3-Hydroxy-Pyridones-(2) From Phenylcyclobutenedione and Enamines", Liebigs Ann. Chem., 1969, 725, 230-233.
Riedel et al., "Glutamate Receptor Function in Learning and Memory", Behavioural Brain Research, 2003, 140(1-2), 1-47.
Riederer et al., "Pharmacotoxic Psychosis After Memantine in Parkinson's Disease", Lancet, 1991, 338, 1022-1023.
Ritzen et al., "Molecular Pharmacology and Therapeutic Prospects of Metabotropic Glutamate Receptor Allosteric Modulators", Basic Clin Pharmacol Toxicol, 2005, 97, 202-213.
Robbe et al., "Role of P/Q-Ca2+ Channels in Metabotropic Glutamate Receptor 2/3-Dependent Presynaptic Long-Term Depression at Nucleus Accumbens Synapses", J Neurosci., 2002, 22(11), 4346-4356.
Robbe et al., "Metabotropic Glutamate Receptor 2 3-Dependent Long-Term Depression in the Nucleus Accumbens is Blocked in Morphine Withdrawn Mice", Eur. J Neurosci., 2002, 16(11), 2231-2235.
Robbins et al., "The Neuropsychopharmacology of Fronto-Executive Function: Monoaminergic Modulation", Annu Rev Neurosci, 2009, 32, 267-287.
Roberts et al., "Pharmacological Tools for the Investigation of Metabotropic Glutamate Receptors (Mglurs): Phenylglycine Derivatives and Other Selective Antagonists—An Update", Neuropharmacology, 1995, 34(8), 813-819.
Robins et al., "Establishment of Diagnostic Validity in Psychiatric Illness: Its Application to Schizophrenia", Amer J Psychiat, 1970, 126(7), 107-111.
Robison et al., "The Rearrangement of Isoquinoline-N-Oxides", J Org Chem, 1957, 21, 1337-1341.
Rodd et al., "The Metabotropic Glutamate 2/3 Receptor Agonist Ly404039 Reduces Alcohol-Seeking But Not Alcohol Self-Administration in Alcohol-Preferring (P) Rats", Behavioural Brain Research, 2006, 171, 207-215.
Rodriguez et al., "Attenuation of Ketamine-Induced Hyperactivity Responses in Rats Following Administration of a Novel Metabotropic Glutamate Receptor 2 Selective Positive Modulator", Annual Meeting of the Society for Neuroscience, Oct. 2004, Abstract No. 798.8, 2 pages.
Rodriguez et al., "Relationships Among Psychosocial Functioning, Diagnostic Comorbidity, and the Recurrence of Generalized Anxiety Disorder, Panic Disorder, and Major Depression", Anxiety Disorders, 2005, 19, 752-766.
Rodriguez-Moreno et al., "Kainate Receptors with a Metabotropic Modus Operandi", Trends Neurosci., 2007, 30(12), 630-637.
Rondard et al., "Coupling of Agonist Binding to Effector Domain Activation in Metabotropic Glutamate-Like Receptors", J Biol. Chem., 2006, 281(34), 24653-24661.
Rorick-Kehn et al., "Improved Bioavailability of the Mglu2/3 Receptor Agonist Ly354740 Using a Prodrug Strategy: In Vivo Pharmacology of Ly544344", J. Pharmacol. Exper. Therapeut., 2006, 316, 905-913.
Rorick-Kehn et al., "In Vivo Pharmacological Characterization of the Structurally Novel, Potent, Selective Mglu2/3 Receptor Agonist Ly404039 in Animal Models of Psychiatric Disorders", Psychopharmacology, 2007, 193, 121-136.
Rorick-Kehn et al., "Pharmacological and Pharmacokinetic Properties of a Structurally Novel, Potent, and Selective Metabotropic Glutamate 2/3 Receptor Agonist: in Vitro Characterization of Agonist (−)-(1r,4s,5s,6s)-4-Amino-2-Sulfonylbicyclo[3.1.0]-Hexane-4,6-Dicarboxylic Acid (Ly404039)" J. Pharmacol. Exper. Therapeut., 2007, 321, 308-317.
Rorick-Kehn et al., "Pharmacological Characterization of Stress-Induced Hyperthermia in Dba/2 Mice Using Metabotropic and Ionotropic Glutamate Receptor Ligands", Psychopharmacology (Berl)., 2005, 183(2), 226-40.
Ross et al., "Expression of Functional Metabotropic and Ionotropic Glutamate Receptors in Baculovirus-Infected Insect Cells", Neuroscience Letters, 1994, 173(1-2), 139-142.
Roth et al., "G Protein-Coupled Receptor (Gpcr) Trafficking in the Central Nervous System: Relevance for Drugs of Abuse", Drug & Alcohol Dependence, 1998, 51(1-2), 73-85.
Roth et al., "Synthesis of Small Molecule Inhibitors of the Orphan Nuclear Receptor Steroidogenic Factor-1 (Nr5a1) Based on Isoquinolinone Scaffolds", Bioorg Med Chem Lett, 2008, 18, 2628-2632.
Rothman et al., "Excitatory and the NMDA Receptor", Trends in Neurosciences, 1987, 10(7), 299-302.
Rovira et al., "Modeling the Binding and Function of Metabotropic Glutamate Receptors", Jpet, 2008, 325, 443-456.
Rowe et al., "Transposition of Three Amino Acids Transforms the Human Metabotropic Glutamate Receptor (Mglur)-3 Positive Allosteric Modulation Site to Mglur2, and Additional Characterization of the Mglur2 Positive Allosteric Modulation Site", J. Pharmacol. Exper. Therapeut., 2008, 326, 240-251.
Roy et al., "A Twin Study of Generalized Anxiety Disorder and Major Depression" Psychological Medicine, 1995, 5, 1037-1049.
Roychowdhury et al., "G Protein Alpha Subunits Activate Tubulin Gtpase and Modulate Microtubule Polymerization Dynamics", J. Biol. Chem., 1999, 274(19), 13485-13490.
Roychowdhury et al., "G Protein Beta1gamma2 Subunits Promote Microtubule Assembly", J. Biol. Chem., 1997, 272(50), 31576-31581.
Rozenfeld et al., "Receptor Heteromerization and Drug Discovery", Trends in Pharmacological Sciences, 2010, 31(3), 124-130.
Rudd et al., "Positive Allosteric Modulators of the Metabotropic Glutamate Receptor Subtype 2 (Mglur2)", Current Topics in Medicinal Chemistry, 2005, 5, 869-884.
Rush et al., "Comorbid Psychiatric Disorders in Depressed Outpatients: Demographic and Clinical Features", Journal of Affective Disorders, 2005, 87, 43-55.

(56) References Cited

OTHER PUBLICATIONS

Rush et al., "Response in Relation to Baseline Anxiety Levels in Major Depressive Disorder Treated with Bupropion Sustained Release or Sertraline", Neuropsychopharmacology, 2001, 25(1), 131-138.
Rush et al., "Sequenced Treatment Alternatives to Relieve Depression (Star*D): Rationale and Design", Controlled Clinical Trials, 2004, 25, 119-142.
Rush et al., "The Inventory for Depressive Symptomatology (Ids): Preliminary Findings", Psychiatry Res, May 1986, 18(1), 65-87.
Rush et al., "The Inventory of Depressive Symptomatology (Ids)—Preliminary Findings", Psychopharmacology Bulletin, 1986, 22(3), 985-990.
Rush et al., "The Inventory of Depressive Symptomatology (Ids): Psychometric Properties", Psycho! Med, May 1996, 26(3), 477-486.
Russell et al., "Amyloid-B Acts as a Regulator of Neurotransmitter Release Disrupting the Interaction Between Synaptophysin and Vamp2", Plos One, 2012, 7(8), E43201, 1-14.
Sackheim et al., "The Impact of Medication Resistance and Continuation Pharmacotherapy on Relapse Following Response to Electroconvulsive Therapy in Major Depression", J Clin Psychpharmacol, Apr. 1990, 10(2), 96-104.
Sagara et al., "The Activation of Metabotropic Glutamate Receptors Protects Nerve Cells from Oxidative Stress", J. Neurosci., 1998, 18(17), 6662-6671.
Sahara et al., "Cellular Localization of Metabotropic Glutamate Receptors Mglur1, 2/3, 5 and 7 in the Main and Accessory Olfactory Bulb of the Rat", Neuroscience Letters, 2001, 312(2), 59-62.
Sahni et al., "Compound A, A Novel, Potent and Selective Metabotropic Glutamate Receptor 2 (Mglur2) Positive Allosteric Modulator: I. Pharmacological Characterization" Poster 767.6 Presented at the $40^{th}$ Annual Meeting of Society for Neuroscience, Nov. 2010, 1 page.
Sajdyk et al., "Measurement of Panic-Like Responses Unit 9.17 Following Intravenous Infusion of Sodium Lactate in Panic-Prone Rats", Current Protocols in Neuroscience, 2003, 9.17.1-9.17.19.
Sakamoto et al., "Condensed Heteroaromatic Ring Systems. VIII. Synthesis 3-Substituted Isocoumarins from O-Halobenzoic Acid Derivatives", Chem. Pharm. Bull., 1986, 34(7), 2754-2759.
Sakharkar et al., "Druggability of Human Disease Genes", Int J Biochem. Cell Biol., 2007, 39(6), 1156-1164.
Salinska et al., "Metabotropic Glutamate Receptors (Mglurs) are Involved in Early Phase of Memory Formation: Possible Role of Modulation of Glutamate Release", Neurochemistry Intl, 2003, 43, 469-474.
Samadi et al., "Basal Ganglia Group II Metabotropic Glutamate Receptors Specific Binding in Non-Human Primate Model of L-Dopa-lnduced Dyskinesias", Neuropharmacology, 2008, 54(2), 258-268.
Samadi et al., "Metabotropic Glutamate Receptor II in the Brains of Parkinsonian Patients", J. Neuropathol. Exp. Neurol., 2009, 68(4), 374-382.
Sanacora et al., "Subtype-Specific Alterations of Gamma-Aminobutyric Acid and Glutamate in Patients with Major Depression", Arch Gen Psychiatry, 2004, 61, 705-713.
Sanacora et al., "Targeting the Glutamatergic System to Develop Novel, Improved Therapeutics for Mood Disorders", Nat Rev Drug Discov, May 2008, 7(5), 426-437.
Sanacora et al., "Towards a Glutamate Hypothesis of Depression: An Emerging Frontier of Neuropsychopharmacology for Mood Disorders", Neuropharmacology, 2012, 62, 63-77.
Sanders et al., "Regulation of Anxiety by Gabaa Receptors in the Rat Amygdala", Pharmacology, Biochemistry and Behavior, 1995, 52(4), 701-706.
Sanderson et al., "Syndrome Comorbidity in Patients with Major Depression or Dysthymia: Prevalence and Temporal Relationships", Am J Psychiatry, Aug. 1990, 147(8), 1025-1028.
Sanger et al., "Pharmacological Profiling of Native Group II Metabotropic Glutamate Receptors in Primary Cortical Neuronal Cultures Using a Flipr", Neuropharmacology 2012, 1-10.
Santi et al., "Temporal and Depolarization-Induced Changes in the Absolute Amounts of Mrnas Encoding Metabotropic Glutamate Receptors in Cerebellar Granule Neurons in Vitro", Journal of Neurochemistry, 1994, 63(4), 1207-1217.
Sareen et al., "Anxiety Disorders and Risk for Suicidal Ideation and Suicide Attempts", Arch Gen Psychiatry, 2005, 62, 1249-1257.
Sarichelou et al., "Metabotropic Glutamate Receptors Regulate Differentiation of Embryonic Stem Cells Into Gabaergic Neurons", Cell Death. Differ., 2008, 15(4), 700-707.
Sarter et al., "Cortical Cholinergic Transmission and Cortical Information Processing in Schizophrenia", Schizophr. Bull, 2005, 31(1), 117-138.
Satow et al., "Pharmacological Effects of the Metabotropic Glutamate Receptor 1 Antagonist Compared with Those of the Metabotropic Glutamate Receptor 5 Antagonist and Metabotropic Glutamate Receptor 2/3 Agonist in Rodents: Detailed Investigations with a Selective Allosteric Metabotropic Glutamate Receptor 1 Antagonist, Ftidc [4-[1-(2-Fluoropyridine-3-Yl)-5-Methyl-1h-1,2,3-Triazol-4-Yl]-Nisopropyl-N-Methyl-3,6-Dihydropyridine-1(2h)-Carboxamider]", J. Pharmacol. Exper. Therapeut., 2008, 326, 577-586.
Saugstad et al., "Cloning and Expression of a New Member of the L-2-Amino-4-Phosphonobutyric Acid-Sensitive Class of Metabotropic Glutamate Receptors", Mol Pharmacol, 1994, 45, 367-372.
Saugstad et al., "Metabotropic Glutamate Receptors Activate G-Protein-Coupled Inwardly Rectifying Potassium Channels in *Xenopus* Oocytes", J. Neurosci., 1996, 16(19), 5979-5985.
Sawamoto et al., "Cognitive Slowing in Parkinson Disease is Accompanied by Hypofunctioning of the Striatum", Neurology, 2007, 68, 1062-1068.
Sawamoto et al., "Cognitive Slowing in Parkinson's Disease: A Behavioral Evaluation Independent of Motor Slowing", J.Neurosci., 2002, 22, 5198-5203.
Scaccianoce et al., "Endogenous Activation of Group-II Metabotropic Glutamate Receptors Inhibits the Hypothalamic-Pituitary-Adrenocortical Axis", Neuropharmacology, 2003, 44, 555-561.
Scanziani et al., "Use-Dependent Increases in Glutamate Concentration Active Presynaptic Metabotropic Glutamate Receptors", Nature, 1997, 385, 630-634.
Schaffhauser et al., "Camp-Dependent Protein Kinase Inhibits Mglur2 Coupling to G-Proteins by Direct Receptor Phosphorylation", J Neurosci., 2000, 20(15), 5663-5670.
Schaffhauser et al., "In Vitro Characterization of N-(4'-(2-Methoxyphenoxy)Phenyl-N-(2,2,2-Trifluoroethylsulfonyl)Pyrid-3-Ylmethylamine (Ly487379) a Selective Mglu2 Receptor Positive Modulator", Neuropharmacology, 2002, 43, 307.
Schaffhauser et al., "Multiple Pathways for Regulation of the Kcl-Induced [3h]-Gaba Release by Metabotropic Glutamate Receptors, in Primary Rat Cortical Cultures", Brain Res., 1998, 782(1-2), 91-104.
Schaffhauser et al., "Pharmacological Characterization of Metabotropic Glutamate Receptors Linked to the Inhibition of Adenylate Cyclase Activity in Rat Striatal Slices", Neuropharmacology, 1997, 36(7), 933-940.
Schapira, "Science, Medicine, and the Future: Parkinson's Disease", Brit.Med.J., 1999, 318, 311-314.
Scheer et al., "Constitutively Active G Protein-Coupled Receptors: Potential Mechanisms of Receptor Activation", Journal of Receptor & Signal Transduction Research, 1997, 17(1-3), 57-73.
Schiffer et al., "Optimizing Experimental Protocols for Quantitative Behavioral Imaging with 18f-Fdg in Rodents", J Nucl Med, 2007, 48, 277-287.
Schlumberger et al., "Comparison of the MgluS Receptor Positive Allosteric Modulator Adx47273 and the Mglu2/3 Receptor Agonist Ly354740 in Tests for Antipsychotic-Like Activity", European Journal of Pharmacology, 2009, 623, 73-83.
Schlumberger et al., "Effects of a Metabotropic Glutamate Receptor Group II Agonist Ly354740 in Animal Models of Positive Schizophrenia Symptoms and Cognition", Behav Pharmacol., 2009, 20, 56-66.

(56) References Cited

OTHER PUBLICATIONS

Schoepp et al., "Ly354740 is a Potent and Highly Selective Group II Metabotropic Glutamate Receptor Agonist in Cells Expressing Human Glutamate Receptors", Neuropharmacology, 1997, 36, 1-11.
Schoepp et al., "Ly354740, An Mglu2/3 Receptor Agonist as a Novel Approach to Treat Anxiety/Stress", Stress, 2003, 6(3), 189-197.
Schoepp et al., "Metabotropic Glutamate Receptors" Pharmacol Biochem Behav, 2002, 74, 255-256.
Schoepp et al., "Potent, Stereoselective, and Brain Region Selective Modulation of Second Messengers in the Rat Brain by (+)Ly354740, A Novel Group II Metabotropic Glutamate Receptor Agonist", Naunyn-Schmiedebergs Archives of Pharmacology, 1998, 358(2), 175-180.
Schoepp, "Unveiling the Functions of Presynaptic Metabotropic Glutamate Receptors in the Central Nervous System", J Pharmacol Exp Ther, 2001, 299, 12-20.
Schoppa et al., "Modulation of Mepscs in Olfactory Bulb Mitral Cells by Metabotropic Glutamate Receptors", J Neurophysiol., 1997, 78(3), 1468-1475.
Schreiber et al., "Ly354740 Affects Startle Responding But Not Sensorimotor Gating or Discriminative Effects of Phencyclidine", Eur. J Pharmacol., 2000, 388(2), R3-R4.
Schulze-Osthoff et al., "Apoptosis Signaling by Death Receptors", European Journal of Biochemistry, 1998, 254(3), 439-459.
Schwartz et al., "Ago-Allosteric Modulation and Other Types of Allostery in Dimeric 7tm Receptors", J Recept. Signal. Transduct. Res., 2006, 26(1-2), 107-128.
Schwartz et al., "Allosteric Enhancers, Allosteric Agonists and Ago-Allosteric Modulators: Where Do They Bind and How Do They Act?", Trends Pharmacol. Sci., 2007, 28(8), 366-373.
Schweitzer et al., "Characterization of [(3)H]-Ly354740 Binding to Rat Mglu2 and Mglu3 Receptors Expressed in Cho Cells Using Semliki Forest Virus Vectors", Neuropharmacology, 2000, 39(10), 1700-1706.
Seebahn et al., "Ranbpm is Expressed in Synaptic Layers of the Mammalian Retina and Binds to Metabotropic Glutamate Receptors",. Febs Lett., 2008, 582(16), 2453-2457.
Seedat et al., "Measuring Anxiety in Patients with Schizophrenia", J Nerv Ment Dis. Apr. 2007, 195(4), 320-324.
Seeman et al., "Dopamine Partial Agonist Actions of the Glutamate Receptor Agonists Ly354740 and Ly379268", Synapse, 2008, 62, 154-158.
Seeman et al., "Glutamate Receptor Mglu2 and Mglu3 Knockout Striata are Dopamine Supersensitive, with Elevated D2(High) Receptors and Marked Supersensitivity to the Dopamine Agonist (+)Phno", Synapse, 2009, 63(3), 247-251.
Seeman, "An Agonist at Glutamate and Dopamine D2 Receptors, Ly404039" Neuropharmacology, 2012, 7 pages.
Seeman, "Glutamate Agonists for Schizophrenia Stimulate D2high Receptors", Schizophrenia Research, 2008, 99, 373-374.
Seeman, "Glutamate and Dopamine Components in Schizophrenia", J Psychiatry Neurosci., 2009, 34(2), 143-149.
Semba et al., "Regional Differences in the Effects of Glutamate Uptake Inhibitor L-Trans-Pyrrolidine-2,4-Dicarboxylic Acid on Extracellular Amino Acids and Dopamine in Rat Brain: An in Vivo Microdialysis Study", General Pharmacology, 1998, 31(3), 399-404.
Semple et al., "3-Aryl Pyridone Derivatives. Potent and Selective Kappa Opioid Receptor Agonists", Bioorganic and Medicinal Chemistry Lett, 2002, 12, 197-200.
Seneca, "Recent Advances in Positron Emission Tomography Imaging of Brain", Drugs of the Future, 2011, 36, 601-613.
Seo et al., "Distinctive Clinical Characteristics and Suicidal Tendencies of Patients with Anxious Depression", J Nerv Ment Dis, 2011, 199, 42-48.
Seroquel XR® Highlights of Prescribing Information 2013.
Shalev, "Neurobiology of Relapse to Heroin and Cocaine Seeking: A Review", Pharmacol. Rev., 2002, 54(1), 1-42.
Sharpe et al., "Systemic Pre-Treatment with a Group II Mglu Agonist, Ly379268, Reduces Hyperalgesia in Vivo", British Journal of Pharmacology, 2002, 135, 1255-1262.

Shear et al., "Multicenter Collaborative Panic Disorder Severity Scale", Am J Psychiatry, Nov. 1997, 154(11), 1571-1575.
Shear et al., "Reliability and Validity of a Structured Interview Guide for the Hamilton Axiety Rating Scale (Sigh-A)", Depress Anxiety, 2001, 13(4), 166-178.
Sheffler et al., "Recent Progress in the Synthesis and Characterization of Group II Metabotropic Glutamate Receptor Allosteric Modulators", Acs Chem Neurosci, 2011, 2, 382-393.
Shekar et al., "Ly354740, a Potent Group II Metabotropic Glutamate Receptor Agonist Prevents Lactate-Induced Panic-Like Response in Panic-Prone Rats", Neuropharmacology, 2000, 39, 1139-1146.
Shekhar, "Gabe Receptors in the Region of the Dorsomedial Hypothalamus of Rats Regulate Anxiety in the Elevated Plus-Maze Test. I. Behavioral Measures", Brain Research, 1993, 627(1), 9-16.
Shekhar et al., "Dorsomedial Hypothalamic Gaba Dysfunction Produces Physiological Arousal Following Sodium Lactate Infusions", Pharmacol Biochem Behav., Oct. 1996, 55(2), 249-256.
Shekhar et al., "Dorsomedial Hypothalamic Gaba Regulates Anxiety in the Social Interaction Test", Pharmacology, Biochemistry and Behavior, 1995, 50(2), 253-258.
Shekhar et al., "The Circumventricular Organs Form a Potential Neural Pathway for Lactate Sensitivity: Implications for Panic Disorder", Journal of Neuroscience, 1997, 17(24), 9726-9735.
Shepherd et al., "Behavioural and Pharmacological Characterisation of the Elevated 'Zero-Maze' as an Animal Model of Anxiety", Psychopharmacology, 1994, 116, 56-64.
Sherbourne et al., "Course of Depression in Patients with Comorbid Anxiety Disorders" Journal of Affective Disorders 1997, 43, 245-250.
Shi et al., "L-Homocysteine Sulfinic Acid and Other Acidic Homocysteine Derivatives are Potent and Selective Metabotropic Glutamate Receptor Agonists", J Pharmacol Exp Ther, 2003, 305(1), 131-142.
Shigemoto et al., "Differential Presynaptic Localization of Metabotropic Glutamate Receptor Subtypes in the Rat Hippocampus", Journal of Neuroscience, 1997, 17(19), 7503-7522.
Shigemoto et al., "Metabotropic Glutamate Receptors—Immunocytochemical and in Situ Hybridization Analysis", Ottersen Op, Storm-Mathisen J (Eds) Handbook of Chemical Neuroanatomy, Elxevier Science, 2000, 63-98.
Shigemoto et al., "Target-Cell-Specific Concentration of a Metabotropic Glutamate Receptor in the Presynaptic Active Zone", Nature, 1996, 381(6582), 523-525.
Shih et al., "Protein Kinase C Deficiency Blocks Recovery From Agonist-Induced Desensitization", J. Biol. Chem., 1996, 271(35), 21478-21483.
Shimazaki et al., "Blockade of the Metabotropic Glutamate 2/3 Receptors Enhances Social Memory via the Ampa Receptor in Rats", Eur.J.Pharmacol., 2007, 575, 94-97.
Shin et al., "Metabotropic Glutamate Receptors (Mglus) and Cellular Transformation", Neuropharmacology, 2008, 55(4), 396-402.
Shin et al., "The Neurocircuitry of Fear, Stress, and Anxiety Disorders", Neuropsychopharmacology, 2010, 35(1), 169-191.
Shipe et al., "Recent Advances in Positive Allosteric Modulators of Metabotropic Glutamate Receptors", Current Opinion in Drug Discovery & Development, 2005, 8(4), 449-457.
Sidique et al., "Orally Active Metabotropic Glutamate Subtype 2 Receptor Positive Allosteric Modulators: Structure-Activity Relationships and Assessment in a Rat Model of Nicotine Dependence", J Med Chem, 2012, 55, 9434-9445.
Silver et al., "Multifunctional Pharmacotherapy: What Can We Learn From Study of Selective Serotonin Reuptake Inhibitor Augmentation of Antipsychotics in Negative-Symptom Schizophrenia?", Neurotherapeutics, 2009, 6, 86-93.
Silverstone et al., "Defining Anxious Depression: Going Beyond Comorbidity", Can J Psychiatry, 2003, 48, 675-680.
Simon et al., "Advances in the Treatment of Anxiety: Targeting Glutamate", Journal of the American Society for Exp Neur, Jan. 2006, 3, 57-68.
Simon et al., "Comparing Anxiety Disorders and Anxiety-Related Traits in Bipolar Disorder and Unipolar Depression", Journal of Psychiatric Research, 2003, 37, 187-192.

(56) References Cited

OTHER PUBLICATIONS

Simonyi et al., "Chronic Ethanol-Induced Subtype- and Subregion-Specific Decrease in the Mrna Expression of Metabotropic Glutamate Receptors in Rat Hippocampus", Alcoholism: Clinical & Experimental Research, 2004, 28(9), 1419-1423.
Simonyi et al., "Expression of Groups I and II Metabotropic Glutamate Receptors in the Rat Brain During Aging", Brain Res, 2005, 1043, 95-106.
Simonyi et al., "Metabotropic Glutamate Receptor Subtype 5 Antagonism in Learning and Memory", European Journal of Pharmacology, 2010, 639, 17-25.
Simpson et al., "A Possible Role for the Striatum in the Pathogenesis of the Cognitive Symptoms of Schizophrenia", Neuron., 2010, 65(5), 585-596.
Siok et al., "Comparative Analysis of the Neurophysiological Profile of Group I Metabotropic Glutamate Receptor Activators and Diazepam: Effects on Hippocampal and Cortical Eeg Patterns in Rats", Neuropharmacology, 2012, 62, 226-236.
Skerry et al., "Glutamate Signalling in Non-Neuronal Tissues", Trends Pharmacol. Sci., 2001, 22(4), 174-181.
Sladeczek et al., "The Metabotropic Glutamate Receptor (Mgr): Pharmacology and Subcellular Location", Journal of Physiology, 1992, 86(1-3), 47-55.
Slattery et al., "Potentiation of Mouse Vagal Afferent Mechanosensitivity by Ionotropic and Metabotropic Glutamate Receptors", J Physiol, 2006, 577(Pt 1), 295-306.
Sleight et al., "Radiolabelling of the Human 5-Ht2a Receptor with an Agonist, a Partial Agonist and an Antagonist: Effects on Apparent Agonist Affinities", Biochemical Pharmacology, 1996, 51, 71-76.
Smalley et al., "Pyrolysis of Aryle Azides in Acetic Anhydride", J. Chem. Soc., 1963, 5571-5572.
Smialowska et al., "The Effect of Intrahippocampal Injection of Group II and III Metobotropic Glutamate Receptor Agonists on Anxiety; the Role of Neuropeptide Y", Neuropsychopharmacology, 2007, 32(6), 1242-1250.
Smith et al., "Ionotropic and Metabotropic Gaba and Glutamate Receptors in Primate Basal Ganglia", Journal of Chemical Neuroanatomy, 2001, 22(1-2), 13-42.
Smith et al., "Is Extended Clonazepam Cotherapy of Fluoxetine Effective for Outpatients with Major Depression?", Journal of Affective Disorders, 2002, 70, 251-259.
Smith et al., "Schizophrenia (Maintenance Treatment)", Clin Evid (Online), 2009, 1007.
Smith et al., "Short-Term Augmentation of Fluoxetine Clonazepam in the Treatment of Depression: A Double-Blind Study", Am J Psychiatry, 1998, 155, 1339-1345.
Smith, "Regulation of Glutamate Uptake in Astrocytes Continuously Exposed to Ethanol", Life Sciences, 1997, 61(25), 2499-2505.
Smits et al., "Outcomes of Acute Phase Cognitive Therapy in Outpatients with Anxious Versus Nonaxious Depression", Psychother Psychosom, 2012, 81, 153-160.
Smolders et al., "In Vivo Modulation of Extracellular Hippocampal Glutamate and Gaba Levels and Limbic Seizures by Group I and II Metabotropic Glutamate Receptor Ligands", Journal of Neurochemistry, 2004, 88(5), 1068-1077.
Sodhi et al., "Role of Glutamate in Schizophrenia: Integrating Excitatory Avenues of Research", Expert Rev Neurother, 2008, 8(9), 1389-1406.
Sokoloff et al., "The [14c]Deoxyglucose Method for the Measurement of Local Cerebral Glucose Utilization: Theory, Procedure, and Normal Values in the Conscious and Anesthetized Albino Rat", J Neurochem, 1977, 28, 897-916.
Sokolowski et al., "The Behavioral Effects of Sertraline, Fluoxetine, and Paroxetine Differ on the Differential-Reinforcement-Of-Low-Rate 72-Second Operant Schedule in the Rat", Psychopharmacology, 1999, 147, 153-161.
Sortino et al., "Immortalized Hypothalamic Neurons Express Metabotropic Glutamate Receptors Positively Coupled to Cyclic Amp Formation", Eur. J Neurosci., 1996, 8(11), 2407-2415.
Souery et al., "Group for the Study of Resistant Depression. Clinical Factors Associated with Treatment Resistance in Major Depressive Disorder: Results From a European Multicenter Study", J. Clin. Psychiatry, Jul. 2007, 68(7), 1062-1070.
South Korean Patent Application No. 2010-053694958: Office Action dated Nov. 25, 2010, 9 pages.
Spencer et al., "Novel Strategies for Alzheimer's Disease Treatment", Expert Opin. Biol. Ther., 2007, 7(12), 1853-1867.
Spiegel et al., "Defects in G Protein-Coupled Signal Transduction in Human Disease", Annual Review of Physiology, 1996, 58, 143-170.
Spiegel et al., "Psychosis Induced by the Interaction of Memantine and Amantadine: Lending Evidence to the Glutamatergic Theory of Schizophrenia", Clinical Schizophrenia & Related Psychoses, 2007, 1(3), 273-276.
Spijker, "The Course of Anxiety and Depression in Nemesis and Nesda", Abstract AS36-04 of the 20th European Congress of Psychiatry, Mar. 2012, 1 page.
Spooren et al., "Anxiolytic-Like Effects of the Prototypical Metabotropic Glutamate Receptor 5 Antagonist 2-Methyl-6-(Phenylethynyl)Pyridine in Rodents", Journal of Pharmacology & Experimental Therapeutics, 2000, 295(3), 1267-1275.
Spooren et al., "Insight Into the Function of Group I and Group II Metabotropic Glutamate (Mglu) Receptors: Behavioural Characterization and Implications for the Treatment of CNS Disorders", Behavioural Pharmacology, 2003, 14(4), 257-277.
Spooren et al., "Lack of Effect of Ly314582 (A Group 2 Metabotropic Glutamate Receptor Agonist) on Phencyclidine-Induced Locomotor Activity in Metabotropic Glutamate Receptor 2 Knockout Mice", Eur J Pharmacol., 2000, 397, R1-R2.
Spooren et al., "Metabotropic Glutamate Receptors: Their Therapeutic Potential in Anxiety", Current Topics in Behavioral Neurosciences, 2010, 2, 391-413.
Spooren et al., "Pharmacological and Endocrinological Characterization of Stress-Induced Hypethermia in Singly Housed Mice Using Classical and Candidate Anxiolytics (Ly314582, Mpep and Nkp608)", Eur J Pharmacol, 2002, 435, 161-170.
Srivastava et al., "Novel Anchorage of Glur2/3 to the Postsynaptic Density by the Ampa Receptor-Binding Protein Abp", Neuron, 1998, 21(3), 581-591.
Stachowicz et al., "Anxiolytic-Like Activity of Mgs0039, A Selective Group II Mglu Receptor Antagonist, Is Serotonin- and Gaba-Dependent", Pharmacological Reports, 2011, 63, 880-887.
Stahl et al., "Negative Symptoms of Schizophrenia: A Problem That Will Not Go Away", Acta Psychiatr. Scand., 2007, 115(1), 4-11.
Star*D Research Methods Section (2001), Available from Http://Www.Edc.Gsph.Pitt.Edu/Stard/Public/Protocol/Star-D%20III%20research%20design%20methods.Pdf, 2001, 50 pages.
Steckler, "Glutamatergic Anxiolytics Are They Any Better?", (Presentation Slides), European College of Neuropsychopharmacology, 2009, 18 pages.
Steckler et al., "Chapter 7—Neuroimaging as a Translational Tool in Animal and Human Models of Schizophrenia", Translational Neuroimaging, 2013, 195-220.
Steckler et al., "Effects of Mglu1 Receptor Blockade on Anxiety-Related Behavior in the Rat Lick Suppression Test", Psychopharmacology, 2005, 179, 198-206.
Steckler et al., "Pharmacological Treatment of PTSD—Established and New Approaches", Neuropharmacology, 2012, 62, 617-627.
Stefani et al., "Activation of Type 5 Metabotropic Glutamate Receptors Attenuates Deficits in Cognitive Flexibility Induced by NMDA Receptor Blockade", European Journal of Pharmacology, 2010, 639, 26-32.
Stefani et al., "The Modulation of Calcium Currents by the Activation of Mglurs. Functional Implications", Molecular Neurobiology, 1996, 13(1), 81-95.
Steinpreis, "The Behavioral and Neurochemical Effects of Phencyclidine in Humans and Animals: Some Implications for Modeling Psychosis", Behavioral Brain Research, 1996, 74, 45-55.
Stella et al., "4. Prodrugs: the Contrul of Drug Delivery via Bioreversible Chemical Modification", Drug Delivery Systems: Characteristics and Biomedical Applications. New York: Oxford University Press, 1980, 67 pages.

(56) References Cited

OTHER PUBLICATIONS

Stella et al., "Prodrugs: Do They Have Advantages in Clinical Practice?", Drugs, 1985, 29, 455-473.
Stepulak et al., "Expression of Glutamate Receptor Subunits in Human Cancers", Histochem. Cell Biol., 2009, 12 pages.
Steru et al., "The Automated Tail Suspension Test: A Computerized Device Which Differentiates Psychotropic Drugs", Prog. Neuropsychopharmacol. Exp. Psychiatry, 1987, 11, 659-671.
Steru et al., "The Tail Suspension Test: A New Method for Screening Antidepressants in Mice", Psychopharmacology, 1985, 85, 367-370.
Stogryn et al., "5-Hetarylmethylene-2,4-Diaminopyrimidines (1)", J. Heterocyclic Chem., Apr. 1974. 11, 251-253.
Stone et al., "Glutamate and Dopamine Dysregulation in Schizophrenia—A Synthesis and Selective Review", J Psychopharmacol., 2007, 21(4), 440-452.
Stone, "Imaging the Glutamate System in Humans: Relevance to Drug Discovery for Schizophrenia", Curr. Pharm. Des, 2009, 15(22), 2594-2602.
Stout et al., "High-Affinity Calcium Indicators Underestimate Increases in Intracellular Calcium Concentrations Associated with Excitotoxic Glutamate Stimulations", Neuroscience, 1999, 89(1), 91-100.
Stowell et al., "Axon/Dendrite Targeting of Metabotropic Glutamate Receptors by Their Cytoplasmic Carboxy-Terminal Domains", Neuron, 1999, 22(3), 525-536.
Straiker et al., "Metabotropic Suppression of Excitation in Murine Autaptic Hippocampal Neurons", J Physiol, 2007, 578(Pt 3), 773-785.
Strange, "Use of the Gtpgs ([35s]Gtpgs and Eu-Gtpgs) Binding Assay for Analysis of Ligand Potency and Efficacy at G Protein-Coupled Receptors", British Journal of Pharmacology, 2010, 161, 1238-1249.
Stroup et al., "Results of Phase 3 of the Catie Schizophrenia Trial", Schizophr Res., 2009, 107(1),1-12.
Structures, "Chemical Abstracts", May 2009. 23 pages.
Stulz et al., "Distinguishing Anxiety and Depression in Self-Report: Purification of the Beck Anxiety Inventory and Beck Depression Inventory—II", J Clin Psychol, 2010, 66, 927-940.
Suh et al., "Hypoglycemic Neuronal Death and Cognitive Impairment are Prevented by Poly(Adp-Ribose) Polymerase Inhibitors Administered After Hypoglycemia", Journal of Neuroscience, 2003, 23(33), 10681-10690.
Sun et al., "Mechanism of Glutamate Receptor Desensitization", Nature, 2002, 417, 245-253.
Sutton et al., "Regulation of Akt and Wnt Signaling by the Group II Metabotropic Glutamate Receptor Antagonist Ly341495 and Agonist Ly379268", Journal of Neurochemistry, 2011, 117, 973-983.
Suzuki et al., "Synthesis of the Selective 5-Hydroxytryptamine 4 (5-Ht4) Receptor Agonist (+)-(S)-2-Chloro-5-Methoxy-4-[5-(2-Piperidylmethyl)-1,2,4-Oxadiazol-3-Yl]Aniline", Chem. Pharm. Bull., 1999, 47(1), 120-122.
Svensson et al., "Ly2607540 (THLLC), A Novel Mglu2 Receptor Potentiator with Potential Anxiolytic/Antidepressant Properties: in Vivo Profiling Suggests a Link Between Behavioral and CNS Neurochemical Changes" Poster 642.4, 40th Annual Meeting of Society for Neuroscience, Nov. 2010, 1 page.
Swanson et al., "A Role for Noradrenergic Transmission in the Actions of Phencyclidine and the Antipsychotic and Antistress Effects of Mglu2/3 Receptor Agonists", Annals of the New York Academy of Sciences, 2003, 1003, 309-17.
Swanson et al., "Metabotropic Glutamate Receptors as Novel Targets for Anxiety and Stress Disorders", Nature Reviews Drug Discovery, 2005, 4, 131-144.
Swanson et al., "The Group II Metabotropic Glutamate Receptor Agonist (−)-2-Oxa-4-Aminobicyclo[3.1.0.]Hexane-4,6-Dicarboxylate (Ly379268) and Clozapine Reverse Phencyclidine-Induced Behaviors in Monoamine-Depleted Rats", Journal of Pharmacology & Experimental Therapeutics, 2002, 303(3), 919-927.

Swerdlow et al., "Assessing the Validity of an Animal Model of Deficient Sensorimotor Gating in Schizophrenic Patients", Arch. Gen. Psychiatry, 1994, 51, 139-154.
Swerdlow et al., "Strain Differences in the Disruption of Prepulse Inhibition of Startle After Systemic and Intra-Accumbens Amphetamine Administration",. Pharmacol. Biochem. Behav., 2007, 87 (1), 1-10.
Szapiro et al., "Facilitation and Inhibition of Retrieval in Two Aversive Tasks in Rats by Intrahippocampal Infusion of Agonists of Specific Glutamate Metabotropic Receptor Subtypes", Psychopharmacology, 2001, 156(4), 397-401.
Taiwanese Patent Application No. 094132375: Office Action dated Aug. 25, 2011, 10 pages.
Taiwanese Patent Application No. 096108666: Office Action, dated 2007, 3 pages.
Takahashi et al., "In Vitro Systems for the Study of Apoptosis", Advances in Pharmacology, 1997, 41, 89-106.
Takahashi et al., "Post-Treatment with an Inhibitor of Poly(Adp-Ribose) Polymerase Attenuates Cerebral Damage in Focal Ischemia", Brain Research, 1999, 829, 46-54.
Takahashi et al., "Role of the Large Extracellular Domain of Metabotropic Glutamate Receptors in Agonist Selectivity Determination", J. Biol. Chem., 1993, 268(26), 19341-19345.
Takamori et al., "Antipsychotic Action of Selective Group II Metabotropic Glutamate Receptor Agonist Mgs0008 and Mgs0028 on Conditioned Avoidance Responses in the Rat", Life Sci., 2003, 73, 1721-1728.
Takamori, "Vgluts: 'Exciting' Times for Glutamatergic Research?", Neuroscience Research, 2006, 55(4), 343-351.
Takumi et al., "The Arrangement of Glutamate Receptors in Excitatory Synapses", Annals of the New York Academy of Sciences, 1999, 868, 474-482.
Tamminga et al., "Glutamate Pharmacology and the Treatment of Schizophrenia: Current Status and Future Directions", Intl Clinical Psychopharmacology, 1995, 10(Suppl-37), 29-37.
Tamminga, "Schizophrenia and Glutamatergic Transmission", Critical Reviews in Neurobiology, 1998, 12(1-2), 21-36.
Tanabe et al., "A Family of Metabotropic Glutamate Receptors", Neuron, 1992, 8(1), 169-179.
Tandon et al., "Schizophrenia, Just the Facts, 5.Treatment and Prevention Past, Present, and Future", Schizophr Res., Jul. 2010, 122, 1-23.
Tang et al., "Metabotropic Glutamate Receptors in the Control of Neuronal Activity and as Targets for Development of Anti-Epileptogenic Drugs", Curr. Med. Chem, 2009, 16(17), 2189-2204.
Tang et al., "Prolonged Anticonvulsant Action of Glutamate Metabotropic Receptor Agonists in Inferior Colliculus of Genetically Epilepsy-Prone Rats", European Journal of Pharmacology, 1997, 327(2-3), 109-115.
Targum et al., "Redefining Affective Disorders: Relevance for Drug Development", CNS Neuroscience and Therapeutics, 2008, 14, 2-9.
Targum et al., "The Relevance of Anxious Depression as a Distinct Entity for Psychopharmacology and Drug Development", US Psychiatry, 2009, 2(1), 29-31.
Tarrier et al., "A Trial of Two Cognitive Behavioural Methods of Treating Drug-Resistant Residual Psychotic Symptoms in Schizophrenic Patients: I. Outcome", Br J Psychiatry, 1993, 162, 524-532.
Tatarczyska et al., "The Antianxiety-Like Effects of Antagonists of Group I and Agonists of Group II and III Metabotropic Glutamate Receptors After Intrahippocampal Administration", Psychopharmacology, 2001, 158, 94-99.
Taylor et al., "Stimulation of Microglial Metabotropic Glutamate Receptor Mglu2 Triggers Tumor Necrosis Factor?-Induced Neurotoxicity in Concert with Microglial-Derived Fas Ligand", Journal of Neuroscience, 2005, 25(11), 2952-2964.
Taylor et al., "The Efficacy of Nefazodone Augmentation for Treatment-Resistant Depression with Anxiety Symptoms or Anxiety Disorder", Depression and Anxiety, 2003, 18, 83-88.
Teitler et al., "4-[125i]Iodo-(2,5-Dimethoxy)Phenylisopropylamine and [3h]Ketanserin Labeling of 5-Hydroxytryptamine2 (5ht2) Receptors in Mammalian Cells Transfected with a Rat 5ht2 Cdna: Evidence for Multiple States and Not Multiple 5ht2 Receptor Subtypes", Molecular Pharmacology, 1990, 38, 594-598.

(56) References Cited

OTHER PUBLICATIONS

Teran et al., "Regioselective Oxidation of 3-Substituted Pyridinium Salts", Molecules, 2000, 5, 1175-1181.
Testa et al., "Immunohistochemical Localization of Metabotropic Glutamate Receptors Mglur1a and Mglur2/3 in the Rat Basal Ganglia", Journal of Comparative Neurology, 1998, 390(1), 5-19.
Testa et al., "Metabotropic Glutamate Receptor Mrna Expression in the Basal Ganglia of the Rat", Journal of Neuroscience, 1994, 14(5), 3005-3018.
Thase et al., "Extended Release Quetiapine Fumarate in Major Depressive Disorder: Analysis in Patients with Anxious Depression", Depression and Anxiety, 2012, 29, 574-586.
Thase et al., "Remission Rates Following Antidepressant Therapy with Bupropion or Selective Serotonin Reuptake Inhibitors: A Meta-Analysis of Original Data From 7 Randomized Controlled Trials", J Clin Psychiatry, 2005, 66(8), 974-981.
Thase, "Augmentation Strategies for Depression: History and Concepts", CNS Spectr, 2007, 12(12), (Suppl 22), 3-5.
Thase, "Depression and Sleep: Pathophysiology and Treatment", Dialogues Clin Neurosci, 2006, 8, 217-226.
Thathiah et al., "The Role of G Protein-Coupled Receptors in the Pathology of Alzheimer's Disease", Nature Reviews Neuroscience, 2011, 12, 73-87.
Theberge, "Glutamate and Glutamine in the Anterior Cingulate and Thalamus of Medicated Patients with Chronic Schizophrenia and Healthy Comparison Subjects Measured with 4.0-T Proton MRS", Am. J. Psychiatry, 2003, 160, 2231-2233.
Theberge, "Glutamate and Glutamine Measured with 4.0t Proton Mrs in Never-Treated Patients with Schizophrenia and Healthy Volunteers", Am. J. Psychiatry, 2002, 159, 1944-1946.
Thompson et al., "Activation of Group II and Group III Metabotropic Glutamate Receptors by Endogenous Ligand(S) and the Modulation of Synaptic Transmission in the Superficial Superior Colliculus", Neuropharmacology, 2004, 47(6), 822-832.
Thomsen et al., "Actions of Phenylglycine Analogs at Subtypes of the Metabotropic Glutamate Receptor Family", European Journal of Pharmacology, 1994, 267(1), 77-84.
Thomsen et al., "Roles of Metabotropic Glutamate Receptor Subtypes in Modulation of Pentylenetetrazole-Induced Seizure Activity in Mice", Neuropharmacology, 1998, 37(12), 1465-1473.
Tiihonen et al., "The Efficacy of Lamotrigine in Clozapine-Resistant Schizophrenia: A Systematic Review and Meta-Analysis", Schizophr Res. 2009, 109(1-3), 10-14.
Tilakaratne et al., "Chronic Fluoxetine or Desmethylimipramine Treatment Alters 5-Ht2 Receptor Mediated C-Fos Gene Expression", European Journal of Pharmacology, 1995, 290(3), 263-266.
Tizzano et al., "Induction or Protection of Limbic Seizures in Mice by Mglur Subtype Selective Agonists", Neuropharmacology, 1995, 34(8), 1063-1067.
Tizzano et al., "The Anxiolytic Action of Mglu2/3 Receptor Agonist, Ly354740, in the Fear-Potentiated Startle Model in Rats is Mechanistically Distinct From Diazepam", Pharmacology, Biochemistry and Behavior, 2002, 73, 367-374.
Tokita et al., "Roles of Glutamate Signaling in Preclinical and/or Mechanistic Models of Depression", Pharmacology, Biochemistry and Behavior, 2012, 100, 688-704.
Tokunaga et al., "Neuroimaging and Physiological Evidence for Involvement of Glutamatergic Transmission in Regulation of the Striatal Dopaminergic System", Journal of Neuroscience, 2009, 29(6), 1887-1896.
Tolchard et al., "Modulation of Synaptic Transmission in the Rat Ventral Septal Area by the Pharmacological Activation of Metabotropic Glutamate Receptors", European Journal of Neuroscience, 2000, 12(5), 1843-1847.
Tollefson et al., "Fluoxetine, Placebo, and Tricyclic Antidepressants in Major Depression with and without Anxious Features", J Clin Psychiatry, 1994, 55(2), 50-59.
Toms et al., "Latest Eruptions in Metabotropic Glutamate Receptors", Trends in Pharmacological Sciences, 1996, 17(12), 429-435.

Tong et al., "Signal Transduction in Neuronal Death", Journal of Neurochemistry, 1998, 71(2), 447-459.
Trabanco et al., "Discovery of 5- and 6-Substituted Isoquinolones: A New Class of Positive Allosteric Modulators of the Metabotropic Glutamate 2 Receptor", XXI'st International Symposium on Medicinal Chemistry, Sep. 2010, 1 page.
Trabanco et al., "Imidazo[1,2-A]Pyridines: Orally Active Positive Allosteric Modulators of the Metabotropic Glutamate 2 Receptor", J Med Chem, 2012, 55, 2688-2701.
Trabanco et al., "Mglur2 Positive Allosteric Modulators (Pams): A Patent Review (2009-Present)", Expert Opin, 2013, 19 pages.
Trabanco et al., "New Positive Allosteric Modulators of the Metabotropic Glutamate Receptor 2 (Mglur2). Identification and Synthesis of N-Propyl-5-Substituted Isoquinolones", Med Chem Commun, 2011, 2, 132-139.
Trabanco et al., "New Positive Allosteric Modulators of the Metabotropic Glutamate Receptor 2 (Mglur2): Identification and Synthesis of N-Propyl-8-Chloro-6-Substituted Isoquinolones", Bioorganic & Medicinal Chemistry Letters, 2011, 21, 971-976.
Trabanco et al., "Progress in the Developement of Positive Allosteric Modulators of the Metabotropic Glutamate Receptor 2", Current Medicinal Chemistry, 2011, 18, 47-68.
Trabanco et al., "Synthesis, Evaluation, and Radiolabeling of New Potent Positive Allosteric Modulators of the Metabotropic Glutamate Receptor 2 as Potential Tracers for Positron Emission Tomography Imaging", J Med Chem, 2012, 55, 8685-8689.
Tresadern et al., "Scaffold Hopping From Pyridones to Imidazo[1,2-A]Pyridines. New Positive Allosteric Modulators of Metabotropic Glutamate 2 Receptor", Bioorganic & Medicinal Chemistry Letters, 2010, 20, 175-179.
Trettel et al., "Endocannabinoid Signalling Selectively Targets Perisomatic Inhibitory Inputs to Pyramidal Neurones in Juvenile Mouse Neocortex", Journal of Physiology, 2004, 556(Pt 1), 95-107.
Treutlein et al., "Dissection of Phenotype Reveals Possible Association Between Schizophrenia and Glutamate Receptor Delta 1 (Grid1) Gene Promoter", Schizophr. Res., 2009, 111(1-3), 123-130.
Trivedi et al., "Adjunctive Aripiprazole in Major Depressive Disorder: Analysis of Efficacy and Safety in Patients with Anxious and Atypical Features", J Clin Psychiatry, 2008, 69, 1928-1936.
Trivedi et al., "Evaluation of Outcomes with Citalopram for Depression Using Measurement-Based Care in Star*D: Implications for Clinical Practice", Am J Psychiatry, 2006; 163, 28-40.
Trofimova et al., "The Lability of Behavior as a Marker of Comorbid Depression and Anxiety", Advances in Bioscience and Biotechnology, 2010, 1, 190-199.
Trullas et al., "Functional Antagonists at the NMDA Receptor Complex Exhibit Antidepressant Actions", Eur J Pharmacol, Aug. 1990, 185(1), 1-10.
Tsai et al., "Immunocytochemical Distribution of N-Acetylaspartylglutamate in the Rat Forebrain and Glutamatergic Pathways", Journal of Chemical Neuroanatomy, 1993, 6(5), 277-292.
Tsai, "Central N-Acetyl Aspartylglutamate Deficit: A Possible Pathogenesis of Schizophrenia", Med Sci. Monit., 2005, 11(9), Hy39-Hy45.
Tsai, "Glutamatergic Mechanisms in Schizophrenia", Ann. Rev. Pharmacol. Toxicol., 2002, 42, 165-179.
Tsiveriotis et al., "Nickel(II) and Cobalt(II) Complexes of 2,4-Diaminothieno[2,3-D]-Pyrimidines", Transition Metal Chemistry, 1994, 19, 335-339.
Tsunoka et al., "Association Analysis of Grm2 and Htr2a with Methamphetamine-Induced Psychosis and Schizophrenia in the Japanese Population", Progress in Neuro-Psychopharmacology & Biological Psychiatry, 2010, 34(4), 639-644.
Tsunoka et al., "Association Analysis of Group II Metabotropic Glutamate Receptor Genes (Grm2 and Grm3) with Mood Disorders and Fluvoxamine Response in a Japanese Population", Progress in Neuro-Psychopharmacology & Biological Psychiatry, 2009, 33(5), 875-879.
Tuominen et al., "Glutamatergic Drugs for Schizophrenia", The Cochrane Collaboration, Cochrane Database Syst Rev., Apr. 2006, 1, 8 pages.

(56) References Cited

OTHER PUBLICATIONS

Tuominen, "Glutamatergic Drugs for Schizophrenia: A Systematic Review and Meta-Analysis", Schiz. Res., 2005, 72, 225-234.
Tyrer, "The Case for Cothymia: Mixed Anxiety and Depression as a Single Diagnosis", British Journal of Psychiatry, 2001, 179, 191-193.
Uher et al., "Differential Efficacy of Escitalopram and Nortriptyline on Dimensional Measures of Depression", British Journal of Psychiatry, 2009, 194, 252-259.
Uher et al., "Melancholic, Atypical and Anxious Depression Subtypes and Outcome of Treatment with Escitalopram and Nortriptyline", Journal of Affective Disorders, 2011, 132, 112-120.
Um et al., "Alzheimer Amyloid-B Oligomer Bound to Postsynaptic Prion Protein Activates Fyn to Impair Neurons", Nature Neuroscience, 2012, 15(9), 1227-1235.
Undine et al., "Molecular Mechanisms of Schizophrenia", Cell Physiol Biochem, 2007, 20, 687-702.
Ung et al., "Synthesis and Biological Activities of Conformationally Restricted Cyclopentenyl-Glutamate Analogues", Journal of Organic Chemistry, 2002, 67(1), 227-233.
Urwyler, "Allosteric Modulation of Family C G-Protein-Coupled Receptors From Molecular Insights to Therapeutic Perspectives", Pharmacol Rev, 2011, 63, 59-126.
Uslaner et al., "Combined Administration of an Mglu2/3 Receptor Agonist and a 5-Ht 2a Receptor Antagonist Markedly Attenuate the Psychomotor-Activating and Neurochemical Effects of Psychostimulants", Psychopharmacology (Berl), 2009, 206(4), 641-651.
Uys et al., "Glutamate: the New Frontier in Pharmacotherapy for Cocaine Addiction", CNS & Neurological Disorders—Drug Targets, 2008, 7, 482-491.
Vaccarino et al., "Symptoms of Anxiety in Depression: Assessment of Item Performance of the Hamilton Anxiety Rating Scale in Patients with Depression", Depression and Anxiety, 2008, 25, 1006-1013.
Valentine et al., "Targeting Glial Physiology and Glutamate Cycling in the Treatment of Depression", Biochem. Pharmacol., 2009, 78(5), 431-439.
Vales et al., "The Difference in Effect of Mglu2/3 and Mglu5 Receptor Agonists on Cognitive Impairment Induced by Mk-801", European Journal of Pharmacology, 2010, 639, 91-98.
Valproate Information Available from Http://Www.Fda.Gov/Drugs/Drugsafety/Postmarketdrugsafetyinformationforpatientsandproviders/Ucm192645.Htm, 2011, 2 pages.
Van Beljouw et al., "The Course of Untreated Anxiety and Depression, and Determinants of Poor On-Year Outcome: A One-Year Cohort Study", BMC Psychiatry, 2010, 10, 86.
Van Berckel et al., "Modulation of Amphetamine-Induced Dopamine Release by Group Ii Metabotropic Glutamate Receptor Agonist Ly354740 in Non-Human Primates Studied with Positron Emission Tomography", Neuropsychopharmacology, 2006, 31, 967-977.
Van Den Pol, "Presynaptic Metabotropic Glutamate Receptors in Adult and Developing Neurons: Autoexcitation in the Olfactory Bulb", Journal of Comparative Neurology, 1995, 359(2), 253-271.
Van Der Linden et al., "In Vitro Chracterization of the Binding of the Mglu2 Receptor Positive Allosteric Modulator [3h]Jnj-40068782 to Native and Recombinant Mglu2 Receptors", 7th Int. Meeting on Metabotropic Glutamate Receptors 2011, 1 page.
Van Tol et al., "Regional Brain Volume in Depression and Anxiety Disorders", Arch Gen Psychiatry, 2010, 67(10), 1002-1011.
Van Valkenberg et al., "Anxious Depressions. Clinical, Family History, and Naturalistic Outcome—Comparisons with Panic and Major Depressive Disorders", Journal of Affective Disorders, 1984, 6(1), 67-82.
Van Vliet et al., "Adaptive Changes in the Number of Gs- and Gi- Proteins Underlie Adenylyl Cyclase Sensitization in Morphine-Treated Rat Striatal Neurons", European Journal of Pharmacology, 1993, 245(1), 23-29.
Vandergriff et al., "The Selective Mglu2/3 Receptor Agonist Ly354740 Attenuates Morphine-Withdrawal-Induced Activation of Locus Coeruleus Neurons and Behavioral Signs of Morphine Withdrawal", Neuropharmacology, 1999, 38, 217-222.
Vandesompele et al., "Accurate Normalization of Real-Time Quantitative Rt-Pcr Data by Geometric Averaging of Multiple Internal Control Genes", Genome Biology, 2002, 3(7), 1-12.
Varney et al., "Metabotropic Glutamate Receptor Involvement in Models of Acute and Persistent Pain: Prospects for the Development of Novel Analgesics", Current Drug Targets—CNS & Neurological Disorders, 2002, 1, 283-296.
Vasilieva, "Clinical-Dynamic Characteristics of Depressive Disorders Comorbid with Anxiety Disorders", Abstract P01-109 of 18th European Congress of Psychiatry, 2010, 1 page.
Vaughan et al., "Reactivity of 3-Alkyl-4-Arylazomethylene-3,4-Dihydro-1,2,3-Benzotriazines in Protic Solvents: 1,4-Addition Reactions and Dimroth Rearrangement", Journal of Heterocyclic Chemistry, Nov. 1991, 1709-1713.
Ver Donck et al., "Low Dose Subchronic Phencyclidine (PCP) Pretreatment Potentiates Acute PCP-Induced Hyperlocomotion in Adult Rats: A Model of Schizophrenia?", Presentation Abstract, Society for Neuroscience, 2011, 2 pages.
Verhagen et al., "Effect of the 5-Httlpr Polymorphism in the Serotonin Transporter Gene on Major Depressive Disorder and Related Comorbid Disorders", Psychiatric Genetics, 2009, 19, 39-44.
Verma et al., "Regulation of Striatal Dopamine Release by Metabotropic Glutamate Receptors", Synapse 1998, 28(3), 220-226.
Vernon et al., "Additive Neuroprotection by Metabotropic Glutamate Receptor Subtype-Selective Ligands in aRat Parkinson's Model", Neuroreport, 2008, 19(4), 475-478.
Versiani et al., "Fluoxetine Versus Amitriptyline in the Treatment of Major Depression with Associated Anxiety (Anxious Depression): A Double-Blind Comparison", International Clinical Psychopharmacology, 1999, 14, 321-327.
Vezina et al., "Metabotropic Glutamate Receptors and the Generation of Locomotor Activity: Interactions with Midbrain Dopamine", Neuroscience & Biobehavioral Reviews, 1999, 23(4), 577-589.
Vinson et al., "Metabotropic Glutamate Receptors as Therapeutic Targets for Schizophrenia", Neuropharmacology, 2012, 62, 1461-1472.
Vogel et al., "A Simple and Reliable Conflict Procedure for Testing Anti-Anxiety Agents", Psychopharmacologia, 1971, 21, 1-7.
Vogel et al., "Drug Effects on Rem Sleep and on Endogenous Depression", Neuroscience & Biobehavioral Reviews, 1990, 14, 49-63.
Vogel et al., "Evidence for REM Sleep Deprivation as the Mechanism of Action of Antidepressant Drugs", Prog Neuropsychopharmacol Biol Psychiatry, 1983, 7(2-3), 343-349.
Vollenweider et al., "A Systems Model of Altered Consciousness: Integrating Natural and Drug-Induced Psychoses", Brain Res. Bull., 2001, 56, 495-507.
Vollenweider et al., "Differential Psychopathology and Patterns of Cerebral Glucose Utilization Produced by (S)- and (R)-Ketamine in Healthy Volunteers Using Positron Emission Tomography (Pet)", Eur Neuropsychopharmacol, 1997, 7, 25-38.
Vollenweider et al., "Effect of Clozapine and Ketanserin on S-Ketamine-Induced Brain Activation and Psychotic Symptoms in Healthy Humans", Abstract, Symposia, 28th Cinp World Congress of Neuropsychopharmacology, 2012, 2 pages.
Vollenweider et al., "Metabolic Hyperfrontality and Psychopathology in the Ketamine Model of Psychosis Using Positron Emission Tomography (Pet) and [18f]fluorodeoxyglucose (Fdg)", Eur Neuropsychopharmacol, 1997, 7, 9-24.
Vollenweider et al., "Psilocybin Induces Schizophrenia-Like Psychosis in Humans via a Serotonin-2 Agonist Action", Neuroreport, 1998, 9, 3897-3902.
Vollenweider, "Positron Emission Tomography and Fluorodeoxyglucose Studies of Metabolic Hyperfrontality and Psychopathology in the Psilocybin Model of Psychosis", Neuropsychopharmacology, 1997, 16, 357-372.
Wachtel et al., "Glutamate: A New Target in Schizophrenia?", Trends in Pharmacological Sciences, 1990, 11(6), 219-220.
Wadenberg, "Conditioned Avoidance Response in the Development of New Antipsychotics", Curr Pharm Des, 2010, 16, 358-370.

(56) References Cited

OTHER PUBLICATIONS

Wadenberg et al., "The Conditioned Avoidance Response Test Re-Evaluated: Is it a Sensitive Test for the Detection of Potentially Atypical Antipsychotics?", Neurosci. Biobehav. Rev., 1999, 23, 851-862.
Wainer, "Finding Time for Allosteric Interactions", Nature Biotechnology, 2004, 22(11), 1376-1377.
Walker et al., "Group II Metabotropic Glutamate Receptors Within the Amygadale Regulate Fear as Assessed with Potentiated Startle in Rats", Behav Neurosci, 2002, 116, 1075-1083.
Walker et al., "The Role of Amygdala Glutamate Receptors in Fear Learning, Fear-Potentiated Startle, and Extinction", Pharmacol. Biochem. Behav., 2002, 71(3), 379-392.
Wang et al., "Allosteric Modulators of G Protein-Coupled Receptors: Future Therapeutics for Complex Physiological Disorders", J Pharmacol. Exp. Ther., 2009, 331(2), 340-348.
Wang et al., "Development of Metabotropic Glutamate Receptor Ligands for Neuroimaging", Curr Med Imaging Rev, 2007, 3, 186-205.
Wang et al., "Radiosynthesis of Pet Radiotracer as a Prodrug for Imaging Group II Metabotropic Glutamate Receptors in Vivo", Bioorganic & Medicinal Chemistry Letters, 2012, 22, 1958-1962.
Warden et al., "The Star*D Project Results: A Comprehensive Review of Findings", Current Psychiatry Reports, 2007, 9, 449-459.
Warnock et al., "In Vivo Evidence for Ligand-Specific Receptor Activation in the Central CRF System, as Measured by Local Cerebral Glucose Utilization", Peptides, 2009, 30, 947-954.
Watanabe et al., "Mglur2 Postsynaptically Senses Granule Cell Inputs at Golgi Cell Synapses" Neuron, 2003, 39, 821-829.
Watkins, "L-Glutamate as a Central Neurotransmitter: Looking Back", Biochem Soc Trans, 2000, 28, 297-310.
Watkins et al., "Structure-Activity Relationships in the Development of Excitatory Amino Acid Receptor Agonists and Competitive Antagonists", Trends in Pharmacological Sciences, 1990, 11(1), 25-33.
Webb et al., "Apoptosis: An Overview of the Process and its Relevance in Disease", Advances in Pharmacology, 1997, 41, 1-34.
Weinberger et al., "Schizophrenia Drug Says Goodbye to Dopamine", Nature Medicine, 2007, 13, 1018-1019.
Weinberger, "The Biological Basis of Schizophrenia: New Directions", Journal of Clinical Psychiatry, 1997, 58(Suppl 10), 22-27.
Weiner et al., "5-Hydroxytryptamine2a Receptor Inverse Agonists as Antipsychotics", Journal of Pharmacology & Experimental Therapeutics, 2001, 299(1), 268-276.
Weisstaub, "Cortical 5-Ht2a Receptor Signaling Modulates Anxiety-Like Behaviors in Mice", Science, 2006, 313, 536-540.
Wheeler et al., "(2s,1's,2'r,3'r)-2(2'-Carboxy-3'-Hydroxymethyl-Cyclopropyl)Glycine-[3h], a Potent and Selective Radioligand for Labeling Group 2 and 3 Metabotropic Glutamate Receptors", Bioorganic & Medicinal Chemistry Letters, 2005, 15, 349-351.
Whitehouse et al., "Clinical Trial Designs for Demonstrating Disease-Course-Altering Effects in Dementia", Alzheimer Disease and Associated Disorders, 1998, 12, 281-294.
Wicke et al., "Effects of Metabotropic Glutamate Receptor (Mglur) 2/3 Agonists and Antagonist on Rat Sleep Eeg", Program No. 839.2/M9, Neuroscience Meeting Planner, Society for Neuroscience, 2009, 2 pages.
Wieronska et al., "Anxiolytic Action of Group II and III Metabotropic Glutamate Receptors Agonists Involves Neuropeptide Y in the Amygdala", Pharmacol. Rep., 2005, 57(6), 734-743.
Wieronska et al., "Glutamate-Based Anxiolytic Ligands in Clinical Trials", Expert Opin Investig Drugs, 2013, 22(8), 1007-1022.
Wieronska et al., "Metabotropic Glutamate Receptor 4 Novel Agonist Lsp1-2111 with Anxiolytic, but not Antidepressant-Like Activity, Mediated by Serotonergic and Gabaergic Systems", Neuropharmacology, 2010, 59, 627-634.
Wieronska et al., "Metabotropic Glutamate Receptors in the Tripartite Synapse as a Target for New Psychotropic Drugs", Neurochem. Int, 2009, 55(1-3), 85-97.
Wieronska et al., "On the Mechanism of Anti-Hyperthermic Effects of Ly379268 and Ly487379, Group II Mglu Receptors Activators, in the Stress-Induced Hyperthermia in Singly Housed Mice", Neuropharmacology, 2012, 62, 322-331.
Wieronska et al., "Opposing Efficacy of Group III Mglu Receptor Activators, Lsp1-2111 and Amn082, in Animal Models of Positive Symptoms of Schizophrenia", Psychopharmacology, Sep. 2011, 14 pages.
Wiethoff et al., "Prevalence and Treatment Outcome in Anxious Versus Nonanxious Depression: Results From the German Algorithm Project", J Clin Psychiatry, 2010, 71(8), 1047-1054.
Wiley et al., "2-Pyrones. XVIII. 5-Aroyl-2-Pyridones", J. Am. Chem. Soc., Jun. 195, 78, 2393-2398.
Williams et al., "Characterization of Polyamines Having Agonist, Antagonist, and Inverse Agonist Effects at the Polyamine Recognition Site of the NMDA Receptor", Neuron, 1990, 5(2), 199-208.
Williams et al., "International Study to Predict Optimized Treatment for Depression (Ispot-D), A Randomized Clinical Trial: Rationale and Protocol", Trials, 2011, 12(4), 17 pages.
Wilsch et al., "Metabotropic Glutamate Receptor Agonist DCG-IV as NMDA Receptor Agonist in Immature Rat Hippocampal Neurons", European Journal of Pharmacology, 1994, 262(3), 287-291.
Wilson et al., "Antidepressants and Sleep: A Qualitative Review of the Literature", Drugs, 2005, 65, 927-947.
Winter et al., "Serotonergic/Glutamatergic Interactions: The Effects of Mglur2/3 Receptor Ligands in Rats Trained with LSD and PCP as Discriminative Stimuli.", Psychopharmacol. (Berl), 2004, 172, 233-240.
Wischhof et al., "Pre-Treatment with the Mglu2/3 Receptor Agonist Ly379268 Attenuates DOI-Induced Impulsive Responding and Regional C-Fos Protein Expression", Psychopharmacology, Aug. 2011, 14 pages.
Witkin et al., "Metabotropic Glutamate Receptors in the Control of Mood Disorders", CNS & Neurological Disorders—Drug Targets, 2007, 6, 87-100.
Wittchen et al., "Disabilities and Quality of Live in Pure and Comorbid Generalized Anxiety Disorder and Major Depression in a National Survey", Intl Clinical Psychopharmacology, 2000, 15, 319-328.
Wittchen et al., "DSM-III-R Generalized Anxiety Disorder in the National Comorbidity Survey", Arch Gen Psychiatry, 1994, 51, 355-364.
Wittchen et al., "The Size and Burden of Mental Disorders and Other Disorders of the Brain in Europe 2010", European Neuropsychopharmacology, 2011, 21, 655-679.
Wittmann et al., "Dopamine Modulates the Function of Group II and Group III Metabotropic Glutamate Receptors in the Substantia Nigra Pars Reticulata", J Pharmacol. Exp. Ther., 2002, 302(2), 433-441.
Wong et al., "The Role of Imaging in Proof of Concept for CNS Drug Discovery and Development", Neuropsychopharmacology, 2009, 34, 187-203.
Woolley et al., "The Mglu2 but not the Mglu3 Receptor Mediates the Actions of the Mglur2/3 Agonist, Ly379268, in Mouse Models Predictive of Antipsychotic Activity", Psychopharmacology, 2008, 196, 431-440.
World Health Organization, "Mental Health: New Understanding, New Hope", 2001, 169 pages.
Wright e al., "[3h]Ly341495 Binding to Group II Metabotropic Glutamate Receptors in Rat Brain", Journal of Pharmacology & Experimental Therapeutics, 2001, 298(2), 453-460.
Wroblewska et al., "N-Acetylaspartylglutamate Activates Cyclic Amp-Coupled Metabotropic Glutamate Receptors in Cerebellar Astrocytes", Glia, 1998, 24(2), 172-179.
Xi et al., "Group II Metabotropic Glutamate Receptors Modulate Extracellular Glutamate in the Nucleus Accumbens", Journal of Pharmacology & Experimental Therapeutics, 2002, 300(1), 162-171.
Xiao et al., "Desensitization of G-Protein-Coupled Receptors. Agonist-Induced Phosphorylation of the Chemoattractant Receptor Car1 Lowers its Intrinsic Affinity for Camp", J. Biol. Chem., 1999, 274(3), 1440-1448.
Xiao et al., "Metabotropic Glutamate Receptor Activation Causes a Rapid Redistribution of Ampa Receptors", Neuropharmacology, 2001, 41(6), 664-671.

(56) References Cited

OTHER PUBLICATIONS

Xu et al., "Neurotransmitter Receptors and Cognitive Dysfunction in Alzheimer's Disease and Parkinson's Disease", Progress in Neurobiology, 2012, 97, 1-13.
Yakovidis et al., "Copper(II) Complexes of Thieno[2,3-D] Pyrimidine Derivatives", Inorganica Chimica Acta, 1988, 151, 165-167.
Yanamala et al., "Preferential Binding of Allosteric Modulators to Active and Inactive Conformational States of Metabotropic Glutamate Receptors", BMC Bioinformatics, 2008, 9(Suppl 1), S16.
Yao et al., "Enhancement of Glutamate Uptake Mediates the Neuroprotection Exerted by Activating Group II or III Metabotropic Glutamate Receptors on Astrocytes", Journal of Neurochemistry, 2005, 92(4), 948-961.
Yasuhara et al., "Metabotropic Glutamate Receptors: Potential Drug Targets for Psychiatric Disorders",Open Medicinal Chemistry Journal, 2010, 4, 20-36.
Ye et al., "Metabotropic Glutamate Receptor Agonists Reduce Glutamate Release From Cultured Astrocytes", Glia, 1999, 25(3), 270-281.
Yokoi et al., "Impairment of Hippocampal Mossy Fiber Ltd in Mice Lacking Mgiur2", Science, 1996, 273, 645-647.
Young et al., "Biomarkers of Oxidative Stress in Schizophrenic and Control Subjects", Prostaglandins Leukot. Essent. Fatty Acids, 2007, 76(2), 73-85.
Young et al., "Evidence for a Role of Metabotropic Glutamate Receptors in Sustained Nociceptive Inputs to Rat Dorsal Horn Neurons," Neuropharmacology, 1994, 33(1), 141-144.
Young et al., "The Involvement of Metabotropic Glutamate Receptors and Their Intracellular Signalling Pathways in Sustained Nociceptive Transmission in Rat Dorsal Horn Neurons", Neuropharmacology, 1995, 34(8), 1033-1041.
Yousif et al., "Studies on Tertiary Amine Oxides. LXXV. Reactions of Aromatic N-Oxides with Meldrum's Acid in the Presence of Acetic Anhydride", Chem. Pharm. Bull., 1982, 30(5), 1680-1691.
Yuan et al., "Glutamate-Induced Swelling of Cultured Astrocytes is Mediated by Metabotropic Glutamate Receptor", Science in China, Series C, Life Sciences, 1996, 39(5), 517-522.
Yucel et al., "Anterior Cingulate Volume In Never-Treated Patients with Major Depressive Disorder", Neuropsychopharmacology, 2008, 33, 3157-3163.
Yui et al., "Studies of Amphetamine or Methamphetamine Psychosis in Japan: Relation of Methamphetamine Psychosis to Schizophrenia", Annals New York Academy of Sciences, 2000, 914, 1-12.
Yuzaki et al., "Pharmacological and Immunocytochemical Characterization of Metabotropic Glutamate Receptors in Cultured Purkinje Cells", J. Neurosci., 1992, 12(11), 4253-4263.

Zarate et al., "An Open-Label Trial of Riluzole in Patients with Treatment-Resistant Major Depression", Am J Psychiatry, 2004, 161, 171-174.
Zarate, "A Randomized Trial of an N-Methyl-D-Aspartate Antagonist in Treatment-Resistant Major Depression," Arch. Gen. Psychiatry, Aug. 2006, 63(8), 856-864.
Zeilhofer et al., "Differential Effects of Ketamine Enantiomers on NMDA Receptor Currents in Cultured Neurons", Eur J Pharmacol, 1992, 213, 155-158.
Zhang et al., "1-[(1-Methyl-1h-Imidazol-2-Yl)Methyl]-4-Phenylpiperidines as Mglur2 Positive Allosteric Modulators for the Treatment of Psychosis", J Med Chem, 2011, 54, 1724-1739.
Zhang et al., "3-(Imidazolyl Methyl)-3-Aza-Bicyclo[3.1.0]Hexan-6-Yl)Methyl Ethers: a Novel Series of Mglur2 Positive Allosteric Modulators", Bioorg Med Chem Lett, 2008, 18, 5493-5496.
Zhang et al., "Neuroprotective Effects of Poly(Adp-Ribose) Polymerase Inhibition on Focal Cerebral Ischemia", Biology of Nitric Oxide, Portland Press Proceedings, 1998, 15, 125.
Zhao et al., "Activation of Group II Metabotropic Glutamate Receptors Attenuates Both Stress and Cue-Induced Ethanol-Seeking and Modulates C-Fos Expression in the Hippocampus and Amygdala", Journal of Neuroscience, 2006, 26(39), 9967-9974.
Zhu et al., "Rapid Enhancement of High Affinity Glutamate Uptake by Glucocorticoids in Rat Cerebral Cortex Synaptosomes and Human Neuroblastoma Clone Sk-N-Sh: Possible Involvement of G-Protein", Biochemical & Biophysical Research Communications, 1998, 247(2), 261-265.
Zhu, "The Competitive and Noncompetitive Antagonism of Receptor-Mediated Drug Actions in the Presence of Spare Receptors", Journal of Pharmacological & Toxicological Methods, 1993, 29(2), 85-91.
Zimmerman et al., "Frequency of Anxiety Disorders in Psychiatric Outpatients with Major Depressive Disorder", Am J Psychiatry, 2000, 157, 1337-1340.
Zuena et al., "Prenatal Restraint Stress Generates Two Distinct Behavioral and Neurochemical Profiles in Male and Female Rats", Plos. One, 2008, 3(5), E2170.
Zusso et al., "Cerebellar Granular Cell Cultures as an In Vitro Model for Antidepressant Drug-Induced Meurogenesis", Critical Reviews in Neurobiology, 2004, 16(1&2), 59-65.
Zwart et al., "Sazetidine-A is a Potent and Selective Agonist at Native and Recombinant A4β2 Nicotinic Acetylcholine Receptors", Mol Pharmacol, 2008, 73, 1838-1843.
Patani et. al. "Bioisosterism: A Rational Approach in Drug Design" Chemical Reviews, 1996, 96, 3147-3176.
Wakefield, "Fluorinated Pharmaceuticals: Fluorinated Compounds are of Increasing Interest as Pharmaceuticals, and an Extensive Range of Techniques for Making Them is Now Available", Innovations in Pharmaceutical Technology, 2003, 74-78.

\* cited by examiner

1,2,4-TRIAZOLO[4,3-A]PYRIDINE DERIVATIVES AND THEIR USE AS POSITIVE ALLOSTERIC MODULATORS OF MGLUR2 RECEPTORS

IN THE CROSS-REFERENCE TO RELATED APPLICATIONS

This application claims priority to European Application No. 09160067.6, filed May 12, 2009, which is hereby incorporated herein by reference in its entirety for all purposes.

FIELD OF THE INVENTION

The present invention relates to novel triazolo[4,3-a]pyridine derivatives which are positive allosteric modulators of the metabotropic glutamate receptor subtype 2 ("mGluR2") and which are useful for the treatment or prevention of neurological and psychiatric disorders associated with glutamate dysfunction and diseases in which the mGluR2 subtype of metabotropic receptors is involved. The invention is also directed to pharmaceutical compositions comprising such compounds, to processes to prepare such compounds and compositions, and to the use of such compounds for the prevention or treatment of neurological and psychiatric disorders and diseases in which mGluR2 is involved.

BACKGROUND OF THE INVENTION

Glutamate is the major amino acid neurotransmitter in the mammalian central nervous system. Glutamate plays a major role in numerous physiological functions, such as learning and memory but also sensory perception, development of synaptic plasticity, motor control, respiration, and regulation of cardiovascular function. Furthermore, glutamate is at the centre of several different neurological and psychiatric diseases, where there is an imbalance in glutamatergic neurotransmission.

Glutamate mediates synaptic neurotransmission through the activation of ionotropic glutamate receptor channels (iGluRs), and the NMDA, AMPA and kainate receptors which are responsible for fast excitatory transmission.

In addition, glutamate activates metabotropic glutamate receptors (mGluRs) which have a more modulatory role that contributes to the fine-tuning of synaptic efficacy.

Glutamate activates the mGluRs through binding to the large extracellular amino-terminal domain of the receptor, herein called the orthosteric binding site. This binding induces a conformational change in the receptor which results in the activation of the G-protein and intracellular signalling pathways.

The mGluR2 subtype is negatively coupled to adenylate cyclase via activation of Gαi-protein, and its activation leads to inhibition of glutamate release in the synapse. In the central nervous system (CNS), mGluR2 receptors are abundant mainly throughout cortex, thalamic regions, accessory olfactory bulb, hippocampus, amygdala, caudate-putamen and nucleus accumbens.

Activating mGluR2 has been shown in clinical trials to be efficacious to treat anxiety disorders. In addition, activating mGluR2 in various animal models was shown to be efficacious, thus representing a potential novel therapeutic approach for the treatment of schizophrenia, epilepsy, drug addiction/dependence, Parkinson's disease, pain, sleep disorders and Huntington's disease.

To date, most of the available pharmacological tools targeting mGluRs are orthosteric ligands which activate several members of the family as they are structural analogs of glutamate.

A new avenue for developing selective compounds acting at mGluRs is to identify compounds that act through allosteric mechanisms, modulating the receptor by binding to a site different from the highly conserved orthosteric binding site.

Positive allosteric modulators of mGluRs have emerged recently as novel pharmacological entities offering this attractive alternative. Various compounds have been described as mGluR2 positive allosteric modulators. None of the specifically disclosed compounds herein are structurally related to the compounds disclosed in the art.

It was demonstrated that such compounds do not activate the receptor by themselves. Rather, they enable the receptor to produce a maximal response to a concentration of glutamate which by itself induces a minimal response. Mutational analysis has demonstrated unequivocally that the binding of mGluR2 positive allosteric modulators does not occur at the orthosteric site, but instead at an allosteric site situated within the seven transmembrane region of the receptor.

Animal data suggest that positive allosteric modulators of mGluR2 have effects in anxiety and psychosis models similar to those obtained with orthosteric agonists. Allosteric modulators of mGluR2 have been shown to be active in fear-potentiated startle, and in stress-induced hyperthermia models of anxiety. Furthermore, such compounds have been shown to be active in reversal of ketamine- or amphetamine-induced hyperlocomotion, and in reversal of amphetamine-induced disruption of prepulse inhibition of the acoustic startle effect models of schizophrenia.

Recent animal studies have further revealed that the selective positive allosteric modulator of metabotropic glutamate receptor subtype 2 biphenyl-indanone (BINA) blocks a hallucinogenic drug model of psychosis, supporting the strategy of targeting mGluR2 receptors for treating glutamatergic dysfunction in schizophrenia.

Positive allosteric modulators enable potentiation of the glutamate response, but they have also been shown to potentiate the response to orthosteric mGluR2 agonists such as LY379268 or DCG-IV. These data provide evidence for yet another novel therapeutic approach to treat the above mentioned neurological and psychiatric diseases involving mGluR2, which would use a combination of a positive allosteric modulator of mGluR2 together with an orthosteric agonist of mGluR2.

The present triazolopyridine derivatives are centrally active, potent compounds providing alternative mGluR2 positive allosteric modulators with improved solubility and salt forming properties.

DETAILED DESCRIPTION OF THE INVENTION

The present invention relates to compounds having metabotropic glutamate receptor 2 modulator activity, said compounds having the Formula (I)

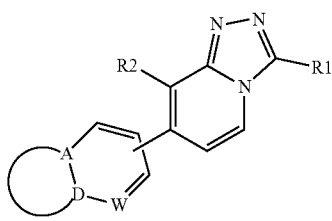

(I)

and the stereochemically isomeric forms thereof, wherein
the bond drawn into the ring indicates that the bond may be attached to any carbon ring atom;

$R^1$ is selected from the group consisting of hydrogen; $C_{1-6}$alkyl; $(C_{1-3}$alkyloxy$)$-$C_{1-3}$alkyl; $[(C_{1-3}$alkyloxy$)$-$C_{1-3}$alkyloxy$]C_{1-3}$alkyl; $C_{1-3}$alkyl substituted with one or more independently selected halo substituents; unsubstituted benzyl; benzyl substituted with one or more substituents each independently selected from the group consisting of halo, $C_{1-3}$alkyl, $(C_{1-3}$alkyloxy$)C_{1-3}$alkyl, $C_{1-3}$alkyloxy, hydroxy$C_{1-3}$alkyl, cyano, hydroxyl, amino, C(=O)R', C(=O)OR', C(=O)NR'R'', mono- or di-$(C_{1-3}$alkyl)amino, morpholinyl, $(C_{3-7}$cycloalkyl$)C_{1-3}$alkyloxy, trifluoromethyl and trifluoromethoxy, wherein R' and R'' are independently selected from hydrogen and $C_{1-6}$alkyl; (benzyloxy)$C_{1-3}$alkyl; unsubstituted $C_{3-7}$cycloalkyl; $C_{3-7}$cycloalkyl substituted with one or more independently selected $C_{1-3}$alkyl substituted with one or more independently selected halo substituents; $(C_{3-7}$cycloalkyl$)C_{1-3}$alkyl; 4-(2,3,4,5-tetrahydro-benzo[f][1,4]oxazepine)methyl; Het$^1$; Het$^1C_{1-3}$alkyl; Het$^2$; and Het$^2C_{1-3}$alkyl;

$R^2$ is selected from the group consisting of cyano; halo; $C_{1-3}$alkyl substituted with one or more independently selected halo substituents; $C_{1-3}$alkyloxy substituted with one or more independently selected halo substituents; $C_{1-3}$alkyl; $C_{3-7}$cycloalkyl; and $(C_{3-7}$cycloalkyl$)C_{1-3}$alkyl;

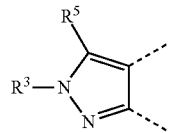

forms a radical selected from (a), (b), (c), (d) and (e):

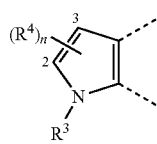

(a)

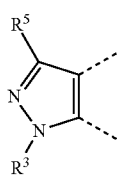

(b)

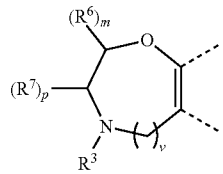

(c)

(d)

(e)

wherein
the bond drawn into (a) indicates that $R^4$ may be attached to any of carbon ring atoms 2 and 3;
each $R^3$ is independently selected from the group consisting of hydrogen; unsubstituted $C_{1-6}$alkyl; $C_{1-6}$alkyl substituted with one or more substituents independently selected from the group consisting of halo, hydroxy, $C_{1-3}$alkoxy and trifluoromethyl; unsubstituted $C_{3-7}$cycloalkyl; $C_{3-7}$cycloalkyl substituted with one or more substituents independently selected from the group consisting of halo, $C_{1-3}$alkyl, hydroxy, $C_{1-3}$alkoxy and trifluoromethyl; $C_{3-7}$cycloalkyl$C_{1-3}$alkyl; unsubstituted phenyl; phenyl substituted with one or more substituents independently selected from the group consisting of halo, $C_{1-3}$alkyl, $C_{1-3}$alkoxy and trifluoromethyl; Het$^3$; and Het$^3C_{1-3}$alkyl;
or
each $R^3$ is independently selected from a cyclic radical of formula (f)

(f)

wherein $R^8$ is selected from hydrogen, $C_{1-3}$alkyl, $C_{1-3}$alkyloxy and hydroxy$C_{1-3}$alkyl;
q is 1 or 2;
X is selected from O, CH$_2$ and CR$^9$(OH), wherein R$^9$ is selected from hydrogen, $C_{1-3}$alkyl and $C_{3-7}$cycloalkyl; or
X is a cyclic radical of formula (g)

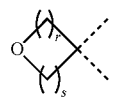

(g)

wherein r and s are independently selected from 0, 1 and 2, provided that r+s≥2;
each $R^4$, $R^6$ and $R^7$ are each independently selected from $C_{1-3}$alkyl and $C_{1-3}$alkyl substituted with one or more independently selected halo substituents;
each $R^5$ is independently selected from the group consisting of hydrogen, $C_{1-3}$alkyl, and $C_{1-3}$alkyl substituted with one or more independently selected halo substituents;

n, m and p are each independently selected from 0, 1 and 2;
v is 0 or 1; and
t and u are each independently selected from 1 and 2;
W is selected from N and $CR^{10}$;
wherein $R^{10}$ is selected from hydrogen, halo and trifluoromethyl;
wherein
each $Het^1$ is a saturated heterocyclic radical selected from pyrrolidinyl; piperidinyl; piperazinyl; and morpholinyl; each of which may be optionally substituted with one or more each independently selected from the group consisting of $C_{1-6}$alkyl; mono-, di- and tri-halo$C_{1-3}$alkyl; unsubstituted phenyl; and phenyl substituted with 1, 2 or 3 substituents independently selected from the group consisting of halo, trifluoromethyl, and trifluoromethoxy;
each $Het^2$ is pyridyl or pyrimidinyl; and
each $Het^3$ is a heterocycle selected from the group consisting of tetrahydropyran, pyridyl; and pyrimidinyl; each of them being optionally substituted with one or more substituents each independently selected from the group consisting of halo, $C_{1-3}$alkyl, $C_{1-3}$alkoxy and trifluoromethyl;
halo is selected from fluoro, chloro, bromo and iodo;
and the pharmaceutically acceptable salts and the solvates thereof.

The names of the compounds of the present invention were generated according to the nomenclature rules agreed upon by the Chemical Abstracts Service (CAS) using Advanced Chemical Development, Inc., software (ACD/Name product version 10.01; Build 15494, 1 Dec. 2006). In case of tautomeric forms, the name of the depicted tautomeric form of the structure was generated. However it should be clear that the other non-depicted tautomeric form is also included within the scope of the present invention.

DEFINITIONS

The notation $C_{1-3}$alkyl or $C_{1-6}$alkyl as used herein alone or as part of a group defines a saturated, straight or branched, hydrocarbon radical having, unless otherwise stated, from 1 to 3 or 1 to 6 carbon atoms, such as methyl, ethyl, 1-propyl, 1-methylethyl, butyl, 2-methyl-1-propyl, 1,1-dimethylethyl, 3-methyl-1-butyl, 1-pentyl, 1-hexyl and the like.

The notation $C_{3-7}$cycloalkyl, as used herein alone or as part of a group, defines a saturated, cyclic hydrocarbon radical having from 3 to 7 carbon atoms, such as cyclopropyl, cyclobutyl, cyclopentyl, cyclohexyl and cycloheptyl.

The term "$C_{3-7}$cycloalkyl$C_{1-3}$alkyl" as employed herein alone or as part of another group, defines a saturated, cyclic hydrocarbon radical having from 3 to 7 carbon atoms bound through a saturated, straight hydrocarbon radical having from 1 to 3 carbon atoms, such as cyclopropylmethyl, cyclopropylethyl, cyclobutylmethyl and the like.

The notation halogen or halo as used herein alone or as part of another group, refers to fluoro, chloro, bromo or iodo, with fluoro or chloro being preferred.

The notation mono-, di- or tri-halo$C_{1-3}$alkyl defines an alkyl group as defined above, substituted with 1, 2 or 3 halogen atoms, such as fluoromethyl; difluoromethyl; trifluoromethyl; 2,2,2-trifluoroethyl; 1,1-difluoroethyl; 3,3,3-trifluoropropyl. Preferred examples of these groups are trifluoromethyl, 2,2,2-trifluoroethyl and 1,1-difluoroethyl.

The notation "$C_{1-3}$alkyl substituted with one or more independently selected halo substituents" as used herein alone or as part of another group, defines an alkyl group as defined above, substituted with 1, 2, 3 or more halogen atoms, such as fluoromethyl; difluoromethyl; trifluoromethyl; 2,2,2-trifluoroethyl; 1,1-difluoroethyl; 3,3,3-trifluoropropyl. Preferred examples of these groups are trifluoromethyl; 2,2,2-trifluoroethyl; 3,3,3-trifluoropropyl and 1,1-difluoroethyl.

Whenever the term "substituted" is used in the present invention, it is meant, unless otherwise is indicated or is clear from the context, to indicate that one or more hydrogens, preferably from 1 to 3 hydrogens, more preferably 1 to 2 hydrogens, more preferably 1 hydrogen, on the atom or radical indicated in the expression using "substituted" are replaced with a selection from the indicated group, provided that the normal valency is not exceeded, and that the substitution results in a chemically stable compound, i.e. a compound that is sufficiently robust to survive isolation to a useful degree of purity from a reaction mixture, and formulation into a therapeutic agent.

The substituents covered by the terms $Het^1$, $Het^2$ or $Het^3$ may be attached to the remainder of the molecule of formula (I) through any available ring carbon or heteroatom as appropriate, if not otherwise specified. Thus, for example, when the $Het^1$ substituent is morpholinyl, it may be 2-morpholinyl, 3-morpholinyl or 4-morpholinyl; when the $Het^2$ or $Het^3$ substituent is pyridyl, it may be 2-pyridyl, 3-pyridyl or 4-pyridyl. Preferred $Het^1$ substituents are those linked to the rest of the molecule through the nitrogen atom.

It will be appreciated that some of the compounds of formula (I) and their pharmaceutically acceptable addition salts and solvates thereof may contain one or more centres of chirality and exist as stereoisomeric forms.

The term "stereoisomeric forms" as used hereinbefore defines all the possible isomeric forms that the compounds of Formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centres may have the R- or S-configuration; substituents on bivalent cyclic (partially) saturated radicals may have either the cis- or trans-configuration. Compounds encompassing double bonds can have an E- or Z-stereochemistry at said double bond. Stereoisomeric forms of the compounds of Formula (I) are embraced within the scope of this invention.

When a specific stereoisomeric form is indicated, this means that said form is substantially free, i.e. associated with less than 50%, preferably less than 20%, more preferably less than 10%, even more preferably less than 5%, in particular less than 2% and most preferably less than 1%, of the other isomers. Thus, when a compound of formula (I) is for instance specified as (R), this means that the compound is substantially free of the (S) isomer.

Following CAS nomenclature conventions, when two stereogenic centres of known absolute configuration are present in a compound, an R or S descriptor is assigned (based on Cahn-Ingold-Prelog sequence rule) to the lowest-numbered chiral centre, the reference centre. The configuration of the second stereogenic centre is indicated using relative descriptors [R*,R*] or [R*,S*], where R* is always specified as the reference centre and [R*,R*] indicates centres with the same chirality and [R*,S*] indicates centres of unlike chirality. For example, if the lowest-numbered chiral centre in the compound has an S-configuration and the second centre is R, the stereo descriptor would be specified as S—[R*,S*].

Preferred features of the compounds of this invention are now set forth.

In an embodiment, the invention relates to compounds of Formula (I) and stereochemically isomeric forms thereof, wherein
$R^1$ is selected from the group consisting of $C_{1-6}$alkyl; ($C_{1-3}$alkyloxy)$C_{1-3}$alkyl; [($C_{1-3}$alkyloxy)-$C_{1-3}$alkyloxy]$C_{1-3}$ alkyl; $C_{1-3}$alkyl substituted with one or more halo substituents; unsubstituted benzyl; (benzyloxy)$C_{1-3}$alkyl; unsubstituted $C_{3-7}$cycloalkyl; $C_{3-7}$cycloalkyl substituted with trihalo$C_{1-3}$alkyl; ($C_{3-7}$cycloalkyl)$C_{1-3}$alkyl; 4-(2,3,4,5-tetrahydro-benzo[f][1,4]oxazepine)methyl; $Het^1C_{1-3}$alkyl; $Het^2$; and $Het^2C_{1-3}$alkyl;

$R^2$ is selected from the group consisting of cyano; halo; $C_{1-3}$alkyl; $C_{3-7}$cycloalkyl; and $C_{1-3}$alkyl substituted with one or more halo substituents; and $C_{1-3}$alkyl substituted with one or more independently selected halo substituents;

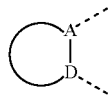

is selected from (a), (b), (c) and (d):

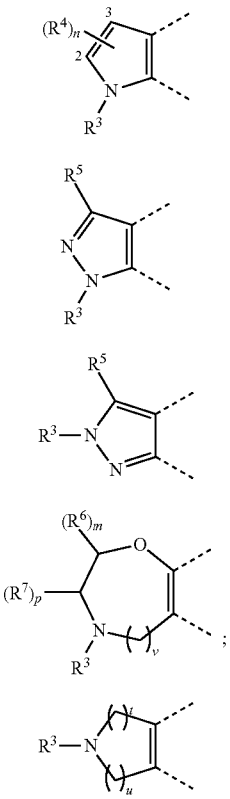

each $R^3$ is independently selected from the group consisting of hydrogen; unsubstituted $C_{1-6}$alkyl; $C_{1-6}$alkyl substituted with one or more substituents independently selected from the group consisting of halo, hydroxyl, $C_{1-3}$alkoxy or trifluoromethyl; unsubstituted $C_{3-7}$cycloalkyl; $C_{3-7}$cycloalkyl substituted with one or more substituents independently selected from the group consisting of halo, $C_{1-3}$alkyl, hydroxyl, $C_{1-3}$alkoxy or trifluoromethyl; ($C_{3-7}$cycloalkyl)$C_{1-3}$alkyl; unsubstituted phenyl; phenyl substituted with one or more independently selected halo substituents; $Het^3$; and $Het^3C_{1-3}$alkyl;

m, n and p are 0;
v is 0 or 1;
t and u are both 1;

each $R^5$ is hydrogen;
W is selected from N and $CR^{10}$;
$R^{10}$ is selected from hydrogen and halo;
$Het^3$ is a heterocycle selected from the group consisting of tetrahydropyran; pyridyl; and pyrimidinyl; each of them being optionally substituted with one or more substituents each independently selected from halo, $C_{1-3}$alkyl, $C_{1-3}$alkoxy and trifluoromethyl; and
halo is selected from fluoro and chloro
and the pharmaceutically acceptable salts and the solvates thereof.

In an embodiment, the invention relates to compounds of Formula (I) and stereochemically isomeric forms thereof, wherein $R^1$ is selected from the group consisting of ($C_{1-3}$alkyloxy)$C_{1-3}$alkyl; $C_{1-3}$alkyl substituted with one or more independently selected halo substituents; and ($C_{3-7}$cycloalkyl)$C_{1-3}$alkyl;

$R^2$ is selected from the group consisting of halo; $C_{1-3}$alkyl; $C_{3-7}$cycloalkyl; and $C_{1-3}$alkyl substituted with one or more independently selected halo substituents;

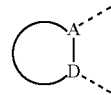

is selected from (a), (b), (c) and (d):

(a)

(b)

(c)

(d)

each $R^3$ is independently selected from the group consisting of hydrogen; $C_{1-6}$alkyl substituted with one or more hydroxyl substituents; unsubstituted $C_{3-7}$cycloalkyl; $C_{3-7}$cycloalkyl substituted with one or more hydroxyl substituents; ($C_{3-7}$cycloalkyl)$C_{1-3}$alkyl; phenyl substituted with one or more independently selected halo substituents; $Het^3$; and $Het^3C_{1-3}$alkyl;

m, n and p are 0;
v is 0 or 1;
each $R^5$ is hydrogen;

W is selected from N and CR[10];

R[10] is selected from hydrogen and halo;

Het[3] is a heterocycle selected from the group consisting of tetrahydropyran; pyridyl; and pyrimidinyl; each of them being optionally substituted with one or more substituents each independently selected from halo and $C_{1-3}$alkyl;

halo is selected from fluoro and chloro;

and the pharmaceutically acceptable salts and the solvates thereof.

In an embodiment, the invention relates to compounds of Formula (I) and stereochemically isomeric forms thereof, wherein

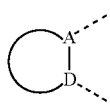

is selected from (a'), (b'), (c') and (d'):

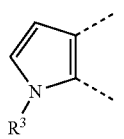
(a')

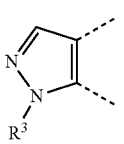
(b')

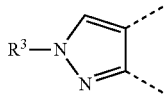
(c')

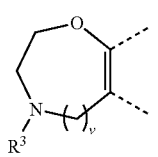
(d')

each R[3] is independently selected from the group consisting of hydrogen; hydroxyC$_{1-6}$alkyl; C$_{3-7}$cycloalkyl substituted with one hydroxy substituent; (C$_{3-7}$cycloalkyl)C$_{1-3}$alkyl; phenyl substituted with one halo substituent; Het[3]; and Het[3]C$_{1-3}$alkyl;

v is 0 or 1;

W is selected from the group consisting of N, CH, CCl and CF;

Het[3] is a heterocycle selected from the group consisting of tetrahydropyran; pyridyl optionally with one substituent selected from halo and $C_{1-3}$alkyl; and pyrimidinyl;

halo is selected from fluoro and chloro;

and the pharmaceutically acceptable salts and the solvates thereof.

In an embodiment, the invention relates to compounds of Formula (I) and stereochemically isomeric forms thereof, wherein

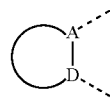

is selected from (a') and (d');

R[1] is C$_{3-7}$cycloalkylC$_{1-3}$alkyl;

R[2] is selected from halo and C$_{1-3}$alkyl substituted with one or more independently selected halo substituents;

R[3] is selected from hydrogen; C$_{3-7}$cycloalkyl substituted with one hydroxy substituent; (C$_{3-7}$cycloalkyl)C$_{1-3}$alkyl; pyridyl optionally with one substituent selected from halo and $C_{1-3}$alkyl; and pyrimidinyl;

W is selected from N, CH and CCl;

v is 0;

halo is selected from fluoro and chloro;

and the pharmaceutically acceptable salts and the solvates thereof.

In an embodiment, the invention relates to compounds of Formula (I) and stereochemically isomeric forms thereof, wherein R[1] is selected from the group consisting of ethoxymethyl; 2,2,2-trifluoroethyl; cyclopropylmethyl;

R[2] is selected from the group consisting of chloro; methyl; trifluoromethyl; and cyclopropyl;

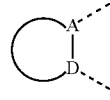

is selected from (a'), (b'), (c') and (d');

each R[3] is independently selected from the group consisting of hydrogen; 2-hydroxy-2-methyl-propyl; cyclopropylmethyl; cyclobutylmethyl; 4-hydroxy-cyclohexyl; 4-fluorophenyl; tetrahydropyran-4-yl; pyridin-2-yl; pyridin-3-yl; pyridin-4-yl; pyrimidin-2-yl; 2-methyl-pyridin-4-yl; 3-fluoro-pyridin-4-yl; 2-methyl-pyridin-5-yl; and pyridin-3-yl-methyl;

v is 0 or 1;

W is selected from the group consisting of N, CH, CF and CCl;

and the pharmaceutically acceptable salts and the solvates thereof.

In an embodiment, the invention relates to compounds of Formula (I) and stereochemically isomeric forms thereof, wherein

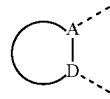

is selected from (a') and (d');

R[1] is cyclopropylmethyl;

R[2] is selected from chloro and trifluoromethyl;

R[3] is selected from hydrogen; cyclopropylmethyl; 4-hydroxy-cyclohexyl; pyridin-3-yl; and pyrimidin-2-yl;

W is selected from N, CH and CCl;

v is 0;

and the pharmaceutically acceptable salts and the solvates thereof.

In an embodiment, the invention relates to compounds of Formula (I) and stereochemically isomeric forms thereof, as previously defined, wherein

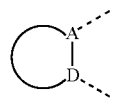

is selected from (a') and W is selected from N, CH, CF and CCl;

is selected from (b') or (c') and W is CH;

is selected from (d'); v is 0 or 1; and W is CH;

is selected from (a') and W is selected from N, CH, CF and CCl;

is selected from (a') and W is selected from N, CH, and CCl;

is selected from (d'); v is 0; and W is CH;

In an embodiment, the invention relates to compounds of Formula (I) and stereoisomeric forms thereof, wherein
the bond drawn into the ring indicates that the bond may be attached to any carbon ring atom;
$R^1$ is selected from hydrogen; $C_{1-6}$alkyl; $(C_{1-3}$alkyloxy)$C_{1-3}$alkyl; $[(C_{1-3}$alkyloxy)-$C_{1-3}$alkyloxy]$C_{1-3}$alkyl; mono-, di- or tri-halo$C_{1-3}$alkyl; unsubstituted benzyl; benzyl substituted with 1, 2 or 3 substituents independently selected from the group consisting of halo, $C_{1-3}$alkyl, $(C_{1-3}$alkyloxy)$C_{1-3}$alkyl, $C_{1-3}$alkyloxy, hydroxy$C_{1-3}$alkyl, cyano, hydroxyl, amino, C(=O)R', C(=O)OR', C(=O)NR'R", mono- or di-$(C_{1-3}$alkyl)amino, morpholinyl, $(C_{3-7}$cycloalkyl)$C_{1-3}$alkyloxy, trifluoromethyl and trifluoromethoxy, wherein R' and R" are independently selected from hydrogen and $C_{1-6}$alkyl; (benzyloxy)$C_{1-3}$alkyl; unsubstituted $C_{3-7}$cycloalkyl; $C_{3-7}$cycloalkyl substituted with trihalo$C_{1-3}$alkyl; $(C_{3-7}$cycloalkyl)$C_{1-3}$alkyl; 4-(2,3,4,5-tetrahydro-benzo[f][1,4]oxazepine)methyl; $Het^1$; $Het^1C_{1-3}$alkyl; $Het^2$ and $Het^2C_{1-3}$alkyl;

$R^2$ is selected from cyano; halo; mono-, di- or tri-halo $C_{1-3}$alkyl; mono-, di- or trihalo$C_{1-3}$alkyloxy; $C_{1-3}$alkyl; $C_{3-7}$cycloalkyl and $(C_{3-7}$cycloalkyl)$C_{1-3}$alkyl;

forms a radical selected from (a), (b), (c) and (d):

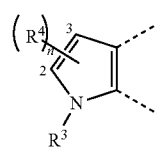

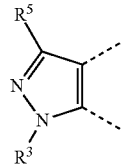

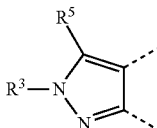

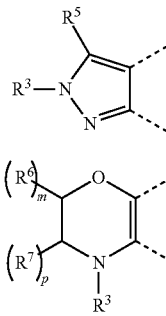

wherein
the bond drawn into (a) indicates that $R^4$ may be attached to any of carbon ring atoms 2 and 3;

$R^3$ is selected from hydrogen; unsubstituted $C_{1-6}$alkyl; $C_{1-6}$alkyl substituted with 1 or 2 substituents independently selected from the group consisting of halo, hydroxy, $C_{1-6}$alkoxy or trifluoromethyl; unsubstituted $C_{3-7}$cycloalkyl; $C_{3-7}$cycloalkyl substituted with 1 or 2 substituents independently selected from the group consisting of halo, $C_{1-3}$alkyl, hydroxy, $C_{1-3}$alkoxy and trifluoromethyl; $C_{3-7}$cycloalkyl $C_{1-3}$alkyl; unsubstituted phenyl; phenyl substituted with 1, 2 or 3 substituents selected from the group consisting of halo, $C_{1-3}$alkyl, $C_{1-3}$alkoxy and trifluoromethyl; $Het^3$ and $Het^3$ $C_{1-3}$alkyl;

or $R^3$ is a cyclic radical of formula (f)

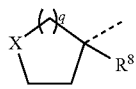
(f)

wherein $R^8$ is selected from hydrogen, $C_{1-3}$alkyl, $C_{1-3}$alkyloxy and hydroxy$C_{1-3}$alkyl;

q is 1 or 2;

X is selected from O, $CH_2$ or $CR^9$(OH) wherein $R^9$ is selected from hydrogen, $C_{1-3}$alkyl and $C_{3-7}$cycloalkyl; or X is a cyclic radical of formula (g)

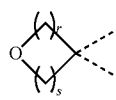
(g)

wherein r and s are independently selected from 0, 1 or 2, provided that r+s≥2;

$R^4$, $R^6$ and $R^7$ are independently selected from $C_{1-3}$alkyl or mono-, di- and tri-halo-$C_{1-3}$alkyl;

$R^5$ is selected from hydrogen, $C_{1-3}$alkyl or mono-, di- and tri-halo$C_{1-3}$alkyl;

n, m and p are independently selected from 0, 1 and 2;

W is selected from N and Ce;

wherein $R^{10}$ is selected from hydrogen, halo and trifluoromethyl;

wherein each $Het^1$ is a saturated heterocyclic radical selected from pyrrolidinyl; piperidinyl; piperazinyl; or morpholinyl; each of which may be optionally substituted with 1 or 2 substituents independently selected from the group consisting of $C_{1-6}$alkyl, mono-, di- or tri-halo$C_{1-3}$alkyl, unsubstituted phenyl or phenyl substituted with 1, 2 or 3 substituents independently selected from the group consisting of halo, trifluoromethyl, and trifluoromethoxy; and each $Het^2$ is an aromatic heterocyclic radical selected from pyridyl or pyrimidinyl; and each $Het^3$ is a heterocycle selected from the group consisting of tetrahydropyran, pyridyl or pyrimidinyl, each of them being optionally substituted with 1 or 2 substituents selected from the group consisting of halo, $C_{1-3}$alkyl, $C_{1-3}$alkoxy and trifluoromethyl;

and the pharmaceutically acceptable salts and the solvates thereof.

In an embodiment, the invention relates to compounds according to Formula (I) and the stereochemically isomeric forms thereof, wherein $R^1$ is selected from $C_{1-6}$alkyl; mono-, di- or tri-halo$C_{1-3}$alkyl; unsubstituted $C_{3-7}$cycloalkyl; $C_{3-7}$cycloalkyl substituted with trihalo$C_{1-3}$alkyl; $(C_{3-7}$cycloalkyl)-$C_{1-3}$alkyl; 4-(2,3,4,5-tetrahydro-benzo[f][1,4]oxazepine)methyl; $Het^1$; $Het^1C_{1-3}$alkyl; and $Het^2C_{1-3}$alkyl;

$R^2$ is selected from halo or mono-, di- and tri-halo$C_{1-3}$alkyl;

forms a radical selected from (a), (b), (c) and (d):

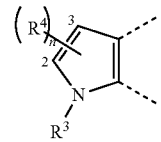
(a)

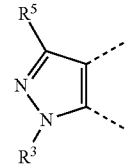
(b)

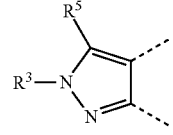
(c)

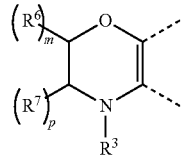
(d)

wherein $R^3$ is selected from hydrogen; unsubstituted $C_{1-6}$alkyl; $C_{1-6}$alkyl substituted with 1 or 2 substituents independently selected from the group consisting of halo, hydroxy, $C_{1-3}$alkoxy and trifluoromethyl; unsubstituted $C_{3-7}$cycloalkyl; $C_{3-7}$cycloalkyl substituted with 1 or 2 substituents independently selected from the group consisting of halo, $C_{1-3}$alkyl, hydroxy, $C_{1-3}$alkoxy or trifluoromethyl; $(C_{3-7}$cycloalkyl)$C_{1-3}$alkyl; $Het^3$ and $Het^3C_{1-3}$alkyl;

$R^4$, $R^6$ and $R^7$ are independently selected from $C_{1-3}$alkyl or mono-, di- and tri-halo-$C_{1-3}$alkyl;

$R^5$ is selected from hydrogen, $C_{1-3}$alkyl or mono-, di- and tri-halo$C_{1-3}$alkyl;

n, m and p are independently selected from 0, 1 and 2;

W is selected from N and $CR^{10}$;

wherein $R^{10}$ is selected from hydrogen and halo;

wherein $Het^1$, $Het^2$, $Het^3$ are as previously defined;

and the pharmaceutically acceptable salts and the solvates thereof.

In the previous embodiment, $R^5$ is preferably hydrogen and n, m and p are preferably, 0.

In an embodiment, the invention relates to compounds according to Formula (I) and the stereochemically isomeric forms thereof, wherein $R^1$ is selected from mono-, di- or tri-halo$C_{1-3}$alkyl; unsubstituted $C_{3-7}$cycloalkyl; $(C_{3-7}$cycloalkyl)$C_{1-3}$alkyl; 4-(2,3,4,5-tetrahydro-benzo[f][1,4]oxazepine)methyl; $Het^1$; $Het^1C_{1-3}$alkyl; and $Het^2C_{1-3}$alkyl;

forms a radical selected from (a'), (b'), and (c'):

wherein

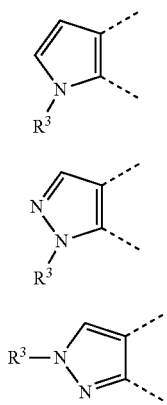

R³ is selected from hydrogen; C₁₋₆alkyl substituted with 1 or 2 substituents independently selected from the group consisting of halo, hydroxy, C₁₋₃alkoxy or trifluoromethyl; C₃₋₇cycloalkyl substituted with 1 or 2 substituents independently selected from the group consisting of halo, C₁₋₃alkyl, hydroxy, C₁₋₃alkoxy or trifluoromethyl; (C₃₋₇cycloalkyl)C₁₋₃alkyl; Het³ and Het³C₁₋₃alkyl;
W is selected from N and CR¹⁰;
wherein R¹⁰ is selected from hydrogen and halo;
wherein R², Het¹, Het², Het³ are as previously defined;
and the pharmaceutically acceptable salts and the solvates thereof.

In an embodiment, the invention relates to compounds according to Formula (I) and the stereochemically isomeric forms thereof, wherein
R¹ is selected from mono-, di- or tri-haloC₁₋₃alkyl; and (C₃₋₇cycloalkyl)C₁₋₃alkyl;

forms a radical selected from (a'), (b'), and (c'):
wherein

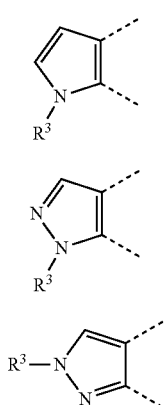

R³ is selected from hydrogen; C₁₋₆alkyl substituted with 1 or 2 substituents independently selected from the group consisting of halo, hydroxy, and trifluoromethyl; C₃₋₇cycloalkyl substituted with 1 or 2 substituents independently selected from the group consisting of halo, hydroxy and trifluoromethyl; (C₃₋₇cycloalkyl)C₁₋₃alkyl; Het³ and Het³C₁₋₃alkyl;
wherein Het³ is selected from tetrahydropyran, pyridyl and pyrimidinyl, each of them being optionally substituted with one or two substituents selected from the group consisting of halo and trifluoromethyl;
and R² and W are as previously defined;
and the pharmaceutically acceptable salts and the solvates thereof.

In an additional embodiment, the invention relates to compounds according to Formula (I) and the stereochemically isomeric forms thereof, wherein
R¹ is selected from CH₂CF₃ and cyclopropylmethyl;
R² is selected from fluoro, chloro and trifluoromethyl;

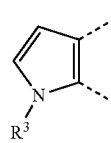

forms a radical selected from (a'), (b'), and (c'):
wherein

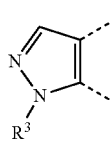

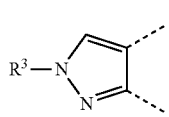

R³ is selected from hydrogen; 2-hydroxy-2-methyl-propyl; 4-hydroxy-cyclohexyl; pyridyl; pyrimidinyl; tetrahydropyranyl; and pyridylmethyl;
W is selected from N and CR¹⁰;
wherein R¹⁰ is selected from hydrogen and chloro;
and the pharmaceutically acceptable salts and the solvates thereof.

In a further embodiment, the invention relates to compounds according to any of the other embodiments wherein R² is chloro or trifluoromethyl and R³ is selected from the group consisting of hydrogen; 2-hydroxy-2-methyl-propyl; 4-hydroxy-cyclohexyl; 2-pyridyl; 2-pyrimidinyl; 4-tetrahydropyranyl; and 3-pyridylmethyl.

In the compounds of formula (I) the bicycle

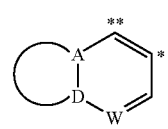

is bound to the rest of the molecule through the * or the ** carbon atom and R¹, R², W, and

are as previously defined, or a pharmaceutically acceptable salt or a solvate thereof. In a particular embodiment, the bicycle may be selected from one of the following:

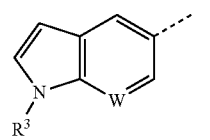
(a'-1)

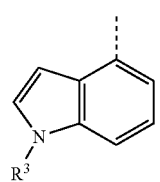
(a'-2)

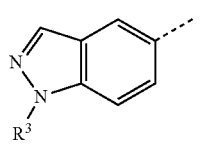
(b'-1)

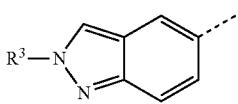
(b'-2)

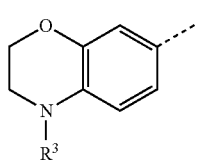
(c'-1)

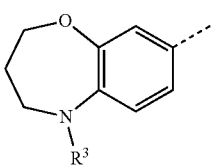
(c'-2)

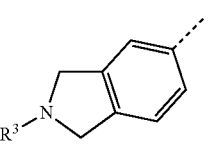
(e'-1)

wherein $R^3$ is as previously defined.

In a more particular embodiment, the bicycle is selected from (a'-1), (c'-1) and (c'-2), wherein $R^3$ and W are as previously defined.

In a further embodiment, the invention relates to compounds according to any of the other embodiments, wherein the bicycle is selected from (a'-1) and $R^3$ is selected from hydrogen; cyclohexyl substituted with a hydroxyl radical; $(C_{3-7}cycloalkyl)C_{1-3}alkyl$ and pyridinyl.

In a further embodiment, the invention relates to compounds according to any of the other embodiments, wherein the bicycle is selected from (c'-1) and $R^3$ is selected from pyrimidinyl.

Particular preferred compounds may be selected from the group of:
8-Chloro-7-[1-(2-pyridinyl)-1H-indol-5-yl]-3-(2,2,2-trifluoroethyl)-1,2,4-triazolo[4,3-a]pyridine;
8-chloro-3-(cyclopropylmethyl)-7-[1-(tetrahydro-2H-pyran-4-yl)-1H-indol-5-yl]-1,2,4-triazolo[4,3-a]pyridine;
3-(cyclopropylmethyl)-7-[1-(tetrahydro-2H-pyran-4-yl)-1H-indol-5-yl]-8-(trifluoromethyl)-1,2,4-triazolo[4,3-a]pyridine;
trans-4-[5-[3-(cyclopropylmethyl)-8-(trifluoromethyl)-1,2,4-triazolo[4,3-a]-pyridine-7-yl]-1H-indol-1-yl]-cyclohexanol;
8-chloro-3-(cyclopropylmethyl)-7-(1H-pyrrolo[2,3-b]pyridine-5-yl)-1,2,4-triazolo[4,3-a]pyridine;
8-chloro-7-[1-(2-pyrimidinyl)-1H-indol-5-yl]-3-(2,2,2-trifluoroethyl)-1,2,4-triazolo[4,3-a]pyridine;
3-(cyclopropylmethyl)-7-[1-(2-pyrimidinyl)-1H-indol-5-yl-8-(trifluoromethyl)-1,2,4-triazolo[4,3-a]pyridine;
8-chloro-7-(7-chloro-1H-indol-5-yl)-3-(cyclopropylmethyl)-1,2,4-triazolo[4,3-a]-pyridine;
5-[8-chloro-3-(cyclopropylmethyl)-1,2,4-triazolo[4,3-a]pyridine-7-yl]-α,α-dimethyl-1H-indole-1-ethanol;
Trans-4-[5-[8-chloro-3-(cyclopropylmethyl)-1,2,4-triazolo[4,3-a]pyridin-7-yl]-1H-indol-1-yl]-cyclohexanol;
8-chloro-3-(cyclopropylmethyl)-7-[2-(3-pyridinylmethyl)-2H-indazol-5-yl]-1,2,4-triazolo[4,3-a]pyridine;
8-chloro-3-(cyclopropylmethyl)-7-[1-(3-pyridinylmethyl)-1H-indazol-5-yl]-1,2,4-triazolo[4,3-a]pyridine;
8-chloro-3-(cyclopropylmethyl)-7-(1H-indol-4-yl)-1,2,4-triazolo[4,3-a]pyridine;
7-(7-chloro-1H-indol-5-yl)-3-(cyclopropylmethyl)-8-(trifluoromethyl)-1,2,4-triazolo[4,3-a]pyridine;
8-chloro-3-(cyclopropylmethyl)-7-[1-(2-pyrimidinyl)-1H-indol-5-yl]-1,2,4-triazolo[4,3-a]pyridine;
8-chloro-3-(cyclopropylmethyl)-7-[1-(2-pyridinyl)-1H-indol-5-yl]-1,2,4-triazolo[4,3-a]pyridine;
8-chloro-3-(cyclopropylmethyl)-7-[1-(3-pyridinyl)-1H-indol-5-yl]-1,2,4-triazolo[4,3-a]pyridine;
8-chloro-3-(ethoxymethyl)-7-[1-(2-pyridinyl)-1H-indol-5-yl]-1,2,4-triazolo[4,3-a]pyridine;
8-chloro-3-(ethoxymethyl)-7-[1-(2-pyrimidinyl)-1H-indol-5-yl]-1,2,4-triazolo[4,3-a]pyridine;
8-chloro-3-(cyclopropylmethyl)-7-(1H-indol-5-yl)-1,2,4-triazolo[4,3-a]pyridine;
8-chloro-3-(cyclopropylmethyl)-7-[1-(6-methyl-3-pyridinyl)-1H-indol-5-yl]-1,2,4-triazolo[4,3-a]pyridine;
8-chloro-3-(cyclopropylmethyl)-7-[1-(cyclopropylmethyl)-1H-pyrrolo[2,3-b]pyridin-5-yl]-1,2,4-triazolo[4,3-a]pyridine;
8-chloro-7-(7-chloro-1H-indol-5-yl)-3-(ethoxymethyl)-1,2,4-triazolo[4,3-a]pyridine;
3-(cyclopropylmethyl)-7-(1H-pyrrolo[2,3-b]pyridin-5-yl)-8-(trifluoromethyl)-1,2,4-triazolo[4,3-a]pyridine;
3-(cyclopropylmethyl)-7-[1-(cyclopropylmethyl)-1H-pyrrolo[2,3-b]pyridin-5-yl]-8-(trifluoromethyl)-1,2,4-triazolo[4,3-a]pyridine;
8-chloro-3-(ethoxymethyl)-7-[1-(3-pyridinyl)-1H-indol-5-yl]-1,2,4-triazolo[4,3-a]pyridine;
8-chloro-3-(ethoxymethyl)-7-[1-(6-methyl-3-pyridinyl)-1H-indol-5-yl]-1,2,4-triazolo[4,3-a]pyridine;
8-chloro-3-(cyclopropylmethyl)-7-(7-fluoro-1H-indol-5-yl)-1,2,4-triazolo[4,3-a]pyridine;
8-chloro-3-(ethoxymethyl)-7-(1H-indol-5-yl)-1,2,4-triazolo[4,3-a]pyridine;
3-(ethoxymethyl)-7-[1-(3-pyridinyl)-M-indol-5-yl]-8-(trifluoromethyl)-1,2,4-triazolo[4,3-a]pyridine;

8-chloro-3-(cyclopropylmethyl)-7-[7-fluoro-1-(6-methyl-3-pyridinyl)-1H-indol-5-yl]-1,2,4-triazolo[4,3-a]pyridine;

3-(ethoxymethyl)-7-[1-(6-methyl-3-pyridinyl)-1H-indol-5-yl]-8-(trifluoromethyl)-1,2,4-triazolo[4,3-a]pyridine;

3-(ethoxymethyl)-7-(1H-indol-5-yl)-8-(trifluoromethyl)-1,2,4-triazolo[4,3-a]pyridine;

3-(cyclopropylmethyl)-7-[1-(3-pyridinyl)-1H-indol-5-yl]-8-(trifluoromethyl)-1,2,4-triazolo[4,3-a]pyridine;

3-(cyclopropylmethyl)-8-methyl-7-[1-(6-methyl-3-pyridinyl)-1H-indol-5-yl]-1,2,4-triazolo[4,3-a]pyridine;

3-(cyclopropylmethyl)-7-[1-(6-methyl-3-pyridinyl)-1H-indol-5-yl]-8-(trifluoromethyl)-1,2,4-triazolo[4,3-a]pyridine;

8-cyclopropyl-3-(cyclopropylmethyl)-7-[1-(6-methyl-3-pyridinyl)-1H-indol-5-yl]-1,2,4-triazolo[4,3-a]pyridine;

3-(cyclopropylmethyl)-7-[7-fluoro-1-(6-methyl-3-pyridinyl)-1H-indol-5-yl]-8-(trifluoromethyl)-1,2,4-triazolo[4,3-a]pyridine;

8-chloro-7-[1-(cyclobutylmethyl)-1H-pyrrolo[2,3-b]pyridin-5-yl]-3-(cyclopropylmethyl)-1,2,4-triazolo[4,3-a]pyridine;

3-(cyclopropylmethyl)-7-[1-(cyclopropylmethyl)-1H-pyrrolo[2,3-b]pyridin-5-yl]-8-methyl-1,2,4-triazolo[4,3-a]pyridine;

8-chloro-3-(cyclopropylmethyl)-7-[1-(2-pyridinyl)-1H-pyrrolo[2,3-b]pyridin-5-yl]-1,2,4-triazolo[4,3-a]pyridine;

8-chloro-3-(cyclopropylmethyl)-7-[1-(3-fluoro-4-pyridinyl)-1H-indol-5-yl]-1,2,4-triazolo[4,3-a]pyridine;

3-(cyclopropylmethyl)-7-[1-(4-pyridinyl)-1H-indol-5-yl]-8-(trifluoromethyl)-1,2,4-triazolo[4,3-a]pyridine;

8-chloro-3-(cyclopropylmethyl)-7-[1-(4-pyridinyl)-1H-indol-5-yl]-1,2,4-triazolo[4,3-a]pyridine;

8-chloro-3-(cyclopropylmethyl)-7-[1-(4-fluorophenyl)-1H-pyrrolo[2,3-b]pyridin-5-yl]-1,2,4-triazolo[4,3-a]pyridine;

3-(cyclopropylmethyl)-7-[1-(2-methyl-4-pyridinyl)-1H-indol-5-yl]-8-(trifluoromethyl)-1,2,4-triazolo[4,3-a]pyridine;

8-chloro-3-(cyclopropylmethyl)-7-[1-(2-methyl-4-pyridinyl)-1H-indol-5-yl]-1,2,4-triazolo[4,3-a]pyridine;

8-chloro-3-(cyclopropylmethyl)-7-[7-fluoro-1-(3-pyridinyl)-1H-indol-5-yl]-1,2,4-triazolo[4,3-a]pyridine;

3-(ethoxymethyl)-8-methyl-7-[1-(6-methyl-3-pyridinyl)-1H-indol-5-yl]-1,2,4-triazolo[4,3-a]pyridine;

7-[3-(cyclopropylmethyl)-8-(trifluoromethyl)-1,2,4-triazolo[4,3-a]pyridin-7-yl]-3,4-dihydro-4-(2-pyrimidinyl)-2H-1,4-benzoxazine;

7-[8-chloro-3-(cyclopropylmethyl)-1,2,4-triazolo[4,3-a]pyridin-7-yl]-3,4-dihydro-4-(2-pyrimidinyl)-2H-1,4-benzoxazine;

7-[8-chloro-3-(cyclopropylmethyl)-1,2,4-triazolo[4,3-a]pyridin-7-yl]-3,4-dihydro-4-(2-pyridinyl)-2H-1,4-benzoxazine;

7-[8-chloro-3-(ethoxymethyl)-1,2,4-triazolo[4,3-a]pyridin-7-yl]-3,4-dihydro-4-(2-pyridinyl)-2H-1,4-benzoxazine;

7-[8-chloro-3-(ethoxymethyl)-1,2,4-triazolo[4,3-a]pyridin-7-yl]-3,4-dihydro-4-(2-pyrimidinyl)-2H-1,4-benzoxazine;

7-[8-chloro-3-(cyclopropylmethyl)-1,2,4-triazolo[4,3-a]pyridin-7-yl]-3,4-dihydro-4-(3-pyridinyl)-2H-1,4-benzoxazine;

7-[3-(cyclopropylmethyl)-8-(trifluoromethyl)-1,2,4-triazolo[4,3-a]pyridin-7-yl]-3,4-dihydro-4-(3-pyridinyl)-2H-1,4-benzoxazine;

7-[3-(cyclopropylmethyl)-8-(trifluoromethyl)-1,2,4-triazolo[4,3-a]pyridin-7-yl]-3,4-dihydro-4-(6-methyl-3-pyridinyl)-2H-1,4-benzoxazine;

7-[8-chloro-3-(cyclopropylmethyl)-1,2,4-triazolo[4,3-a]pyridin-7-yl]-3,4-dihydro-4-(6-methyl-3-pyridinyl)-2H-1,4-benzoxazine;

7-[3-(cyclopropylmethyl)-8-(trifluoromethyl)-1,2,4-triazolo[4,3-a]pyridin-7-yl]-3,4-dihydro-4-(4-pyridinyl)-2H-1,4-benzoxazine;

7-[3-(cyclopropylmethyl)-8-(trifluoromethyl)-1,2,4-triazolo[4,3-a]pyridin-7-yl]-3,4-dihydro-4-(2-methyl-4-pyridinyl)-2H-1,4-benzoxazine;

8-(3-Cyclopropylmethyl-8-trifluoromethyl-[1,2,4]triazolo[4,3-a]pyridin-7-yl)-2,3,4,5-tetrahydro-benzo[f][1,4]oxazepine; and 3-(cyclopropylmethyl)-7-(2,3-dihydro-1H-isoindol-5-yl)-8-(trifluoromethyl)-1,2,4-triazolo[4,3-a]pyridine;

and the stereoisomeric forms, acid addition salts and solvates thereof.

In an embodiment, the compound of Formula (I) is selected from the group of:

trans-4-[5-[3-(cyclopropylmethyl)-8-(trifluoromethyl)-1,2,4-triazolo[4,3-a]-pyridine-7-yl]-1H-indol-1-yl]-cyclohexanol;

8-chloro-7-(7-chloro-1H-indol-5-yl)-3-(cyclopropylmethyl)-1,2,4-triazolo[4,3-a]-pyridine;

8-chloro-3-(cyclopropylmethyl)-7-[1-(3-pyridinyl)-1H-indol-5-yl]-1,2,4-triazolo[4,3-a]pyridine;

8-chloro-3-(cyclopropylmethyl)-7-[1-(cyclopropylmethyl)-1H-pyrrolo[2,3-b]pyridin-5-yl]-1,2,4-triazolo[4,3-a]pyridine; and 7-[8-chloro-3-(cyclopropylmethyl)-1,2,4-triazolo[4,3-a]pyridin-7-yl]-3,4-dihydro-4-(2-pyrimidinyl)-2H-1,4-benzoxazine;

and the stereoisomeric forms, acid addition salts and solvates thereof.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not, are included within the ambit of the present invention.

The pharmaceutically acceptable acid and base addition salts as mentioned hereinabove or hereinafter are meant to comprise the therapeutically active non-toxic acid and base addition salt forms which the compounds of Formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids. Conversely said salt forms can be converted by treatment with an appropriate base into the free base form.

The compounds of Formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline; the benzathine, N-methyl-D-glucamine, hydrabamine salts, and salts with amino acids such as, for example, arginine, lysine and the like. Conversely the salt form can be converted by treatment with acid into the free acid form.

The term solvate comprises the solvent addition forms as well as the salts thereof, which the compounds of formula (I) are able to form. Examples of such solvent addition forms are e.g. hydrates, alcoholates and the like.

In the framework of this application, an element, in particular when mentioned in relation to a compound according to Formula (I), comprises all isotopes and isotopic mixtures of this element, either naturally occurring or synthetically produced, either with natural abundance or in an isotopically enriched form. Radiolabelled compounds of Formula (I) may comprise a radioactive isotope selected from the group of $^3$H, $^{11}$C, $^{15}$F, $^{122}$I, $^{123}$I, $^{125}$I, $^{131}$I, $^{75}$Br, $^{76}$Br, $^{77}$Br and $^{82}$Br. Preferably, the radioactive isotope is selected from the group of $^3$H, $^{11}$C and $^{18}$F.

Preparation

The compounds according to the invention can be generally prepared by a succession of steps, each of which is known to the skilled person. In particular, the compounds can be prepared according to the following synthesis methods.

The compounds of Formula (I) may be synthesized in the form of racemic mixtures of enantiomers, which can be separated from one another following art-known resolution procedures. The racemic compounds of Formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of Formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically.

A. Preparation of the Final Compounds

Experimental Procedure 1

Final compounds according to Formula (I), can be prepared by reacting an intermediate compound of Formula (II) with a compound of Formula (III) according to reaction scheme (1), a reaction that is performed in a suitable reaction-inert solvent, such as, for example, 1,4-dioxane or mixtures of inert solvents such as, for example, 1,4-dioxane/DMF, in the presence of a suitable base, such as, for example, aqueous NaHCO$_3$ or Na$_2$CO$_3$, a Pd-complex catalyst such as, for example, Pd(PPh$_3$)$_4$ under thermal conditions such as, for example, heating the reaction mixture at 150° C. under microwave irradiation, for example for 10 min. In reaction scheme (1), all variables are as defined in Formula (I) and halo is chloro, bromo or iodo. R$^{11}$ and R$^{12}$ may be hydrogen or alkyl, or may be taken together to form for example a bivalent radical of formula —CH$_2$CH$_2$—, —CH$_2$CH$_2$CH$_2$—, or —C(CH$_3$)$_2$C(CH$_3$)$_2$—.

Reaction Scheme 1

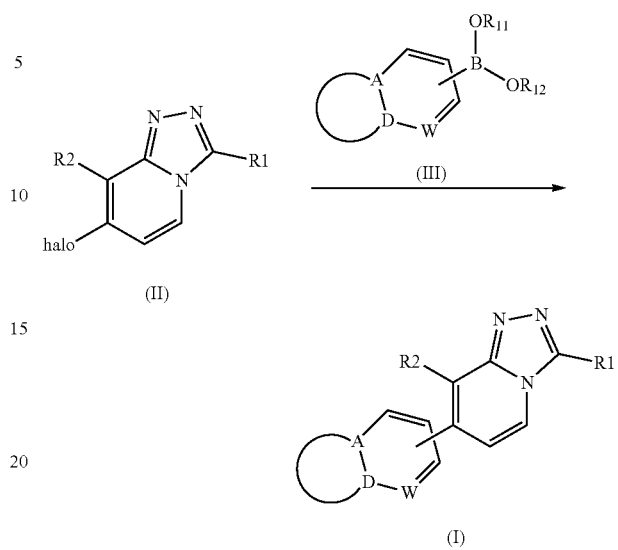

Experimental Procedure 2

Final compounds according to Formula (I) can be prepared following art known procedures by cyclization of intermediate compound of Formula (IV) in the presence of a halogenating agent such as for example phosphorus (V) oxychloride (POCl$_3$) or trichloroacetonitrile-triphenylphosphine mixture in a suitable solvent such as for example dichloroethane or acetonitrile stirred under microwave irradiation, for a suitable period of time that allows the completion of the reaction, as for example 50 min at a temperature between 140-200° C.

Alternatively, final compounds of Formula (I) can be prepared by heating the intermediate compound of Formula (IV) for a suitable period of time that allows the completion of the reaction, as for example 1 h at a temperature between 140-200° C. In reaction scheme (2), all variables are defined as in Formula (I).

Reaction Scheme 2

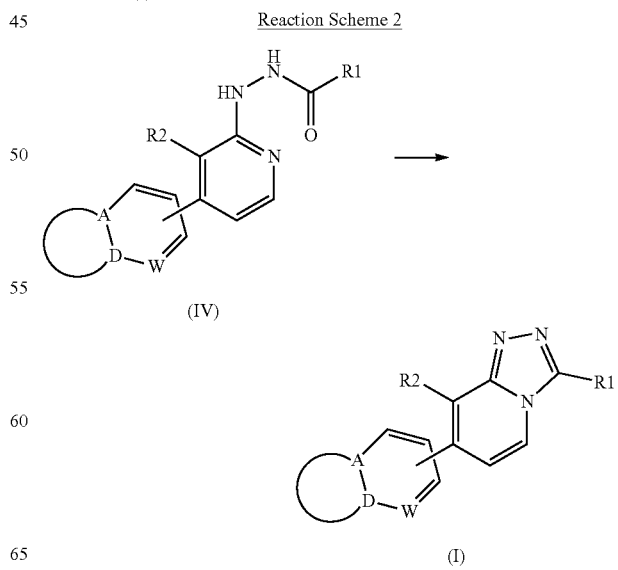

Experimental Procedure 3

Final compounds according to Formula (I) can be prepared by art known procedures in analogy to the syntheses described in *J. Org. Chem.*, 1966, 31, 251, or *J. Heterocycl. Chem.*, 1970, 7, 1019, by cyclization of intermediate compounds of Formula (V) under suitable conditions in the presence of a suitable ortho-ester of Formula (VI), wherein R is a suitable substituent like, for example, a methyl group according to reaction scheme (3). The reaction can be carried out in a suitable solvent such as, for example, xylene. Typically, the mixture can be stirred for 1 to 48 h at a temperature between 100-200° C. In reaction scheme (3), all variables are defined as in Formula (I).

Alternatively, final compounds according to Formula (I) can be prepared by art known procedures in analogy to the synthesis described in *Tetrahedron Lett.*, 2007, 48, 2237-2240 by reaction of intermediate compound of Formula (V) with carboxylic acids of Formula (VII) or acid equivalents such as acid halides of Formula (VIII) to afford final compounds of Formula (I). The reaction can be carried out using a halogenating agent such as, for example, a trichloroacetonitrile-triphenylphosphine mixture in the presence of suitable solvent such as for example dichloroethane, stirred at a temperature between 100-200° C. for 1 to 48 h or under microwave irradiation for 20 min. In reaction scheme (3), all variables are defined as in Formula (I).

Reaction Scheme 3

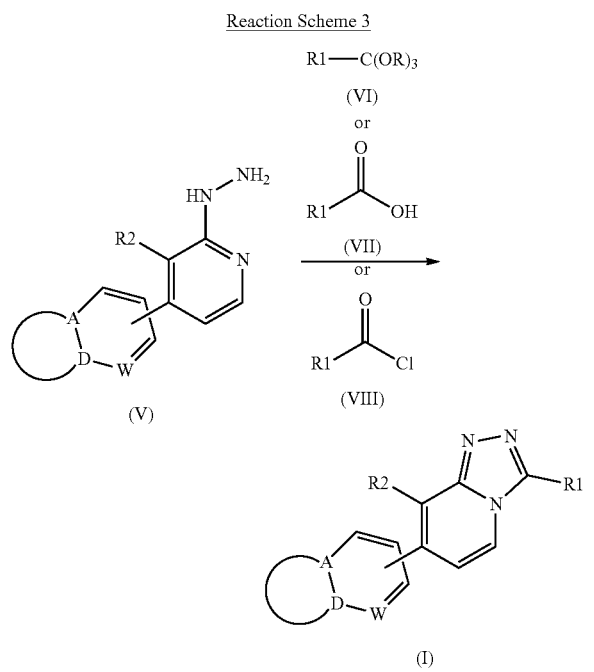

Experimental Procedure 4

Final compounds according to Formula (I), wherein $R^1$ is $Het^1$-$C_1$alkyl or a 4-(2,3,4,5-tetrahydro-benzo[f][1,4]oxazepin)methyl substituent as previously defined wherein $Het^1$ is hereby represented as

and bound through the nitrogen atom, hereby named (I-a), can be prepared by art known procedures by reaction of intermediate compound of Formula (IX) under standard Mannich conditions with intermediate compound of Formula (X), wherein

is as defined above. The reaction can be carried out in the presence of formaldehyde with a suitable solvent such as for example, AcOH stirred at a suitable temperature, for example 80° C., for a period of time that allows completion of the reaction, for example 16 h. In reaction scheme (4), all variables are defined as in Formula (I).

Reaction Scheme 4

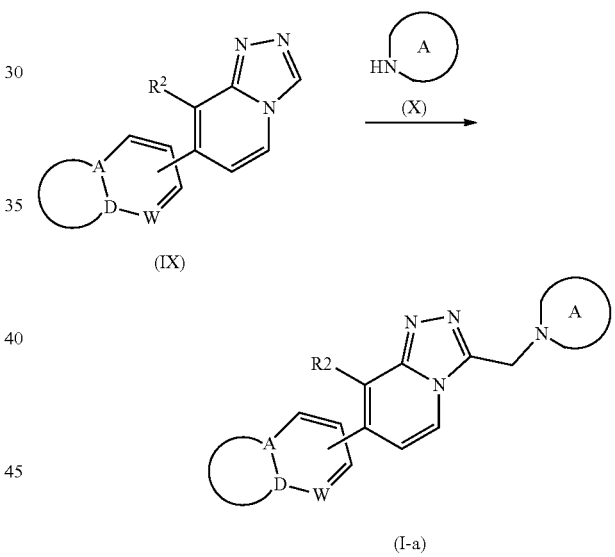

Experimental Procedure 5

Alternatively final compounds according to Formula (I) wherein $R^1$ is $Het^1$-$C_1$alkyl or a 4-(2,3,4,5-tetrahydro-benzo[f][1,4]oxazepin)methyl substituent as previously defined wherein $Het^1$ is bound through the nitrogen atom, hereby named (I-a), can be prepared by reacting an intermediate of Formula (X) with an intermediate of Formula (XI) under reductive amination conditions that are known to those skilled in the art. This is illustrated in reaction scheme (5) wherein all variables are defined as in Formula (I). The reaction may be performed, for example, in the presence of triacetoxy borohydride in a suitable reaction-inert solvent such as, for example, DCE, at a suitable temperature, typically at room temperature, for a suitable period of time that allows the completion of the reaction.

Reaction Scheme 5

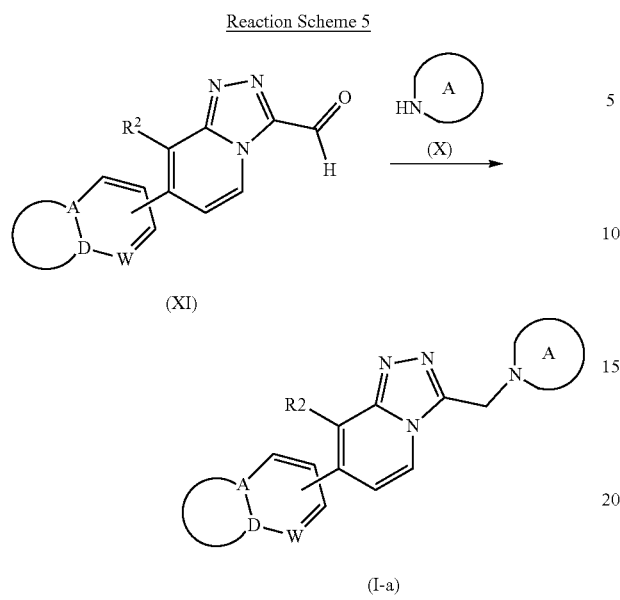

The transformations of different functional groups present in the final compounds, into other functional groups according to Formula (I), can be performed by synthesis methods well known by the person skilled in the art. For example, compounds of Formula (I) that contain carbamate function in their structure, could be hydrolysed following art known procedures for a person skilled in the art to give Final compounds of Formula (I) containing an amino B. Preparation of the Intermediate Compounds Experimental Procedure 6

Intermediate compounds according to Formula (IV) can be prepared by art known procedures in analogy to the syntheses described in *J. Org. Chem.*, 1966, 31, 251, or *J. Heterocycl. Chem.*, 1970, 7, 1019, by reaction of intermediate compounds of Formula (V) under suitable conditions in the presence of a suitable ortho-ester of Formula (VI) wherein R is a suitable group like for example methyl, according to reaction scheme (6). The reaction can be carried out in a suitable solvent such as, for example, xylene. Typically, the mixture can be stirred for 1 to 48 h at a temperature between 100-200° C. In reaction scheme (6), all variables are defined as in Formula (I). Alternatively, final compounds according to Formula (IV) can be prepared by art known procedures in analogy to the synthesis described in *Tetrahedron Lett.*, 2007, 48, 2237-2240 by reaction of intermediate compound of Formula (V) with carboxylic acids of Formula (VII) or acid equivalent such as acid halides of Formula (VIII) to afford final compounds of Formula (IV). The reaction can be carried out using a halogenating agent such as for example trichloroacetonitrile-triphenylphosphine mixture in the presence of a suitable solvent such as, for example, dichloroethane stirred at a temperature between 100-200° C. for 1 to 48 hours or under microwave irradiation for 20 min. In reaction scheme (6), all variables are defined as in Formula (I).

Reaction Scheme 6

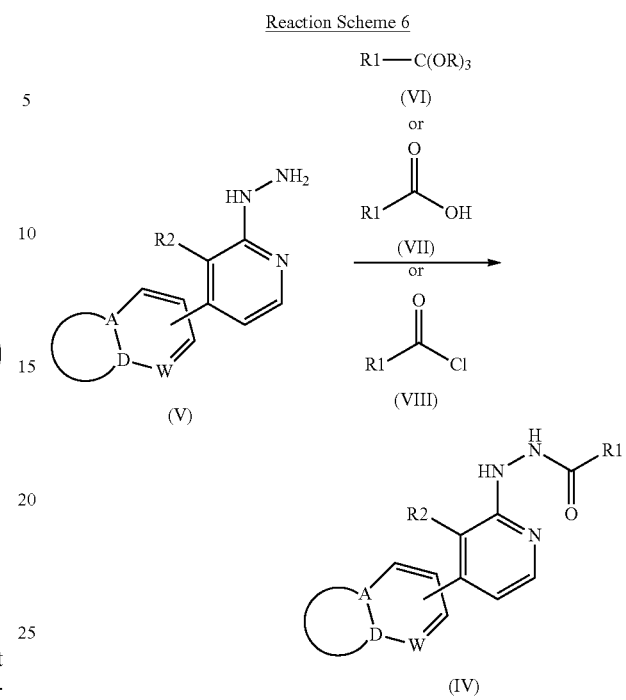

Experimental Procedure 7

Intermediate compounds according to Formula (V) can be prepared by reacting an intermediate compound of Formula (XII) with hydrazine according to reaction scheme (7), a reaction that is performed in a suitable reaction-inert solvent, such as, for example, ethanol or THF under thermal conditions such as, for example, heating the reaction mixture for example at 160° C. under microwave irradiation for 20 min or classical thermal heating at 90° C. for 16 h. In reaction scheme (7), all variables are defined as in Formula (I) and halo is chloro, bromo or iodo.

Reaction Scheme 7

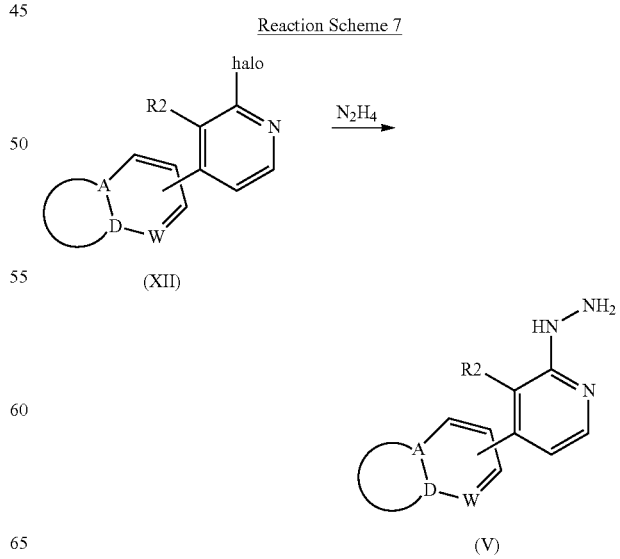

Experimental Procedure 8

Intermediate compounds of Formula (XII) can be prepared by reacting an intermediate compound of Formula (XIII) with a compound of Formula (III) according to reaction scheme (8). All variables are defined as in Formula (I) and (III) and halo is chloro, bromo or iodo.

Reaction Scheme 8

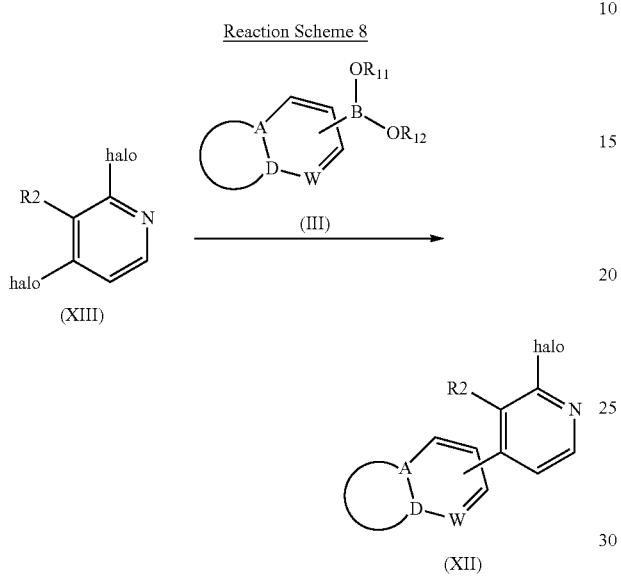

Experimental Procedure 9

Intermediate compounds according to Formula (IX) can be prepared by art known procedures in analogy to the syntheses described in *J. Org. Chem.*, 1966, 31, 251, or *J. Heterocycl. Chem.*, 1970, 7, 1019, by cyclization of intermediate compound of Formula (V) under suitable conditions in the presence of a suitable ortho-ester of formula (VI), such as for example methylorthoformate wherein $R^1$ is H and R is methyl, according to reaction scheme (9). The reaction can be carried out neat or in a suitable solvent such as, for example, xylene. Typically, the mixture can be stirred for 1 to 48 h at a temperature between 100-200° C. In reaction scheme (9), all variables are defined as in Formula (I).

Reaction Scheme 9

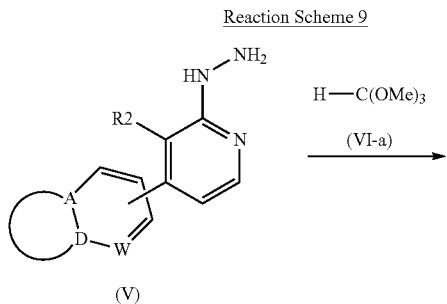

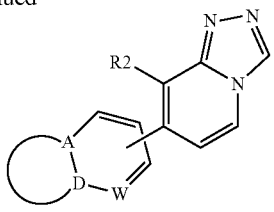

Experimental Procedure 10

Intermediate compounds of Formula (XI) can be prepared by reacting an intermediate compound of Formula (IX) under standard Vilsmeier-Haack reaction conditions such as, for example, DMF and phosphorus (V) oxychloride ($POCl_3$) from room temperature to 140° C. under classical thermal heating or under microwave irradiation, for a suitable period of time that allows the completion of the reaction, as for example 1 h. In reaction scheme (10), all variables are defined as in Formula (I).

Reaction Scheme 10

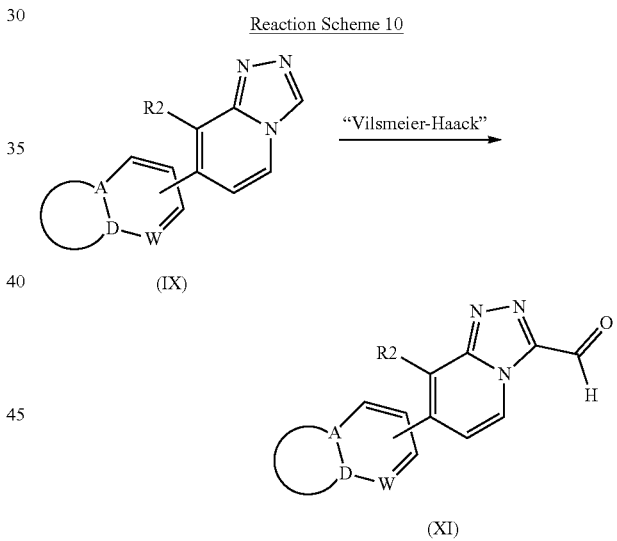

Experimental Procedure 11

Intermediate compounds of Formula (II) can be prepared following art known procedures by cyclization of intermediate compound of Formula (XIV) in the presence of a halogenating agent such as for example phosphorus (V) oxychloride ($POCl_3$) in a suitable solvent such as for example, dichloroethane, stirred under microwave irradiation, for a suitable period of time that allows the completion of the reaction, as for example, 5 min at a temperature between 140-200° C. In reaction scheme (11), all variables are defined as in Formula (I) and halo is chloro, bromo or iodo.

Reaction Scheme 11

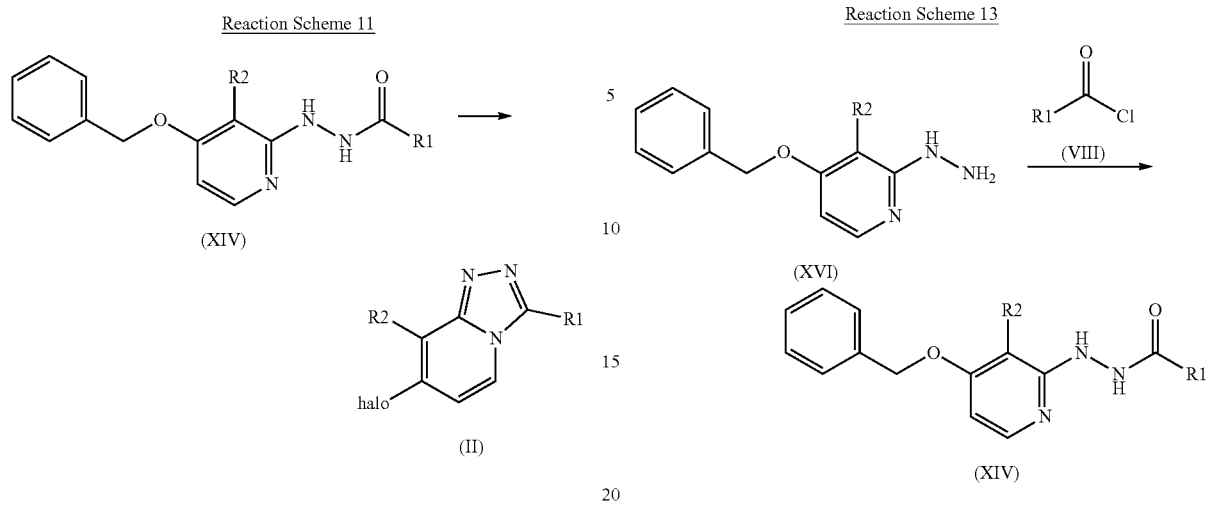

Experimental Procedure 12

Alternatively, intermediate compounds of Formula (II) can be prepared following art known procedures by cyclization of intermediate compound of Formula (XV) under heating for a suitable period of time that allows the completion of the reaction, as for example 1 h at a temperature between 140-200° C. In reaction scheme (12), all variables are defined as in Formula (I) and halo is chloro, bromo or iodo

Reaction Scheme 12

Experimental Procedure 13

Intermediate compounds according to Formula (XIV) can be prepared by art known procedures by reaction of intermediate compound of Formula (XVI) with acid halides of Formula (VIII). The reaction can be carried out using an inert-solvent such as for example, DCM in the presence of a base such as for example, TEA, for example at room temperature for a suitable period of time that allows completion of the reaction, for example 20 min. In reaction scheme (13), all variables are defined as in Formula (I).

Reaction Scheme 13

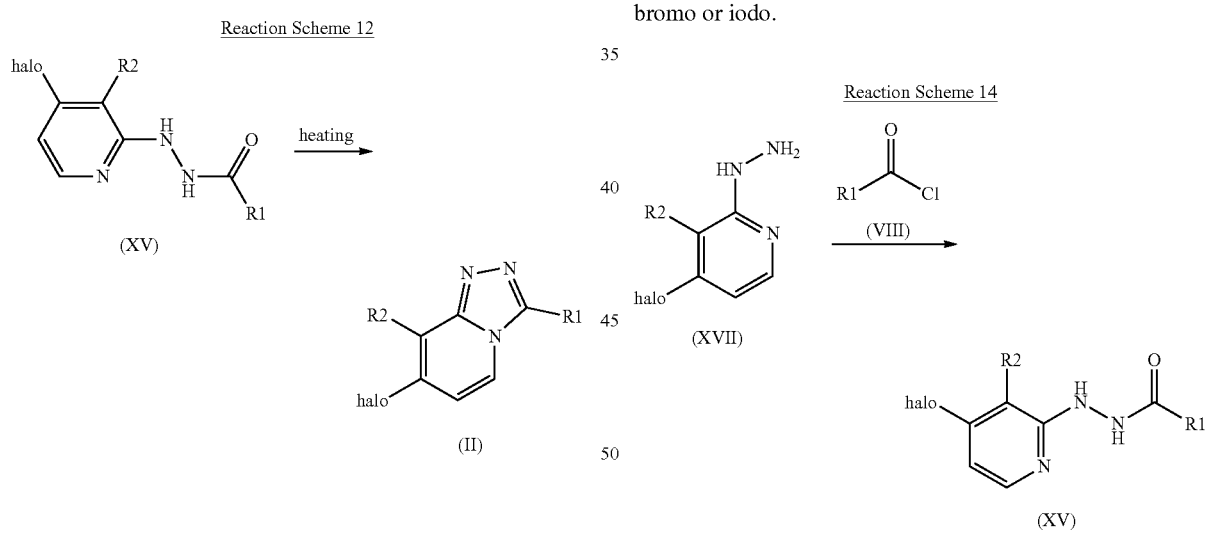

Experimental Procedure 14

Intermediate compounds according to Formula (XV) can be prepared by art known procedures by reaction of intermediate compounds of Formula (XVII) with acid halides of Formula (VIII). The reaction can be carried out using a inert-solvent such as for example DCM in the presence of a base such as for example, TEA, for example at room temperature for a suitable period of time that allows completion of the reaction, for example 20 min. In reaction scheme (14), all variables are defined as in Formula (I) and halo is chloro, bromo or iodo.

Reaction Scheme 14

Experimental Procedure 15

Intermediate compounds according to Formula (XVII) can be prepared by reacting an intermediate compound of Formula (XIII) with hydrazine according to reaction scheme (15), a reaction that is performed in a suitable reaction-inert solvent, such as, for example, ethanol, THF or 1,4-dioxane under thermal conditions such as, for example, heating the reaction mixture for example at 160° C. under microwave irradiation for 30 min or classical thermal heating at 70° C. for 16 h. In reaction scheme (15), $R^2$ is as defined in Formula (I) and halo is chloro, bromo or iodo.

Reaction Scheme 15

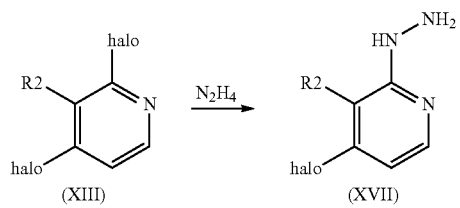

Experimental Procedure 16

Intermediate compounds according to Formula (XVI) can be prepared by reacting an intermediate compound of Formula (XVIII) with hydrazine according to reaction scheme (16), a reaction that is performed in a suitable reaction-inert solvent, such as, for example, ethanol, THF or 1,4-dioxane under thermal conditions such as, for example, heating the reaction mixture for example at 160° C. under microwave irradiation for 30 minutes or classical thermal heating at 70° C. for 16 h. In reaction scheme (16), $R^2$ is as defined in Formula (I) and halo is chloro, bromo or iodo

Reaction Scheme 16

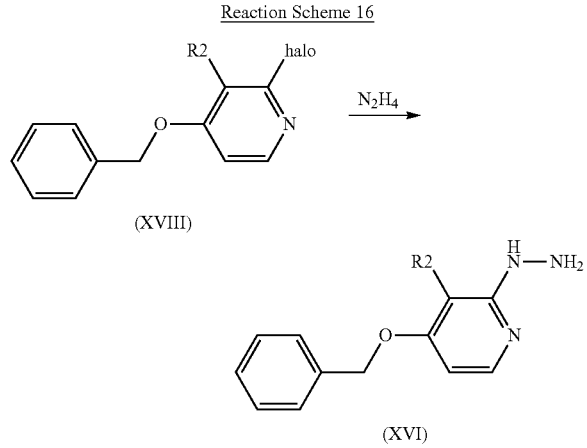

Experimental Procedure 17

Intermediate compounds according to Formula (XVIII) can be prepared by reacting an intermediate compound of Formula (XIII) with benzyl alcohol according to reaction scheme (17), a reaction that is performed in a suitable reaction-inert solvent, such as, for example, N,N-dimethylformamide in the presence of a suitable base, such as for example sodium hydride at room temperature for a suitable period of time that allows the completion of the reaction, such as for example 1 h. In reaction scheme (17), $R^2$ is as defined in Formula (I) and halo is chloro, bromo or iodo.

Reaction Scheme 17

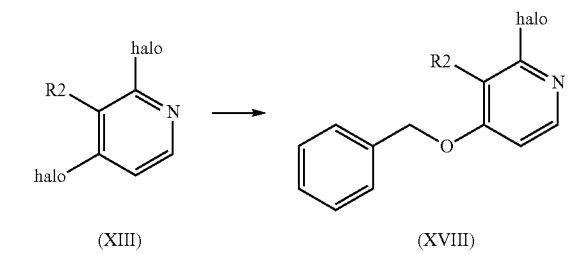

Experimental Procedure 18

Intermediate compounds of Formula (XIII) wherein $R^2$ is trifluoromethyl, hereby named (XIII-a), can be prepared by reacting an intermediate of Formula (XIII) wherein $R^2$ is iodine, hereby named (XIII-b), with a suitable trifluoromethylating agent, such as for example, fluorosulfonyl(difluoro)acetic acid methyl ester, according to reaction scheme (18). This reaction is performed in a suitable reaction-inert solvent such as, for example, N,N-dimethylformamide in the presence of a suitable coupling agent such as for example, copper iodide, under thermal conditions such as, for example, heating the reaction mixture for example at 160° C. under microwave irradiation for 45 min. In reaction scheme (18), halo is chloro, bromo or iodo.

Reaction Scheme 18

Experimental Procedure 19

Intermediate compounds of Formula (XIII) wherein $R^2$ is iodine, hereby named (XIII-b), can be prepared by reacting an intermediate compound of Formula (XIX) with a strong base such as, for example, n-butyllithium, and further treatment with an iodinating agent such as, for example, iodine. This reaction is performed in a suitable reaction-inert solvent such as, for example, THF at a temperature of for example, −78° C. for a period of time that allows the completion of the reaction such as for example 2 h. In reaction scheme (19), halo may be chloro, bromo or iodo.

Reaction Scheme 19

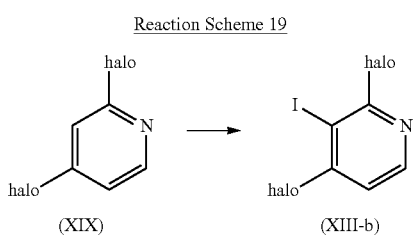

Experimental Procedure 20

Intermediates of Formula (III) can be prepared by art known procedures by reacting an intermediate of Formula (XX) with a suitable boron source such as, for example, bis(pinacolato)diboron in the presence of a palladium catalyst such as, for example, 1,1'-bis(diphenylphosphino)ferrocene-palladium(II)dichloride in a reaction-inert solvent such as, for example, DCM, as shown in reaction scheme (20). The reaction may be carried out in the presence of a suitable salt such as, for example, potassium acetate at a temperature of, for example, 110° C. during, for example, 16 h.

Additionally, intermediates of Formula (III) can be prepared by art known procedures of halogen-metal exchange and subsequent reaction with an appropriate boron source from intermediates of Formula (XX). This type of reaction can be carried out by using, for example, an intermediate of Formula (XX) and an organolithium compound such as, for example, n-butyllithium. The reaction can be performed at a temperature of, for example, −40° C. in an inert solvent such as, for example, THF. This reaction is followed by subsequent reaction with an appropriate boron source such as, for example, trimethoxyborane.

In reaction scheme (20), all variables are defined as in Formula (I), $R^{11}$ and $R^{12}$ may be hydrogen or alkyl, or may be taken together to form for example a bivalent radical of formula —$CH_2CH_2$—, —$CH_2CH_2CH_2$—, or —$C(CH_3)_2C(CH_3)_2$—, and halo is a suitable halogen such as, for example, bromo.

Reaction Scheme 20

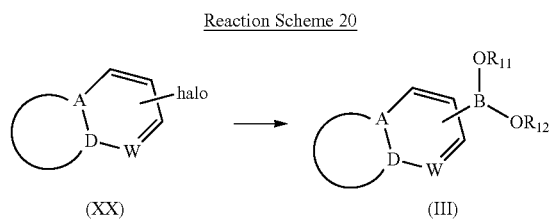

Experimental Procedure 21

Intermediates of Formula (XX) wherein forms a radical selected from (a), (b), (c), (d) or (e) and wherein $R^3$ is as defined in Formula (I) but other than hydrogen, hereby named (XXI) or (XXII), can be prepared following art known procedures by reacting an intermediate of Formula (XXI-a) or (XXII-a) wherein $R^3$ is hydrogen, with an intermediate compound of Formula (XXIII) under alkylation conditions, for example, in the presence of a base such as, for example, $K_2CO_3$ or NaH in a suitable reaction-inert solvent such as, for example, DMF. The reaction may be carried out under microwave irradiation at a suitable temperature, typically 150° C., for a suitable period of time that allows the completion of the reaction. In reaction scheme (21), all variables are defined as in Formula (I), LG is a suitable leaving group for alkylation reactions such as for example, halo, tosyl and mesyl, and halo may be chloro, bromo or iodo.

Reaction Scheme 21

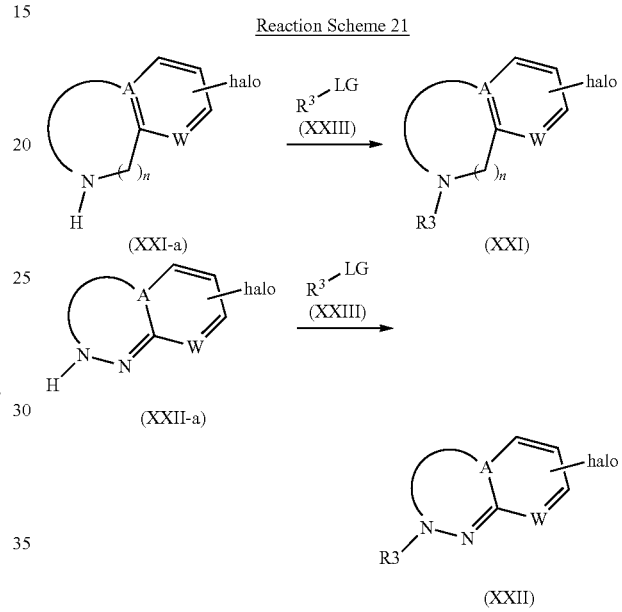

Experimental Procedure 22

Intermediates of Formula (XXI) wherein n is zero, hereby name (XXI-b) and (XXII) where halo is bromo or iodo can be prepared following art known procedures by reacting an intermediate of Formula (XXIV) or (XXV) with a suitable halogenating agent. This reaction is shown in reaction scheme (22). The reaction can be carried out with halogenating agents such as N-bromosuccinimide, N-iodosuccinimide, at temperatures ranging from room temperature to reflux temperature, in a reaction-inert solvent such as DMF, DCM, $CHCl_3$ or AcOH. Typically, the reaction mixture can be stirred for 15 minutes to 48 h at a temperature between 0-100° C. In reaction scheme (22), all variables are defined as in Formula (I) and halo may be chloro, bromo or iodo.

Reaction Scheme 22

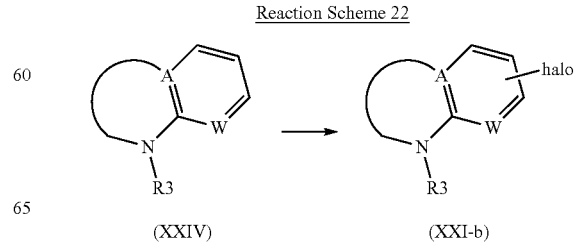

-continued

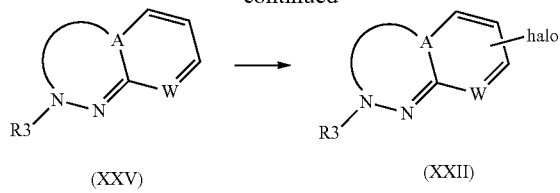

(XXV) → (XXII)

Experimental Procedure 23

Intermediates of Formula (XXIV) or (XXV) wherein $R^3$ is as defined in Formula (I) but other than hydrogen, can be prepared by art known procedures by reacting an intermediate of Formula (XXIV) or (XXV) wherein $R^3$ is hydrogen, hereby named (XXIV-a) or (XXV-a), with an intermediate compound of Formula (XXIII) under alkylation conditions, as illustrated in reaction scheme (23). In reaction scheme (23), all variables are defined as in Formula (I), LG is a suitable leaving group for alkylation such as for example halo, tosyl, mesyl and halo may be chloro, bromo or iodo.

Reaction Scheme 23

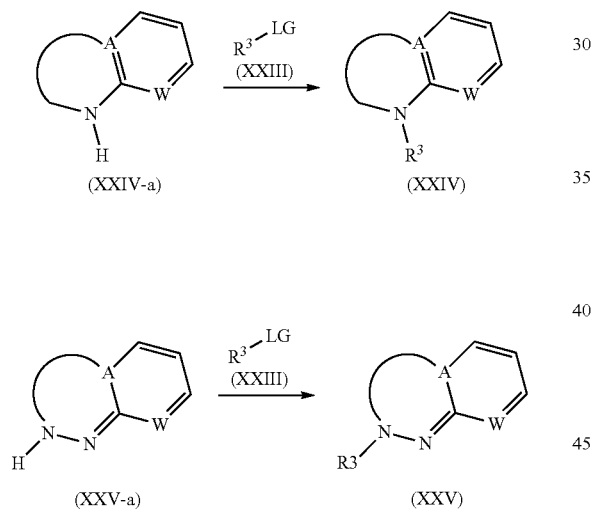

Experimental Procedure 24

Intermediates of Formula (XXIV) or (XXV) wherein $R^3$ is 4-hydroxy-4-alkylcyclohexan-1-yl, hereby named (XXIV-b) or (XXV-b), can be prepared by art known procedures by reacting an intermediate of Formula (XXIV-c) or (XXV-c) with a suitable organometallic alkyl source such as, for example, $R^9$MgHal or $R^9$Li, wherein Hal is a halide. This reaction is shown in reaction scheme (24). The reaction can be carried out in an inert solvent such as, for example, THF, diethyl ether or 1,4-dioxane. Typically, the mixture can be stirred from 1 to 48 h at a temperature between 0-100° C. In reaction scheme (24), all variables are defined as in Formula (I), halo may be chloro or bromo and $R^9$ is $C_{1-3}$alkyl or $C_{3-7}$cycloalkyl.

Reaction Scheme 24

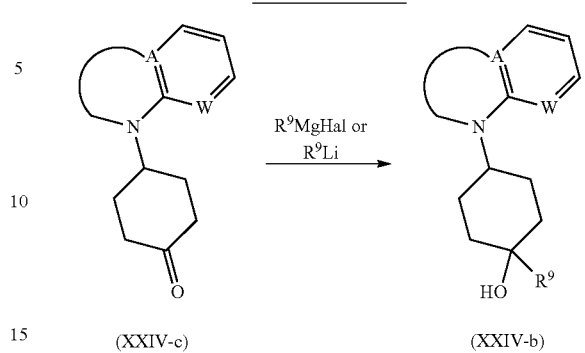

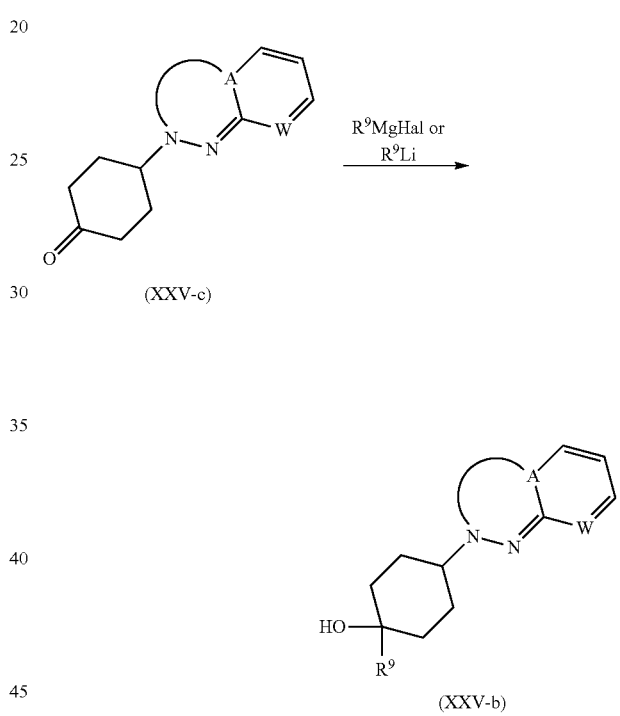

Experimental Procedure 25

Intermediates of Formula (XXI) and (XXII) wherein $R^3$ is 4-hydroxy-cyclohexan-1-yl, hereby named (XXI-c) and (XXII-c), can be prepared by reacting an intermediate of Formula (XXI-d) or (XXII-d) under reductive conditions that are known to those skilled in the art. The reaction is illustrated in reaction scheme (25). The reaction can be carried out in the presence of a reducing agent such as for example, sodium borohydride in a suitable solvent such as, for example, methanol. The reaction may be performed at a suitable temperature, typically room temperature, for a suitable period of time that allows the completion of the reaction. In reaction scheme (25), all variables are defined as in Formula (I) and halo may be chloro, bromo or iodo.

Reaction Scheme 25

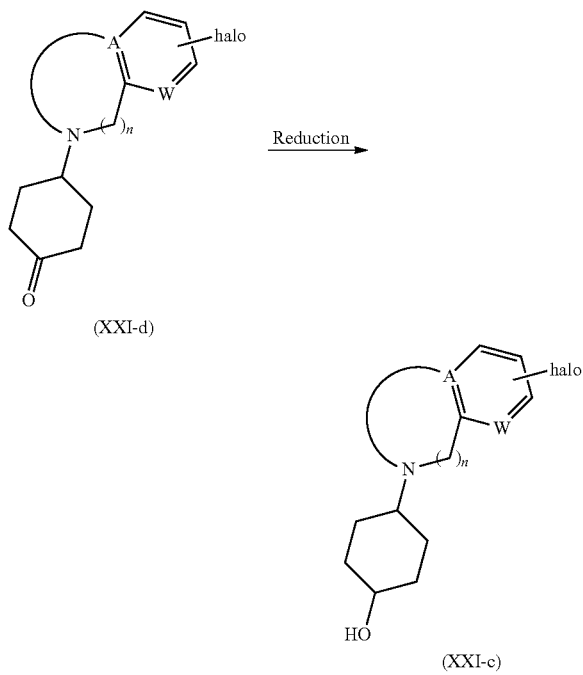

Reaction Scheme 26

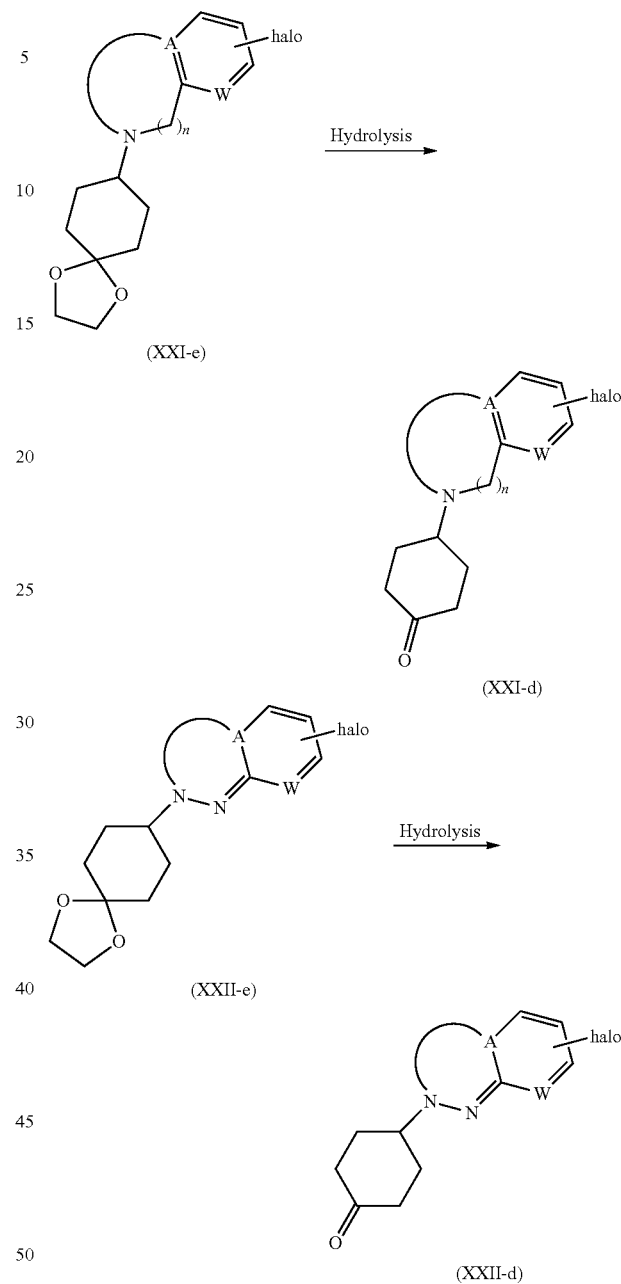

Experimental Procedure 26

Intermediates of Formula (XXI) and (XXII) wherein $R^3$ is 4-oxo-cyclohexan-1-yl, hereby named (XXI-d) and (XXII-d), can be prepared by subjecting an acetal intermediate of Formula (XXI-e) or (XXII-e) to suitable deprotection conditions for the carbonyl function known to those skilled in the art. This reaction is illustrated in reaction scheme (26). The reaction can be performed in the presence of an acid such as, for example, p-toluenesulfonic acid, in a suitable reaction solvent such as, for example, acetone. The reaction may conveniently be carried out under microwave irradiation at a suitable temperature, typically at 100° C., for a suitable period of time that allows the completion of the reaction. In reaction scheme (26), all variables are defined as in Formula (I) and halo may be chloro, bromo or iodo.

Experimental Procedure 27

Intermediates of Formula (XXI) or (XXII) wherein

is a radical of formula (a), (b), (c) (d) or (e) and R³ is

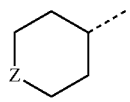

wherein Z is —O—,

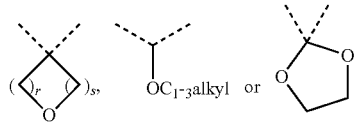

and each r and s is as defined in Formula (I), hereby named (XXI-c) or (XXI'-c) can be prepared by reacting an intermediate of Formula (XXI) wherein

is a radical of formula (a), (b), (c) (d) or (e) and R³ is H, hereby named (XXI-f) or (XXI'-f) with an intermediate of Formula R³-LG (XXIII) wherein R³ is as defined hereinbefore, hereby named (XXIII-a) according to reaction scheme (27). The reaction can be carried out under alkylation conditions that are known to those skilled in the art such as, for example, in the presence of base such as, for example, potassium hydroxide in a suitable reaction solvent such as, for example, dimethylsulphoxide. The reaction may be performed at a suitable temperature, typically at 60° C., for a suitable period of time that allows the completion of the reaction. In reaction scheme (27), all variables are defined as in Formula (I), LG is a suitable leaving group for alkylation such as for example halo, tosyl, mesyl and halo may be chloro, bromo or iodo.

Reaction Scheme 27

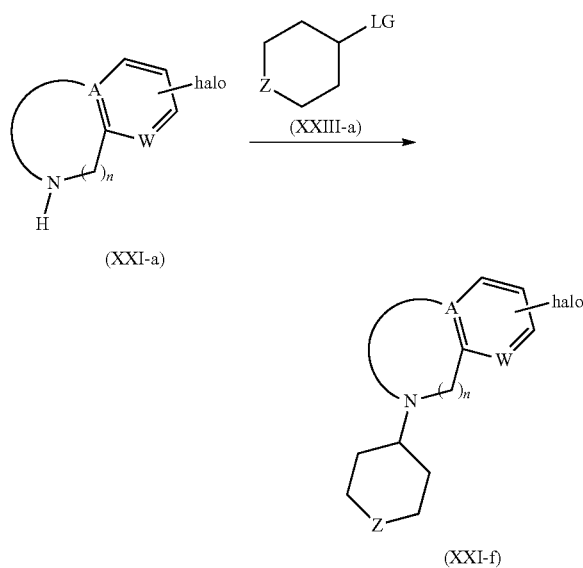

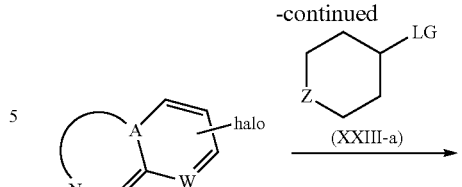

Experimental Procedure 28

Intermediates of Formula (XXI) wherein

is a radical of formula (d), hereby named (XXI-g), can be prepared by reacting an ortho-aminophenol derivative of Formula (XXVI) with commercially available 1,2-dibromoethane under alkylation conditions, such as for example, performing the reaction in the presence of a base such as for example $K_2CO_3$ in a suitable reaction-inert solvent such as, for example, DMF. The reaction may be carried out under microwave irradiation at a suitable temperature, typically 180° C., for a suitable period of time that allows the completion of the reaction. In reaction scheme (28), all variables are defined as in Formula (I) and halo may be chloro, bromo or iodo.

Reaction Scheme 28

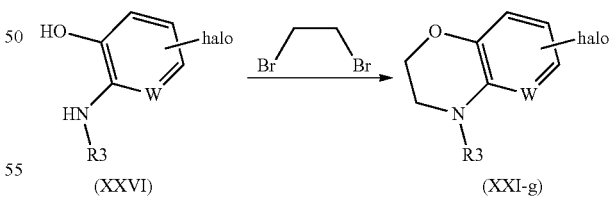

Experimental Procedure 29

Intermediates of Formula (XXVI) can be prepared by reacting an intermediate of Formula (XXVII) with an N-halosuccinimide such as N-chloro- (NCS), N-bromo- (NBS) or N-iodosuccinimide (NIS) according to reaction scheme (29). This reaction can be performed in a suitable reaction-inert solvent such as, for example, DMF, DCM or AcOH. The reaction typically can be carried out at room temperature for 1 to 24 h. In reaction scheme (29), all variables are defined as in Formula (I) and halo may be chloro, bromo or iodo.

Reaction Scheme 29

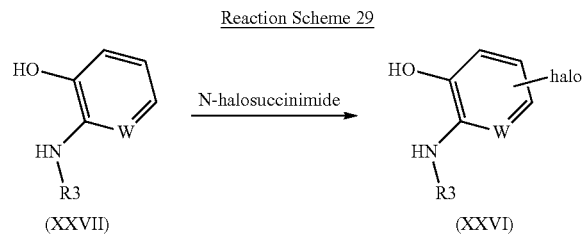

Experimental Procedure 30

Intermediates of Formula (XXVII) wherein $R^3$ is

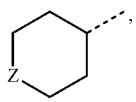

hereby named (XXVII-a) can be prepared by reacting an intermediate of Formula (XVIII) wherein $R^3$ is H, hereby named (XXVII-b) with a cyclic ketone derivative of Formula (XXVIII) under reductive amination conditions that are known to those skilled in the art. This is illustrated in reaction scheme (30). The reaction may be performed, for example, in the presence of sodium triacetoxyborohydride in a suitable reaction-inert solvent such as, for example, DCE, at a suitable reaction temperature, typically at room temperature, for a suitable period of time that allows the completion of the reaction. In reaction scheme (30), all variables are defined as in Formula (I), and Z is as defined in experimental procedure (27).

Reaction Scheme 30

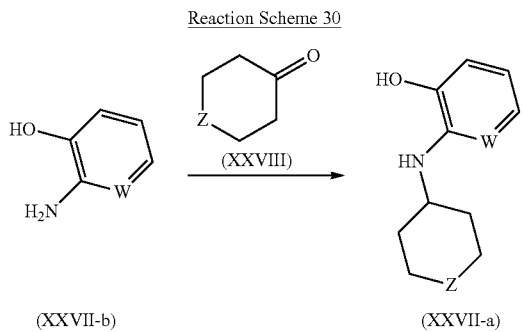

Intermediates of Formula, (VI), (VII), (VIII), (XX), (XXII-a), (XXIII), (XXIII-a) (XXVII-b) and (XXVIII) are commercially available or can be prepared according to conventional reaction procedures generally known to those skilled in the art.

Pharmacology

The compounds provided in this invention are positive allosteric modulators (PAMs) of metabotropic glutamate receptors, in particular they are positive allosteric modulators of mGluR2. The compounds of the present invention do not appear to bind to the glutamate recognition site, the orthosteric ligand site, but instead to an allosteric site within the seven transmembrane region of the receptor. In the presence of glutamate or an agonist of mGluR2, the compounds of this invention increase the mGluR2 response. The compounds provided in this invention are expected to have their effect at mGluR2 by virtue of their ability to increase the response of such receptors to glutamate or mGluR2 agonists, enhancing the response of the receptor.

As used herein, the term "treatment" is intended to refer to all processes, wherein there may be a slowing, interrupting, arresting, or stopping of the progression of a disease, but does not necessarily indicate a total elimination of all symptoms.

Hence, the present invention relates to a compound according to the general Formula (I), the stereoisomeric forms thereof and the pharmaceutically acceptable acid or base addition salts and the solvates thereof, for use as a medicament.

The invention also relates to the use of a compound according to the general Formula (I), the stereoisomeric forms thereof and the pharmaceutically acceptable acid or base addition salts and the solvates thereof, or a pharmaceutical composition according to the invention for the manufacture of a medicament.

The present invention also relates to a compound according to the general Formula (I), the stereoisomeric forms thereof and the pharmaceutically acceptable acid or base addition salts and the solvates thereof, or a pharmaceutical composition according to the invention for use in the treatment or prevention of, in particular treatment of, a condition in a mammal, including a human, the treatment or prevention of which is affected or facilitated by the neuromodulatory effect of allosteric modulators of mGluR2, in particular positive allosteric modulators thereof.

The present invention also relates to the use of a compound according to the general Formula (I), the stereoisomeric forms thereof and the pharmaceutically acceptable acid or base addition salts and the solvates thereof, or a pharmaceutical composition according to the invention for the manufacture of a medicament for the treatment or prevention of, in particular treatment of, a condition in a mammal, including a human, the treatment or prevention of which is affected or facilitated by the neuromodulatory effect of allosteric modulators of mGluR2, in particular positive allosteric modulators thereof.

The present invention also relates to a compound according to the general Formula (I), the stereoisomeric forms thereof and the pharmaceutically acceptable acid or base addition salts and the solvates thereof, or a pharmaceutical composition according to the invention for use in the treatment, prevention, amelioration, control or reduction of the risk of various neurological and psychiatric disorders associated with glutamate dysfunction in a mammal, including a human, the treatment or prevention of which is altered or facilitated by the neuromodulatory effect of positive allosteric modulators of mGluR2.

Also, the present invention relates to the use of a compound according to the general Formula (I), the stereoisomeric forms thereof and the pharmaceutically acceptable acid or base addition salts and the solvates thereof, or a pharmaceutical composition according to the invention for the manufacture of a medicament for treating, preventing, ameliorating, controlling or reducing the risk of various neurological and psychiatric disorders associated with glutamate dysfunction in a mammal, including a human, the treatment or prevention of which is affected or facilitated by the neuromodulatory effect of positive allosteric modulators of mGluR2.

In particular, the neurological and psychiatric disorders associated with glutamate dysfunction, include one or more of the following conditions or diseases: acute neurological and psychiatric disorders such as, for example, cerebral deficits subsequent to cardiac bypass surgery and grafting, stroke, cerebral ischemia, spinal cord trauma, head trauma, perinatal hypoxia, cardiac arrest, hypoglycemic neuronal damage, dementia (including AIDS-induced dementia), Alzheimer's disease, Huntington's Chorea, amyotrophic lateral sclerosis, ocular damage, retinopathy, cognitive disorders, idiopathic and drug-induced Parkinson's disease, muscular spasms and disorders associated with muscular spasticity including tremors, epilepsy, convulsions, migraine (including migraine headache), urinary incontinence, substance dependence/abuse, substance withdrawal (including substances such as, for example, opiates, nicotine, tobacco products, alcohol, benzodiazepines, cocaine, sedatives, hypnotics, etc.), psychosis, schizophrenia, anxiety (including generalized anxiety disorder, panic disorder, and obsessive compulsive disorder), mood disorders (including depression, major depressive disorder, treatment resistant depression, mania, bipolar disorders, such as bipolar mania), posttraumatic stress disorder, trigeminal neuralgia, hearing loss, tinnitus, macular degeneration of the eye, emesis, brain edema, pain (including acute and chronic states, severe pain, intractable pain, neuropathic pain, and post-traumatic pain), tardive dyskinesia, sleep disorders (including narcolepsy), attention deficit/hyperactivity disorder, and conduct disorder.

In particular, the condition or disease is a central nervous system disorder selected from the group of anxiety disorders, psychotic disorders, personality disorders, substance-related disorders, eating disorders, mood disorders, migraine, epilepsy or convulsive disorders, childhood disorders, cognitive disorders, neurodegeneration, neurotoxicity and ischemia.

Preferably, the central nervous system disorder is an anxiety disorder, selected from the group of agoraphobia, generalized anxiety disorder (GAD), mixed anxiety and depression, obsessive-compulsive disorder (OCD), panic disorder, posttraumatic stress disorder (PTSD), social phobia and other phobias.

Preferably, the central nervous system disorder is a psychotic disorder selected from the group of schizophrenia, delusional disorder, schizoaffective disorder, schizophreniform disorder and substance-induced psychotic disorder.

Preferably, the central nervous system disorder is a personality disorder selected from the group of obsessive-compulsive personality disorder and schizoid, schizotypal disorder.

Preferably, the central nervous system disorder is a substance abuse or substance-related disorder selected from the group of alcohol abuse, alcohol dependence, alcohol withdrawal, alcohol withdrawal delirium, alcohol-induced psychotic disorder, amphetamine dependence, amphetamine withdrawal, cocaine dependence, cocaine withdrawal, nicotine dependence, nicotine withdrawal, opioid dependence and opioid withdrawal.

Preferably, the central nervous system disorder is an eating disorder selected from the group of anorexia nervosa and bulimia nervosa.

Preferably, the central nervous system disorder is a mood disorder selected from the group of bipolar disorders (I & II), cyclothymic disorder, depression, dysthymic disorder, major depressive disorder, treatment resistant depression, bipolar depression, and substance-induced mood disorder.

Preferably, the central nervous system disorder is migraine.

Preferably, the central nervous system disorder is epilepsy or a convulsive disorder selected from the group of generalized nonconvulsive epilepsy, generalized convulsive epilepsy, petit mal status epilepticus, grand mal status epilepticus, partial epilepsy with or without impairment of consciousness, infantile spasms, epilepsy partialis continua, and other forms of epilepsy.

Preferably, the central nervous system disorder is attention-deficit/hyperactivity disorder.

Preferably, the central nervous system disorder is a cognitive disorder selected from the group of delirium, substance-induced persisting delirium, dementia, dementia due to HIV disease, dementia due to Huntington's disease, dementia due to Parkinson's disease, dementia of the Alzheimer's type, behavioural and psychological symptoms of dementia, substance-induced persisting dementia and mild cognitive impairment.

Of the disorders mentioned above, the treatment of psychosis, such as schizophrenia, behavioural and psychological symptoms of dementia, major depressive disorder, treatment resistant depression, bipolar depression, anxiety, depression, generalized anxiety disorder, post-traumatic stress disorder, bipolar mania, substance abuse and mixed anxiety and depression, are of particular importance.

Of the disorders mentioned above, the treatment of anxiety, schizophrenia, migraine, depression, and epilepsy are of particular importance.

At present, the fourth edition of the Diagnostic & Statistical Manual of Mental Disorders (DSM-IV) of the American Psychiatric Association provides a diagnostic tool for the identification of the disorders described herein. The person skilled in the art will recognize that alternative nomenclatures, nosologies, and classification systems for neurological and psychiatric disorders described herein exist, and that these evolve with medical and scientific progresses.

Therefore, the invention also relates to a compound according to the general Formula (I), the stereoisomeric forms thereof and the pharmaceutically acceptable acid or base addition salts and the solvates thereof, for the treatment of any one of the diseases mentioned hereinbefore.

The invention also relates to a compound according to the general Formula (I), the stereoisomeric forms thereof and the pharmaceutically acceptable acid or base addition salts and the solvates thereof, for use in treating any one of the diseases mentioned hereinbefore.

The invention also relates to a compound according to the general formula (I), the stereoisomeric forms thereof and the pharmaceutically acceptable acid or base addition salts and the solvates thereof, for the treatment or prevention, in particular treatment, of any one of the diseases mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment or prevention of any one of the disease conditions mentioned hereinbefore.

The invention also relates to the use of a compound according to the general Formula (I), the stereoisomeric forms thereof and the pharmaceutically acceptable acid or base addition salts and the solvates thereof, for the manufacture of a medicament for the treatment of any one of the disease conditions mentioned hereinbefore.

The compounds of the present invention can be administered to mammals, preferably humans for the treatment or prevention of any one of the diseases mentioned hereinbefore.

In view of the utility of the compounds of Formula (I), there is provided a method of treating warm-blooded animals, including humans, suffering from any one of the diseases mentioned hereinbefore and a method of preventing in warm-blooded animals, including humans, any one of the diseases mentioned hereinbefore.

Said methods comprise the administration, i.e. the systemic or topical administration, preferably oral administration, of a therapeutically effective amount of a compound of Formula (I), a stereoisomeric form thereof and a pharmaceutically acceptable addition salt or solvate thereof, to warm-blooded animals, including humans.

Therefore, the invention also relates to a method for the prevention and/or treatment of any one of the diseases mentioned hereinbefore comprising administering a therapeutically effective amount of compound according to the invention to a patient in need thereof.

One skilled in the art will recognize that a therapeutically effective amount of the PAMs of the present invention is the amount sufficient to modulate the activity of the mGluR2 and that this amount varies inter alia, depending on the type of disease, the concentration of the compound in the therapeutic formulation, and the condition of the patient. Generally, an amount of PAM to be administered as a therapeutic agent for treating diseases in which modulation of the mGluR2 is beneficial, such as the disorders described herein, will be determined on a case by case by an attending physician.

Generally, a suitable dose is one that results in a concentration of the PAM at the treatment site in the range of 0.5 nM to 200 µM, and more usually 5 nM to 50 µM. To obtain these treatment concentrations, a patient in need of treatment likely will be administered an effective therapeutic daily amount of about 0.01 mg/kg to about 50 mg/kg body weight, preferably from about 0.01 mg/kg to about 25 mg/kg body weight, more preferably from about 0.01 mg/kg to about 10 mg/kg body weight, more preferably from about 0.01 mg/kg to about 2.5 mg/kg body weight, even more preferably from about 0.05 mg/kg to about 1 mg/kg body weight, more preferably from about 0.1 mg/kg to about 0.5 mg/kg body weight. The amount of a compound according to the present invention, also referred to here as the active ingredient, which is required to achieve a therapeutically effect will, of course vary on case-by-case basis, vary with the particular compound, the route of administration, the age and condition of the recipient, and the particular disorder or disease being treated. A method of treatment may also include administering the active ingredient on a regimen of between one and four intakes per day. In these methods of treatment the compounds according to the invention are preferably formulated prior to admission. As described herein below, suitable pharmaceutical formulations are prepared by known procedures using well known and readily available ingredients.

Because such positive allosteric modulators of mGluR2, including compounds of Formula (I), enhance the response of mGluR2 to glutamate, it is an advantage that the present methods utilize endogenous glutamate.

Because positive allosteric modulators of mGluR2, including compounds of Formula (I), enhance the response of mGluR2 to agonists, it is understood that the present invention extends to the treatment of neurological and psychiatric disorders associated with glutamate dysfunction by administering an effective amount of a positive allosteric modulator of mGluR2, including compounds of Formula (I), in combination with an mGluR2 agonist. Examples of mGluR2 agonists include, for example, LY-379268; DCG-IV; LY-354740; LY-404039; LY-544344; LY-2140023; LY-181837; LY-389795; LY-446433; LY-450477; talaglumetad; MGS0028; MGS0039; (−)-2-oxa-4-aminobicyclo[3.1.0] hexane-4,6-dicarboxylate; (+)-4-amino-2-sulfonylbicyclo [3.1.0]hexane-4,6-dicarboxylic acid; (+)-2-amino-4-fluoro-bicyclo[3.1.0]hexane-2,6-dicarboxylic acid; 1S,2R,5S,6S-2-amino-6-fluoro-4-oxobicyclo[3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R, 3R,5S,6S-2-amino-3-fluorobicyclo[3.1.0]hexane-2,6-dicarboxylic acid; 1S,2R,3S,5S,6S-2-amino-6-fluoro-3-hydroxybicyclo[3.1.0]hexane-2,6-dicarboxylic acid; (+)-4-amino-2-sulfonylbicyclo[3.1.0]hexane-4,6-dicarboxylic acid; (+)-2-amino-4-fluorobicyclo[3.1.0]hexane-2,6-dicarboxylic acid; 1S,2R,5S,6S-2-amino-6-fluoro-4-oxobicyclo [3.1.0]hexane-2,6-dicarboxylic acid; 1S,2R,4S,5S,6S-2-amino-6-fluoro-4-hydroxybicyclo[3.1.0]hexane-2,6-dicarboxylic acid; 1S,2R,3R,5S,6S-2-amino-3-fluorobicyclo [3.1.0]hexane-2,6-dicarboxylic acid; or 1S,2R,3S,5S,6S-2-amino-6-fluoro-3-hydroxybicyclo[3.1.0]hexane-2,6-dicarboxylic acid. More preferable mGluR2 agonists include LY-379268; DCG-IV; LY-354740; LY-404039; LY-544344; or LY-2140023.

The compounds of the present invention may be utilized in combination with one or more other drugs in the treatment, prevention, control, amelioration, or reduction of risk of diseases or conditions for which compounds of Formula (I) or the other drugs may have utility, where the combination of the drugs together are safer or more effective than either drug alone.

Pharmaceutical Compositions

The present invention also provides compositions for preventing or treating diseases in which modulation of the mGluR2 receptor is beneficial, such as the disorders described herein. While it is possible for the active ingredient to be administered alone, it is preferable to present it as a pharmaceutical composition. Accordingly, the present invention also relates to a pharmaceutical composition comprising a pharmaceutically acceptable carrier or diluent and, as active ingredient, a therapeutically effective amount of a compound according to the invention, in particular a compound according to Formula (I), a pharmaceutically acceptable salt thereof, a solvate thereof or a stereochemically isomeric form thereof. The carrier or diluent must be "acceptable" in the sense of being compatible with the other ingredients of the composition and not deleterious to the recipients thereof.

The compounds according to the invention, in particular the compounds according to Formula (I), the pharmaceutically acceptable salts thereof, the solvates and the stereochemically isomeric forms thereof, or any subgroup or combination thereof may be formulated into various pharmaceutical forms for administration purposes. As appropriate compositions there may be cited all compositions usually employed for systemically administering drugs.

The pharmaceutical compositions of this invention may be prepared by any methods well known in the art of pharmacy, for example, using methods such as those described in Gennaro et al. Remington's Pharmaceutical Sciences (18$^{th}$ ed., Mack Publishing Company, 1990, see especially Part 8: Pharmaceutical preparations and their Manufacture). To prepare the pharmaceutical compositions of this invention, a therapeutically effective amount of the particular compound, optionally in salt form, as the active ingredient is combined in intimate admixture with a pharmaceutically acceptable carrier or diluent, which carrier or diluent may take a wide variety of forms depending on the form of preparation desired for administration. These pharmaceutical compositions are desirable in unitary dosage form suitable, in particular, for oral, topical, rectal or percutaneous administration, by parenteral injection or by inhalation. For example, in preparing the compositions in oral dosage form, any of the usual pharmaceutical media may be employed such as, for example, water, glycols, oils, alcohols and the like in the case of oral liquid preparations such as, for example, suspensions, syrups, elixirs, emulsions and solutions; or solid carriers such as, for example, starches, sugars, kaolin, diluents, lubricants, binders, disintegrating agents and the like in the case of powders, pills, capsules and tablets. Because of the ease in administration, oral administration is preferred, and tablets and capsules represent the most advantageous oral dosage unit forms in which case solid pharmaceutical carriers are obviously employed. For parenteral compositions, the carrier will usually comprise sterile water, at least in large part, though other ingredients, for example surfactants, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations that are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, teaspoonfuls, tablespoonfuls, and segregated multiples thereof.

Since the compounds according to the invention are orally administrable compounds, pharmaceutical compositions comprising aid compounds for oral administration are especially advantageous.

In order to enhance the solubility and/or the stability of the compounds of Formula (I) in pharmaceutical compositions, it can be advantageous to employ α-, β- or γ-cyclodextrins or their derivatives, in particular hydroxyalkyl substituted cyclodextrins, e.g. 2-hydroxypropyl-β-cyclodextrin or sulfobutyl-β-cyclodextrin. Also co-solvents such as alcohols may improve the solubility and/or the stability of the compounds according to the invention in pharmaceutical compositions.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention.

Depending on the mode of administration, the pharmaceutical composition will comprise from 0.05 to 99% by weight, preferably from 0.1 to 70% by weight, more preferably from 0.1 to 50% by weight of the active ingredient, and, from 1 to 99.95% by weight, preferably from 30 to 99.9% by weight, more preferably from 50 to 99.9% by weight of a pharmaceutically acceptable carrier, all percentages being based on the total weight of the composition.

As already mentioned, the invention also relates to a pharmaceutical composition comprising the compounds according to the invention and one or more other drugs for use as a medicament or for use in the treatment, prevention, control, amelioration, or reduction of risk of diseases or conditions for which compounds of Formula (I) or the other drugs may have utility as well. The use of such a composition for the manufacture of a medicament, as well as the use of such a composition for the manufacture of a medicament in the treatment, prevention, control, amelioration, or reduction of risk of diseases or conditions for which compounds of Formula (I) or the other drugs may have utility, are also contemplated. The present invention also relates to a combination of a compound according to the present invention and a mGluR2 orthosteric agonist. The present invention also relates to such a combination for use as a medicine. The present invention also relates to a product comprising (a) a compound according to the present invention, a pharmaceutically acceptable salt thereof or a solvate thereof, and (b) a mGluR2 orthosteric agonist, as a combined preparation for simultaneous, separate or sequential use in the treatment or prevention of a condition in a mammal, including a human, the treatment or prevention of which is affected or facilitated by the neuromodulatory effect of mGluR2 allosteric modulators, in particular positive mGluR2 allosteric modulators. The different drugs of such a combination or product may be combined in a single preparation together with pharmaceutically acceptable carriers or diluents, or they may each be present in a separate preparation together with pharmaceutically acceptable carriers or diluents.

The following examples are intended to illustrate but not to limit the scope of the present invention.

Chemistry

Several methods for preparing the compounds of this invention are illustrated in the following Examples. Unless otherwise noted, all starting materials were obtained from commercial suppliers and used without further purification.

Hereinafter, "CI" means chemical ionisation; "DAD" means diode-array detector; "THF" means tetrahydrofuran; "DMF" means N,N-dimethylformamide; "EtOAc" means ethyl acetate; "DCM" means dichloromethane; "DCE" means dichloroethane; "BINAP" means 1,1'-[1,1'-binaphthalene]-2,2'-diylbis[1,1-diphenyl-phosphine]; "DBU" means 1,8-diaza-7-bicyclo[5.4.0]undecene; "l" or "L" means liter; "LRMS" means low-resolution mass spectrometry/spectra; "HRMS" means high-resolution mass spectra/spectrometry; "NH$_4$Ac" means ammonium acetate; "NH$_4$OH" means ammonium hydroxide; "NaHCO$_3$" means sodium hydrogencarbonate; "Et$_2$O" means diethyl ether; "DIPE" means diisopropylether; "MgSO$_4$" means magnesium sulphate; "EtOH" means ethanol; "Na$_2$SO$_4$" means sodium sulphate; "CH$_3$CN" means acetonitrile; "NaH" means sodium hydride; "MeOH" means methanol; "NH$_3$" means ammonia; "Na$_2$S$_2$O$_3$" means sodium thiosulphate; "AcOH" means acetic acid; "mp" means melting point; "min" means minutes; "h" means hours; "s" means second(s); "Et$_3$N" or "TEA" mean triethylamine; "ES" means electrospray; "TOF" means time of flight; "NH$_4$Cl" means ammonium chloride; "K$_2$CO$_3$" means potassium carbonate; "Pd(PPh$_3$)$_4$" means tetrakis(triphenylphosphine)palladium(0); "S-Phos" means 2-dicyclohexylphosphino-2',6'-dimethoxybiphenyl Microwave assisted reactions were performed in a single-mode reactor: Initiator™ Sixty EXP microwave reactor (Biotage AB), or in a multimode reactor: MicroSYNTH Labstation (Milestone, Inc.).

Thin layer chromatography (TLC) was carried out on silica gel 60 F254 plates (Merck) using reagent grade solvents. Flash column chromatography was performed on silica gel, particle size 60 Å, mesh=230-400 (Merck) using standard techniques. Automated flash column chromatography was performed using ready-to-connect cartridges from Merck, on irregular silica gel, particle size 15-40 μm (normal phase disposable flash columns) on a SPOT or FLASH system from Armen Instrument.

Description 1

2,3-Dichloro-4-iodo-pyridine (D1)

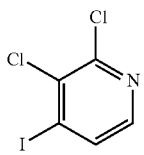

To a solution of n-butyllithium (27.6 ml, 69 mmol, 2.5 M in hexanes) in dry Et$_2$O (150 ml) cooled at −78° C., under nitrogen atmosphere, was added 2,2,6,6-tetramethylpiperidine (11.64 ml, 69 mmol) dropwise. The resulting reaction mixture was stirred at −78° C. for 10 min, and then a solution of 2,3-dichloropyridine (10 g, 67.57 mmol) in dry THF (75 ml) was added dropwise. The mixture was stirred at −78° C. for 30 min and then a solution of iodine (25.38 g, 100 mmol) in dry THF (75 ml) was added. The mixture was allowed to warm to room temperature overnight, quenched with Na$_2$S$_2$O$_3$ (aqueous sat. solution) and extracted twice with EtOAc. The combined organic extracts were washed with NaHCO$_3$ (aqueous sat. solution), dried (Na$_2$SO$_4$) and concentrated in vacuo. The crude residue was precipitated with heptane, filtered off and concentrated to yield intermediate compound D1 (8.21 g, 44%) as a pale cream solid.

Description 2

(3-Chloro-4-iodo-pyridin-2-yl)-hydrazine (D2)

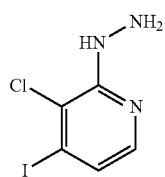

To a solution of compound D1 (8 g, 29.21 mmol) in 1,4-dioxane (450 ml), was added hydrazine monohydrate (14.169 ml, 175.255 mmol). The reaction mixture was heated in a sealed tube at 70° C. for 16 h. After cooling, NH$_4$OH (32% aqueous solution) was added and the resulting mixture was concentrated in vacuo. The white solid residue thus obtained was taken up in EtOH to obtain a suspension which was heated and filtered. The filtrate was cooled and the precipitate thus obtained was filtered off. The resulting filtrate was concentrated in vacuo to yield intermediate compound D2 (2.67 g, 52%) as a white solid.

Description 3

N'-(3-chloro-4-iodo-pyridin-2-yl)-2-cyclopropylacetohydrazide (D3)

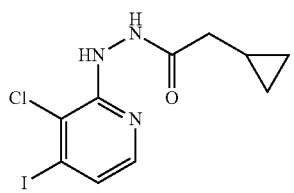 [SMILES: O=C(CC1CC1)NNc1nccc(I)c1Cl]

To a solution of D2 (0.73 g, 2.709 mmol) in dry DCM (8 ml), cooled at 0° C., were added Et$_3$N (0.562 ml, 4.064 mmol) and cyclopropyl-acetyl chloride (0.385 g, 3.251 mmol). The resulting reaction mixture was stirred at room temperature for 16 h. To this mixture was then added NaHCO$_3$ (aqueous sat. solution). The resulting solution was then extracted with DCM. The organic layer was separated, dried (MgSO$_4$) and concentrated in vacuo to yield intermediate compound D3 (0.94 g, 99%).

Description 4

8-Chloro-3-cyclopropylmethyl-7-iodo-1,2,4-triazolo[4,3-a]pyridine (D4)

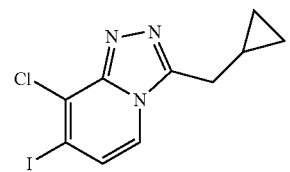

D3 (0.74 g, 2.389 mmol) was heated at 160° C. for 40 min. After cooling, the brown gum was triturated with DIPE yielding intermediate compound D4 (0.74 g, 93%), which was used without further purification.

Description 5

2,4-Dichloro-3-iodo-pyridine (D5)

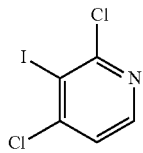

To a solution of 2,4-dichloropyridine (5.2 g, 35.137 mmol) and DIPEA (3.911 g, 38.651 mmol) in dry THF (40 ml) cooled at −78° C. under a nitrogen atmosphere, was added n-butyllithium (24.157 ml, 38.651 mmol, 1.6 M in hexanes) dropwise. The resulting reaction mixture was stirred at −78°

C. for 45 min. and then a solution of iodine (9.81 g, 38.651 mmol) in dry THF (20 ml) was added dropwise. The mixture was stirred at −78° C. for 1 h. The mixture was allowed to warm to room temperature, diluted with EtOAc and quenched with NH₄Cl (aqueous sat. solution) and Na₂S₂O₃ (aqueous sat. solution). The combined organic extracts were separated, washed with NaHCO₃ (aqueous sat. solution), dried (Na₂SO₄) and concentrated in vacuo. The crude product was purified by column chromatography (silica gel; Heptane/DCM up to 20% as eluent). The desired fractions were collected and concentrated in vacuo to yield intermediate compound D5 (7.8 g, 81%).

Description 6

2,4-Dichloro-3-trifluoromethyl-pyridine (D6)

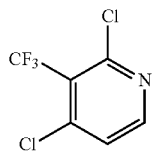

To a mixture of compound D5 (2 g, 7.302 mmol) in DMF (50 ml) were added fluorosulfonyl-difluoro-acetic acid methyl ester (1.858 ml, 14.605 mmol) [C.A.S. 680-15-9] and copper (I) iodide (2.796. g, 14.605 mmol). The reaction mixture was heated in a sealed tube at 100° C. for 5 h. After cooling, the solvent was evaporated in vacuo. The crude product was purified by column chromatography (silica gel; DCM as eluent). The desired fractions were collected and concentrated in vacuo to yield intermediate compound D6 (1.5 g, 95%).

Description 7

4-Benzyloxy-3-trifluoromethyl-2-chloro-pyridine (D7)

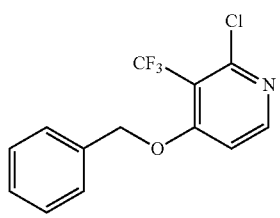 [SMILES: FC(F)(F)c1c(OCc2ccccc2)ccnc1Cl]

To a suspension of NaH (0.487 g, 12.732 mmol, 60% mineral oil) in DMF (50 ml) cooled at 0° C., was added benzyl alcohol (1.262 ml, 12.2 mmol). The resulting mixture was stirred for 2 min. Then, intermediate compound D6 (2.5 g, 11.575 mmol) was added. The resulting reaction mixture was gradually warmed to room temperature and stirred for 1 h. The reaction mixture was quenched with water and extracted with Et₂O. The organic layer was separated, dried (Na₂SO₄) and concentrated in vacuo. The crude product was purified by column chromatography (silica gel; Heptane/DCM gradient as eluent). The desired fractions were collected and concentrated in vacuo to yield intermediate compound D7 (1.1 g, 33%).

Description 8

(4-Benzyloxy-3-trifluoromethyl-pyridin-2-yl)-hydrazine (D8)

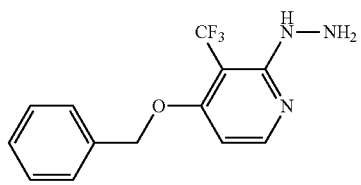 [SMILES: NNc1nccc(OCc2ccccc2)c1C(F)(F)F]

To a suspension of compound D7 (1.09 g g, 3.789 mmol) in 1,4-dioxane (9 ml), was added hydrazine monohydrate (3.676 ml, 75.78 mmol). The reaction mixture was heated at 160° C. under microwave irradiation for 30 min. After cooling the resulting solution was concentrated in vacuo. The residue thus obtained was dissolved in DCM and washed with NaHCO₃ (aqueous sat. solution). The organic layer was separated, dried (Na₂SO₄) and concentrated in vacuo to yield intermediate compound D8 (0.890 g, 83%) as a white solid.

Description 9

N'-(4-benzyloxy-3-trifluoromethyl-pyridin-2-yl)-2-cylclopropylacetohydrazide (D9)

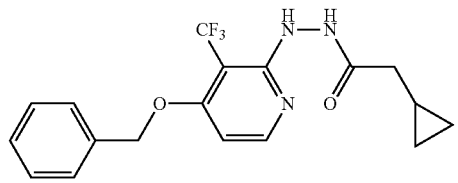 [SMILES: O=C(CC1CC1)NNc1nccc(OCc2ccccc2)c1C(F)(F)F]

To a solution of D8 (0.890 g, 3.142 mmol) in dry DCM (3 ml) were added Et₃N (0.653 ml, 4.713 mmol) and cyclopropyl-acetyl chloride [C.A.S. 543222-65-5] (0.373 g, 3.142 mmol). The resulting reaction mixture was stirred at 0° C. for 20 min, then concentrated in vacuo to yield intermediate compound D9 (1.1 g, 96%), which was used without further purification.

Description 10

7-Chloro-8-trifluoromethyl-3-cyclopropylmethyl-1,2,4-triazolo[4,3-a]pyridine (D10)

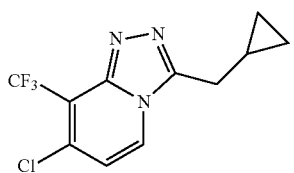 [SMILES: FC(F)(F)c1c(Cl)ccn2c(CC3CC3)nnc12]

D9 (1.14 g, 1.872 mmol) and phosphorous (V) oxychloride (0.349 g, 3.744 mmol) in CH₃CN (10 ml) was heated at 150° C. under microwave irradiation for 10 min. After cooling, the resulting reaction mixture was diluted with DCM and washed with NaHCO₃ (aqueous sat. solution), dried (Na₂SO₄) and concentrated in vacuo. The crude product was purified by column chromatography (silica gel; DCM/7M solution of NH₃ in MeOH up to 20% as eluent). The desired fractions were collected and concentrated in vacuo to yield intermediate compound D10 (0.261 g, 51%) as a white solid.

Description 11

5-Bromo-1-(1,4-dioxa-spiro[4.5]dec-8-yl)-1H-indole (D11)

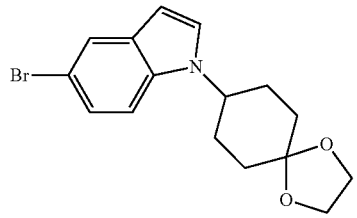 [SMILES: Brc1ccc2c(ccn2C2CCC3(CC2)OCCO3)c1]

A mixture of 5-bromoindole (8.472 g, 43.216 mmol), [CAS: 10075-50-0]), toluene-4-sulfonic acid, 1,4-dioxa-spiro[4.5] dec-8-yl ester (13.5 g, 43.216 mmol) [C.A.S. 23551-05-9]; (prepared according to the procedure described in J. Chem. Soc., Perkin Trans. 1 2002, 20, 2251-2255) and powdered potassium hydroxide (13.239 g, 235.958 mmol) in DMSO (300 ml) was stirred at 80° C. for 6 h. Subsequently, the mixture was cooled to room temperature and poured into ice water. The resulting aqueous mixture was extracted with Et₂O, dried (Na₂SO₄), and the volatiles were evaporated in vacuo. The crude residue was purified by column chromatography (silica gel; DCM/heptane 1:1 as eluent). The desired fractions were collected and concentrated in vacuo to yield intermediate compound D11 (2.897 g, 19.93%) as a white solid.

Description 12

4-(5-Bromo-indol-1-yl)-cyclohexanone (D12)

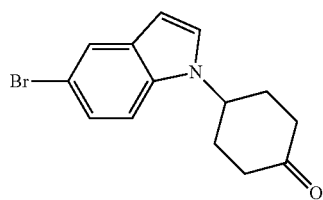 [SMILES: O=C1CCC(n2ccc3cc(Br)ccc32)CC1]

A mixture of intermediate D11 (24 g, 71.38 mmol) and p-toluenesulfonic acid (0.679 mg, 3.569 mmol) in water (72 ml) and acetone (168 ml) was heated at 100° C. under microwave irradiation for 15 min. After cooling to room temperature, the reaction mixture was diluted with DCM and washed with NaHCO₃ (aqueous sat. solution), dried (Na₂SO₄), and the solvent was evaporated in vacuo. The residue was triturated with a mixture of Et₂O (100 ml)/acetone (30 ml). The solid was filtered off and the filtrate was concentrated in vacuo to yield intermediate compound D12 (18.13 g, 73%) as a yellow oil.

Description 13

4-(5-Bromo-indol-1-yl)-cyclohexanol (D13)

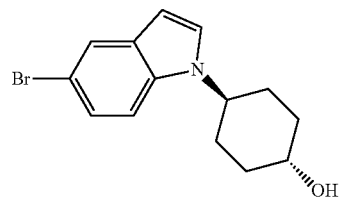

trans-D13

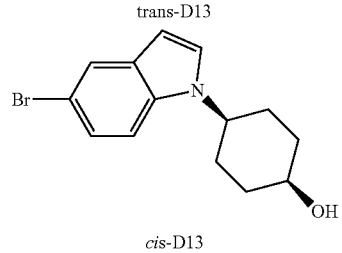

cis-D13

To a mixture of intermediate D12 (2.074 g, 7.098 mmol) in MeOH (50 ml) stirred at 0° C., was added sodium borohydride (62.198 mg, 1.644 mmol). The resulting reaction mixture was warmed to room temperature and further stirred for 1 h. Subsequently, the mixture was concentrated in vacuo and the residue was dissolved in DCM. This solution was washed with NH₄Cl (aqueous sat. solution). The organic layer was separated, dried (Na₂SO₄), and the solvent was evaporated in vacuo. The residue was purified by column chromatography (silica gel; EtOAc/heptane gradient from 0:100 to 30:70 as eluent). The desired fractions were collected and the solvent was evaporated in vacuo to yield intermediate compound trans-D13 (1.809 g, 86.6%) and intermediate compound cis-D13 (0.110 g, 5.27%).

Description Trans-14 trans-4-[5-(4,4,5,5-Tetramethyl-[1,3,2]dioxaborolan-2-yl)-indol-1-yl]-cyclohexanol (trans-D14)

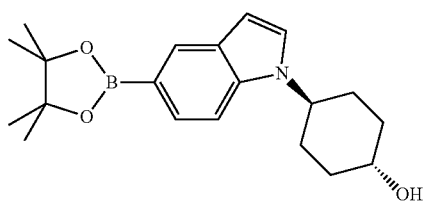 [SMILES: CC1(C)OB(c2ccc3c(ccn3[C@H]3CC[C@H](O)CC3)c2)OC1(C)C]

To a solution of intermediate trans-D13 (0.300 g, 1.02 mmol) in 1,4-dioxane (12 ml) and DMF (2 ml) were added bis (pinacolato)diboron (0.829 g, 3.263 mmol) and potassium acetate (0.300 g, 3.059 mmol). A nitrogen stream was bubbled through the mixture and then [1,1'-bis(diphenylphosphino)-ferrocene]-dichloropalladium(II)-complex with DCM (1:1) (0.0374 g, 0.051 mmol) was added. The reaction mixture was heated at 160° C. under microwave irradiation for 1 h. After cooling to room temperature, the reaction mixture was filtered through diatomaceous earth. The filtrate was concentrated in vacuo. The residue was purified by column chromatography (silica gel; eluent: DCM/EtOAc gradient from 100:0 to 60:40). The desired fractions were collected and the solvent was evaporated in vacuo to yield intermediate compound trans-D14 (0.260 g, 74.6%).

Description 15

1-(Tetrahydro-pyran-4-yl)-5-(4,4,5,5-tetramethyl-[1,3,2]dioxaborolan-2-yl)-1H-indole (D15)

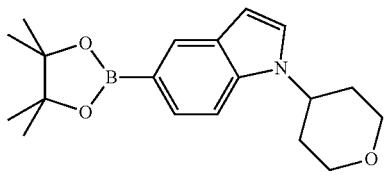 [SMILES: CC1(C)OB(c2ccc3c(ccn3C3CCOCC3)c2)OC1(C)C]

To a solution of 5-Bromo-1-(tetrahydro-pyran-4-yl)-1H-indole [C.A.S. 954387-14-5] (0.380 g, 1.356 mmol) in 1,4-dioxane (5 ml) were added, bis(pinacolato)diboron (0.482 g, 1.899 mmol) and potassium acetate (0.399 g, 4.069 mmol). A nitrogen stream was bubbled through the mixture and then [1,1'-bis(diphenylphosphino)-ferrocene]-dichloropalladium (II)-complex with DCM (1:1) (0.0597 g, 0.0814 mmol) was added. The reaction mixture was heated at 95° C. overnight. After cooling to room temperature, the reaction mixture was filtered through diatomaceous earth and washed with EtOAc. The filtrate was concentrated in vacuo. The residue was purified by column chromatography (silica gel; eluent: DCM). The desired fractions were collected and the solvent was evaporated in vacuo to yield intermediate compound D15 (0.312 g, 74.6%) as a white solid.

Description 16

1-Pyridin-2-yl-5-(4,4,5,5-tetramethyl-[1,3,2]dioxaborolan-2-yl)-1H-indole (D16)

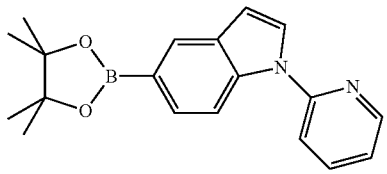 [SMILES: CC1(C)OB(c2ccc3c(ccn3-c3ccccn3)c2)OC1(C)C]

To a solution of 5-Bromo-1-pyridin-2-yl-1H-indole [CA.S. 504424-71-9] (1.73 g, 6.334 mmol) in DMSO (13 ml) were added bis(pinacolato)diboron (0.482 g, 1.899 mmol) and potassium acetate (1.865 g, 19.002 mmol). A nitrogen stream was bubbled through the mixture and then [1,1'-bis(diphenylphosphino)-ferrocene]-dichloropalladium(II)-complex with DCM (1:1) (0.139 g, 0.19 mmol) was added. The reaction mixture was heated at 110° C. overnight. After cooling to room temperature, the reaction mixture was refilled with [1,1'-bis(diphenylphosphino)-ferrocene]-dichloropalladium (II)-complex with DCM (1:1) (0.280 g) and stirred at 110° C. for 2 days. After cooling to room temperature, the reaction mixture was filtered through diatomaceous earth and washed with EtOAc. The filtrate was washed with water and NaCl (aqueous sat. solution). The organic layer was separated, dried ($Na_2SO_4$), and the solvent was evaporated in vacuo. The residue was purified by column chromatography (silica gel; eluent:Heptane/EtOAc 9:1 as eluent). The desired fractions were collected and the solvent was evaporated in vacuo to yield intermediate compound D16 (0.868 g, 42.8%) as a white solid.

Description 17

5-(2,3-Dichloro-pyridin-4-yl)-1-pyridin-2-yl-M-indole (D17)

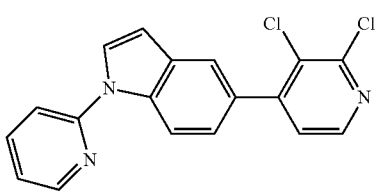 [SMILES: Clc1nccc(-c2ccc3c(ccn3-c3ccccn3)c2)c1Cl]

To a mixture of intermediate compound D1 (0.5 g, 1.826 mmol) in 1,4-dioxane (11.25 ml) under a nitrogen atmosphere were added intermediate compound D16 (0.684 g, 2.136 mmol), $Pd(PPh_3)_4$ (0.105 g, 0.0913 mmol) and $NaHCO_3$ (3.75 ml, aqueous sat. solution). The reaction mixture was heated at 150° C. under microwave irradiation for 5 min. After cooling, the mixture was filtered through a pad of diatomaceous earth and washed with EtOAc. The filtrate was washed with water and NaCl (aqueous sat. solution). The organic layer was separated, dried ($Na_2SO_4$), and the solvent was evaporated in vacuo. The residue was purified by column chromatography (silica gel; eluent:Heptane/EtOAc up to 20% as eluent). The desired fractions were collected and the solvent was evaporated in vacuo to yield intermediate compound D17 (0.489 g, 79%).

Description 18

[3-Chloro-4-(1-pyridin-2-yl-1H-indol-5-yl)-pyridin-2-yl]-hydrazine (D18)

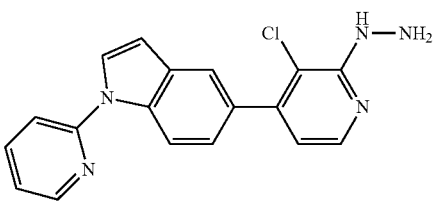 [SMILES: NNc1nccc(-c2ccc3c(ccn3-c3ccccn3)c2)c1Cl]

To a solution of intermediate compound D17 (0.489 g, 1.438 mmol) in EtOH (4 ml), was added hydrazine monohydrate (2.537 ml, 28.765 mmol). The reaction mixture was heated at 90° C. for 16 hours. Then, after cooling to room temperature, the reaction mixture was refilled with hydrazine monohydrate (2.5 ml) and heated again at 100° C. for 16 hours. After cooling to room temperature, the precipitate that developed was collected and washed with water, EtOH and DIPE to yield intermediate compound D18 (0.388 g, 80%) as a white solid. M.P. 173.3° C.

Description 19

2-[3-chloro-4-[1-(2-pyridinyl)-1H-indol-5-yl]-2-pyridinyl]hydrazide 3,3,3-trifluoropropionic acid (D19)

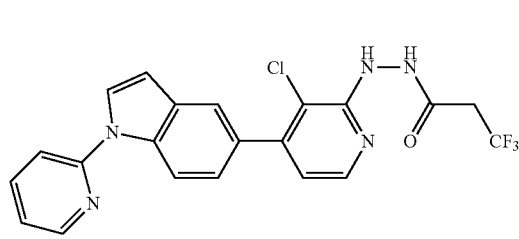 [SMILES: O=C(CC(F)(F)F)NNc1nccc(-c2ccc3c(ccn3-c3ccccn3)c2)c1Cl]

To a solution of intermediate compound D18 (0.388 g, 1.155 mmol) in dry DCM (8 ml) at 0° C. were added trietylamine (0.126 ml, 0.902 mmol) and 3,3,3-trifluoro-propionyl chloride [C.A.S. 41463-83-6] (0.203 g, 1.387 mmol) was added. The resulting reaction mixture was gradually warmed to room temperature and stirred for 16 h. Additional trietylamine (0.22 ml) was added and the mixture was further stirred for 2 hours. The mixture was then washed with NaHCO₃ (aqueous sat. solution), the organic layer was separated, dried (Na₂SO₄), and the solvent was evaporated in vacuo to yield intermediate compound D19 (0.46 g, 66%), which was used without further purification.

Description 20

5-Bromo-1-(3-fluoro-pyridin-4-yl)-1H-indole (D20)

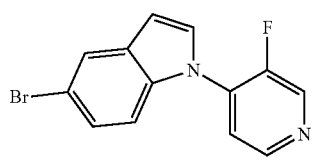 [SMILES: Fc1cnccc1-n1ccc2cc(Br)ccc21]

5-Bromo-1H-indole [CA.S. 10075-50-0] (2 g, 10.202 mmol) was dissolved in DMF (16 ml). A nitrogen stream was bubbled through the mixture and then were added 3-Fluoro-4-iodopyridine [CA.S. 22282-75-3] (2.502 g, 11.222 mmol), lithium chloride (0.432 g, 10.202 mmol), copper(I) iodide (0.0195 g, 0.102 mmol) and K₂CO₃ (4.23 g, 30.605 mmol). The reaction mixture was heated at 120° C. for 2 days. After cooling to room temperature, the reaction mixture was refilled with lithium chloride (0.100 g) and (copper(I) iodide (0.010) stirred at 120° C. for 16 h. After cooling to room temperature, the reaction mixture was washed with NH₃ (aqueous sat. solution) and extracted with DCM. The organic layer was separated, washed with water, dried (Na₂SO₄), and the solvent was evaporated in vacuo. The residue was purified by column chromatography (silica gel; eluent:Heptane/EtOAc up to 15% as eluent). The desired fractions were collected and the solvent was evaporated in vacuo to yield intermediate compound D20 (1.37 g, 46%).

Description 21

1-(3-Fluoro-pyridin-4-yl)-5-(4,4,5,5-tetramethyl-[1,3,2]dioxaborolan-2-yl)-1H-indole

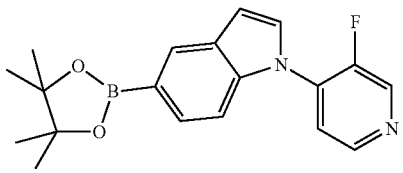 [SMILES: CC1(C)OB(c2ccc3c(ccn3-c3ccncc3F)c2)OC1(C)C]

To a solution of intermediate compound D20 (1.3 g, 4.465 mmol) in 1,4-dioxane (10 ml) were added bis(pinacolato)diboron (1.701 g, 6.698 mmol) and potassium acetate (1.315 g, 13.396 mmol). A nitrogen stream was bubbled through the mixture and then [1,1'-bis(diphenylphosphino)-ferrocene]-dichloropalladium(II)-complex with DCM (1:1) (0.197 g, 0.268 mmol) was added. The reaction mixture was heated at 95° C. overnight. After cooling to room temperature, the reaction mixture was refilled with bis(pinacolato)diboron (0.100 g) and [1,1'-bis(diphenylphosphino)-ferrocene]-dichloropalladium(II)-complex with DCM (1:1) (0.05 g) and stirred at 95° C. for 2 day overnight. After cooling to room temperature, the reaction mixture was filtered through diatomaceous earth and washed with DCM. The solvent was evaporated in vacuo. The residue was purified by column chromatography (silica gel; eluent:Heptane/EtOAc up to 4% as eluent). The desired fractions were collected and the solvent was evaporated in vacuo to yield intermediate compound D21 (1.18 g, 78%).

Description 22

5-Bromo-1-cyclopropylmethyl-M-pyrrolo[2,3-b]pyridine (D22)

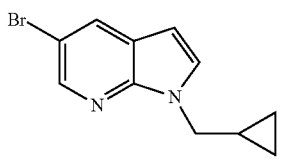 [SMILES: Brc1cnc2c(ccn2CC2CC2)c1]

To a solution of 5-Bromo-1H-pyrrolo[2,3-b]pyridine [CA.S. 183208-35-7] (0.95 g, 4.821 mmol) in DMF (8 ml) cooled at 0° C. was added portionwise NaH (0.289 g, 7.232 mmol, 60% mineral oil). The resulting mixture was stirred for 15 min., then, cyclopropylmethyl bromide [CA.S. 7051-34-5] (0.716 g, 5.304 mmol) was added. The resulting reaction mixture was gradually warmed to room temperature and stirred for 1 h. The reaction mixture was refilled with cyclopropylmethyl bromide (0.430 mg) and stirred at room temperature for 1 hour. The reaction mixture was quenched with water and extracted with DCM. The organic layer was separated, dried (Na$_2$SO$_4$) and concentrated in vacuo to yield intermediate compound D22 (1.2 g, 99%).

Description 23

1-Cyclopropylmethyl-5-(4,4,5,5-tetramethyl-[1,3,2] dioxaborolan-2-yl)-1H-pyrrolo[2,3-b]pyridine (D23)

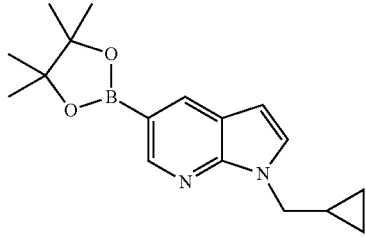 [SMILES: CC1(C)OB(c2cnc3c(ccn3CC3CC3)c2)OC1(C)C]

To a solution of intermediate compound D22 (1.2 g, 4.778 mmol) in 1,4-dioxane (10 ml) were added bis(pinacolato) diboron (1.82 g, 7.168 mmol) and potassium acetate (1.407 g, 14.335 mmol). A nitrogen stream was bubbled through the mixture and then [1,1'-bis(diphenylphosphino)-ferrocene]-dichloropalladium(ID-complex with DCM (1:1) (0.21 g, 0.287 mmol) was added. The reaction mixture was heated at 95° C. overnight. After cooling to room temperature, the reaction mixture was filtered through diatomaceous earth and washed with DCM. The solvent was evaporated in vacuo. The residue was purified by column chromatography (silica gel; eluent:Heptane/EtOAc up to 3% as eluent). The desired fractions were collected and the solvent was evaporated in vacuo to yield intermediate compound D23 (1.02 g, 71%).

Description 24

4-Pyrimidin-2-yl-3,4-dihydro-2H-benzo[1,4]oxazine (D24)

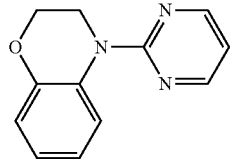 [SMILES: c1cnc(N2CCOc3ccccc32)nc1]

A nitrogen stream was bubbled through a mixture of 2-chloropyrimidine (1 g, 8.731 mmol), and potassium acetate (0.098 g, 0.437 mmol), racemic-2,2'-bis(diphenylphosphino)-1,1'-binaphthyl (0.407 g, 0.655 mmol) and Cs$_2$CO$_3$ (5.689 g, 17.462 mmol). Then, 3,4-dihydro-2H-1,4-benzoxazino [CA.S. 5735-53-5] (1.77 g, 13.097 mmol) in THF (0.5 ml) was added. The reaction mixture was heated at 110° C. under microwave irradiation for 10 min. After cooling to room temperature, the reaction mixture was washed with EtOAc. The organic layer was separated, washed with water, dried (Na$_2$SO$_4$), and the solvent was evaporated in vacuo. The residue was purified by column chromatography (silica gel; eluent: DCM/Heptane up to 20% as eluent). The desired fractions were collected and the solvent was evaporated in vacuo to yield intermediate compound D24 (1.9 g, 81%).

Description 25

7-Bromo-4-pyrimidin-2-yl-3,4-dihydro-2H-benzo[1,4]oxazine (D25)

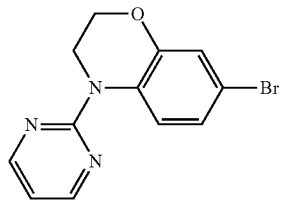 [SMILES: Brc1ccc2c(c1)OCCN2c1ncccn1]

To a solution of intermediate compound D24 (1.67 g, 7.832 mmol) in DMF (10 ml) was added N-bromosuccinimide (1.533 g, 8.615 mmol). The reaction mixture was heated at 180° C. under microwave irradiation for 20 min. After cooling to room temperature, the reaction mixture was refiled with N-bromosuccinimide (1.53 g) and heated at 180° C. under microwave irradiation for 20 min. After cooling, the reaction mixture was washed with NaHCO$_3$ (aqueous sat. solution) and extracted with DCM. The organic layer was separated, dried (Na$_2$SO$_4$) and the solvent evaporated in vacuo. The crude product was purified by column chromatography (silica gel; Heptane/DCM/EtOAc from 100/0 up to 40/60 as eluent). The desired fractions were collected and evaporated in vacuo to yield intermediate compound D25 (1.2 g, 52%) as an orange oil Description 26

4-Pyrimidin-2-yl-7-(4,4,5,5-tetramethyl-[1,3,2]dioxaborolan-2-yl)-3,4-dihydro-2H-benzo[1,4]oxazine (D26)

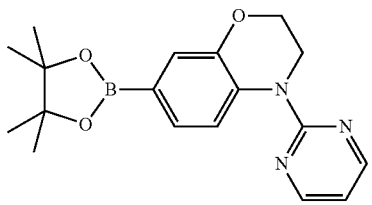 [SMILES: CC1(C)OB(c2ccc3c(c2)OCCN3c2ncccn2)OC1(C)C]

To a solution of intermediate compound D25 (1.1 g, 3.765 mmol) in 1,4-dioxane (14 ml) were added bis(pinacolato) diboron (1.434 g, 5.648 mmol) and potassium acetate (1.109 g, 11.296 mmol). A nitrogen stream was bubbled through the mixture and then [1,1'-bis(diphenylphosphino)-ferrocene]-dichloropalladium(II)-complex with DCM (1:1) (0.138 g, 0.188 mmol) was added. The reaction mixture was heated at 100° C. overnight. After cooling to room temperature, the reaction mixture was filtered through diatomaceous earth and washed with EtOAc. The solvent was evaporated in vacuo. The residue was purified by column chromatography (silica gel; eluent: DCM as eluent). The desired fractions were collected and the solvent was evaporated in vacuo to yield intermediate compound D26 (1.11 g, 86%) as pale yellow oil which became a solid upon standing

Description 27

1-Pyridin-3-yl-5-(4,4,5,5-tetramethyl-[1,3,2]dioxaborolan-2-yl)-1H-indole (D27)

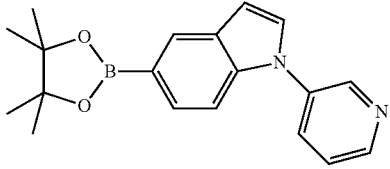 [SMILES: CC1(C)OB(c2ccc3c(ccn3-c3cccnc3)c2)OC1(C)C]

To a solution of 5-Bromo-1-pyridin-3-yl-1H-indole [CA.S. 95519-86-1] (1.1 g, 4.027 mmol) in 1,4-dioxane (8 ml) were added bis(pinacolato)diboron (0.125 g, 4.43 mmol) and potassium acetate (1.186 g, 12.082 mmol). A nitrogen stream was bubbled through the mixture and then [1,1'-bis(diphenylphosphino)-ferrocene]-dichloropalladium(II)-complex with DCM (1:1) (0.177 g, 0.242 mmol) was added. The reaction mixture was heated at 90° C. overnight. After cooling to room temperature, the reaction mixture was filtered through diatomaceous earth and washed with 1,4-dioxane and the solvent was evaporated in vacuo. The residue was purified by column chromatography (silica gel; eluent:Heptane/EtOAc from 100/0 to 85/15 as eluent). The desired fractions were collected and the solvent was evaporated in vacuo to yield intermediate compound D27 (0.96 g, 74%) as a white solid.

Description 28

1-(2-Methylpyridin-5-yl)-5-(4,4,5,5-tetramethyl-[1,3,2]dioxaborolan-2-yl)-1H-indole (D28)

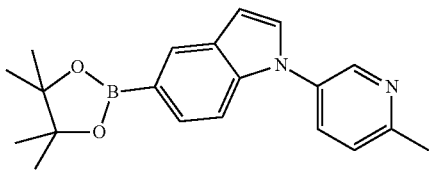

To a stirred solution of 5-Bromo-1-(2-methyl-5-pyridin-3-yl-1H-indole [CA.S. 504424-81-1] (2 g, 6.965 mmol) in 1,4-dioxane (10 ml) were added bis(pinacolato)diboron (1.946 g, 7.661 mmol) and potassium acetate (2.051 g, 20.894 mmol). A nitrogen stream was bubbled through the mixture and then [1,1'-bis(diphenylphosphino)-ferrocene]-dichloropalladium (II)-complex with DCM (1:1) (0.307 g, 0.418 mmol) was added. The reaction mixture was heated at 90° C. overnight. After cooling to room temperature, the reaction mixture was filtered through diatomaceous earth and washed with 1,4-dioxane and the solvent was evaporated in vacuo. The residue was purified by column chromatography (silica gel; eluent: Heptane/EtOAc from 100/0 to 85/15 as eluent). The desired fractions were collected and the solvent was evaporated in vacuo to yield intermediate compound D28 (1.025 g, 44%).

Description 29

4-(6-Methyl-pyridin-3-yl)-3,4-dihydro-2H-benzo[1,4]oxazine (D29)

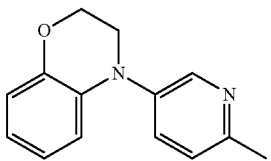 [SMILES: Cc1ccc(N2CCOc3ccccc32)cn1]

A nitrogen stream was bubbled through a mixture of 5-bromo-2-methylpyridine (3.818 g, 22.195 mmol) in toluene (28 ml), then, $^t$BuONa (6.186 g, 64.365 mmol), 1,1'-bis (diphenylphosphino)ferrocene (0.615 g, 1.11 mmol), bis (dibenzylideneacetonato)palladium (0.383 g, 0.666 mmol) and 3,4-dihydro-2H-1,4-benzoxazino [CA.S. 5735-53-5] (1.77 g, 13.097 mmol) were added. The reaction mixture was heated at 80° C. overnight. After cooling to room temperature, the reaction mixture was filtered through diatomaceous earth and washed with EtOAc. The solvent was evaporated in vacuo. The residue was purified by column chromatography (silica gel; eluent:DCM/EtOAc from 100/0 to 80/10 as eluent). The desired fractions were collected and the solvent was evaporated in vacuo to yield intermediate compound D29 (3.812 g, 75%) as a yellow oil.

Description 30

7-Bromo-4-(6-methyl-pyridin-3-yl)-3,4-dihydro-2H-benzo[1,4]oxazine (D30)

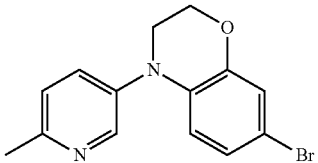 [SMILES: Cc1ccc(N2CCOc3cc(Br)ccc32)cn1]

To a solution of intermediate compound D29 (3.756 g, 16.559 mmol) in DMF (50 ml) was added N-bromosuccinimide (3.25 g, 18.259 mmol). The reaction mixture was washed with NaHCO$_3$ (aqueous sat. solution) and extracted with EtOAc. The organic layer was separated, dried (Na$_2$SO$_4$) and the solvent evaporated in vacuo. The crude product was purified by column chromatography (silica gel; DCM/AcOEt up to 3% as eluent). The desired fractions were collected and concentrated in vacuo to yield intermediate compound D30 (4.58 g, 90% as a yellow oil

Description 31

4-(6-Methyl-pyridin-3-yl)-7-(4,4,5,5-tetramethyl-[1,3,2]dioxaborolan-2-yl)-3,4-dihydro-2H-benzo[1,4]oxazine (D31)

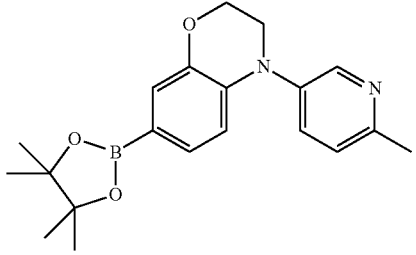

To a solution of intermediate compound D30 (4.58 g, 15.008 mmol) in 1,4-dioxane (28 ml) were added bis(pinacolato)diboron (4.192 g, 16.509 mmol) and potassium acetate (2.209 g, 22.512 mmol). A nitrogen stream was bubbled through the mixture and then [1,1'-bis(diphenylphosphino)-ferrocene]-dichloropalladium(II)-complex with DCM (1:1) (0.551 g, 0.75 mmol) was added. The reaction mixture was heated at 100° C. overnight. After cooling to room temperature, the reaction mixture was filtered through diatomaceous earth and washed with 1,4-dioxane. The solvent was evaporated in vacuo. The residue was purified by column chromatography (silica gel; eluent: DCM/EtOAc up to 50% as eluent). The desired fractions were collected and the solvent was evaporated in vacuo to yield intermediate compound D31 (5.23 g, 98%)

Description 32

(4-Chloro-3-iodo-pyridin-2-yl)-hydrazine (D32)

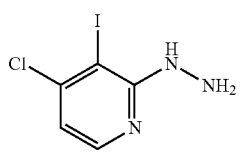

To a solution of 2,4-dichloro-3-iodopyridine [CAS 343781-36-3] (4.7 g, 17.16 mmol) in 1,4-dioxane (240 ml), was added hydrazine monohydrate (5.096 ml, 102.962 mmol). The reaction mixture was heated in a sealed tube at 80° C. for 16 h. After cooling, the solvent was concentrated in vacuo. The white solid residue thus obtained was dissolved in DCM and washed with NaHCO$_3$ (aqueous saturated solution). The organic layer was separated, dried (Na$_2$SO$_4$) and concentrated in vacuo. The residue was washed with Et$_2$O. The solid thus obtained was discarded. The mother liquours were concentrated in vacuo to yield intermediate compound D32 (2.31 g, 49%)

Description 33

N'-(4-chloro-3-iodo-pyridin-2-yl)-2-cyclopropylcetohydrazide (D33)

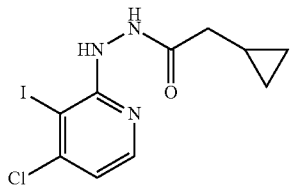

To a solution of intermediate compound D32 (3.46 g, 12.84 mmol) in dry DCM (40 ml), cooled at 0° C., were added Et$_3$N (3.553 ml, 25.68 mmol) and 2-cyclopropyl-acetyl chloride (1.827 g, 15.408 mmol). The resulting reaction mixture was stirred at room temperature overnight. To this mixture was then added NaHCO$_3$ (aqueous sat. solution). The organic layer was separated, dried (Na$_2$SO$_4$) and concentrated in vacuo to yield intermediate compound D33 (4.5 g, 99%).

Description 34

7-Chloro-3-cyclopropylmethyl-8-iodo-[1,2,4]triazolo[4,3-a]pyridine (D34)

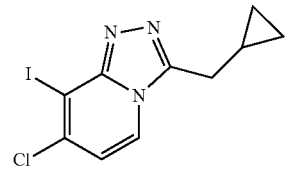 [SMILES: Clc1ccn2c(CC3CC3)nnc2c1I]

Intermediate compound D33 (13.5 g, 38.399 mmol) was heated at 160° C. for 2 h. After cooling, the brown gum was purified by column chromatography (silica gel; DCM/EtOAc from 100/0 up to 50/50 as eluent). The desired fractions were collected and concentrated in vacuo to yield intermediate compound D34 (7 g, 54%) as a yellow solid. M.P.: 246.7° C.

Description 35

7-Chloro-3-cyclopropylmethyl-8-methyl-[1,2,4]triazolo[4,3-a]pyridine (D35)

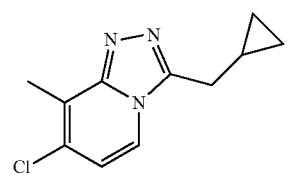

To a mixture of intermediate compound D34 (0.600 g, 1.799 mmol) in toluene (15 ml) under a nitrogen atmosphere were added methylboronic acid (0.538 g, 8.994 mmol), dicyclohexyl(2',6'-dimethoxybiphenyl-2-yl)phosphine; S-Phos (0.171 g, 0.36 mmol), Palladium(II) acetate (0.0410 g, 0.18 mmol) and K$_2$CO$_3$ (0.745 g, 5.396 mmol). The reaction mixture was heated at 100° C. overnight. After cooling, the mixture was diluted with EtOAc and washed with water. The organic layer was separated and concentrated in vacuo. The residue was purified by column chromatography (silica gel; DCM/EtOAc from 100/0 to 20/80 as eluent). The desired fractions were collected and concentrated in vacuo to yield intermediate compound D35 (0.105 g, 24%) as a cream solid Example 1

8-Chloro-7,8-dihydro-7-[1-(2-pyridinyl)-1H-indol-5-yl]-3-(2,2,2-trifluoroethyl)-1,2,4-triazolo[4,3-a]pyridine (E1)

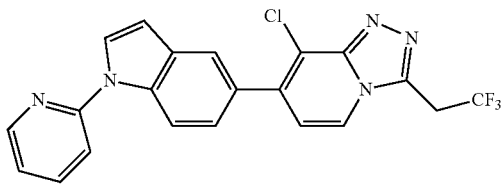 [SMILES: FC(F)(F)Cc1nnc2c(Cl)c(-c3ccc4c(ccn4-c4ccccn4)c3)ccn12]

A mixture of intermediate compound D19 (0.46 g, 0.774 mmol) and phosphorus(V) oxychloride (0.144 ml, 1.548 mmol) in CH$_3$CN (9.5 ml) was heated at 150° C. under microwave irradiation for 5 min. After cooling, NaHCO$_3$ (aqueous sat. solution) was added. The resulting mixture was extracted with EtOAc. The organic layer was separated, dried (Na$_2$SO$_4$) and concentrated in vacuo. The crude product was purified by column chromatography (silica gel; DCM/AcOEt up to 100% as eluent). The desired fractions were collected and concentrated in vacuo to yield final compound E1 (0.137 g, 41% as a white solid.

Example 2

8-Chloro-3-(cyclopropylmethyl)-7,8-dihydro-7-[1-(tetrahydro-2H-pyran-4-yl)-1H-indol-5-yl]-1,2,4-triazolo[4,3-a]pyridine (E2)

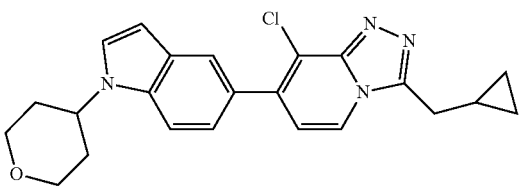 [SMILES: Clc1c(-c2ccc3c(ccn3C3CCOCC3)c2)ccn2c(CC3CC3)nnc12]

To a mixture of intermediate compound D4 (0.2 g, 0.6 mmol) in 1,4-dioxane (3 ml) under a nitrogen atmosphere were added intermediate compound D15 (0.255 g, 0.779 mmol), Pd(PPh$_3$)$_4$ (0.035 g, 0.03 mmol) and NaHCO$_3$ (0.75 ml, aqueous sat. solution). The reaction mixture was heated at 150° C. under microwave irradiation for 10 min. After cooling, the mixture was filtered through a pad of celite and washed with EtOAc. The filtrate was concentrated in vacuo and the residue was purified by column chromatography (silica gel; DCM/MeOH(NH$_3$) up to 9% as eluent). The desired fractions were collected and concentrated in vacuo to yield a residue that was subjected to a second purification by column chromatography (silica gel; DCM/AcOEt up to 80% as eluent) to yield final compound E2 (0.110 g, 45%).

Example 3

3-(Cyclopropylmethyl)-7,8-dihydro-7-[1-(tetrahydro-2H-pyran-4-yl)-1H-indol-5-yl]-8-(trifluoromethyl)-1,2,4-triazolo[4,3-a]pyridine (E3)

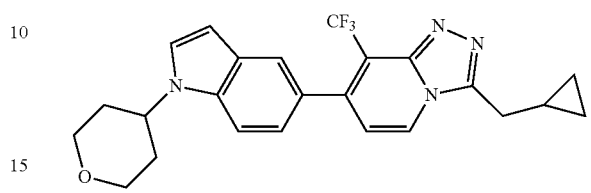

To a mixture of intermediate compound D10 (0.180 g, 0.653 mmol) in 1,4-dioxane (4 ml) under a nitrogen atmosphere were added intermediate compound D15 (0.231 g, 0.66 mmol), Pd(PPh$_3$)$_4$ (0.075 g, 0.065 mmol) and NaHCO$_3$ (1 ml, aqueous sat. solution). The reaction mixture was heated at 150° C. under microwave irradiation for 7 min. After cooling, the mixture was filtered through a pad of diatomaceous earth and washed with AcOEt. The filtrate was concentrated in vacuo and the residue was purified by column chromatography (silica gel; DCM/7M solution of NH$_3$ in MeOH up to 3% as eluent). The desired fractions were collected and concentrated in vacuo to yield final compound E3 (0.09 g, 31%).

Example 4

Trans-4-[5-(3-cyclopropylmethyl)-7,8-dihydro-8-(trifluoromethyl)-1,2,4-triazolo[4,3-a]pyridin-7-yl]-1H-indol-1-yl]-cyclohexanol (E4)

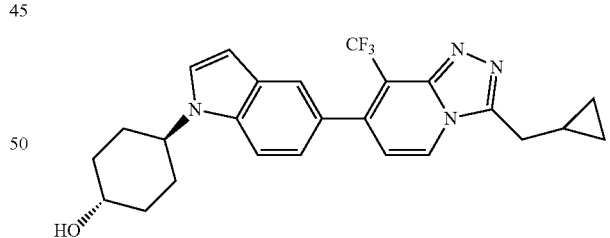

To a mixture of compound D10 (0.200 g, 0.726 mmol) in 1,4-dioxane (5 ml) under a nitrogen atmosphere were added compound trans-D14 (0.309 g, 0.907 mmol), Pd(PPh$_3$)$_4$ (0.083 g, 0.0726 mmol) and NaHCO$_3$ (1.25 ml, aqueous sat. solution). The reaction mixture was heated at 150° C. under microwave irradiation for 7 min. After cooling, the mixture was filtered through a pad of diatomaceous earth and washed with EtOAc. The filtrate was concentrated in vacuo and the residue was purified by column chromatography (silica gel; DCM/7M solution of NH$_3$ in MeOH up to 3% as eluent). The desired fractions were collected and concentrated in vacuo to yield final compound E4 (0.113 g, 40%).

Example 17

8-Chloro-3-cyclopropylmethyl-7-[1-(pyridin-3-yl)-1H-indol-5-yl]-[1,2,4]triazolo[4,3-a]pyridine (E17)

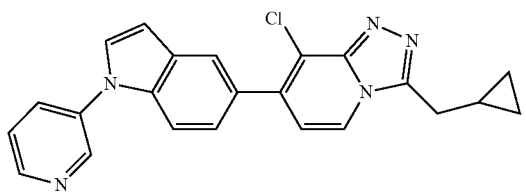 [SMILES: Clc1c(-c2ccc3c(ccn3-c3cccnc3)c2)ccn2c(CC3CC3)nnc12]

To a mixture of intermediate compound D4 (0.6 g, 1.799 mmol) in 1,4-dioxane (5 ml) under a nitrogen atmosphere were added intermediate compound D27 (0.634 g, 1.979 mmol), Pd(PPh$_3$)$_4$ (0.166 g, 0.144 mmol) and NaHCO$_3$ (2 ml, aqueous sat. solution). The reaction mixture was heated at 150° C. under microwave irradiation for 10 min. After cooling to room temperature, the reaction mixture was refilled with Pd(PPh$_3$)$_4$ (0.050 g) and irradiated at 150° C. for 10 min. After cooling, the mixture was filtered through a pad of diatomaceous earth and washed with 1,4-dioxane. The filtrate was concentrated in vacuo and the residue was purified by column chromatography (silica gel; DCM/MeOH up to 4% as eluent). The desired fractions were collected and concentrated in vacuo to yield a residue that was triturated with Et$_2$O/DIPE mixtures to give a solid that was purified by column chromatography (silica gel; DCM/EtOAc from 100/0 to 40/50 as eluent). The desired fractions were collected and concentrated in vacuo to yield final compound E17 (0.410 g, 57%)

Example 21

8-Chloro-3-cyclopropylmethyl-7-[1-(2-methylpyridin-5-yl)-1H-indol-5-yl]-[1,2,4]triazolo[4,3-a]pyridine (E21)

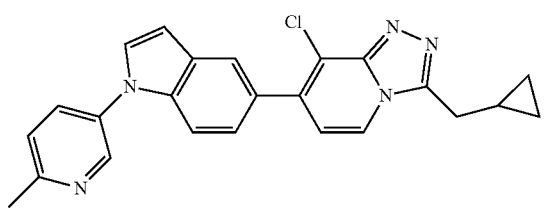 [SMILES: Cc1ccc(-n2ccc3cc(-c4ccn5c(CC6CC6)nnc5c4Cl)ccc32)cn1]

To a mixture of intermediate compound D4 (0.335 g, 1.005 mmol) in 1,4-dioxane (6 ml) under a nitrogen atmosphere were added intermediate compound D28 (0.37 g, 1.106 mmol), Pd(PPh$_3$)$_4$ (0.058 g, 0.050 mmol) and NaHCO$_3$ (2 ml, aqueous sat. solution). The reaction mixture was heated at 150° C. under microwave irradiation for 15 min. After cooling, the mixture was filtered through a pad of diatomaceous earth and washed with 1,4-dioxane. The filtrate was concentrated in vacuo and the residue was purified by column chromatography (silica gel; DCM/7M solution of NH$_3$ in MeOH up to 10% as eluent). The desired fractions were collected and concentrated in vacuo to yield a residue that was triturated with Et$_2$O to give a solid that was purified by reversed phase chromatography on C18XBridge 30×100 5 μm) to yield final compound E21 (0.046 g, 11%)

Example 22

8-Chloro-3-cyclopropylmethyl-7-(1-cyclopropylmethyl-1H-pyrrolo[2,3-b]pyridin-5-yl)-[1,2,4]triazolo[4,3-a]pyridine (E22)

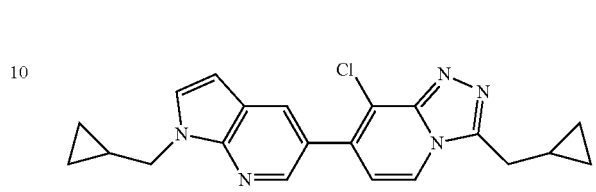

To a mixture of intermediate compound D4 (0.3 g, 0.899 mmol) in 1,4-dioxane (4 ml) under a nitrogen atmosphere were added intermediate compound D23 (0.295 g, 0.989 mmol), Pd(PPh$_3$)$_4$ (0.052 g, 0.045 mmol) and NaHCO$_3$ (1 ml, aqueous sat. solution). The reaction mixture was heated at 150° C. under microwave irradiation for 10 min. After cooling, the mixture was filtered through a pad of diatomaceous earth and washed with DCM. The filtrate was concentrated in vacuo and the residue was purified by column chromatography (silica gel; DCM/7M solution of NH$_3$ in MeOH up to 2% as eluent). The desired fractions were collected and concentrated in vacuo to yield a residue that was triturated with Et$_2$O to give final compound E22 (0.180 g, 52%) as a white solid

Example 35

8-Methyl-3-cyclopropylmethyl-7-[1-(2-methylpyridin-5-yl)-1H-indol-5-yl]-[1,2,4]triazolo[4,3-a]pyridine (E35)

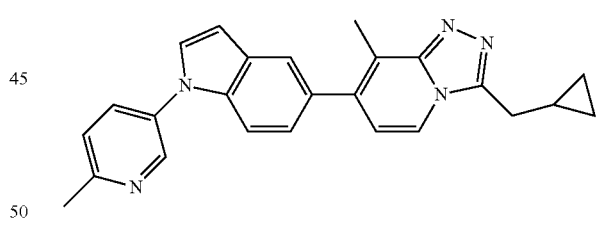

To a mixture of intermediate compound D35 (0.070 g, 0.316 mmol) in 1,4-dioxane (2 ml) under a nitrogen atmosphere were added intermediate compound D28 (0.137 g, 0.41 mmol), Pd(PPh$_3$)$_4$ (0.036 g, 0.031 mmol) and NaHCO$_3$ (1 ml, aqueous sat. solution). The reaction mixture was heated at 150° C. under microwave irradiation for 10 min. After cooling, the mixture was filtered through a pad of diatomaceous earth and washed with NaHCO$_3$ (1 ml, aqueous sat. solution). The solvent was concentrated in vacuo and the residue was purified by column chromatography (silica gel; DCM/AcOEt up to 100% as eluent). The desired fractions were collected and concentrated in vacuo to yield a residue that was triturated with DIPE to give a solid that was purified by reversed phase chromatography on C18XBridge 19×100 5 μm) to yield final compound E35 (0.025 g, 25%)

Example 42

8-Chloro-3-cyclopropylmethyl-7-[1-(3-fluoro-pyridin-4-yl)-1H-indol-5-yl]-[1,2,4]triazolo[4,3-a]pyridine (E42)

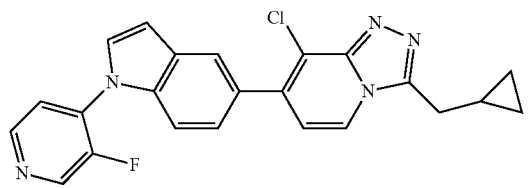 [SMILES: Fc1cnccc1-n1ccc2cc(-c3ccn4c(CC5CC5)nnc4c3Cl)ccc21]

To a mixture of intermediate compound D4 (0.3 g, 0.899 mmol) in 1,4-dioxane (4 ml) under a nitrogen atmosphere were added intermediate compound D21 (0.335 g, 0.989 mmol), Pd(PPh$_3$)$_4$ (0.083 g, 0.0726 mmol) and NaHCO$_3$ (1 ml, aqueous sat. solution). The reaction mixture was heated at 150° C. under microwave irradiation for 15 min. After cooling to room temperature, the reaction mixture was refilled with Pd(PPh$_3$)$_4$ (0.020 g) and irradiated at 150° C. for 15 min. After cooling, the mixture was filtered through a pad of diatomaceous earth and washed with DCM. The filtrate was concentrated in vacuo and the residue was purified by column chromatography (silica gel; DCM/MeOH up to 4% as eluent). The desired fractions were collected and concentrated in vacuo to yield a residue that was triturated with Et$_2$O to give final compound E42 (0.270 g, 71%) as a white solid

Example 50

8-Trifluoromethyl-3-cyclopropylmethyl-7-[4-pyrimidin-2-yl-3,4-dihydro-2H-benzo[1,4]oxazin-6-yl]-[1,2,4]triazolo[4,3-a]pyridine (E50)

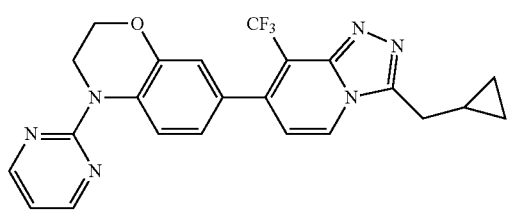 [SMILES: FC(F)(F)c1c(-c2ccc3c(c2)OCCN3c2ncccn2)ccn2c(CC3CC3)nnc12]

To a mixture of intermediate compound D10 (0.812 g, 2.946 mmol) in 1,4-dioxane (10 ml) under a nitrogen atmosphere were added intermediate compound D26 (0.335 g, 0.989 mmol), Pd(PPh$_3$)$_4$ (0.170 g, 0.147 mmol) and NaHCO$_3$ (2.5 ml, aqueous sat. solution). The reaction mixture was heated at 150° C. under microwave irradiation for 7 min. After cooling to room temperature, the reaction mixture was refilled with Pd(PPh$_3$)$_4$ (0.100 g) and irradiated at 150° C. for 7 min. After cooling to room temperature, the reaction mixture was refilled again with Pd(PPh$_3$)$_4$ (0.050 g) and irradiated at 150° C. for 7 min After cooling, the mixture was washed with NaHCO$_3$. The organic layer was separated, dried (Na$_2$SO$_4$) and concentrated in vacuo. The crude product was purified by column chromatography (silica gel; DCM/AcOEt from 100/0 up to 50/50 as eluent). The desired fractions were collected and concentrated in vacuo to yield final compound E50 (0.680 g, 51% as a white solid.

Example 51

8-Chloro-3-cyclopropylmethyl-7-[4-pyrimidin-2-yl-3,4-dihydro-2H-benzo[1,4]oxazin-6-yl]-[1,2,4]-triazolo[4,3-a]pyridine (E51)

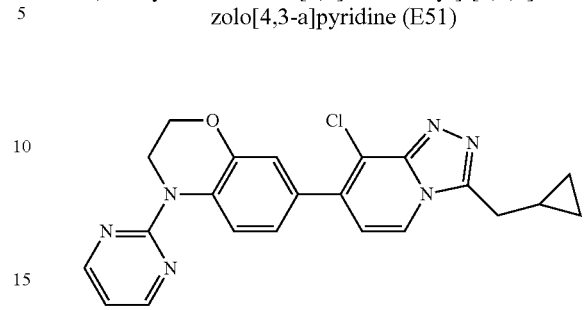

To a mixture of intermediate compound D4 (0.300 g, 0.899 mmol) in 1,4-dioxane (6 ml) under a nitrogen atmosphere were added intermediate compound D26 (0.366 g, 1.079 mmol), Pd(PPh$_3$)$_4$ (0.051 g, 0.045 mmol) and NaHCO$_3$ (1.5 ml, aqueous sat. solution). The reaction mixture was heated at 150° C. under microwave irradiation for 10 min. After cooling, the mixture was washed with NaHCO$_3$. The organic layer was separated, dried (Na$_2$SO$_4$) and concentrated in vacuo. The crude product was purified by column chromatography (silica gel; DCM/AcOEt from 100/0 up to 40/60 as eluent). The desired fractions were collected and concentrated in vacuo to give a residue that was crystallized from Et$_2$O to yield final compound E51 (0.180 g, 47% as a white solid.

Example 57

8-Trifluoromethyl-3-cyclopropylmethyl-7-[4-(6-methyl-pyridin-3-yl)-3,4-dihydro-2H-benzo[1,4]oxazin-6-yl]-[1,2,4]triazolo[4,3-a]pyridine (E57)

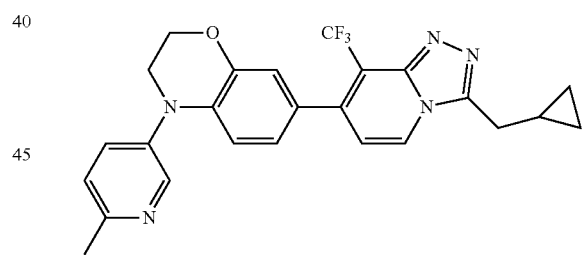

To a mixture of intermediate compound D10 (0.180 g, 0.653 mmol) in 1,4-dioxane (6 ml) under a nitrogen atmosphere were added intermediate compound D31 (0.189 g, 0.539 mmol), Pd(PPh$_3$)$_4$ (0.037 g, 0.032 mmol) and NaHCO$_3$ (1.5 ml, aqueous sat. solution). The reaction mixture was heated at 150° C. under microwave irradiation for 10 min. After cooling to room temperature, the reaction mixture was refilled with D31 (0.22 equ.) and irradiated at 150° C. for 10 min. After cooling to room temperature, the reaction mixture was refilled again with D31 (0.11 equ.) and irradiated at 150° C. for 10 min. After cooling, the mixture was filtered through a pad of diatomaceous earth and washed with NaHCO$_3$. The mixture was extracted with AcOEt. The organic layer was separated, dried (Na$_2$SO$_4$) and concentrated in vacuo. The crude product was purified by column chromatography (silica gel; DCM/7M solution of NH$_3$ in MeOH up to 2% as eluent). The desired fractions were collected and concentrated in vacuo to give a residue that was triturated with DIPE to yield final compound E57 (0.072 g, 23%) as a yellow solid.

TABLE 1a

Compounds prepared according to Formula (I).

| Co. Nr. | Exp nr. | R¹ | R² | R³ | W |
|---|---|---|---|---|---|
| 1 | E1* | —CH$_2$CF$_3$ | —Cl | 2-pyridyl | CH |
| 2 | E2* | cyclopropylmethyl | —Cl | tetrahydropyran-4-yl | CH |
| 3 | E3* | cyclopropylmethyl | —CF$_3$ | tetrahydropyran-4-yl | CH |
| 4 | E4* | cyclopropylmethyl | —CF$_3$ | trans-4-hydroxycyclohexyl | CH |
| 5 | E2 | cyclopropylmethyl | —Cl | H | N |
| 6 | E1 | —CH$_2$CF$_3$ | —Cl | pyrimidin-2-yl | CH |
| 7 | E2 | cyclopropylmethyl | —CF$_3$ | pyrimidin-2-yl | CH |
| 8 | E2 | cyclopropylmethyl | —Cl | H | C—Cl |
| 9 | E2 | cyclopropylmethyl | —Cl | 2-hydroxy-2-methylpropyl | CH |
| 10 | E2 | cyclopropylmethyl | —Cl | trans-4-hydroxycyclohexyl | CH |
| 14 | E2 | cyclopropylmethyl | —CF$_3$ | H | C—Cl |
| 15 | E2 | cyclopropylmethyl | —Cl | pyrimidin-2-yl | CH |
| 16 | E2 | cyclopropylmethyl | —Cl | 2-pyridyl | CH |
| 17 | E17* | cyclopropylmethyl | —Cl | 3-pyridyl | CH |
| 18 | E1 | ethoxyethyl | —Cl | 2-pyridyl | CH |
| 19 | E1 | ethoxyethyl | —Cl | pyrimidin-2-yl | CH |
| 20 | E2 | cyclopropylmethyl | —Cl | H | CH |
| 21 | E21* | cyclopropylmethyl | —Cl | 6-methylpyridin-3-yl | CH |
| 22 | E22* | cyclopropylmethyl | —Cl | cyclopropylmethyl | N |

TABLE 1a-continued

Compounds prepared according to Formula (I).

| Co. Nr. | Exp nr. | R¹ | R² | R³ | W |
|---|---|---|---|---|---|
| 23 | E1 | -CH₂-O-CH₂CH₃ | -Cl | H | C—Cl |
| 24 | E2 | -CH₂-cyclopropyl | -CF₃ | H | N |
| 25 | E2 | -CH₂-cyclopropyl | -CF₃ | -CH₂-cyclopropyl | N |
| 26 | E1 | -CH₂-O-CH₂CH₃ | -Cl | pyridin-3-yl | CH |
| 27 | E1 | -CH₂-O-CH₂CH₃ | -Cl | 6-methylpyridin-3-yl | CH |
| 28 | E2 | -CH₂-cyclopropyl | -Cl | H | C—F |
| 29 | E1 | -CH₂-O-CH₂CH₃ | -Cl | H | CH |
| 30 | E1 | -CH₂-O-CH₂CH₃ | -CF₃ | pyridin-3-yl | CH |
| 31 | E2 | -CH₂-cyclopropyl | -Cl | 6-methylpyridin-3-yl | C—F |
| 32 | E1 | -CH₂-O-CH₂CH₃ | -CF₃ | 6-methylpyridin-3-yl | CH |
| 33 | E1 | -CH₂-O-CH₂CH₃ | -CF₃ | H | CH |
| 34 | E2 | -CH₂-cyclopropyl | -CF₃ | pyridin-3-yl | CH |
| 35 | E35* | -CH₂-cyclopropyl | -CH₃ | 6-methylpyridin-3-yl | CH |
| 36 | E2 | -CH₂-cyclopropyl | -CF₃ | 6-methylpyridin-3-yl | CH |
| 37 | E2 | -CH₂-cyclopropyl | -cyclopropyl | 6-methylpyridin-3-yl | CH |
| 38 | E2 | -CH₂-cyclopropyl | -CF₃ | 6-methylpyridin-3-yl | C—F |
| 39 | E2 | -CH₂-cyclopropyl | -Cl | -CH₂-cyclobutyl | N |
| 40 | E2 | -CH₂-cyclopropyl | -CH₃ | -CH₂-cyclopropyl | N |
| 41 | E2 | -CH₂-cyclopropyl | -Cl | pyridin-2-yl | N |
| 42 | E42* | -CH₂-cyclopropyl | -Cl | 3-fluoropyridin-4-yl | CH |

TABLE 1a-continued

Compounds prepared according to Formula (I).

| Co. Nr. | Exp nr. | R¹ | R² | R³ | W |
|---|---|---|---|---|---|
| 43 | E2 | cyclopropylmethyl | —CF₃ | pyridin-4-yl | CH |
| 44 | E2 | cyclopropylmethyl | —Cl | pyridin-4-yl | CH |
| 45 | E2 | cyclopropylmethyl | —Cl | 4-fluorophenyl | N |
| 46 | E2 | cyclopropylmethyl | —CF₃ | 2-methylpyridin-4-yl | CH |
| 47 | E2 | cyclopropylmethyl | —Cl | 2-methylpyridin-4-yl | CH |
| 48 | E2 | cyclopropylmethyl | —Cl | pyridin-3-yl | C—F |
| 49 | E2 | ethoxymethyl | —CH₃ | 6-methylpyridin-3-yl | CH |

TABLE 1b

Compounds prepared according to Formula (I).

| Co. nr. | Exp nr. | R¹ | R² | R³ | W |
|---|---|---|---|---|---|
| 11 | E2 | cyclopropylmethyl | —Cl | pyridin-3-ylmethyl (pos 2) | CH |
| 12 | E2 | —Cl | —Cl | pyridin-3-ylmethyl (pos 1) | CH | wherein in R³, the "1" and "2" mean the binding position at the indazole ring.

TABLE 1c

Compounds prepared according to Formula (I).

| Co. nr. | Exp nr. | R¹ | R² | R³ | W |
|---|---|---|---|---|---|
| 13 | E2 | cyclopropylmethyl | —Cl | H | CH |

TABLE 1d

Compounds prepared according to Formula (I).

| Co. nr. | Exp nr. | R¹ | R2 | R3 | W | v |
|---|---|---|---|---|---|---|
| 50 | E50* | cyclopropylmethyl | —CF₃ | pyrimidin-2-yl | CH | 0 |

*means exemplified procedure according to which additional compounds were prepared.

TABLE 1d-continued

Compounds prepared according to Formula (I).

[Structure: R3-N-containing oxepine fused to pyridine-triazole core with R1, R2, W, v substituents]

| Co. nr. | Exp nr. | R¹ | R2 | R3 | W | v |
|---|---|---|---|---|---|---|
| 51 | E51* | cyclopropylmethyl | —Cl | 2-pyrimidinyl | CH | 0 |
| 52 | E2 | cyclopropylmethyl | —Cl | 2-pyridinyl | CH | 0 |
| 53 | E2 | ethoxymethyl | —Cl | 2-pyridinyl | CH | 0 |
| 54 | E2 | ethoxymethyl | —Cl | 2-pyrimidinyl | CH | 0 |
| 55 | E2 | cyclopropylmethyl | —Cl | 3-pyridinyl | CH | 0 |
| 56 | E2 | cyclopropylmethyl | —CF₃ | 3-pyridazinyl | CH | 0 |
| 57 | E2 | cyclopropylmethyl | —CF₃ | 6-methyl-3-pyridinyl | CH | 0 |
| 58 | E2 | cyclopropylmethyl | —Cl | 6-methyl-3-pyridinyl | CH | 0 |
| 59 | E2 | cyclopropylmethyl | —CF₃ | 4-pyridinyl | CH | 0 |
| 60 | E2 | cyclopropylmethyl | —CF₃ | 2-methyl-4-pyridinyl | CH | 0 |
| 61 | E2 | cyclopropylmethyl | —CF₃ | H | CH | 1 |

TABLE 1e

Compound prepared according to Formula (I).

[Structure: isoindoline-containing compound with R1, R2, R3 substituents]

| Co. nr. | Exp. nr. | R¹ | R² | R³ |
|---|---|---|---|---|
| 62 | E2 | cyclopropylmethyl | —CF₃ | —H |

C. Analytical Part

Melting Points

Values are peak values, and are obtained with experimental uncertainties that are commonly associated with this analytical method. For a number of compounds, melting points were determined in open capillary tubes either on a Mettler FP62 or on a Mettler FP81HT-FP90 apparatus. Melting points were measured with a temperature gradient of 10° C./min. Maximum temperature was 300° C. The melting point was read from a digital display.

LCMS

General Procedure for Waters MS Instruments (TOF, ZQ, SQD, Platform)

The HPLC measurement was performed using a HP 1100 from Agilent Technologies comprising a pump (quaternary or binary) with degasser, an autosampler, a column oven, a diode-array detector (DAD) and a column as specified in the respective methods below. Flow from the column was split to the MS spectrometer. The MS detector was configured with either an electrospray ionization source or an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure for Agilent MS Instrument (MSD)

The HPLC measurement was performed using a HP 1100 from Agilent Technologies comprising a binary pump with degasser, an autosampler, a column oven, a diode-array detector (DAD) and a column as specified in the respective methods below. Flow from the column was split to a MS spectrometer. The MS detector was configured with an ESCI dual ionization source (electrospray combined with atmospheric pressure chemical ionization). Nitrogen was used as the nebulizer gas. The source temperature was maintained at 100° C. Data acquisition was performed with Chemsation-Agilent Data Browser software.

General Procedure for Waters MS Instruments (Acquity-SQD)

The HPLC measurement was performed using an Acquity system from Waters comprising a sampler organizer, a binary pump with degasser, a four column's oven, a diode-array detector (DAD) and a column as specified in the respective methods below. Column flow is used without split to the MS detector. The MS detector is configured with an ESCI dual ionization source (electrospray combined with atmospheric pressure chemical ionization). Nitrogen was used as the nebulizer gas. The source temperature was maintained at 140° C. Data acquisition was performed with MassLynx-Openlynx software.

General Procedure for HP 1100-MS Instruments (TOF, SQD or MSD)

The HPLC measurement was performed using an HP 1100 (Agilent Technologies) system comprising a pump (quaternary or binary) with degasser, an autosampler, a column oven, a diode-array detector (DAD) and a column as specified in the respective methods. The MS detector was configured with either an electrospray ionization source or an ESCI dual ionization source (electrospray combined with atmospheric pressure chemical ionization). Nitrogen was used as the nebulizer gas. The source temperature was maintained either at 140° C. or 100° C. Data acquisition was performed either with MassLynx-Openlynx software or Chemsation-Agilent Data Browser software.

MS Procedure for LC Method 3&5:

Low-resolution mass spectra (single quadrupole, SQD detector) were acquired only in positive ionization mode or in positive/negative modes by scanning from 100 to 1000 umas. The capillary needle voltage was 3 kV. For positive ionization mode the cone voltage was 20V, 25V or 20V/50V. For negative ionization mode the cone voltage was 30V.

Method 1

In addition to the general procedure: Reversed phase HPLC was carried out on a BEH-C18 column (1.7 µm, 2.1×50 mm) from Waters, with a flow rate of 0.8 ml/min, at 60° C. without split to the MS detector. The gradient conditions used are: 95% A (0.5 g/l ammonium acetate solution+5% $CH_3CN$), 5% B (mixture of $CH_3CN$/MeOH, 1/1), to 20% A, 80% B in 4.9 min, to 100% B in 5.3 min, kept till 5.8 min and equilibrated to initial conditions at 6.0 min until 7.0 min. Injection volume 0.5 µl. Low-resolution mass spectra (quadrupole, SQD) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

Method 2

In addition to the general procedure: Reversed phase HPLC was carried out on a Sunfire-C18 column (2.5 µm, 2.1×30 mm) from Waters, with a flow rate of 1.0 ml/min, at 60° C. The gradient conditions used are: 95% A (0.5 g/l ammonium acetate solution+5% of $CH_3CN$), 2.5% B ($CH_3CN$), 2.5% C (MeOH) to 50% B, 50% C in 6.5 min, kept till 7.0 min and equilibrated to initial conditions at 7.3 min until 9.0 min. Injection volume 2 µl. High-resolution mass spectra (Time of Flight, TOF) were acquired by scanning from 100 to 750 in 0.5 seconds using a dwell time of 0.3 seconds. The capillary needle voltage was 2.5 kV for positive ionization mode and 2.9 kV for negative ionization mode. The cone voltage was 20 V for both positive and negative ionization modes. Leucine-Enkephaline was the standard substance used for the lock mass calibration.

Method 3

In addition to the general procedure: Reversed phase HPLC was carried out on a BEH-C18 column (1.7 µm, 2.1×50 mm) from Waters, with a flow rate of 1.0 ml/min, at 50° C. The gradient conditions used are: 95% A (0.5 g/l ammonium acetate solution+5% $CH_3CN$), 5% B ($CH_3CN$), to 40% A, 60% B, then to 5% A, 95% B and equilibrated to initial conditions up to 7 and 5 min run; 0.5 or 2 µl injection volume.

Method 4

In addition to the general procedure: Reversed phase HPLC was carried out on an Eclipse Plus-C18 column (3.5 µm, 2.1×30 mm) from Agilent, with a flow rate of 1.0 ml/min, at 60° C. without split to the MS detector. The gradient conditions used are: 95% A (0.5 g/l ammonium acetate solution+5% $CH_3CN$), 5% B (mixture of $CH_3CN$/MeOH, 1/1), to 100% B at 6.5 min, kept till 7.0 min and equilibrated to initial conditions at 7.3 min until 9.0 min. Injection volume 2 µl. Low-resolution mass spectra (single quadrupole, SQD detector) were acquired by scanning from 100 to 1000 in 0.1 seconds using an inter-channel delay of 0.08 second. The capillary needle voltage was 3 kV. The cone voltage was 20 V for positive ionization mode and 30 V for negative ionization mode.

Method 5

In addition to the general procedure: Reversed phase HPLC was carried out on a BEH-C18 column (1.7 µm, 2.1×50 mm) from Waters, with a flow rate of 0.8 ml/min, at 50° C. The gradient conditions used are: 95% A (formic acid solution, 0.1%), 5% B (MeOH), to 40% A, 60% B, then to 5% A, 95% B and equilibrated to initial conditions up to 7.0 min run; 0.5 injection volume.

TABLE 2

Physico-chemical data for some compounds (nd = not determined).

| Co. No. | mp (° C.) | $R_t$ | [MH$^+$] | LCMS Method |
|---|---|---|---|---|
| 1 | >300 | 3.32 | 428 | 1 |
| 2 | >300 | 3.32 | 407 | 2 |
| 3 | 193.1 | 3.48 | 441 | 2 |
| 4 | 206.9 | 2.98 | 455 | 1 |
| 5 | >300 | 2.03 | 324 | 1 |
| 6 | n.d. | 3.43 | 429 | 1 |
| 7 | n.d. | 3.3 | 435 | 3 |
| 8 | 233.5 | 3.68 | 357 | 2 |
| 9 | n.d. | 2.82 | 395 | 1 |
| 10 | >300 | 2.95 | 421 | 1 |
| 11 | n.d. | 2.2 | 415 | 1 |
| 12 | n.d. | 2.38 | 415 | 1 |
| 13 | >300 | 2.39 | 323 | 1 |
| 14 | >300 | 3.25 | 391 | 4 |
| 15 | >300 | 3.11 | 401 | 3 |
| 16 | 197.1 | 3.05 | 400 | 3 |
| 17 | n.d. | 1.81 | 400 | 3 |

TABLE 2-continued

Physico-chemical data for some compounds (nd = not determined).

| Co. No. | mp (° C.) | $R_t$ | [MH$^+$] | LCMS Method |
|---|---|---|---|---|
| 18 | 235 | 2.96 | 404 | 3 |
| 19 | n.d. | 3.05 | 405 | 3 |
| 20 | >300 | 2.18 | 323 | 3 |
| 21 | 137.2 | 2.80 | 414 | 3 |
| 22 | 184.7 | 2.84 | 378 | 3 |
| 23 | n.d. | 2.37 | 361 | 3 |
| 24 | >300 | 1.85 | 358 | 3 |
| 25 | >300 | 3.02 | 412 | 3 |
| 26 | 233.2 | 4.20 | 404 | 5 |
| 27 | 188.9 | 2.70 | 418 | 3 |
| 28 | 235.5 | 3.54 | 341 | 2 |
| 29 | 176.4 | 2.01 | 327 | 3 |
| 30 | 182.4 | 2.60 | 438 | 3 |
| 31 | 243.8 | 2.86 | 432 | 3 |
| 32 | 163.1 | 2.87 | 452 | 3 |
| 33 | 200.1 | 2.22 | 361 | 3 |
| 34 | 144.3 | 2.68 | 434 | 3 |
| 35 | 263.3 | 2.83 | 394 | 3 |
| 36 | 204 | 2.90 | 448 | 3 |
| 37 | >300 | 3.21 | 420 | 3 |
| 38 | >300 | 2.97 | 466 | 3 |
| 39 | >300 | 2.29 | 392 | 3 |
| 40 | >300 | 2.04 | 358 | 3 |
| 41 | >300 | 1.59 | 401 | 3 |
| 42 | >300 | 1.93 | 418 | 3 |
| 43 | >300 | 1.88 | 434 | 3 |
| 44 | >300 | 1.76 | 400 | 3 |
| 45 | >300 | 3.16 | 418 | 3 |
| 46 | >300 | 2.01 | 448 | 3 |
| 47 | >300 | 1.91 | 414 | 3 |
| 48 | 195.6 | 1.88 | 418 | 3 |
| 49 | 108.5 | 1.94 | 398 | 3 |
| 50 | >300 | 2.86 | 453 | 3 |
| 51 | 194.9 | 2.62 | 419 | 3 |
| 52 | 194.9 | 2.82 | 418 | 3 |
| 53 | 138.4 | 2.70 | 422 | 3 |
| 54 | 278.5 | 2.59 | 423 | 3 |
| 55 | 251.2 | 3.75 | 418 | 2 |
| 56 | 247.1 | 2.52 | 452 | 3 |
| 57 | >300 | 2.76 | 466 | 3 |
| 58 | 205.5 | 2.61 | 432 | 3 |
| 59 | >300 | 2.24 | 452 | 3 |
| 60 | 248.9 | 2.31 | 466 | 3 |
| 61 | 154.9 | 1.21 | 389 | 3 |
| 62 | >300 | 1.57 | 359 | 4 |

Nuclear Magnetic Resonance (NMR)

For a number of compounds, $^1$H NMR spectra were recorded either on a Bruker DPX-400 or on a Bruker AV-500 spectrometer with standard pulse sequences, operating at 360 MHz, 400 MHz and 500 MHz, respectively. Chemical shifts (δ) are reported in parts per million (ppm) downfield from tetramethylsilane (TMS), which was used as internal standard.

Co. No. 1: $^1$H NMR (500 MHz, CDCl$_3$) δ ppm 4.11 (q, J=9.8 Hz, 2H), 6.81 (d, J=3.5 Hz, 1H), 7.11 (d, J=6.9 Hz, 1H), 7.23 (ddd, J=7.5, 4.9, 0.9 Hz, 1H), 7.47 (dd, J=8.7, 1.7 Hz, 1H), 7.53 (d, J=8.1 Hz, 1H), 7.80 (d, J=3.5 Hz, 1H), 7.85 (d, J=1.4 Hz, 1H), 7.86-7.90 (m, 1H), 8.00 (d, J=6.9 Hz, 1H), 8.38 (d, J=8.7 Hz, 1H), 8.59-8.63 (m, 1H).

Co. No. 2: $^1$H NMR (500 MHz, CDCl$_3$) δ ppm 0.32-0.42 (m, 2H), 0.59-0.70 (m, 2H), 1.18-1.29 (m, 1H), 2.06-2.11 (m, 2H), 2.11-2.21 (m, 2H), 3.13 (d, J=6.9 Hz, 2H), 3.65 (td, J=11.8, 2.0 Hz, 2H), 4.19 (dd, J=11.3, 4.0 Hz, 2H), 4.53 (tt, J=11.6, 4.3 Hz, 1H), 6.64 (d, J=3.2 Hz, 1H), 6.99 (d, J=6.9 Hz, 1H), 7.32 (d, J=3.2 Hz, 1H), 7.41 (dd, J=8.4, 1.4 Hz, 1H), 7.52 (d, J=8.4 Hz, 1H), 7.82 (d, J=1.2 Hz, 1H), 7.95 (d, J=7.2 Hz, 1H).

Co. No. 3: $^1$H NMR (400 MHz, CDCl$_3$) δ ppm 0.32-0.44 (m, 2H), 0.59-0.72 (m, 2H), 1.17-1.29 (m, 1H), 2.04-2.22 (m, 4H), 3.15 (d, J=6.5 Hz, 2H), 3.65 (td, J=11.8, 2.8 Hz, 2H), 4.19 (dd, J=10.9, 3.7 Hz, 2H), 4.46-4.57 (m, 1H), 6.61 (d, J=3.2 Hz, 1H), 6.89 (d, J=6.9 Hz, 1H), 7.21 (dd, J=8.3, 1.2 Hz, 1H), 7.32 (d, J=3.5 Hz, 1H), 7.47 (d, J=8.6 Hz, 1H), 7.64 (d, J=1.4 Hz, 1H), 8.06 (d, J=7.2 Hz, 1H).

Co. No. 4: $^1$H NMR (400 MHz, CDCl$_3$) δ ppm 0.33-0.42 (m, 2H), 0.61-0.70 (m, 2H), 1.18-1.29 (m, 1H), 1.52-1.68 (m, 3H), 1.81-1.96 (m, 2H), 2.22 (br d, J=10.4 Hz, 4H), 3.15 (d, J=6.7 Hz, 2H), 3.75-3.88 (m, 1H), 4.24-4.38 (m, 1H), 6.58 (d, J=3.2 Hz, 1H), 6.89 (d, J=7.2 Hz, 1H), 7.20 (dd, J=8.4, 1.0 Hz, 1H), 7.28 (d, J=3.2 Hz, 1H), 7.44 (d, J=8.6 Hz, 1H), 7.62 (d, J=1.2 Hz, 1H), 8.05 (d, J=7.2 Hz, 1H).

Co. No. 17: $^1$H NMR (500 MHz, CDCl$_3$) δ ppm 0.32-0.43 (m, 2H), 0.59-0.71 (m, 2H), 1.15-1.34 (m, 1H), 3.14 (d, J=6.9 Hz, 2H), 6.84 (d, J=3.2 Hz, 1H), 7.00 (d, J=7.2 Hz, 1H), 7.33-7.48 (m, 2H), 7.52 (dd, J=8.1, 4.9 Hz, 1H), 7.63 (d, J=8.7 Hz, 1H), 7.83-7.93 (m, 2H), 7.97 (d, J=7.2 Hz, 1H), 8.67 (dd, J=4.8, 1.3 Hz, 1H), 8.88 (d, J=2.6 Hz, 1H).

Co. No. 21: $^1$H NMR (400 MHz, CDCl$_3$) δ ppm 0.32-0.44 (m, 2H), 0.58-0.72 (m, 2H), 1.17-1.31 (m, 1H), 2.68 (s, 3H), 3.14 (d, J=6.7 Hz, 2H), 6.81 (dd, J=3.2, 0.7 Hz, 1H), 6.99 (d, J=6.9 Hz, 1H), 7.36 (d, J=8.3 Hz, 1H), 7.39 (d, J=3.2 Hz, 1H), 7.41 (dd, J=8.6, 1.6 Hz, 1H), 7.58 (d, J=8.6 Hz, 1H), 7.76 (dd, J=8.2, 2.7 Hz, 1H), 7.88 (d, J=1.2 Hz, 1H), 7.96 (d, J=6.9 Hz, 1H), 8.73 (d, J=2.5 Hz, 1H).

Co. No. 22: $^1$H NMR (500 MHz, CDCl$_3$) δ ppm 0.26-0.42 (m, 2H), 0.42-0.55 (m, 2H), 0.55-0.71 (m, 4H), 1.19-1.29 (m, 1H), 1.30-1.40 (m, 1H), 3.14 (d, J=6.6 Hz, 2H), 4.22 (d, J=6.9 Hz, 2H), 6.57 (d, J=3.8 Hz, 1H), 6.96 (d, J=7.2 Hz, 1H), 7.46 (d, J=3.5 Hz, 1H), 7.99 (d, J=6.9 Hz, 1H), 8.12 (d, J=2.0 Hz, 1H), 8.47 (d, J=2.0 Hz, 1H).

Co. No. 35: $^1$H NMR (400 MHz, CDCl$_3$) δ ppm 0.29-0.43 (m, 2H), 0.54-0.70 (m, 2H), 1.19-1.31 (m, 1H), 2.67 (s, 3H), 2.68 (s, 3H), 3.12 (d, J=6.7 Hz, 2H), 6.79 (d, J=3.2 Hz, 1H), 6.90 (d, J=7.2 Hz, 1H), 7.25 (dd, J=8.6, 1.6 Hz, 1H), 7.36 (d, J=8.3 Hz, 1H), 7.38 (d, J=3.2 Hz, 1H), 7.56 (d, J=8.6 Hz, 1H), 7.69 (d, J=1.4 Hz, 1H), 7.77 (dd, J=8.2, 2.7 Hz, 1H), 7.88 (d, J=6.9 Hz, 1H), 8.74 (d, J=2.5 Hz, 1H).

Co. No. 45: $^1$H NMR (500 MHz, CDCl$_3$) δ ppm 0.31-0.44 (m, 2H), 0.57-0.72 (m, 2H), 1.16-1.32 (m, 1H), 3.14 (d, J=6.9 Hz, 2H), 6.87 (d, J=3.5 Hz, 1H), 6.99 (d, J=6.9 Hz, 1H), 7.41-7.50 (m, 2H), 7.52-7.65 (m, 2H), 7.88 (d, J=1.2 Hz, 1H), 7.98 (d, J=6.9 Hz, 1H), 8.59 (d, J=4.9 Hz, 1H), 8.73 (d, J=2.6 Hz, 1H).

Co. No. 50: $^1$H NMR (500 MHz, CDCl$_3$) δ ppm 0.27-0.43 (m, 2H), 0.57-0.76 (m, 2H), 1.11-1.31 (m, 1H), 3.14 (d, J=6.6 Hz, 2H), 4.24-4.49 (m, 4H), 6.79 (t, J=4.8 Hz, 1H), 6.84 (d, J=6.9 Hz, 1H), 6.92 (dd, J=8.7, 2.0 Hz, 1H), 6.95 (d, J=2.0 Hz, 1H), 8.07 (d, J=7.2 Hz, 1H), 8.21 (d, J=8.7 Hz, 1H), 8.50 (d, J=4.6 Hz, 2H).

Co. No. 51: $^1$H NMR (500 MHz, CDCl$_3$) δ ppm 0.26-0.44 (m, 2H), 0.56-0.70 (m, 2H), 1.12-1.31 (m, 1H), 3.12 (d, J=6.6 Hz, 2H), 4.28-4.46 (m, 4H), 6.80 (t, J=4.8 Hz, 1H), 6.92 (d, J=7.2 Hz, 1H), 7.12 (dd, J=8.4, 2.0 Hz, 1H), 7.17 (d, J=2.0 Hz, 1H), 7.94 (d, J=7.2 Hz, 1H), 8.21 (d, J=8.4 Hz, 1H), 8.50 (d, J=4.6 Hz, 2H).

Co. No. 57: $^1$H NMR (400 MHz, CDCl$_3$) δ ppm 0.29-0.46 (m, 2H), 0.54-0.71 (m, 2H), 1.15-1.24 (m, 1H), 2.58 (s, 3H), 3.12 (d, J=6.7 Hz, 2H), 3.77 (t, J=4.4 Hz, 2H), 4.39 (dd, J=4.6, 4.2 Hz, 2H), 6.74 (dd, J=8.3, 1.8 Hz, 1H), 6.81 (d, J=8.6 Hz, 2H), 6.92 (d, J=1.8 Hz, 1H), 7.20 (d, J=8.3 Hz, 1H), 7.53 (dd, J=8.3, 2.5 Hz, 1H), 8.04 (d, J=7.2 Hz, 1H), 8.48 (d, J=2.5 Hz, 1H).

D. Pharmacological Examples

The compounds provided in the present invention are positive allosteric modulators of mGluR2. These compounds appear to potentiate glutamate responses by binding to an allosteric site other than the glutamate binding site. The response of mGluR2 to a concentration of glutamate is increased when compounds of Formula (I) are present. Compounds of Formula (I) are expected to have their effect substantially at mGluR2 by virtue of their ability to enhance the function of the receptor. The behaviour of positive allosteric modulators tested at mGluR2 using the [$^{35}$S]GTPγS binding assay method described below and which is suitable for the identification of such compounds, and more particularly the compounds according to Formula (I), are shown in Table 3.

[$^{35}$S]GTPγS Binding Assay

The [$^{35}$S]GTPγS binding assay is a functional membrane-based assay used to study G-protein coupled receptor (GPCR) function whereby incorporation of a non-hydrolysable form of GTP, [$^{35}$S]GTPγS (guanosine 5'-triphosphate, labelled with gamma-emitting $^{35}$S), is measured. The G-protein α subunit catalyzes the exchange of guanosine 5'-diphosphate (GDP) by guanosine triphosphate (GTP) and on activation of the GPCR by an agonist, [$^{35}$S]GTPγS, becomes incorporated and cannot be cleaved to continue the exchange cycle (Harper (1998) Current Protocols in Pharmacology 2.6.1-10, John Wiley & Sons, Inc.). The amount of radioactive [$^{35}$S]GTPγS incorporation is a direct measure of the activity of the G-protein and hence the activity of the agonist can be determined. mGluR2 receptors are shown to be preferentially coupled to Gαi-protein, a preferential coupling for this method, and hence it is widely used to study receptor activation of mGluR2 receptors both in recombinant cell lines and in tissues. Here we describe the use of the [$^{35}$S]GTPγS binding assay using membranes from cells transfected with the human mGluR2 receptor and adapted from Schaffhauser et al. ((2003) Molecular Pharmacology 4:798-810) for the detection of the positive allosteric modulation (PAM) properties of the compounds of this invention.

Membrane Preparation

CHO-cells were cultured to pre-confluence and stimulated with 5 mM butyrate for 24 h, prior to washing in PBS, and then collected by scraping in homogenisation buffer (50 mM Tris-HCl buffer, pH 7.4, 4° C.). Cell lysates were homogenized briefly using an ultra-turrax homogenizer. The homogenate was centrifuged at 16,000 RPM (Sorvall RC-5C plus rotor SS-34) for 10 minutes and the supernatant discarded. The pellet was resuspended in 5 mM Tris-HCl, pH 7.4 and centrifuged again (18,000 RPM, 20 min, 4° C.). The final pellet was resuspended in 50 mM Tris-HCl, pH 7.4 and stored at −80° C. in appropriate aliquots before use. Protein concentration was determined by the Bradford method (Bio-Rad, USA) with bovine serum albumin as standard.

[$^{35}$S]GTPγS Binding Assay

Measurement of mGluR2 positive allosteric modulatory activity of test compounds was performed as follows. Test compounds and glutamate were diluted in assay buffer containing 10 mM HEPES acid, 10 mM HEPES salt, pH 7.4, 100 mM NaCl, 3 mM MgCl$_2$ and 10 μM GDP. Human mGlu2 receptor-containing membranes were thawed on ice and diluted in assay buffer supplemented with 14 μg/ml saponin. Membranes were pre-incubated with compound alone or together with a predefined ($\sim$EC$_{20}$) concentration of glutamate (PAM assay) for 30 min at 30° C. After addition of [$^{35}$S]GTPγS (f.c. 0.1 nM) microplates were shaken briefly and further incubated to allow [$^{35}$S]GTPγS incorporation on activation (30 minutes, 30° C.). Final assay mixtures contained 7 μg of membrane protein in 10 mM HEPES acid, 10 mM HEPES salt, pH 7.4, 100 mM NaCl, 3 mM MgCl$_2$, 10 μM GDP and 10 μg/ml saponin. Total reaction volume was 200 μl. Reactions were terminated by rapid filtration through Unifilter-96 GF/B filter plates (Packard, Meriden, Conn.) using a 96-well Packard filtermate harvester. Filters were washed 6 times with ice-cold 10 mM NaH$_2$PO$_4$/10 mM Na$_2$HPO$_4$, pH 7.4. Filters were then air-dried, and 40 μl of liquid scintillation cocktail (Microscint-O) was added to each well. Membrane-bound radioactivity was counted in a Microplate Scintillation and Luminescence Counter from Packard.

Data Analysis

The concentration-response curves of representative compounds of the present invention—obtained in the presence of EC$_{20}$ of mGluR2 agonist glutamate to determine positive allosteric modulation (PAM)—were generated using the Lexis software interface (developed at J&J). Data were calculated as % of the control glutamate response, defined as the maximal response that is generated upon addition of glutamate alone. Sigmoid concentration-response curves plotting these percentages versus the log concentration of the test compound were analyzed using non-linear regression analysis. The concentration producing half-maximal effect is then calculated as EC$_{50}$. The pEC$_{50}$ values below are calculated as the −log EC$_{50}$ (wherein EC$_{50}$ is expressed in mol/L). The results of this test are shown in table 3 below.

Motor Activity (Video Tracking)

Apparatus and General Procedure

On the day of experiments, the mice were brought into the procedural room. They were housed individually and allowed to acclimate for at least a half hour prior to testing. Although the studies were conducted during the light cycle (from 8:00 to 16:00 h), the procedure room was only sparsely lit (3 to 30 LUX) to provide better contrast for the video tracking. Local lighting was used for the injection procedures. During each trial, an individual mouse was placed in an open field arena (grey PVC cylinder with a height of 40 cm and a diameter of 22.5 cm). Each arena was placed on an infrared LED (8×8 LEDs)-lit box (white PVC squared box; 40×40 cm$^2$; height 12.5 cm). Each mouse was placed in the center of the arena and allowed to explore freely for 30 min. After each trial, the arena was cleaned with a wet and subsequently with a dry cleaning cloth. An infrared sensitive tube camera and a white light source (in arena: 4-7 LUX) were mounted to the ceiling above the observation chamber to record and input activity to a computer. Animal behavior was recorded and analyzed using the Noldus Ethovision XT Video Tracking System (Version 3.1; Noldus, Wageningen, The Netherlands). The total distance traveled (cm) was calculated. Data were then exported to data management systems for further analysis and reporting.

Phencyclidine (PCP)-Induced Hyperlocomotion in Mice

Test compound or solvent was administered at a pre-defined time before measurement (standard: 30 min) to male NMRI mice that were challenged with phencyclidine (PCP; 5 mg/kg, s.c.) 30 min before measurement. Activity was measured for a period of 30 min. Criterion for drug-induced inhibition of hyperlocomotion: total distance<5500 counts (3.9% false positives in controls; n=154). The results are shown in table 4 below.

Conditioned Avoidance Response (CAR) Test

Apparatus

The apparatus consisted of an inner box surrounded by an outer box. The inner box was composed of four walls of transparent, synthetic material (length×width×height: 30×30×30 cm), an open top, and a grid floor made of 15 pairs of iron bars (2 mm diameter; 6 mm inter-bar distance). Odd and even bars were connected with a source of alternative current (1.0 mA; Coulbourn Instruments Solid State Shocker/Distributor), which could be interrupted by a switch. The outer box was composed of the same material (length×width× height: 40×40×36 cm), also with an open top, with a distance of 5 cm between the inner and outer box on all sides. To decrease the amount of environmental stimuli, three walls of the outer box were made non-transparent. The front wall was left transparent to allow the necessary inspection of the animal during the test. The upper edge of the outer and inner box served as a target for the rats on which to jump with fore- and hind-paws, respectively.

Avoidance Conditioning and Selection of Animals

From their arrival in the laboratory on the experimental day, male Wiga Wistar rats (230±30 g) were housed in individual cages provided with bedding material. The rats received 5 training sessions at 15-min time intervals over a 1-h period during which, the rats were conditioned to avoid an electric shock: the rat was placed on the non-electrified grid floor and the grid was electrified 10 s later for not more than 30 s, if the rat did not jump out of the box. Only rats that showed correct avoidance responses in all the last 3 training sessions were included for further experiments, and received the test compound or solvent immediately after the last training session.

Experimental Sessions

The rats were tested 3 times, i.e. at 60, 90 and 120 min after the injection of test compound or solvent. Latency to avoidance was recorded. The median avoidance response obtained over the three experimental sessions for each rat were used for further calculations. A median avoidance latency >8 s was selected as an all-or-none criterion for drug-induced inhibition of avoidance (occurring in only 1.5% of solvent-pre-treated control rats; n=66). The results of this test are shown in table 4 below.

Sleep Wake Electroencephalography (SW-EEG) in Rats

SW-EEG analyses are a highly sensitive read-out of a compound's central functional activity that may provide additional insight in the potential therapeutic application (i.e. via drug classification fingerprinting). Systemic administration of an mGlu2/3 receptor agonist and PAM has been shown to selectively suppress rapid eye movement (REM) sleep in rat. Internal efforts have confirmed that this effect is mGlu2 receptor-mediated, i.e. is absent in mGlu2 KO mice. Sleep abnormalities are often associated with CNS disorders; as such, the potential use of mGlu2 modulators could also have benefit in the treatment of CNS disorders in which (REM) sleep aberrations are manifested. More specifically, the combination of a persistent reduction in REM occurrence and an increase in REM latency is one of the key features of the typical SW architecture fingerprint of most clinically active antidepressants.

We investigated the effects of oral administration of compounds according to the invention on SW organization in rats. The mGlu2/3 receptor agonist LY404039 was also evaluated to allow comparison.

Compound 17 was found to dose-dependently decrease REM sleep (lowest active dose was 10 mg/kg, p.o.); compound LY404039 was found to affect REM sleep (3 mg/kg, p.o.) qualitatively in a comparable way.

TABLE 3

Pharmacological data for compounds according to the invention in the [$^{35}$S]GTPγS binding assay.

| Co. No. | GTPγS-hR2 PAM pEC$_{50}$ |
|---|---|
| 1 | 7.36 |
| 2 | 7.19 |
| 3 | 7.55 |
| 4 | 7.95 |
| 5 | n.c. |
| 6 | 7.47 |
| 7 | 7.94 |
| 8 | 7.60 |
| 9 | 6.80 |
| 10 | 7.28 |
| 11 | 6.06 |
| 12 | 6.45 |
| 13 | 6.09 |
| 14 | 7.96 |
| 15 | 7.27 |
| 16 | 7.17 |
| 17 | 7.10 |
| 18 | 6.54 |
| 19 | 6.90 |
| 20 | 6.60 |
| 21 | 7.63 |
| 22 | 6.49 |
| 23 | 7.02 |
| 24 | 5.85 |
| 25 | 6.74 |
| 26 | 6.74 |
| 27 | 7.25 |
| 28 | 6.93 |
| 29 | 5.90 |
| 30 | 7.47 |
| 31 | 7.64 |
| 32 | 7.76 |
| 33 | 6.76 |
| 34 | 7.52 |
| 35 | 7.15 |
| 36 | 8.03 |
| 37 | 7.40 |
| 38 | 7.77 |
| 39 | 6.90 |
| 40 | 6.39 |
| 41 | 6.22 |
| 42 | 7.54 |
| 43 | 7.78 |
| 44 | 7.18 |
| 45 | 6.82 |
| 46 | 8.09 |
| 47 | 7.40 |
| 48 | 7.33 |
| 49 | 6.76 |
| 50 | 6.89 |
| 51 | 6.60 |
| 52 | 6.86 |
| 53 | 6.48 |
| 54 | 6.13 |
| 55 | 7.18 |
| 56 | 7.85 |
| 57 | 8.43 |
| 58 | 7.92 |
| 59 | 7.50 |
| 60 | 7.50 |
| 61 | n.c. | n.c. means not calculated

EC$_{50}$ values were not calculated in cases where the concentration-response curve did not reach a plateau level. By definition, the EC$_{50}$ value of a compound is the concentration needed to reach 50% of the maximal response.

All compounds were tested in presence of mGluR2 agonist, glutamate at a predetermined EC$_{20}$ concentration, to determine positive allosteric modulation (GTPγS-PAM). pEC$_{50}$ values were calculated from a concentration-response experiment of at least 10 concentrations. If more experiments were performed, the average pEC$_{50}$ value is reported and error deviation was <0.5.

TABLE 4

Pharmacological data for compounds according to the invention in the PCP-induced hyperlocomotion test in mice and CAR test in rats.

| Co. No. | ED$_{50}$ (mg/kg) | |
|---|---|---|
| | Mice PCP-Inh. | Rats CAR-Inh. |
| 4 | 13.2 | 20 |
| 17 | 10.7 | ≥40* 20* |
| 31 | 7.1 | n.t. |

Inh. means inhibition;
*means the compound was administered orally;
n.t. means not tested.
ED$_{50}$ is the dose (mg/kg body weight) at which 50% of the tested animals show the effect.

Compounds 4, 17 and 31 inhibited PCP-induced hyperlocomotion in mice and compounds 4 and 17 also inhibited the conditioned avoidance response in rats, attesting to their possible antipsychotic potential.

E. Composition Examples

"Active ingredient" as used throughout these examples relates to a final compound of formula (I), the pharmaceutically acceptable salts thereof, the solvates and the stereochemically isomeric forms thereof.
Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced with the same amount of any of the compounds according to the present invention, in particular by the same amount of any of the exemplified compounds.

2. Suspension
An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 ml.

3. Injectable
A parenteral composition is prepared by stirring 1.5% by weight of active ingredient of the invention in 10% by volume propylene glycol in water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.
Reasonable variations are not to be regarded as a departure from the scope of the invention. It will be obvious that the thus described invention may be varied in many ways by those skilled in the art.

The invention claimed is:
1. A compound having the formula (I)

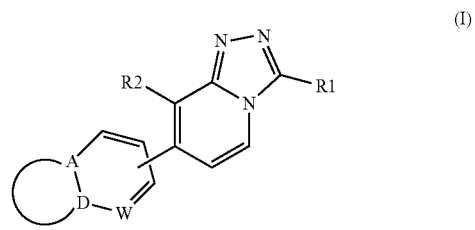

or a stereochemically isomeric form thereof, wherein
the bond drawn into the ring indicates that the bond may be attached to any carbon ring atom;
$R^1$ is selected from the group consisting of hydrogen; $C_{1-6}$alkyl; $(C_{1-3}$alkyloxy$)$-$C_{1-3}$alkyl; $[(C_{1-3}$alkyloxy$)$-$C_{1-3}$alkyloxy$]C_{1-3}$alkyl; $C_{1-3}$alkyl substituted with one or more independently selected halo substituents; unsubstituted benzyl; benzyl substituted with one or more substituents each independently selected from the group consisting of halo, $C_{1-3}$alkyl, $(C_{1-3}$alkyloxy$)C_{1-3}$alkyl, $C_{1-3}$alkyloxy, hydroxy$C_{1-3}$alkyl, cyano, hydroxyl, amino, (C=O)R', (C=O)OR', (C=O)NR'R", mono- or di-$(C_{1-3}$alkyl)amino, morpholinyl, $(C_{3-7}$cycloalkyl$)C_{1-3}$alkyloxy, trifluoromethyl and trifluoromethoxy, wherein R' and R" are independently selected from hydrogen and $C_{1-6}$alkyl; (benzyloxy)$C_{1-3}$alkyl; unsubstituted $C_{3-7}$cycloalkyl; $C_{3-7}$cycloalkyl substituted with one or more independently selected $C_{1-3}$alkyl substituted with one or more independently selected halo substituents; $(C_{3-7}$cycloalkyl$)C_{1-3}$alkyl; 4-(2,3,4,5-tetrahydro-benzo[f][1,4]oxazepine)methyl; Het$^1$; Het$^1C_{1-3}$alkyl; Het$^2$; and Het$^2C_{1-3}$alkyl;
$R^2$ is selected from the group consisting of cyano; halo; $C_{1-3}$alkyl substituted with one or more independently selected halo substituents; $C_{1-3}$alkyloxy substituted with one or more independently selected halo substituents; $C_{1-3}$alkyl; $C_{3-7}$cycloalkyl; and $(C_{3-7}$cycloalkyl$)C_{1-3}$alkyl;

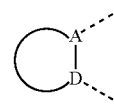

forms a radical selected from (a), (b), (c), (d) and (e):

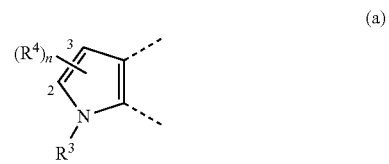

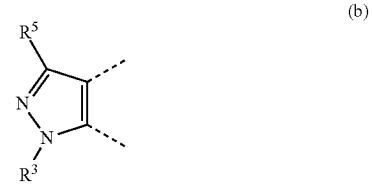

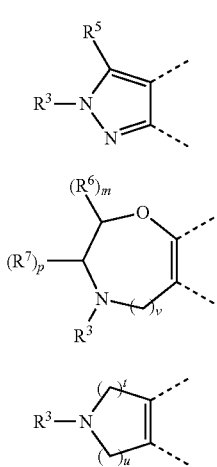

wherein
the bond drawn into (a) indicates that $R^4$ may be attached to any of carbon ring atoms 2 and 3;

each $R^3$ is independently selected from the group consisting of hydrogen; unsubstituted $C_{1-6}$alkyl; $C_{1-6}$alkyl substituted with one or more substituents independently selected from the group consisting of halo, hydroxy, $C_{1-3}$alkoxy and trifluoromethyl; unsubstituted $C_{3-7}$cycloalkyl; $C_{3-7}$cycloalkyl substituted with one or more substituents independently selected from the group consisting of halo, $C_{1-3}$alkyl, hydroxy, $C_{1-3}$alkoxy and trifluoromethyl; $C_{3-7}$cycloalkyl$C_{1-3}$alkyl; unsubstituted phenyl; phenyl substituted with one or more substituents independently selected from the group consisting of halo, $C_{1-3}$alkyl, $C_{1-3}$alkoxy and trifluoromethyl; $Het^3$; and $Het^3C_{1-3}$alkyl;
or
each $R^3$ is independently selected from a cyclic radical of formula (f)

wherein $R^8$ is selected from hydrogen, $C_{1-3}$alkyl, $C_{1-3}$alkyloxy and hydroxy$C_{1-3}$alkyl;
q is 1 or 2; X is selected from O, $CH_2$ and $CR^9(OH)$, wherein $R^9$ is selected from hydrogen, $C_{1-3}$alkyl and $C_{3-7}$cycloalkyl; or
X is a cyclic radical of formula (g)

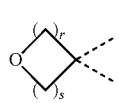

wherein r and s are independently selected from 0, 1 and 2, provided that r+s≥2;
each $R^4$, $R^6$ and $R^7$ are each independently selected from $C_{1-3}$alkyl and $C_{1-3}$alkyl substituted with one or more independently selected halo substituents;

each $R^5$ is independently selected from the group consisting of hydrogen, $C_{1-3}$alkyl, and $C_{1-3}$alkyl substituted with one or more independently selected halo substituents;
n, m and p are each independently selected from 0, 1 and 2;
v is 0 or 1;
t and u are each independently selected from 1 and 2;
W is selected from N and $C^{10}$;
wherein $R^{10}$ is selected from hydrogen, halo and trifluoromethyl;
each $Het^1$ is a saturated heterocyclic radical selected from pyrrolidinyl; piperidinyl;
piperazinyl; and morpholinyl; each of which may be optionally substituted with one or more each independently selected from the group consisting of $C_{1-6}$alkyl; mono-, di- and tri-halo$C_{1-3}$alkyl; unsubstituted phenyl; and phenyl substituted with 1, 2 or 3 substituents independently selected from the group consisting of halo, trifluoromethyl, and trifluoromethoxy;
each $Het^2$ is pyridyl or pyrimidinyl; and
each $Het^3$ is a heterocycle selected from the group consisting of tetrahydropyran, pyridyl; and pyrimidinyl; each of them being optionally substituted with one or more substituents each independently selected from the group consisting of halo, $C_{1-3}$alkyl, $C_{1-3}$alkoxy and trifluoromethyl; and
halo is selected from fluoro, chloro, bromo and iodo;
or a pharmaceutically acceptable salt thereof.

2. The compound of formula (I) according to claim 1, or a stereochemically isomeric form thereof, wherein
$R^1$ is selected from the group consisting of ($C_{1-3}$alkyloxy)$C_{1-3}$alkyl; $C_{1-3}$alkyl substituted with one or more independently selected halo substituents; and ($C_{3-7}$cycloalkyl)$C_{1-3}$alkyl;
$R^2$ is selected from the group consisting of halo; $C_{1-3}$alkyl; $C_{3-7}$cycloalkyl; and $C_{1-3}$alkyl substituted with one or more independently selected halo substituents;

is selected from (a), (b), (c) and (d):

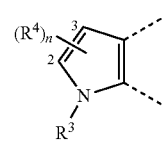

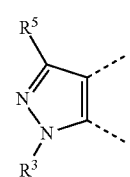

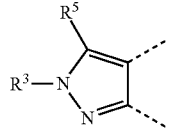

-continued

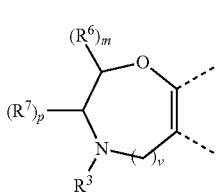
(d)

each R³ is independently selected from the group consisting of hydrogen; $C_{1-6}$alkyl substituted with one or more hydroxyl substituents; unsubstituted $C_{3-7}$cycloalkyl; $C_{3-7}$cycloalkyl substituted with one or more hydroxyl substituents; $(C_{3-7}$cycloalkyl)$C_{1-3}$alkyl; phenyl substituted with one or more independently selected halo substituents; Het³; and Het³ $C_{1-3}$alkyl;
m, n and p are 0;
v is 0 or 1;
each R⁵ is hydrogen;
W is selected from N and $C^{10}$;
$R^{10}$ is selected from hydrogen and halo;
Het³ is a heterocycle selected from the group consisting of tetrahydropyran; pyridyl; and
pyrimidinyl; each of them being optionally substituted with one or more substituents each independently selected from halo and $C_{1-3}$alkyl; and
halo is selected from fluoro and chloro;
or a pharmaceutically acceptable salt thereof.

3. The compound of claim 1, or a stereochemically isomeric form thereof, wherein

is selected from (a'), (b'), (c') and (d'):

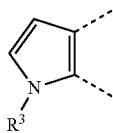
(a')

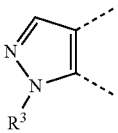
(b')

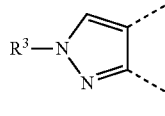
(c')

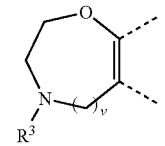
(d')

each R³ is independently selected from the group consisting of hydrogen; hydroxy$C_{1-6}$alkyl; $C_{3-7}$cycloalkyl substituted with one hydroxy substituent; $(C_{3-7}$cycloalkyl)$C_{1-3}$alkyl; phenyl substituted with one halo substituent; Het³; and Het³$C_{1-3}$alkyl;
v is 0 or 1;
W is selected from the group consisting of N, CH, CCl and CF;
Het³ is a heterocycle selected from the group consisting of tetrahydropyran; pyridyl optionally with one substituent selected from halo and $C_{1-3}$alkyl; and pyrimidinyl;
halo is selected from fluoro and chloro;
and R¹ and R² are as defined in claim 1;
or a pharmaceutically acceptable salt thereof.

4. The compound according to claim 1, wherein

is selected from (a') and (d'):

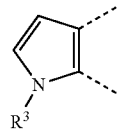
(a')

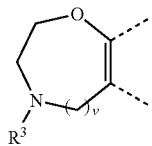
(d')

R¹ is $C_{3-7}$cycloalkyl$C_{1-3}$alkyl;
R² is selected from halo and $C_{1-3}$alkyl substituted with one or more independently selected halo substituents;
R³ is selected from hydrogen; $C_{3-7}$cycloalkyl substituted with one hydroxy substituent; $(C_{3-7}$cycloalkyl)$C_{1-3}$alkyl; pyridyl optionally substituted with one substituent selected from halo and $C_{1-3}$alkyl; and pyrimidinyl;
W is selected from N, CH and CCl;
v is 0; and
halo is selected from fluoro and chloro;
or a pharmaceutically acceptable salt thereof.

5. The compound according to claim 1, or a stereochemically isomeric form thereof, wherein
the bond drawn into the ring indicates that the bond may be attached to any carbon ring atom;
R¹ is selected from hydrogen; $C_{1-6}$alkyl; $(C_{1-3}$alkyloxy)$C_{1-3}$alkyl; $[(C_{1-3}$alkyloxy)-$C_{1-3}$alkyloxy]$C_{1-3}$alkyl; mono-, di- or tri-halo$C_{1-3}$alkyl; unsubstituted benzyl; benzyl substituted with 1, 2 or 3 substituents independently selected from the group consisting of halo, $C_{1-3}$alkyl, $(C_{1-3}$alkyloxy)$C_{1-3}$alkyl, $C_{1-3}$alkyloxy, hydroxy$C_{1-3}$alkyl, cyano, hydroxyl, amino, (C=O)R', C(=O)OR', C(=O)NR'R", mono- or di-($C_{1-3}$alkyl)amino, morpholinyl, $(C_{3-7}$cycloalkyl)$C_{1-3}$alkyloxy, trifluoromethyl and trifluoromethoxy, wherein R' and R" are independently selected from hydrogen and $C_{1-6}$alkyl; (benzyloxy)$C_{1-3}$alkyl; unsubstituted $C_{3-7}$cycloalkyl; $C_{3-7}$cycloalkyl substituted with trihalo$C_{1-3}$alkyl; $(C_{3-7}$cycloalkyl)$C_{1-3}$alkyl; 4-(2,3,4,5-tetrahydrobenzo[f][1,4]oxazepine)methyl; Het¹; Het¹$C_{1-3}$alkyl; Het² and Het²$C_{1-3}$alkyl;

$R^2$ is selected from cyano; halo; mono-, di- or tri-halo $C_{1-3}$alkyl; mono-, di- or tri-halo$C_{1-3}$alkyloxy; $C_{1-3}$alkyl; $C_{3-7}$cycloalkyl and $(C_{3-7}$cycloalkyl$)C_{1-3}$alkyl;

forms a radical selected from (a"), (b"), (c") and (d"):

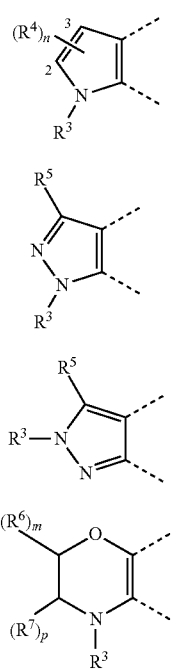

wherein the bond drawn into (a) indicates that $R^4$ may be attached to any of carbon ring atoms 2 and 3;

$R^3$ is selected from hydrogen; unsubstituted $C_{1-6}$alkyl; $C_{1-6}$alkyl substituted with 1 or 2 substituents independently selected from the group consisting of halo, hydroxy, $C_{1-3}$alkoxy or trifluoromethyl; unsubstituted $C_{3-7}$cycloalkyl; $C_{3-7}$cycloalkyl substituted with 1 or 2 substituents independently selected from the group consisting of halo, $C_{1-3}$alkyl, hydroxy, $C_{1-3}$alkoxy and trifluoromethyl; $C_{3-7}$cycloalkyl$C_{1-3}$alkyl; unsubstituted phenyl; phenyl substituted with 1, 2 or 3 substituents selected from the group consisting of halo, $C_{1-3}$alkyl, $C_{1-3}$alkoxy and trifluoromethyl; Het$^3$ and Het$^3$$C_{1-3}$alkyl; or $R^3$ is a cyclic radical of formula (f)

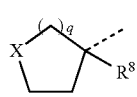

wherein $R^8$ is selected from hydrogen, $C_{1-3}$alkyl, $C_{1-3}$alkyloxy and hydroxy$C_{1-3}$alkyl;

q is 1 or 2;

X is selected from O, $CH_2$ and $CR^9$(OH) wherein $R^9$ is selected from hydrogen, $C_{1-3}$alkyl and $C_{3-7}$cycloalkyl; or X is a cyclic radical of formula (g)

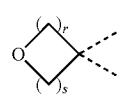

wherein r and s are independently selected from 0, 1 and 2, provided that r+s≥2;

$R^4$, $R^6$ and $R^7$ are independently selected from $C_{1-3}$alkyl and mono-, di- and tri-halo-$C_{1-3}$alkyl;

$R^5$ is selected from hydrogen, $C_{1-3}$alkyl and mono-, di- and tri-halo$C_{1-3}$alkyl;

n, m and p are independently selected from 0, 1 and 2;

W is selected from N and $C_{10}$; wherein $R^{10}$ is selected from hydrogen, halo and trifluoromethyl;

each Het$^1$ is a saturated heterocyclic radical selected from pyrrolidinyl; piperidinyl; piperazinyl; and morpholinyl; each of which may be optionally substituted with 1 or 2 substituents independently selected from the group consisting of $C_{1-6}$alkyl, mono-, di- or tri-halo$C_{1-3}$alkyl, unsubstituted phenyl and phenyl substituted with 1, 2 or 3 substituents independently selected from the group consisting of halo, trifluoromethyl, and trifluoromethoxy;

each Het$^2$ is pyridyl or pyrimidinyl; and each Het$^3$ is selected from the group consisting of tetrahydropyran, pyridyl and pyrimidinyl, each of them being optionally substituted with 1 or 2 substituents selected from the group consisting of halo, $C_{1-3}$alkyl, $C_{1-3}$alkoxy and trifluoromethyl;

or a pharmaceutically acceptable salt thereof.

6. The compound according to claim 1, including any stereochemically isomeric form thereof, wherein said compound is selected from the group consisting of:

trans-4-[5-[3-(cyclopropylmethyl)-8-(trifluoromethyl)-1, 2,4-triazolo[4,3-a]-pyridine-7-yl]-1H-indol-1-yl]-cyclohexanol;

8-chloro-7-(7-chloro-1H-indol-5-yl)-3-(cyclopropylmethyl)-1,2,4-triazolo[4,3-a]-pyridine;

8-chloro-3-(cyclopropylmethyl)-7-[1-(3-pyridinyl)-1H-indol-5-yl]-1,2,4-triazolo[4,3-a]pyridine;

8-chloro-3-(cyclopropylmethyl)-7-[1-(cyclopropylmethyl)-1H-pyrrolo[2,3-b]-pyridin-5-yl]-1,2,4-triazolo[4,3-a]pyridine; and 7-[8-chloro-3-(cyclopropylmethyl)-1,2,4-triazolo[4,3-a] pyridin-7-yl]-3,4-dihydro-4-(2-pyrimidinyl)-2H-1,4-benzoxazine;

and the pharmaceutically acceptable salts thereof.

7. A pharmaceutical composition comprising a therapeutically effective amount of a compound of claim 1 and a pharmaceutically acceptable carrier.

8. A method of treating, controlling, or ameliorating the symptoms of generalized anxiety disorder disorder (GAD) or schizophrenia in a human patient, said method comprising administering therapeutic effective amount of a compound of claim 1 in combination with an orthosteric agonist of mGluR2 to a patient in need of such treatment.

9. A process for preparing a pharmaceutical composition characterized in that a pharmaceutically acceptable carrier is mixed with a therapeutically effective amount of a compound of claim 1.

10. A product comprising
(a) a compound of claim 1; and
(b) a mGluR2 orthosteric agonist.

11. A method of treating, controlling, or ameliorating the symptoms of a central nervous system disorder selected from the group of anxiety disorders; psychotic disorders selected from the group of schizophrenia, schizoaffective disorder and schizophreniform disorder; mood disorders; epilepsy or convulsive disorders; and dementia of the Alzheimer's type said method comprising administering to a subject in need thereof a therapeutically effective amount of a compound of claim 1.

12. A method of treating, controlling, or ameliorating the symptoms of schizophrenia or generalized anxiety disorder in a human patient, said method comprising administering a therapeutically effective amount of a compound of claim 6 in combination with an orthosteric agonist of mGluR2 to a patient in need of such treatment.

13. The method of claim 8, wherein the disorder is generalized anxiety disorder (GAD).

14. A method of claim 11, wherein the disorder is generalized anxiety disorder (GAD).

15. The method of claim 11, wherein the disorder is major depressive disorder.

16. The method of claim 12, wherein the disorder is generalized anxiety disorder (GAD).

17. The method of claim 12, wherein the disorder is schizophrenia.

18. The method of claim 11, wherein the disorder is epilepsy.

19. The method of claim 11, wherein the disorder is bipolar disorder.

20. The method of claim 11, wherein the disorder is obsessive compulsive disorder.

21. The method of claim 8, wherein the compound of claim 1 is
   trans-4-[5-[3-(cyclopropylmethyl)-8-(trifluoromethyl)-1,2,4-triazolo[4,3-a]-pyridine-7-yl]-1H-indol-1-yl]-cyclohexanol;
   8-chloro-7-(7-chloro-1H-indol-5-yl)-3-(cyclopropylmethyl)-1,2,4-triazolo[4,3-a]-pyridine;
   8-chloro-3-(cyclopropylmethyl)-7-[1-(3-pyridinyl)-1H-indol-5-yl]-1,2,4-triazolo[4,3-a]pyridine;
   8-chloro-3-(cyclopropylmethyl)-7-[1-(cyclopropylmethyl)-1H-pyrrolo[2,3-b]-pyridin-5-yl]-1,2,4-triazolo[4,3-a]pyridine; or
   7-[8-chloro-3-(cyclopropylmethyl)-1,2,4-triazolo[4,3-a]pyridin-7-yl]-3,4-dihydro-4-(2-pyrimidinyl)-2H-1,4-benzoxazine;
   or a pharmaceutically acceptable salt thereof.

22. The method of claim 11, wherein the compound of claim 1 is
   trans-4-[5-[3-(cyclopropylmethyl)-8-(trifluoromethyl)-1,2,4-triazolo[4,3-a]-pyridine-7-yl]-1H-indol-1-yl]-cyclohexanol;
   8-chloro-7-(7-chloro-1H-indol-5-yl)-3-(cyclopropylmethyl)-1,2,4-triazolo[4,3-a]-pyridine;
   8-chloro-3-(cyclopropylmethyl)-7-[1-(3-pyridinyl)-1H-indol-5-yl]-1,2,4-triazolo[4,3-a]pyridine;
   8-chloro-3-(cyclopropylmethyl)-7-[1-(cyclopropylmethyl)-1H-pyrrolo[2,3-b]-pyridin-5-yl]-1,2,4-triazolo[4,3-a ]pyridine; or
   7-[8-chloro-3-(cyclopropylmethyl)-1,2,4-triazolo[4,3-a]pyridin-7-yl]-3,4-dihydro-4-(2-pyrimidinyl)-2H-1,4-benzoxazine;
   or a pharmaceutically acceptable salt thereof.

23. The method of claim 12, wherein the compound of claim 1 is
   trans-4-[5-[3-(cyclopropylmethyl)-8-(trifluoromethyl)-1,2,4-triazolo[4,3-a]-pyridine-7-yl]-1H-indol-1-yl]-cyclohexanol;
   8-chloro-7-(7-chloro-1H-indol-5-yl)-3-(cyclopropylmethyl)-1,2,4-triazolo[4,3-a]-pyridine;
   8-chloro-3-(cyclopropylmethyl)-7-[1-(3-pyridinyl)-1H-indol-5-yl]-1,2,4-triazolo[4,3-a]pyridine;
   8-chloro-3-(cyclopropylmethyl)-7-[1-(cyclopropylmethyl)-1H-pyrrolo[2,3-b]-pyridin-5-yl]-1,2,4-triazolo[4,3-a]pyridine; or
   7-[8-chloro-3-(cyclopropylmethyl)-1,2,4-triazolo[4,3-a]pyridin-7-yl]-3,4-dihydro-4-(2-pyrimidinyl)-2H-1,4-benzoxazine;
   or the pharmaceutically acceptable salt or solvate thereof.

24. The method of claim 11, wherein the disorder is dementia of the Alzheimer's type.

25. The method of claim 11, wherein the disorder is schizophrenia.

\* \* \* \* \*